United States Patent
Trotter et al.

(10) Patent No.: US 10,996,215 B2
(45) Date of Patent: May 4, 2021

(54) METHODS FOR DETERMINING DRUG EFFICACY FOR THE TREATMENT OF DIFFUSE LARGE B-CELL LYMPHOMA, MULTIPLE MYELOMA, AND MYELOID CANCERS

(71) Applicant: CELGENE CORPORATION, Summit, NJ (US)

(72) Inventors: Matthew William Burnell Trotter, Seville (ES); Patrick Hagner, Sparta, NJ (US); Courtney G. Havens, Morristown, NJ (US); Rajesh Chopra, Summit, NJ (US); Anita Gandhi, Bernardsville, NJ (US); Anke Klippel, Westfield, NJ (US); Maria Yinglin Wang, San Diego, CA (US); Mike Breider, Cardiff-by-the-Sea, CA (US); Suzana Sturlini Couto, La Jolla, CA (US); Yan Ren, San Diego, CA (US); Paul Hollenbach, Castro Valley, CA (US); Kyle Macbeth, San Francisco, CA (US)

(73) Assignee: CELGENE CORPORATION, Summit, NJ (US)

( * ) Notice: Subject to any disclaimer, the term of this patent is extended or adjusted under 35 U.S.C. 154(b) by 42 days.

(21) Appl. No.: 15/946,618

(22) Filed: Apr. 5, 2018

(65) Prior Publication Data

US 2019/0004033 A1 Jan. 3, 2019

Related U.S. Application Data

(62) Division of application No. 15/101,869, filed as application No. PCT/US2014/068795 on Dec. 5, 2014, now abandoned.

(60) Provisional application No. 62/087,111, filed on Dec. 3, 2014, provisional application No. 62/077,835, filed on Nov. 10, 2014, provisional application No. 62/064,413, filed on Oct. 15, 2014, provisional application No. 62/061,050, filed on Oct. 7, 2014, provisional application No. 61/990,621, filed on May 8, 2014, provisional application No. 61/947,963, filed on Mar. 4, 2014, provisional application No. 61/913,003, filed on Dec. 6, 2013.

(51) Int. Cl.
| | |
|---|---|
| G01N 33/50 | (2006.01) |
| A61K 31/517 | (2006.01) |
| G01N 33/68 | (2006.01) |
| A61K 31/454 | (2006.01) |
| A61K 31/5377 | (2006.01) |
| A61K 38/21 | (2006.01) |
| C12Q 1/6883 | (2018.01) |
| C12Q 1/6886 | (2018.01) |
| G01N 33/574 | (2006.01) |

(52) U.S. Cl.
CPC ........ *G01N 33/5011* (2013.01); *A61K 31/454* (2013.01); *A61K 31/517* (2013.01); *A61K 31/5377* (2013.01); *A61K 38/21* (2013.01); *C12Q 1/6883* (2013.01); *C12Q 1/6886* (2013.01); *C12Y 207/11001* (2013.01); *G01N 33/5743* (2013.01); *G01N 33/57407* (2013.01); *G01N 33/57426* (2013.01); *G01N 33/57484* (2013.01); *G01N 33/57492* (2013.01); *G01N 33/6863* (2013.01); *G01N 33/6866* (2013.01); *C12Q 2600/106* (2013.01); *C12Q 2600/118* (2013.01); *C12Q 2600/136* (2013.01); *C12Q 2600/158* (2013.01); *G01N 2333/4703* (2013.01); *G01N 2333/4704* (2013.01); *G01N 2333/555* (2013.01); *G01N 2333/91205* (2013.01); *G01N 2800/24* (2013.01); *G01N 2800/26* (2013.01); *G01N 2800/285* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,365,640 B2 * | 6/2016 | Lopez-Girona | ........ C07K 16/18 |
| 9,857,359 B2 | 1/2018 | Schafer et al. | |
| 10,047,151 B2 | 8/2018 | Lopez-Girona et al. | |

(Continued)

FOREIGN PATENT DOCUMENTS

| | | |
|---|---|---|
| CA | 2662508 A1 | 7/2008 |
| JP | 2012031141 A | 2/2012 |

(Continued)

OTHER PUBLICATIONS

Lu et al (Science, 2014, 343:305-309).*

(Continued)

*Primary Examiner* — Laura B Goddard
(74) *Attorney, Agent, or Firm* — Jones Day

(57) ABSTRACT

Provided herein, in some embodiments, are methods of using certain cereblon-associated proteins, such as Aiolos, Ikaros, interferon (IFN), and IFN pathway proteins, casein kinase 1, alpha 1 (CSNK1A1), and ZFP9, as biomarkers for use in predicting and monitoring clinical sensitivity and therapeutic response to certain compounds in patients having various diseases and disorders, such as cancers (e.g., diffuse large B-cell lymphoma (DLBCL), multiple myeloma (MM), myelodysplasia syndromes (MDS) and acute myeloid leukemia (AML)) and IFN-associated disorders. Also provided herein, in certain embodiments, are methods of determining the efficacy of an immunomodulatory compound.

21 Claims, 67 Drawing Sheets

(56) References Cited

U.S. PATENT DOCUMENTS

| | | |
|---|---|---|
| 10,338,077 B2 | 7/2019 | Iha et al. |
| 10,648,983 B2 | 5/2020 | Filvaroff et al. |
| 10,689,708 B2 | 6/2020 | Trotter et al. |
| 2007/0065888 A1 | 3/2007 | Ring et al. |
| 2007/0099209 A1 | 5/2007 | Clarke et al. |
| 2009/0023149 A1 | 1/2009 | Steen |
| 2009/0142297 A1 | 6/2009 | Muller et al. |
| 2009/0148853 A1 | 6/2009 | Schafer et al. |
| 2009/0325176 A1 | 12/2009 | O'Toole et al. |
| 2010/0190656 A1 | 7/2010 | Li et al. |
| 2012/0035347 A1 | 2/2012 | Yver |
| 2012/0322073 A1 | 12/2012 | Lopez-Girona et al. |
| 2013/0177644 A1 | 7/2013 | Zeldis |
| 2013/0302323 A1 | 11/2013 | Zeldis |
| 2014/0045843 A1 | 2/2014 | Schafer et al. |
| 2014/0162282 A1 | 6/2014 | Schafer et al. |
| 2014/0314752 A1 | 10/2014 | Lopez-Girona et al. |
| 2016/0139005 A1 | 5/2016 | Young et al. |
| 2016/0282354 A1* | 9/2016 | Ebert .................. C12Q 1/6886 |
| 2016/0312292 A1 | 10/2016 | Trotter |
| 2016/0313300 A1 | 10/2016 | Trotter et al. |
| 2016/0356778 A1 | 12/2016 | Iha et al. |
| 2017/0038387 A1 | 2/2017 | Gandhi et al. |
| 2017/0088901 A1 | 3/2017 | Trotter et al. |
| 2017/0199193 A1 | 7/2017 | Filvaroff et al. |
| 2017/0242014 A1 | 8/2017 | Hagner et al. |
| 2018/0209961 A1 | 7/2018 | Schafer et al. |
| 2018/0231561 A1 | 8/2018 | Gandhi et al. |

FOREIGN PATENT DOCUMENTS

| | | |
|---|---|---|
| JP | 2013519675 A | 5/2013 |
| JP | 2014514579 A | 6/2014 |
| WO | WO 2008027542 A2 | 3/2008 |
| WO | WO 2008027542 A3 | 3/2008 |
| WO | WO 2010053732 A1 | 5/2010 |
| WO | WO 2011100380 A1 | 8/2011 |
| WO | WO 2012/149299 A2 | 11/2012 |
| WO | WO 2014/004990 A2 | 1/2014 |
| WO | WO 2016/060702 A1 | 4/2016 |
| WO | WO 2017027672 A1 | 2/2017 |

OTHER PUBLICATIONS

Lu et al (Science, 2014, 343:305-309) Supplementary Materials, published online Nov. 2013.*

Sperling et al (Blood, 2019, 134:160-170).*

International Search Report and Written Opinion in corresponding PCT Application PCT/US2014/068795 dated Mar. 16, 2015 (18 pages).

Piya et al., 2011, "Suppression of IRF4 by IRF1, 3, and 7 in Noxa expression is a necessary event for IFN-γ-mediated tumor elimination," Mol Cancer Res., 9(10):1356-1365.

International Search Report and Written Opinion of International Patent Application No. PCT/US2015/054227 (Pub. No. WO 2016/057503) dated Jan. 7, 2016 (9 pages).

Ito et al., 2010, "Identification of a primary target of thalidomide teratogenicity," Science, 327(5971):1345-1350.

* cited by examiner

| Gene Name | Full Name |
|---|---|
| IFIT3 | interferon-induced protein with tetratricopeptide repeats 3 [Source:HGNC Symbol;Acc:5411] |
| IFIT1 | interferon-induced protein with tetratricopeptide repeats 1 [Source:HGNC Symbol;Acc:5407] |
| IFI27 | interferon, alpha-inducible protein 27 [Source:HGNC Symbol;Acc:5397] |
| IFIT5 | interferon-induced protein with tetratricopeptide repeats 5 [Source:HGNC Symbol;Acc:13328] |
| IFIT1 | interferon-induced protein with tetratricopeptide repeats 1 [Source:HGNC Symbol;Acc:5407] |
| IFIT2 | interferon-induced protein with tetratricopeptide repeats 2 [Source:HGNC Symbol;Acc:5409] |
| IFIT3 | interferon-induced protein with tetratricopeptide repeats 3 [Source:HGNC Symbol;Acc:5411] |
| DDX58 | DEAD (Asp-Glu-Ala-Asp) box polypeptide 58 [Source:HGNC Symbol;Acc:19102] |
| IFIT3 | interferon-induced protein with tetratricopeptide repeats 3 [Source:HGNC Symbol;Acc:5411] |
| TLR3 | toll-like receptor 3 [Source:HGNC Symbol;Acc:11849] |
| OAS1 | 2'-5'-oligoadenylate synthetase 1, 40/46kDa [Source:HGNC Symbol;Acc:8086] |
| ISG15 | ISG15 ubiquitin-like modifier [Source:HGNC Symbol;Acc:4053] |
| MX1 | myxovirus (influenza virus) resistance 1, interferon-inducible protein p78 (mouse) [Source:HGNC Symbol;Acc:7532] |
| IFI44L | interferon-induced protein 44-like [Source:HGNC Symbol;Acc:17817] |
| IFI44 | interferon-induced protein 44 [Source:HGNC Symbol;Acc:16938] |
| OAS3 | 2'-5'-oligoadenylate synthetase 3, 100kDa [Source:HGNC Symbol;Acc:8088] |
| OAS2 | 2'-5'-oligoadenylate synthetase 2, 69/71kDa [Source:HGNC Symbol;Acc:8087] |
| MX2 | myxovirus (influenza virus) resistance 2 (mouse) [Source:HGNC Symbol;Acc:7533] |
| ISG20 | interferon stimulated exonuclease gene 20kDa [Source:HGNC Symbol;Acc:6130] |
| GBP1 | guanylate binding protein 1, interferon-inducible [Source:HGNC Symbol;Acc:4182] |
| IFI6 | interferon, alpha-inducible protein 6 [Source:HGNC Symbol;Acc:4054] |
| IFIT5 | interferon-induced protein with tetratricopeptide repeats 5 [Source:HGNC Symbol;Acc:13328] |
| DDX60 | DEAD (Asp-Glu-Ala-Asp) box polypeptide 60 [Source:HGNC Symbol;Acc:25942] |
| DDX60L | DEAD (Asp-Glu-Ala-Asp) box polypeptide 60-like [Source:HGNC Symbol;Acc:26429] |
| IFIH1 | interferon induced with helicase C domain 1 [Source:HGNC Symbol;Acc:18873] |
| IFI35 | interferon-induced protein 35 [Source:HGNC Symbol;Acc:5399] |
| IFI16 | interferon, gamma-inducible protein 16 [Source:HGNC Symbol;Acc:5395] |
| IFI27 | interferon, alpha-inducible protein 27 [Source:HGNC Symbol;Acc:5397] |
| IFI6 | interferon, alpha-inducible protein 6 [Source:HGNC Symbol;Acc:4054] |

Figure 12

| Gene Name | Full Name |
|---|---|
| IFI27 | interferon, alpha-inducible protein 27 [Source:HGNC Symbol;Acc:5397] |
| IFI6 | interferon, alpha-inducible protein 6 [Source:HGNC Symbol;Acc:4054] |
| OASL | 2'-5'-oligoadenylate synthetase-like [Source:HGNC Symbol;Acc:8090] |
| DDX60 | DEAD (Asp-Glu-Ala-Asp) box polypeptide 60 [Source:HGNC Symbol;Acc:25942] |
| OAS1 | 2'-5'-oligoadenylate synthetase 1, 40/46kDa [Source:HGNC Symbol;Acc:8086] |
| OAS3 | 2'-5'-oligoadenylate synthetase 3, 100kDa [Source:HGNC Symbol;Acc:8088] |
| IFI44 | interferon-induced protein 44 [Source:HGNC Symbol;Acc:16938] |
| IFI44 | interferon-induced protein 44 [Source:HGNC Symbol;Acc:16938] |
| DDX60L | DEAD (Asp-Glu-Ala-Asp) box polypeptide 60-like [Source:HGNC Symbol;Acc:26429] |
| IFIT1 | interferon-induced protein with tetratricopeptide repeats 1 [Source:HGNC Symbol;Acc:5407] |
| TLR1 | toll-like receptor 1 [Source:HGNC Symbol;Acc:11847] |
| TLR4 | toll-like receptor 4 [Source:HGNC Symbol;Acc:11850] |
| IFIH1 | interferon induced with helicase C domain 1 [Source:HGNC Symbol;Acc:18873] |
| TLR7 | toll-like receptor 8 [Source:HGNC Symbol;Acc:15632] |
| TLR8 | toll-like receptor 8 [Source:HGNC Symbol;Acc:15632] |
| OASL | 2'-5'-oligoadenylate synthetase-like [Source:HGNC Symbol;Acc:8090] |
| OAS2 | 2'-5'-oligoadenylate synthetase 2, 69/71kDa [Source:HGNC Symbol;Acc:8087] |
| TLR3 | toll-like receptor 3 [Source:HGNC Symbol;Acc:11849] |
| IFIT5 | interferon-induced protein with tetratricopeptide repeats 5 [Source:HGNC Symbol;Acc:13328] |
| IRF8 | interferon regulatory factor 8 [Source:HGNC Symbol;Acc:5358] |
| DDX60 | DEAD (Asp-Glu-Ala-Asp) box polypeptide 60 [Source:HGNC Symbol;Acc:25942] |
| IRF8 | interferon regulatory factor 8 [Source:HGNC Symbol;Acc:5358] |
| MX2 | myxovirus (influenza virus) resistance 2 (mouse) [Source:HGNC Symbol;Acc:7533] |
| ISG20 | interferon stimulated exonuclease gene 20kDa [Source:HGNC Symbol;Acc:6130] |
| IFIT2 | interferon-induced protein with tetratricopeptide repeats 2 [Source:HGNC Symbol;Acc:5409] |
| IFI27 | interferon, alpha-inducible protein 27 [Source:HGNC Symbol;Acc:5397] |
| IRF7 | interferon regulatory factor 7 [Source:HGNC Symbol;Acc:6122] |
| DDX58 | DEAD (Asp-Glu-Ala-Asp) box polypeptide 58 [Source:HGNC Symbol;Acc:19102] |

Figure 12 (Cont'd)

| Gene Name | Full Name |
|---|---|
| ISG15 | ISG15 ubiquitin-like modifier [Source:HGNC Symbol;Acc:4053] |
| IFITM2 | interferon induced transmembrane protein 2 [Source:HGNC Symbol;Acc:5413] |
| MX2 | myxovirus (influenza virus) resistance 2 (mouse) [Source:HGNC Symbol;Acc:7533] |
| TLR8 | toll-like receptor 8 [Source:HGNC Symbol;Acc:15632] |
| IRF2 | interferon regulatory factor 2 [Source:HGNC Symbol;Acc:6117] |
| IRF1 | interferon regulatory factor 1 [Source:HGNC Symbol;Acc:6116] |
| IRF8 | interferon regulatory factor 8 [Source:HGNC Symbol;Acc:5358] |
| GBP1 | guanylate binding protein 1, interferon-inducible [Source:HGNC Symbol;Acc:4182] |
| IRF1 | interferon regulatory factor 1 [Source:HGNC Symbol;Acc:6116] |
| OAS3 | 2'-5'-oligoadenylate synthetase 3, 100kDa [Source:HGNC Symbol;Acc:8088] |
| IFI44L | interferon-induced protein 44-like [Source:HGNC Symbol;Acc:17817] |
| IFNA16 | interferon, alpha 16 [Source:HGNC Symbol;Acc:5421] |
| TLR4 | toll-like receptor 4 [Source:HGNC Symbol;Acc:11850] |
| IFITM2 | interferon induced transmembrane protein 2 [Source:HGNC Symbol;Acc:5413] |
| IFNA5 | interferon, alpha 5 [Source:HGNC Symbol;Acc:5426] |
| IFI35 | interferon-induced protein 35 [Source:HGNC Symbol;Acc:5399] |
| IFNG | interferon, gamma [Source:HGNC Symbol;Acc:5438] |
| IFI16 | interferon, gamma-inducible protein 16 [Source:HGNC Symbol;Acc:5395] |
| IFNGR1 | interferon gamma receptor 1 [Source:HGNC Symbol;Acc:5439] |
| TLR3 | toll-like receptor 3 [Source:HGNC Symbol;Acc:11849] |
| IFI27L2 | interferon, alpha-inducible protein 27-like 2 [Source:HGNC Symbol;Acc:19753] |
| IFIT3 | interferon-induced protein with tetratricopeptide repeats 3 [Source:HGNC Symbol;Acc:5411] |
| IRF4 | interferon regulatory factor 4 [Source:HGNC Symbol;Acc:6119] |

Figure 12 (Cont'd)

| Cell proliferation after 4d treatment (% control) | 10µM CC-5013 |
|---|---|
| AML-193 | 102.13 +/- 12.18 |
| F-36P | 55.13 +/- 26.95 |
| HL-60 | 91.97 +/- 8.2 |
| HNT-34 | 15.06 +/- 1.08 |
| K-562 | 101.65 +/- 6.8 |
| KASUMI-1 | 67.95 +/- 5.3 |
| KASUMI-3 | 65.05 +/- 2.21 |
| KG-1 | 73.78 +/- 8.63 |
| KG-1a | 91.53 +/- 2.76 |
| MOLM-13 | 107.23 +/- 9.01 |
| OCI-AML3 | 77.28 +/- 11.8 |
| THP-1 | 114.85 +/- 5.56 |
| MDS-L | 25.15 +/- 5.75 |
| U266 | 21.28 +/- 3.76 |

| Cell line | BrdU assay, % viable +/- range LEN (10 µM) | 3H-thymidine assay EC$_{50}$, µM LEN | 3H-thymidine assay EC$_{50}$, µM Compound A |
|---|---|---|---|
| HNT-34 | 15.06 +/- 1.08 | 0.64 | >10 |
| MDS-L | 25.15 +/- 5.75 | 1.50 | 0.66 |
| KG-1 | 73.78 +/- 8.63 | >10 | >10 |
| HL-60 | 91.97 +/- 8.2 | >10 | >10 |
| THP-1 | 114.85 +/- 5.56 | >10 | >10 |
| MOLM-13 | 107.23 +/- 9.01 | >10 | >10 |

AML, acute myeloid leukemia; AMoL, acute monocytic leukemia; APL, acute promyelocytic leukemia; BrdU, bromodeoxyuridine; Compound A, cereblon-binding analog; CML, chronic myeloid leukemia; del, deletion; EC$_{50}$, half maximal effective concentration; LEN, lenalidomide; MDS, myelodysplastic syndromes.

Figure 22C

| Protein Id | Gene symbol | Protein description | # of quantified peptides | BH adjusted p value | Log2(Ratio) Len/DMSO | Log2(Ratio) CC122/DMSO |
|---|---|---|---|---|---|---|
| sp\|Q13422\|IKZF1_HUMAN | IKZF1 | IKZF1_HUMAN DNA-binding protein Ikaros | 10 | 8.09E-08 | 2.4063 | -3.1211 |
| sp\|P48729-2\|KC1A_HUMAN | CSNK1A1 | KC1A_HUMAN Isoform 2 of Casein kinase I isoform alpha | 11 | 2.43E-06 | -1.4921 | -0.0826 |

Figure 23B

| | HNT-34 | MDS-L | KG-1 | HL-60 | MOLM-13 | THP-1 |
|---|---|---|---|---|---|---|
| Sensitivity to LEN | Yes | Yes | No | No | No | No |
| del(5q) | No | Yes | Yes | Yes | No | No |
| CRBN expression | Yes | Yes | Yes | Low | Low | Low |
| CK1α expression | Yes | Yes | Yes | Yes | Yes | Yes |
| CK1α regulation by LEN | Yes | Yes | Yes | Yes | No | No |
| Ikaros expression | Yes | Yes | Yes | No | No | Yes |
| Ikaros regulation by LEN | Yes | Yes | Yes | NA | NA | No |

CK1α, casein kinase 1α; CRBN, cereblon; del(5q), deletion 5q; LEN, lenalidomide; NA, not applicable.

Figure 25B

METHODS FOR DETERMINING DRUG EFFICACY FOR THE TREATMENT OF DIFFUSE LARGE B-CELL LYMPHOMA, MULTIPLE MYELOMA, AND MYELOID CANCERS

CROSS-REFERENCE TO RELATED APPLICATIONS

This application is a divisional of U.S. application Ser. No. 15/101,869 filed Jun. 3, 2016, now abandoned, which is a U.S. National Stage Application under 35 U.S.C. § 371 of International Patent Application No. PCT/US14/68795 filed Dec. 5, 2014, which claims the benefit of priority to U.S. Provisional Application No. 61/913,003 filed Dec. 6, 2013, U.S. Provisional Application No. 61/947,963 filed Mar. 4, 2014, U.S. Provisional Application No. 61/990,621 filed May 8, 2014, U.S. Provisional Application No. 62/061,050 filed Oct. 7, 2014, U.S. Provisional Application No. 62/064,413 filed Oct. 15, 2014, U.S. Provisional Application No. 62/077,835 filed Nov. 10, 2014, and U.S. Provisional Application No. 62/087,111 filed Dec. 3, 2014, each of which is incorporated herein by reference in its entirety.

1 FIELD

Provided herein, in some embodiments, are methods of using certain cereblon-associated proteins, such as Aiolos, Ikaros, interferon (IFN), and IFN pathway proteins, casein kinase 1, alpha 1 (CSNK1A1 or CK1α), and ZFP91 as biomarkers for use in predicting and monitoring clinical sensitivity and therapeutic response to certain compounds in patients having various diseases and disorders, such as cancers (e.g., diffuse large B-cell lymphoma (DLBCL), multiple myeloma (MM), myelodysplastic syndromes (MDS) and acute myeloid leukemia (AML)) and IFN-associated disorders. Further provided are kits for carrying out the methods. Also provided herein, in certain embodiments, are methods of determining the efficacy of an immunomodulatory compound.

2 BACKGROUND

2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., Immunology, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, blood and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes-B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatments of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, DLBCL, mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the U.S. population. Id. Clarke C A, et al., *Cancer* 2002; 94(7):2015-2023.

DLBCL accounts for approximately one-third of non-Hodgkin's lymphomas. While some DLBCL patients are cured with traditional chemotherapy, the remainders die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in DLBCL.

DLBCL can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17$^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17$^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloid leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual*, 949-952 (17$^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

Bone marrow stromal cells are well known to support CLL disease progression and resistance to chemotherapy. Disrupting the interactions between CLL cells and stromal cells is an additional target of CLL chemotherapy.

In addition to the acute and chronic categorization, neoplasms are also categorized based upon the cells giving rise to such disorder into precursor or peripheral. See e.g., U.S. patent Publication No. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, DLBCL and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

Myelodysplastic syndrome (MDS) refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See The Merck Manual 953 (17th ed. 1999) and List et al., 1990, *J Clin. Oncol.* 8:1424. The treatment of MDS using immunomodulatory compounds is described in U.S. Patent Publication No. 2004/0220144, the entirety of which is hereby incorporated by reference.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., *Ann Oncol* 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. *Nature Rev.,* 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. The oncogenic transcription factor MYC has also been linked to tumor cell metabolism, specifically glycolysis. Id. MYC also promotes cell proliferation by glutamine metabolic pathways. Id.

AMP-activated protein kinase (AMPK) functions as a metabolic check point which tumor cells must overcome in order to proliferate. Id. Several mutations have been identified which suppress AMPK signaling in tumor cells. See Shackelford, D. B. & Shaw, R. J., *Nature Rev. Cancer,* 2009, 9: 563-575. STK11 has been identified as a tumor suppressor gene related to the role of AMPK. See Cairns, R. A., et al. *Nature Rev.,* 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.,* 2009, 361: 1058-1066; Parsons, D. W. et al., *Science,* 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, fibrosis, arthritis and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control and/or inhibit unwanted angiogenesis or inhibit the production of certain cytokines, including TNF-α, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, for example, Stockdale, 1998, *Medicine,* vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics,* Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective methods of treating, preventing and managing cancer, particularly for cancers that are refractory to standard treatments, such as surgery, radiation therapy, chemotherapy and hormonal therapy, while reducing or avoiding the toxicities and/or side effects associated with the conventional therapies. The present invention satisfies these and other needs.

2.3 Cereblon

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (ClC-2) in the retina with AMPK1 and DDB1. See Jo, S. et al., *J. Neurochem*, 2005, 94:1212-1224; Hohberger B. et al., *FEBS Lett*, 2009, 583:633-637; Angers S. et al., *Nature*, 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

CRBN has recently been identified as a key molecular target that binds to thalidomide to cause birth defects. See Ito, T. et al., *Science*, 2010, 327:1345-1350. DDB1 was found to interact with CRBN and, thus, was indirectly associated with thalidomide. Moreover, thalidomide was able to inhibit auto-ubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A were both defective for thalidomide binding, with the double point mutant having the lowest thalidomide-binding activity. Id. A link between CRBN and the teratogenic effect of thalidomide was confirmed in animal models of zebra-fish and chick embryos. Id.

Whether binding to CRBN, the CRBN E3 ubiquitin-ligase complex, or one or more substrates of CRBN, is required for the beneficial effects of thalidomide and other drugs is yet to be established. Understanding these interactions with thalidomide and other drug targets will allow the definition of the molecular mechanisms of efficacy and/or toxicity and may lead to drugs with improved efficacy and toxicity profiles.

2.4 Compounds

A number of studies have been conducted with the aim of providing compounds that can safely and effectively be used to treat diseases associated with abnormal production of TNF-α. See, e.g., Marriott, J. B., et al., *Expert Opin. Biol. Ther.*, 2001, 1(4): 1-8; G. W. Muller, et al., *J Med Chem.*, 1996, 39(17): 3238-3240; and G. W. Muller, et al., *Bioorg & Med Chem Lett.*, 1998, 8: 2669-2674. Some studies have focused on a group of compounds selected for their capacity to potently inhibit TNF-α production by LPS stimulated PBMC. L. G. Corral, et al., *Ann. Rheum. Dis.*, 1999, 58: (Suppl I) 1107-1113. These compounds show not only potent inhibition of TNF-α but also marked inhibition of LPS induced monocyte IL13 and IL12 production. LPS induced IL6 is also inhibited by such compounds, albeit partially. These compounds are potent stimulators of LPS induced IL10. Id.

Compounds for the methods provided herein include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al. Still other specific compounds disclosed herein belong to a class of isoindole-imides disclosed in U.S. Pat. Nos. 6,395,754, 6,555,554, 7,091,353, U.S. Publication No. 2004/0029832, and International Publication No. WO 98/54170, each of which is incorporated herein by reference.

Thalidomide, lenalidomide and pomalidomide have shown remarkable responses in patients with multiple myeloma, lymphoma and other hematological diseases such as myelodysplastic syndrome. See Galustian C, et al., *Expert Opin Pharmacother.*, 2009, 10:125-133. These drugs display a broad spectrum of activity, including anti-angiogenic properties, modulation of pro-inflammatory cytokines, co-stimulation of T cells, increased NK cell toxicity, direct anti-tumor effects and modulation of stem cell differentiation.

For example, thalidomide and lenalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide may also be administered in combination with dexamethasone. U.S. Patent Publication No. 2004/0029832 A1, the disclosure of which is hereby incorporated in its entirety, discloses the treatment of multiple myeloma.

Another compound provided herein is 3-(5-amino-2-methyl-4-oxo-4H-quinazolin-3-yl)-piperidine-2,6-dione ("Compound A"), which has the following structure:

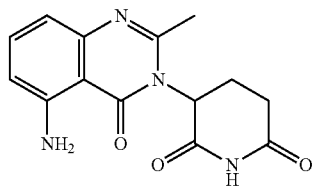

or an enantiomer or a mixture of enantiomers thereof; or a pharmaceutically acceptable salt, solvate, hydrate, co-crystal, clathrate, or polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional Pat. App. No. 61/451,995, filed Mar. 11, 2011, which is incorporated herein by reference in its entirety.

Yet another compound provided herein is 3-[4-(4-Morpholin-4-ylmethyl-benzyloxy)-1-oxo-1,3-dihydro-isoindol-2-yl]-piperidine-2,6-dione ("Compound B"), which has the following structure:

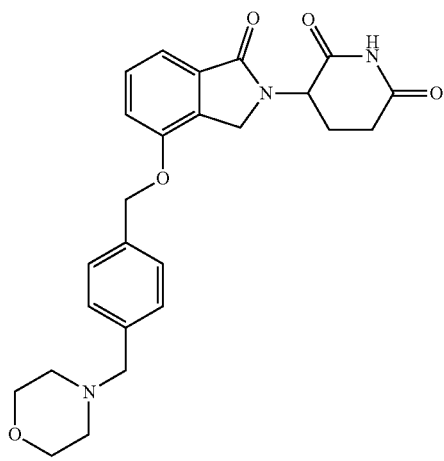

or an enantiomer or a mixture of enantiomers thereof; or a pharmaceutically acceptable salt, solvate, hydrate, co-crystal, clathrate, or polymorph thereof.

The conventional methods of assessing the effects of immunomodulatory compounds require live cellular assays or lengthy clinical endpoints. These cellular tests are cumbersome and often require the use of various stimulants (e.g., lipopolysaccharide or anti-CD3 antibody). Indirect endpoints such as cytokine production are evaluated, which can be influenced via multiple pathways. Further, clinical efficacy of these compounds could not be correctly predicted, as it could only be measured in terms of patient response, which usually requires a minimum of several months of treatment. In view of the deficiencies of the conventional methods, there is a need to develop an efficient, sensitive and accurate method to detect, quantify and characterize the pharmacodynamic activity of immunomodulatory compounds.

3 SUMMARY OF THE INVENTION

In one aspect, provided herein is a method of determining whether a compound is immunomodulatory, comprising:
a. contacting a first cell with the compound;
b. obtaining a first sample from the first cell from step (a);
c. determining the level of a biomarker in the first sample, and
d. comparing the level of the biomarker from step (c) to the level of the same protein obtained from a reference sample, wherein a change in the biomarker level as compared to the reference sample is indicative of the efficacy of the compound as an immunomodulatory compound.

In some embodiments, the cancer is diffuse large B-cell lymphoma (DLBCL). In other embodiments, the cancer is multiple myeloma (MM). In certain embodiments, the cancer is myelodysplastic syndrome (MDS) (e.g., a MDS with deletion of chromosome 5q (del(5q)). In certain embodiments, the cancer is acute myeloid leukemia (AML). In certain embodiments, the cell is a cancer cell. In another embodiment, the cell is an immune cell.

In other embodiments, provided herein is a method of treating a cancer, comprising a method of determining whether a compound is immunomodulatory provided herein, wherein the method further comprises (e) administering to the subject a therapeutically effective amount of the compound when the compound is indicated as likely to be efficacious as an immunomodulatory compound. In other embodiments, provided herein is a method of treating a cancer, comprising a method of determining whether a compound is immunomodulatory provided herein, wherein the method further comprises (e) administering to the subject a therapeutically effective amount of a therapy other than the compound when the compound is indicated as unlikely to be efficacious as an immunomodulatory compound.

In another aspect, provided herein is a method of determining whether a compound is effective as an anti-tumor (or anti-cancer) agent, comprising:
a. contacting a first cell with the compound;
b. obtaining a first sample from the first cell from step (a);
c. determining the level of a biomarker in the first sample; and
d. comparing the level of the biomarker from step (c) to the level of the same protein(s) obtained from a reference sample, wherein a change in the biomarker level as compared to the reference sample is indicative of the efficacy of the compound as an anti-tumor (or anti-cancer) agent.

In some embodiments, the cancer is DLBCL. In other embodiments, the cancer is MM. In another embodiment, the cancer is MDS. In yet another embodiment, the cancer is AML. In certain embodiments, the cell is a cancer cell. In another embodiment, the cell is an immune cell.

In certain embodiments, provided herein is a method of treating a cancer, comprising the method of method of determining whether a compound is effective as an anti-tumor (or anti-cancer) agent provided herein, wherein the method further comprises (e) administering to the subject a therapeutically effective amount of the compound when the compound is indicated as likely to be efficacious as an anti-tumor agent. In some embodiments, provided herein is a method of treating a cancer, comprising the method of method of determining whether a compound is effective as an anti-tumor (or anti-cancer) agent provided herein, wherein the method further comprises (e) administering to the subject a therapeutically effective amount of a therapy other than the compound when the compound is indicated to be as unlikely to be efficacious as an anti-tumor agent.

In another aspect, provided herein is a method of assessing the efficacy of a compound in treating cancer, comprising:
a. administering a compound to a subject having cancer;
b. obtaining a first sample from the subject;
c. determining the level of a biomarker in the first sample; and
d. comparing the level of the biomarker from step (c) to the level of the same protein obtained from a reference sample, wherein a change in the biomarker level as compared to the reference sample is indicative of the efficacy of the compound in treating the cancer.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of assessing the efficacy of a compound in treating cancer provided herein, wherein the method further comprises (e) administering to the subject a therapeutically effective amount of the compound when the compound is indicated as likely to be efficacious in treating the cancer. In certain embodiments, provided herein is a method of treating a cancer, comprising the method of assessing the efficacy of a compound in treating cancer provided herein, wherein the method further comprises (e) administering to the subject a therapeutically effective amount of a therapy other than the compound when the compound is indicated as unlikely to be efficacious in treating the cancer.

In another aspect, provided herein is a method of selecting a group of cancer subjects for the purposes of predicting clinical response, monitoring clinical response, or monitoring patient compliance to dosing by a compound, comprising:
a. administering a compound to a subject;
b. obtaining a first sample from the subject;
c. determining the level of a biomarker in the first sample; and
d. diagnosing the subject as being likely to be responsive to the compound if the level of the biomarker in the first sample is different than the level in a reference sample.

In some embodiments, the cancer is DLBCL. In other embodiments, the cancer is MM. In another embodiment, the cancer is MDS. In yet another embodiment, the cancer is AML.

In some embodiments, the method is a method of selecting a group of cancer subjects for the purposes of predicting clinical response to dosing by a compound. In some embodiments, the method is a method of selecting a group of cancer subjects for the purposes of monitoring clinical response to dosing by a compound. In some embodiments, the method is a method of selecting a group of cancer subjects for the purposes of monitoring patient compliance to dosing by a compound. In certain embodiments, provided herein is a method of treating a cancer, comprising the method of selecting a group of cancer subjects for the purposes of predicting clinical response, monitoring clinical response, or monitoring patient compliance to dosing by a compound provided herein, wherein the method further comprises (e) administering to the subject a therapeutically effective amount of the compound when the subject is indicated as likely to be to be responsive to the compound. In certain embodiments, provided herein is a method of treating a cancer, comprising the method of selecting a group of cancer subjects for the purposes of predicting clinical response, monitoring clinical response, or monitoring patient compliance to dosing by a compound provided herein, wherein the method further comprises (e) administering to the subject a therapeutically effective amount of a therapy other than the compound when the subject is indicated as unlikely to be to be responsive to the compound.

In another aspect, provided herein is a method of identifying a subject having a cancer who is likely to be responsive to a treatment compound, comprising:
a. administering the treatment compound to a subject having the cancer;
b. obtaining a sample from the subject;
c. determining the level of a biomarker in the sample from the subject; and
d. diagnosing the subject as being likely to be responsive to the treatment compound if the level of the biomarker in the sample of the subject changes as compared to a level of the biomarker in a reference sample.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of identifying a subject having a cancer who is likely to be responsive to a treatment compound provided herein, wherein the method further comprises (e) administering to the subject a therapeutically effective amount of the compound when the subject is diagnosed as likely to be responsive to the treatment compound. In certain embodiments, provided herein is a method of treating a cancer, comprising the method of identifying a subject having a cancer who is likely to be responsive to a treatment compound provided herein, wherein the method further comprises (e) administering to the subject a therapeutically effective amount of a therapy other than the compound when the subject is diagnosed as unlikely to be responsive to the treatment compound.

In another aspect, provided herein is a method of predicting the responsiveness of a subject having or suspected of having a cancer to a treatment compound, comprising:
a. administering the treatment compound to the subject;
b. obtaining a sample from the subject;
c. determining the level of a biomarker in the sample from the subject; and
d. predicting or diagnosing the subject as being likely to be responsive to the treatment compound if the level of the biomarker in the sample changes as compared to the level of the biomarker obtained from a reference sample.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of predicting the responsiveness of a subject having or suspected of having a cancer to a treatment compound provided herein, wherein the method further comprises (e) administering to the subject a therapeutically effective amount of the compound when the subject is diagnosed as likely to be responsive to the treatment compound. In certain embodiments, provided herein is a method of treating a cancer, comprising the method of predicting the responsiveness of a subject having or suspected of having a cancer to a treatment compound provided herein, wherein the method further comprises (e) administering to the subject a therapeutically effective amount of a therapy other than the compound when the subject is diagnosed as unlikely to be responsive to the treatment compound.

In another aspect, provided herein is a method of monitoring the efficacy of a treatment of a cancer in a subject with a treatment compound, comprising:
 a. administering the treatment compound to a subject having cancer;
 b. obtaining a sample from the subject;
 c. determining the level of a biomarker in the sample from the subject; and
 d. comparing the level of the biomarker in the sample with the level of the biomarker obtained from a reference sample, wherein a change in the level as compared to the reference sample is indicative of the efficacy of the treatment compound in treating the cancer in the subject.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of monitoring the efficacy of a treatment of a cancer in a subject with a treatment compound provided herein, wherein the method further comprises (e) administering to the subject a therapeutically effective amount of the compound when the compound is indicated to be efficacious in treating the cancer in the subject. In certain embodiments, provided herein is a method of treating a cancer, comprising the method of monitoring the efficacy of a treatment of a cancer in a subject with a treatment compound provided herein, wherein the method further comprises (e) administering to the subject a therapeutically effective amount of a therapy other than the compound when the compound is indicated to have a lack of efficacy in treating the cancer in the subject.

In another aspect, provided herein is a method of predicting patient response to compound treatment in a cancer patient, the method comprising:
 a. obtaining a sample comprising cells from the patient,
 b. culturing the cells in the presence or absence of the compound,
 c. purifying protein or nucleic acid (e.g., a RNA, such as mRNA, or DNA) from the cultured cells, and
 d. measuring the presence or absence of a biomarker.

In some embodiments, the cancer is DLBCL. In other embodiments, the cancer is MM. In another embodiment, the cancer is MDS. In yet another embodiment, the cancer is AML. In certain embodiments, the cells are cancer cells. In another embodiment, the cells are immune cells.

In certain embodiments, provided herein is a method of treating a cancer, comprising the method of predicting patient response to compound treatment in a cancer patient provided herein, wherein the method further comprises (e) administering to the subject a therapeutically effective amount of the compound when a patient is predicted to have a response to the compound treatment. In certain embodiments, provided herein is a method of treating a cancer, comprising the method of predicting patient response to compound treatment in a cancer patient provided herein, wherein the method further comprises (e) administering to the subject a therapeutically effective amount of a therapy other than the compound when a patient is not predicted to have a response to the compound treatment.

In another aspect, provided herein is a method of monitoring tumor response to compound treatment in a cancer patient, the method comprising
 a. obtaining a first sample from the patient,
 b. measuring the expression of a biomarker in the first sample,
 c. administering a compound to the patient,
 d. thereafter, obtaining a second sample from the patient,
 e. measuring biomarker expression in the second sample, and
 f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of monitoring tumor response to compound treatment in a cancer patient provided herein, wherein the method further comprises (g) administering to the subject a therapeutically effective amount of the compound when there is a likelihood of an effective tumor response. In certain embodiments, provided herein is a method of treating a cancer, comprising the method of monitoring tumor response to compound treatment in a cancer patient provided herein, wherein the method further comprises (g) administering to the subject a therapeutically effective amount of a therapy other than the compound when there is not a likelihood of an effective tumor response.

In another aspect, provided herein is a method of treating a subject with a compound, the method comprising
 a. obtaining a first sample from the patient,
 b. measuring the expression of a biomarker in the first sample,
 c. administering a compound to the patient,
 d. thereafter, obtaining a second sample from the patient,
 e. measuring biomarker expression in the second sample,
 f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In certain embodiments, the method further comprises (g) administering to the subject a therapeutically effective amount of the compound when there is a likelihood of an effective tumor response. In other embodiments, a decreased level of biomarker expression in the second sample after compound administration indicates a decreased likelihood of an effective tumor response. In certain embodiments, the method further comprises (g) administering to the subject a therapeutically effective amount of a therapy other than the compound when there is not a likelihood of an effective tumor response.

In another aspect, provided herein is a method of monitoring IFN therapy treatment response to compound treatment in a cancer patient, the method comprising
 a. obtaining a first sample from the patient,
 b. measuring the expression of a biomarker in the first sample,
 c. administering one or more compounds to the patient,
 d. thereafter, obtaining a second sample from the patient, e. measuring biomarker expression in the second sample, and f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In certain embodiments, provided herein is a method of treating a cancer, comprising the method of monitoring IFN therapy treatment response to compound treatment in a cancer patient provided herein, wherein the method further comprises (g) administering to the subject a therapeutically effective amount of the compound when there is a likelihood of an effective IFN therapy treatment response. In certain embodiments, provided herein is a method of treating a cancer, comprising the method of monitoring IFN therapy treatment response to compound treatment in a cancer patient provided herein, wherein the method further comprises (g) administering to the subject a therapeutically effective amount of a therapy other than the compound when there is not a likelihood of an effective IFN therapy treatment response.

In certain embodiments of the various methods provided herein, the cancer is diffuse large B-cell lymphoma (DLBCL). In certain embodiments of the various methods provided herein, the cancer is multiple myeloma (MM). In certain embodiments of the various methods provided herein, the cancer is myelodysplastic syndrome (MDS). In some embodiments, the MDS is a MDS with deletion of chromosome 5q (del(5q)). In certain embodiments of the various methods provided herein, the cancer is acute myeloid leukemia (AML). In some embodiments of the various methods provided herein, the cancer is mantle cell lymphoma (MCL). In other embodiments of the various methods provided herein, the cancer is follicular lymphoma (FL). In some embodiments of the various methods provided herein, the cancer is chronic lymphocytic leukemia (CLL). In other embodiments of the various methods provided herein, the cancer is non-Hodgkin's lymphoma (NHL). In certain embodiments of the various methods provided herein, the cancer is hairy cell leukemia. In some embodiments of the various methods provided herein, the cancer is chronic myelogenous leukemia (CML). In certain embodiments of the various methods provided herein, the cancer is AIDS-related Kaposi sarcoma. In other embodiments of the various methods provided herein, the cancer is a malignant melanoma.

In another aspect, provided herein is a method of monitoring IFN therapy treatment response to compound treatment in a patient having an IFN-associated disorder, the method comprising a. obtaining a first sample from the patient, b. measuring the expression of a biomarker in the first sample, c. administering one or more compounds to the patient, d. thereafter, obtaining a second sample from the patient, e. measuring biomarker expression in the second sample, and f. comparing the levels of biomarker expression in the first and second samples.

In certain embodiments, provided herein is a method of treating an IFN-associated disorder, comprising the method of monitoring IFN therapy treatment response to compound treatment in a patient having an IFN-associated disorder, wherein the method further comprises (g) administering to the subject a therapeutically effective amount of the compound when there is a likelihood of an effective IFN therapy treatment response. In certain embodiments, provided herein is a method of treating an IFN-associated disorder, comprising the method of monitoring IFN therapy treatment response to compound treatment in a patient having an IFN-associated disorder, wherein the method further comprises (g) administering to the subject a therapeutically effective amount of a therapy other than the compound when there is not a likelihood of an effective IFN therapy treatment response.

In certain embodiments, the IFN-associated disorder is conyloma accuminata. In some embodiments, the IFN-associated disorder is chronic hepatitis B. In other embodiments, the IFN-associated disorder is chronic hepatitis C. In certain embodiments, the IFN-associated disorder is relapsing-remitting multiple sclerosis. In some embodiments, the IFN-associated disorder is chronic granulomatous disease. In some embodiments, the IFN-associated disorder is a cancer.

In specific embodiments of the various methods provided herein, the biomarker is a cereblon (CRBN)-associated protein (CAP).

In certain embodiments, CAP is ABCE1, ACLY, ACTB, ALDOA, ARID1A, C7ORF42, COPS6, CPSF6, CSNK1A1, CSNK2A1, CTPS, CRBN, DDB1, DDIT4, DDX17, DDX21, DDX58, DDX58, DDX60, DDX60L, DHX9, DNAJC1, DUT, EEF1A1, EEF1AL3, EEF1G, EIF2S1, EIF2S2, EIF3J, EIF4A1, EWSR1, FASN, FBXO21, FERMT3, FUBP1, G3BP1, G3BP2, GBE1, GBP1, GNAS, GNB2L1, GNB3, H2AFJ, H2AFX, H2AFZ, HIST1H1A, HIST1H1B, HIST1H1C, HIST1H1D, HIST1H1E, HIST1H2AA, HNRNPA2B1, HNRNPC, HNRNPH2, HNRNPR, HSPA1A, HSPA1B, HSPA8, HSPA9, IFI16, IFI27, IFI27L2, IFI35, IFI44, IFI44L, IFI6, IFIH1, IFIT1, IFIT2, IFIT3, IFIT5, IFITM2, IFITM3, IFN, IFNA16, IFNA5, IFNG, IFNGR1, IGF2BP2, IKKE, IKZF1 (Ikaros), IKZF3 (Aiolos), ILF3, IPO5, IRF1, IRF2, IRF3, IRF4, IRF7, IRF8, IRF9, ISG15, ISG20, KCNAB2, MACF1, MCM2, MCM7, MX1, MX2, MYH10, NACA, NAP1L2, NCL, NEDD8, NUP88, OAS1, OAS2, OAS3, OASL, PABPC1, PABPC4, PCM1, PDXK, PPAT, PRKDC, PTPRC, PTRH2, RPL10A, RPL11, RPL12, RPL13A, RPL14, RPL15, RPL18A, RPL19, RPL21, RPL3, RPL30, RPL4, RPL7, RPL7A, RPL9, RPLP1, RPLP2, RPS13, RPS16, RPS19, RPS2, RPS6, SEC23B, SEC24A, SEC24C, SMC4, SND1, a STAT, a STAT-PO$_4$, STAT3, SYNCRIP, TBK1, TBK1-PO$_4$, TBL1XR1, TLR1, TLR3, TLR4, TLR7, TLR8, TPD52, TUBA1A, TUBA1B, TUBA1C, UAP1, UBA52, UBAP2L, UBB, UBE2O, UBE2Q1, USP15, VAPA, XAF1, XRCC6, YWHAE, ZFP91, or any combination thereof. In certain embodiments, the CAP is an IFN pathway protein. In other embodiments of the various methods provided herein, the biomarker is one or more proteins listed in Table 1 or 3-8. In other embodiments of the various methods provided herein, the biomarker is one or more proteins listed in Table 1 and/or Table 3 and/or Table 4 and/or Table 5 and/or Table 6 and/or Table 7 and/or Table 8

In specific embodiments of the various methods provided herein the compound is a CRBN-binding compound (CBC). In some embodiments of the various methods provided herein, the compound is an IMiD® immunomodulatory drug (from Celgene Corporation). In some embodiments, the compound is lenalidomide, pomalidomide, thalidomide, 3-(5-amino-2-methyl-4-oxo-4H-quinazolin-3-yl)-piperidine-2,6-dione (Compound A), or 3-(4-((4-(morpholinomethyl)benzyl)oxy)-1-oxoisoindolin-2-yl)piperidine-2,6-dione (Compound B).

Various combinations of one or more compound (e.g., one or more CRBN-binding compound) and one or more biomarkers (e.g., one or more CAP) are contemplated for use in the various methods provided herein.

In another aspect, provided herein is an array of antibodies for determining the levels of two or more biomarkers in a sample. In certain embodiments, the levels of the biomarkers are used in the various methods provided herein, for example, to select a subject for treatment with a compound; predict or monitor the responsiveness of a subject to the treatment; or monitor the compliance of a subject with the treatment.

In another aspect, provided herein is an array of probes for determining the levels of two or more biomarkers in a sample by hybridizing with one or more of the polynucleotides of the biomarkers under stringent condition. In some embodiments, the levels of the biomarkers are used in the various methods provided herein, for example, to select a subject for treatment with a compound; predict or monitor the responsiveness of a subject to the treatment; or monitor the compliance of a subject with the treatment.

In another aspect, provided herein is an array of probes for determining the levels of two or more biomarkers in a sample by hybridizing with one or more of mRNAs of the biomarkers under stringent condition. In some embodiments, the levels of the biomarkers are used in the various methods provided herein, for example, to select a subject for treatment with a compound; predict or monitor the responsiveness of a subject to the treatment; or monitor the compliance of a subject with the treatment.

In another aspect, provided herein is a panel of isolated biomarkers comprising one or more biomarkers, wherein one biomarker is a CAP. In a specific embodiment, the CAP is CSNK1A1. In one embodiment, the CAP is CRBN. In one embodiment, the CAP is Ikaros. In one embodiment, the CAP is Aiolos. In one embodiment, the CAP is an IFN pathway protein. In one embodiment, the CAP is an IFN. In one embodiment, the CAP is a STAT. In one embodiment, the CAP is ZFP91.

In another aspect, herein is a kit for determining the level of a biomarker in a sample from a subject, wherein the biomarker is a CAP. In certain embodiments, the sample is a biological sample.

In another aspect, provided herein are kits for carrying out the methods provided herein.

4 BRIEF DESCRIPTION OF THE FIGURES

FIGS. 1A-C depict that Aiolos and Ikaros are CRBN substrates in ABC and GCB DLBCL. DLBCL cells were treated with DMSO, Lenalidomide or Compound A for 1, 6, 12 or 72 hours and then levels of Aiolos, Ikaros, IRF4 or 3-actin were assessed. (A) Lenalidomide and Compound A are biochemically active in both GCB and ABC DLBCL subsets. (B) and (C) Aiolos and Ikaros are substrates of the CRBN complex in DLBCL; and lenalidomide and Compound A reduce IRF4 levels within 72 hours.

FIGS. 2A-B depict that Aiolos and Ikaros are CRL4$^{CRBN}$ substrates in vivo. WSU-DLCL2 xenograft SCID mice were treated with either vehicle or 30 mg/kg Compound A qd. Tumor samples were harvested at indicated time points after last dose. Tissues were then subjected to FFPE IHC for Aiolos, and Ikaros. (A) Compound A induces Aiolos degradation within 6 hours of treatment in WSU-DLCL2 xenograft SCID mice. (B) Compound A induces Ikaros degradation within 6 hours of treatment in WSU-DLCL2 xenograft SCID mice.

FIGS. 3A-C depicts Aiolos is a driver of lymphoma proliferation and regulates c-Myc. Inducible Aiolos shRNA cell lines were treated with 0-100 ng/ml of doxycycline for 72 hours and Aiolos, c-myc, IRF4 or 3-actin protein levels were assessed. (A) At least three out of five Aiolos shRNAs result in decreased Aiolos protein levels. (B) and (C) Three Aiolos shRNAs also decrease proliferation and c-Myc levels. Aiolos shRNA results in the significant decrease of c-myc but not IRF4. Proliferation assays indicate that shRNA targeting Aiolos inhibit proliferation of cells at 3 and 5 days post-doxycycline treatment.

FIG. 4A-C depicts the generation of DLBCL cell lines resistant to lenalidomide and Compound A. Cell lines were made resistant to Lenalidomide and Compound A through chronic exposure to both compounds. Proliferation of resistant and parental cells were assessed through tritiated thymidine incorporation assays. (A)-(C) Resistant Lenalidomide ("Len") or Compound A cell lines demonstrate resistance compared to parental cells after a 10 day washout period indicating resistance was now an inherent trait of the resistant cell.

FIGS. 5A-B depict the resistance to lenalidomide and Compound A mechanism of action. (A) Acquired resistance in DLBCL does not involve downregulation of CRBN levels as is observed in multiple myeloma. However, Aiolos and Ikaros levels are slightly decreased in WSU-DLCL2 resistant cells compared to parental. Additionally, c-Myc levels are decreased in both WSU-DLCL2 and TMD8 resistant cells while CD44, a marker of aggressive disease, is increased in the ABC DLBCL cell line (TMD8). (B) The rate of destruction of Aiolos in the WSU-DLCL2 CmpA-R (Compound A resistant) cell line is decreased compared to the parental cell line.

FIG. 6A-C depict the dynamic range of expression levels of CRBN, Aiolos and Ikaros in DLBCL patients. IHC of a FFPE samples from 90 patients for CRBN, Aiolos and Ikaros indicates a wide range of expression levels in primary DLBCL. (A) Range of CRBN expression in three exemplary clinical trial patients, C4, F2 and B9. CRBN staining was observed in 76/90 cases (84%). Nuclear CRBN was observed in 23/76 positive CRBN tumors. (B) Range of Aiolos expression in two exemplary clinical trial patients, E2 and G4. Aiolos staining was observed in 85/90 cases (94%). Aiolos was strongly expressed in 61/85 patients. (C) Range of Ikaros expression in two exemplary clinical trial patients, E2 and G4. Ikaros staining was observed in 76/90 cases (84%). The dynamic range of CRBN, Aiolos and Ikaros in DLBCL can be used as a positive inclusion process for participation in a Compound A (or other compound) clinical trial.

FIGS. 7A-C depict the differential activity of lenalidomide and Compound A in GCB and ABC DLBCL. Multiple DLBCL cell lines were culture with either Lenalidomide or COMPOUND A for 3 days. Proliferation was assessed through tritiated thymidine incorporation. Three phenomena were observed; inherent resistance, differential activity of COMPOUND A compared to Lenalidomide or a distinct potency difference between the two molecules. (A) and (B) Differential activity of Compound A is observed in some GCB DLBCL compared to lenalidomide. (C) Compound A is more potent than lenalidomide in ABC DLBCL FIGS. 8A-B depict lenalidomide competes with Compound A and 1-(3-chloro-4-methylphenyl)-3-((2-(2,6-dioxopiperidin-3-yl)-1-oxoisoindolin-5-yl)methyl)urea ("Compound C" or Cmp C) for CRBN. (A) and (B) Co-treatment of lenalidomide with either Compound A or Compound C blocks the anti-proliferative effects of either drug through competition of binding to the CRBN complex in both ABC and GCB DLBCL. Co-culture of Lenalidomide with either Compound A or Compound C dampens the activity of these compounds as they target the same binding pocket with relative affinity.

FIG. 9 depicts the differentiation of lenalidomide and Compound A in DLBCL using TMT mass spectrometry. GCB and ABC cell lines were treated with either lenalidomide or Compound A for 24 and 72 hours. Aiolos protein levels were analyzed and shown to decrease in a dose-dependent manner in as little as 24 hours in both ABC and GCB DLBCL (bottom panels). Proteins from these cells can also be labeled and analyzed with tandem mass Tag proteomics for signature responses (top panels).

FIGS. 10A-B show IFN pathway protein responses. FIG. 10A shows that Compound A up-regulates IFN response gene expression and upregulates IRF7 protein expression. FIG. 10B shows that shAiolos upregulates IRF7 protein expression.

FIG. 12 illustrates a list of IFN pathway proteins that can be affected by exposure to Compound A and/or lenalidomide.

Figure 13A:
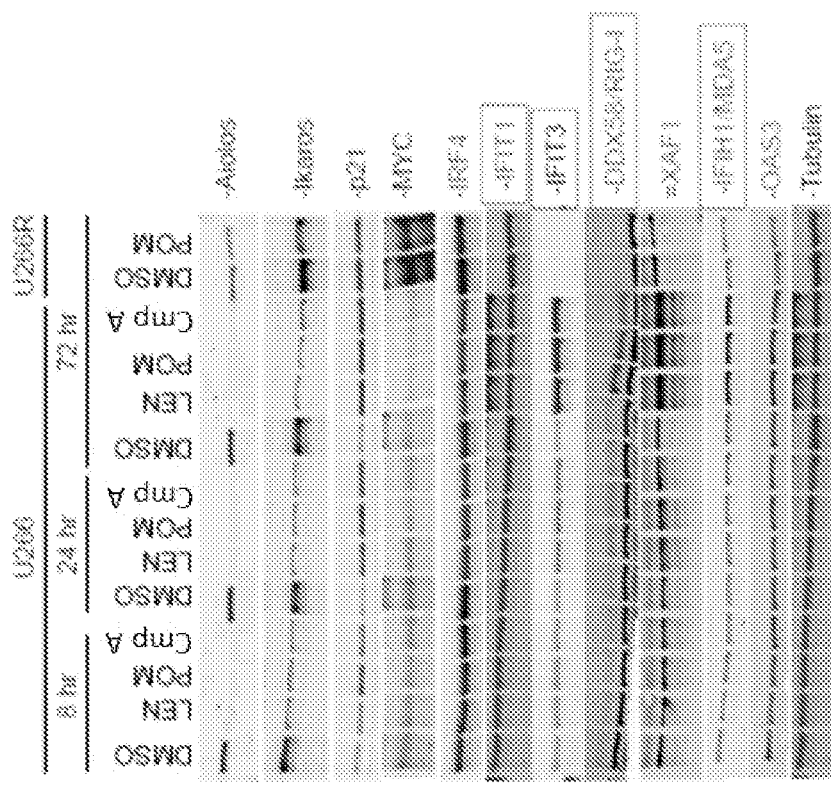
Figure 13B:
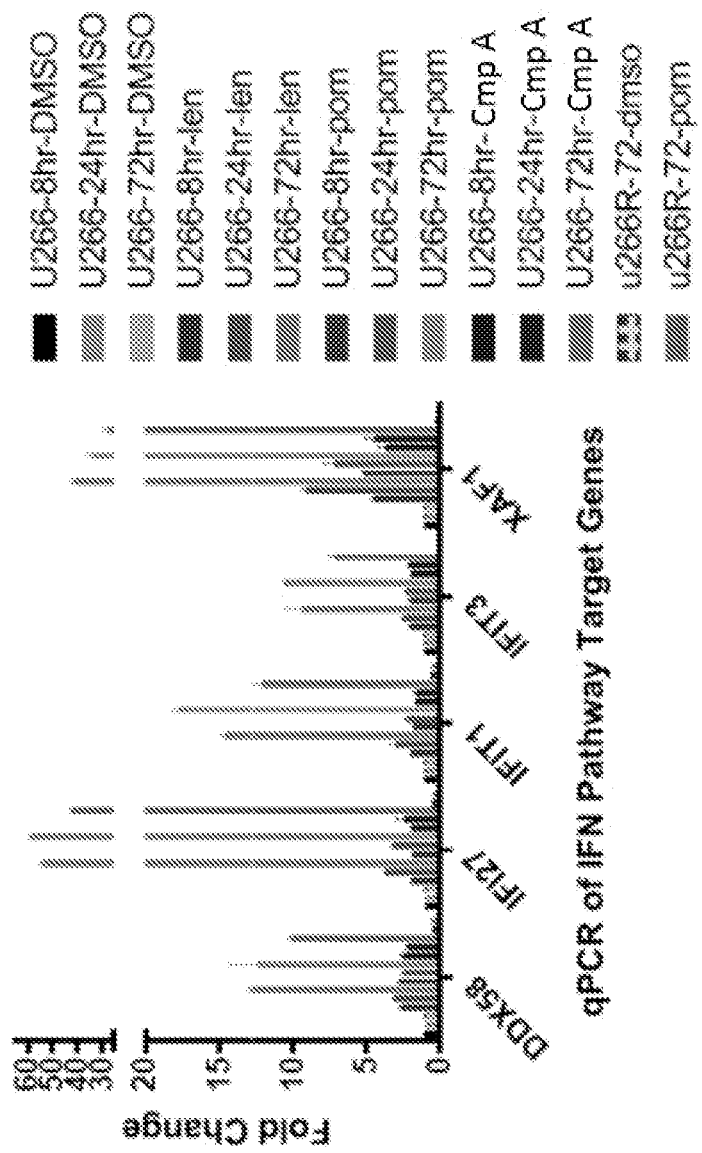
Figure 13C:
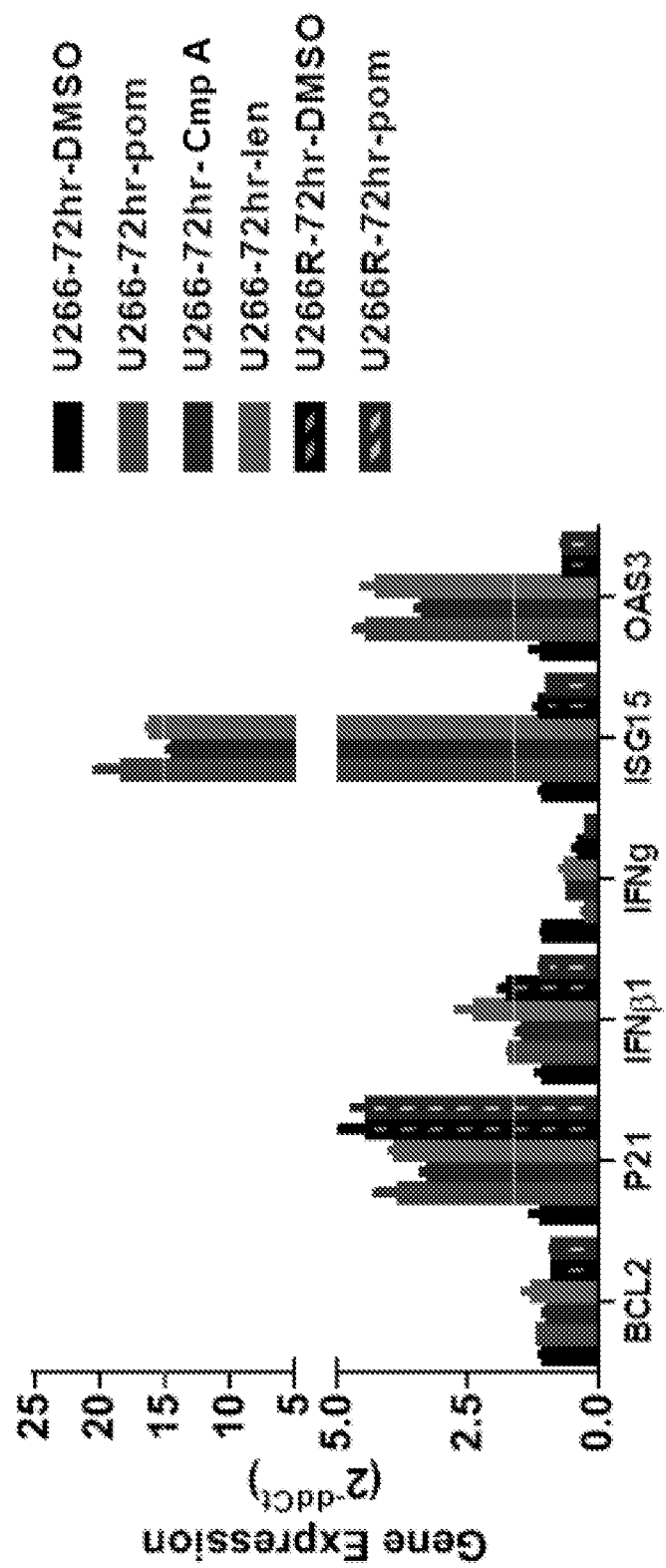
Figure 13D:
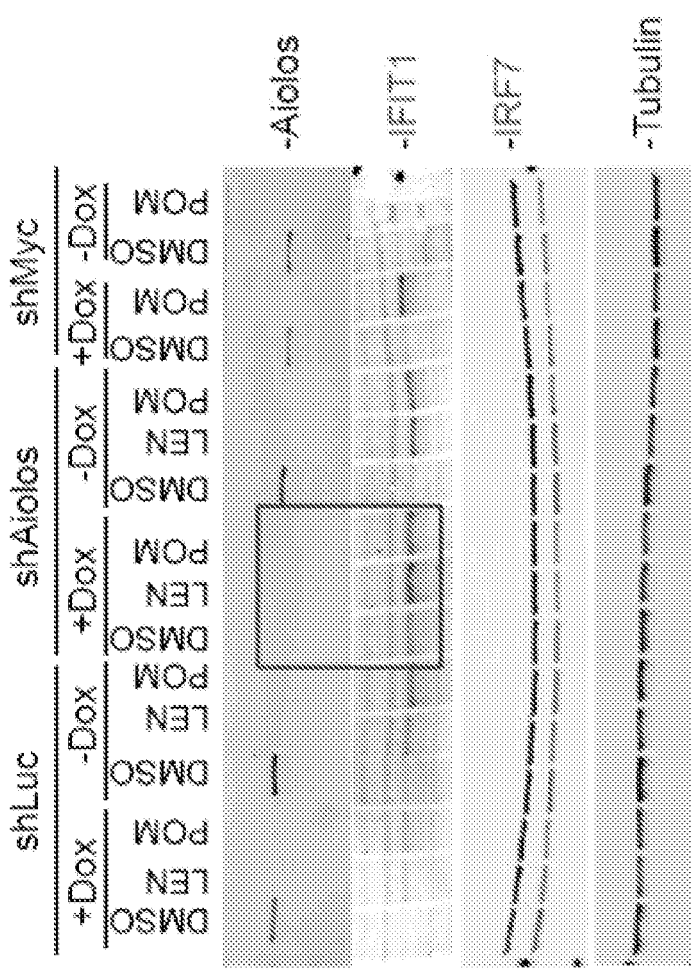
Figure 13E:
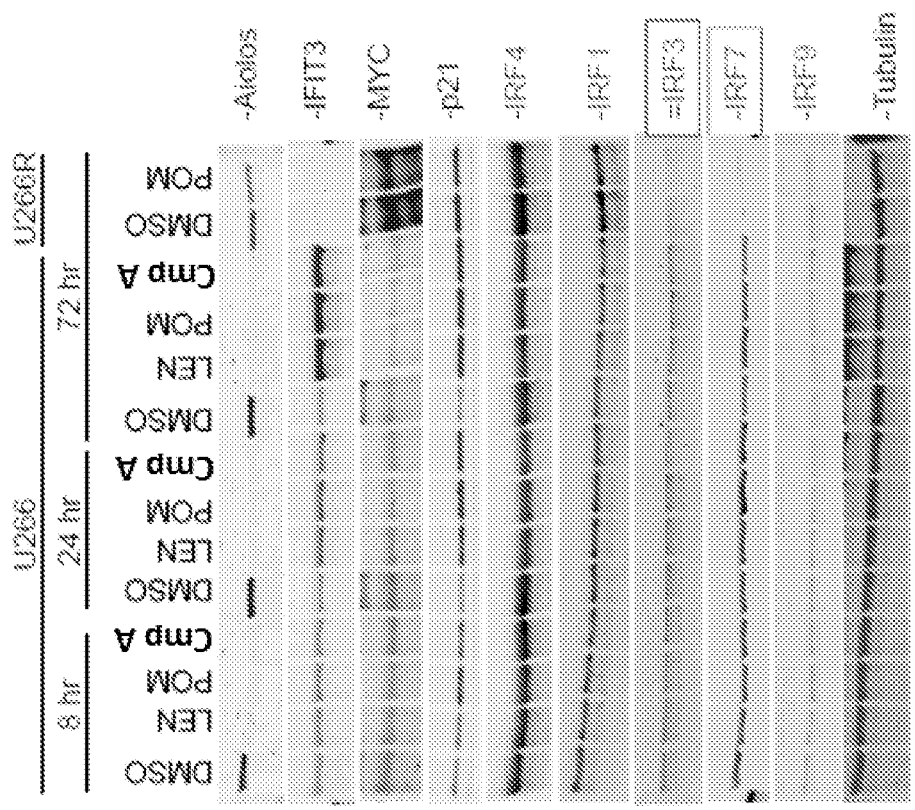
Figure 13F:
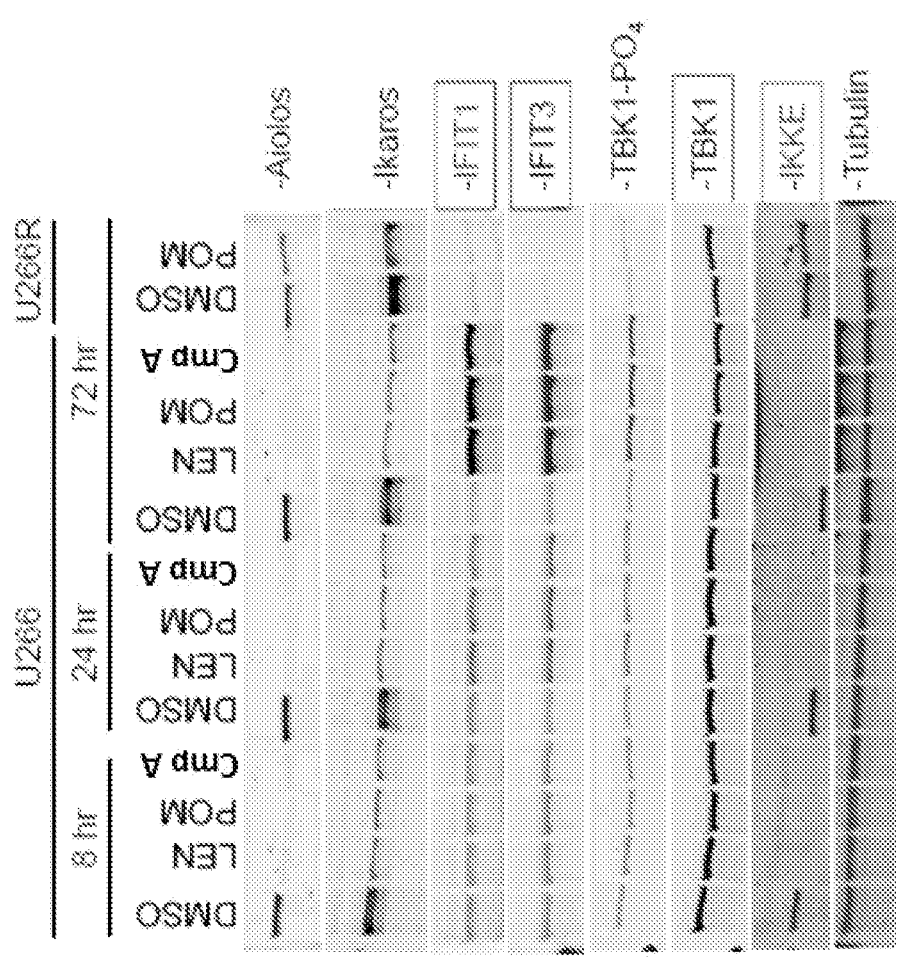
Figure 13G:
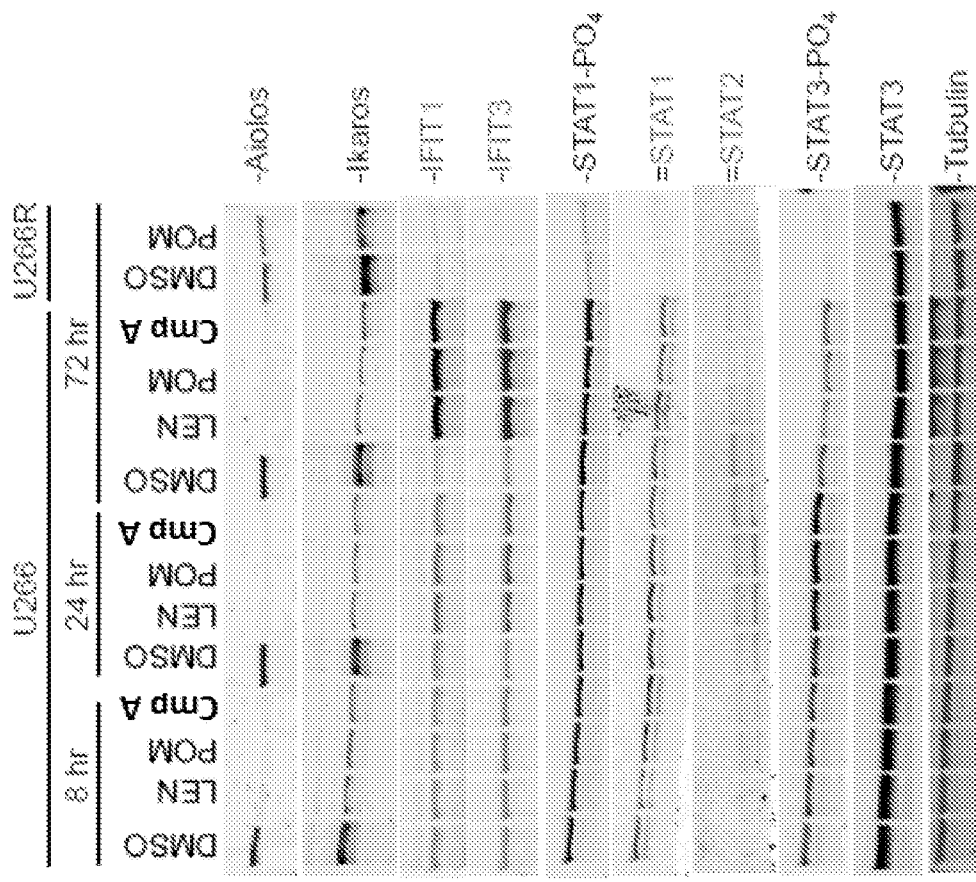

FIG. 13A-G depict the effect of lenalidomide, pomalidomide, or Compound A on IFN pathway. FIG. 13A shows that lenalidomide, pomalidomide, or Compound A upregulates IFIT1, IFIT3, DDX58, XAF1, IFIH1, and OAS3 protein expression. FIG. 13B shows that lenalidomide, pomalidomide, or Compound A upregulates DDX58, IFI27, IFIT1, IFIT3, DDX58, and XAF1 gene expression. FIG. 13C shows that lenalidomide, pomalidomide, or Compound A upregulates ISG15 and OAS3 gene expression. FIG. 13D shows that shAiolos induces IFN pathway proteins and upregulates IFIT1 protein level. FIG. 13E shows that lenalidomide, pomalidomide, or Compound A induces changes of IRF level. FIG. 13F shows that lenalidomide, pomalidomide, or Compound A upregulates IFIT1 and IFIT3 protein expression, upregulates TBK1 phosphorylation (TBK1-PO$_4$), and reduces IKKE protein level. FIG. 13G shows that lenalidomide, pomalidomide, or Compound A upregulates IFIT1 and IFIT3 protein expression, induces STAT changes.

Figure 14A:
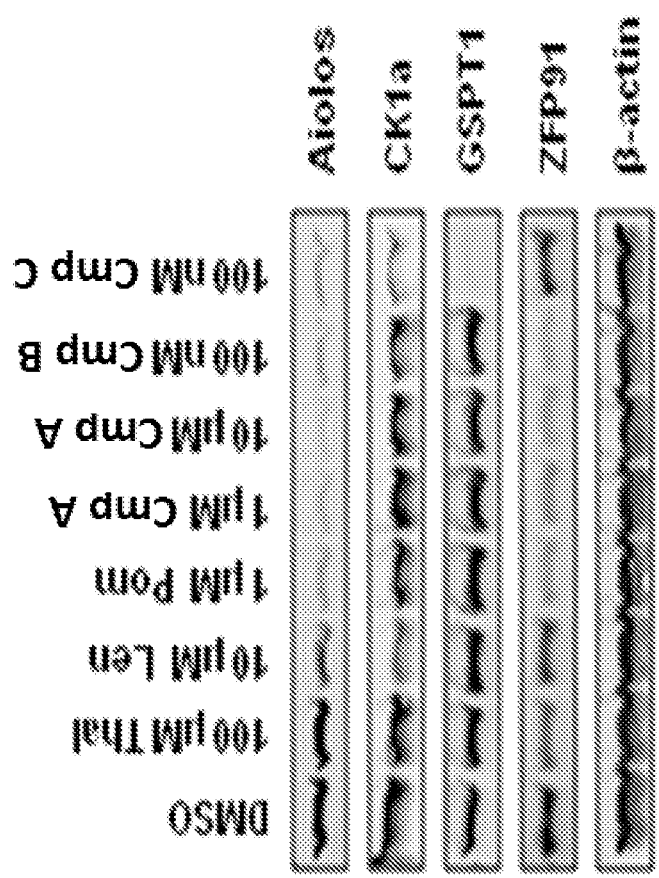
Figure 14B:
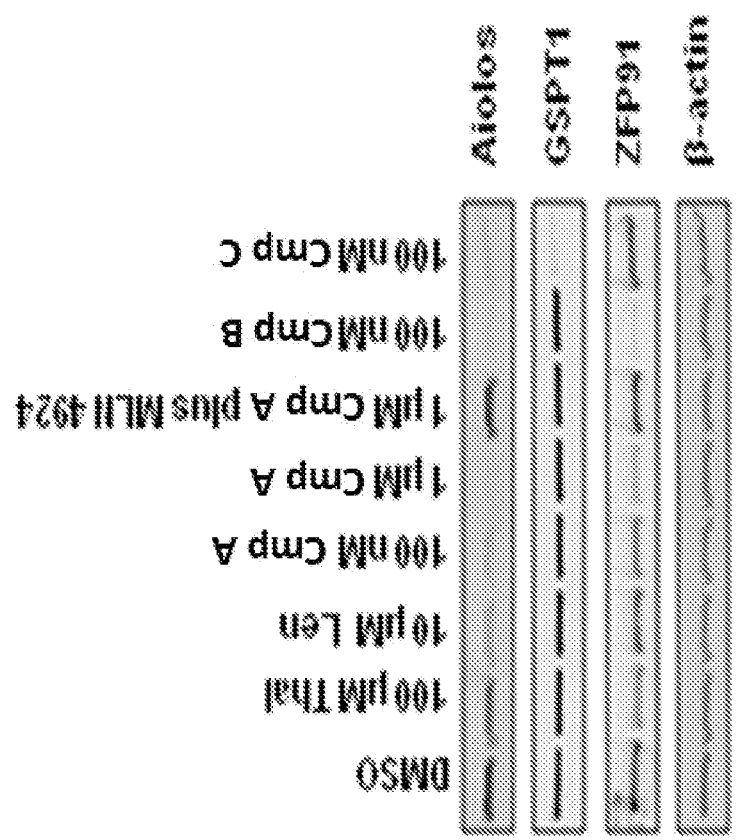

FIG. 14A-B show the levels of ZFP91 and Aiolos reduce in response to treatment with various compounds in lymphoma cell lines using western blot analysis.

Figure 15:
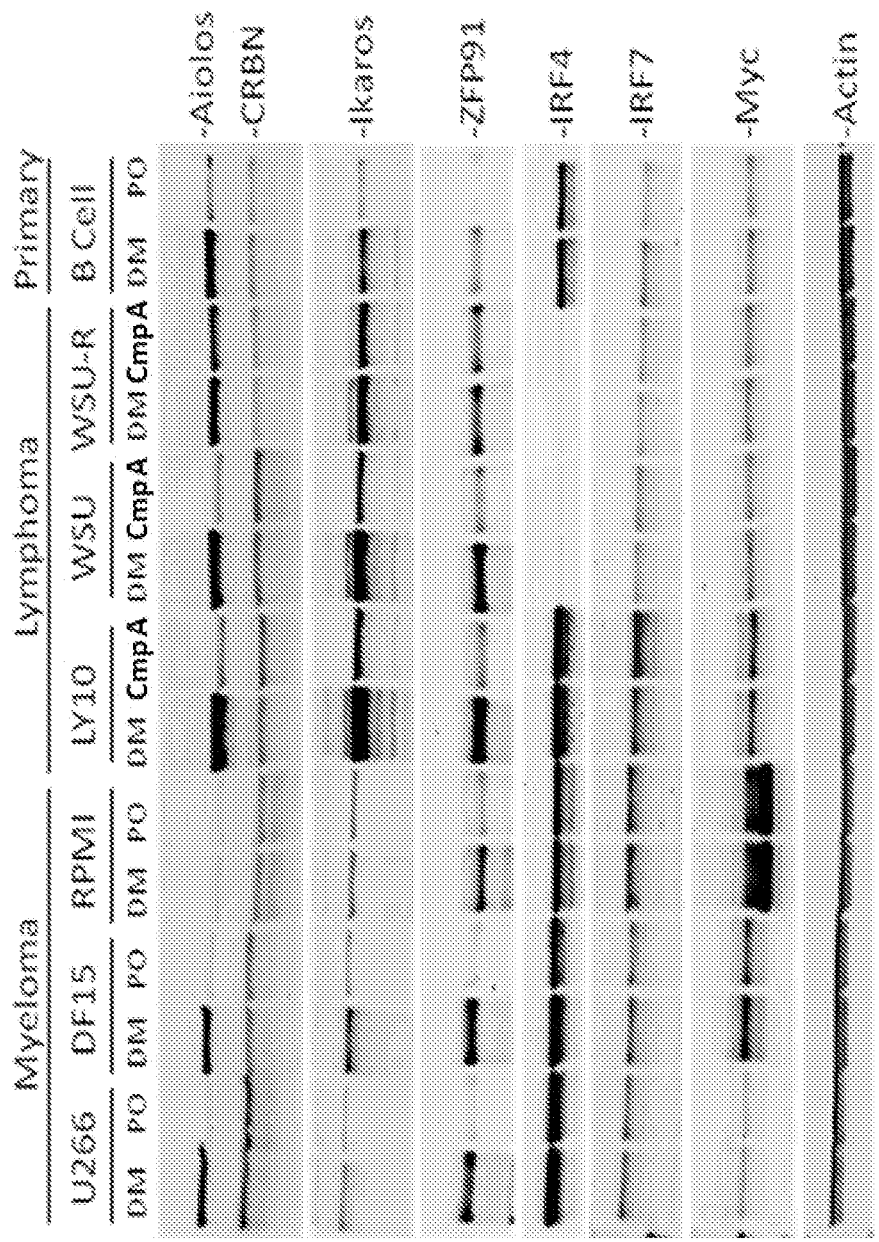

FIG. 15 shows the levels of ZFP91, CRBN, Ikaros, and Aiolos change in response to treatment with compounds in myeloma, lymphoma, and primary B cell lines using western blot analysis.

Figure 16A:
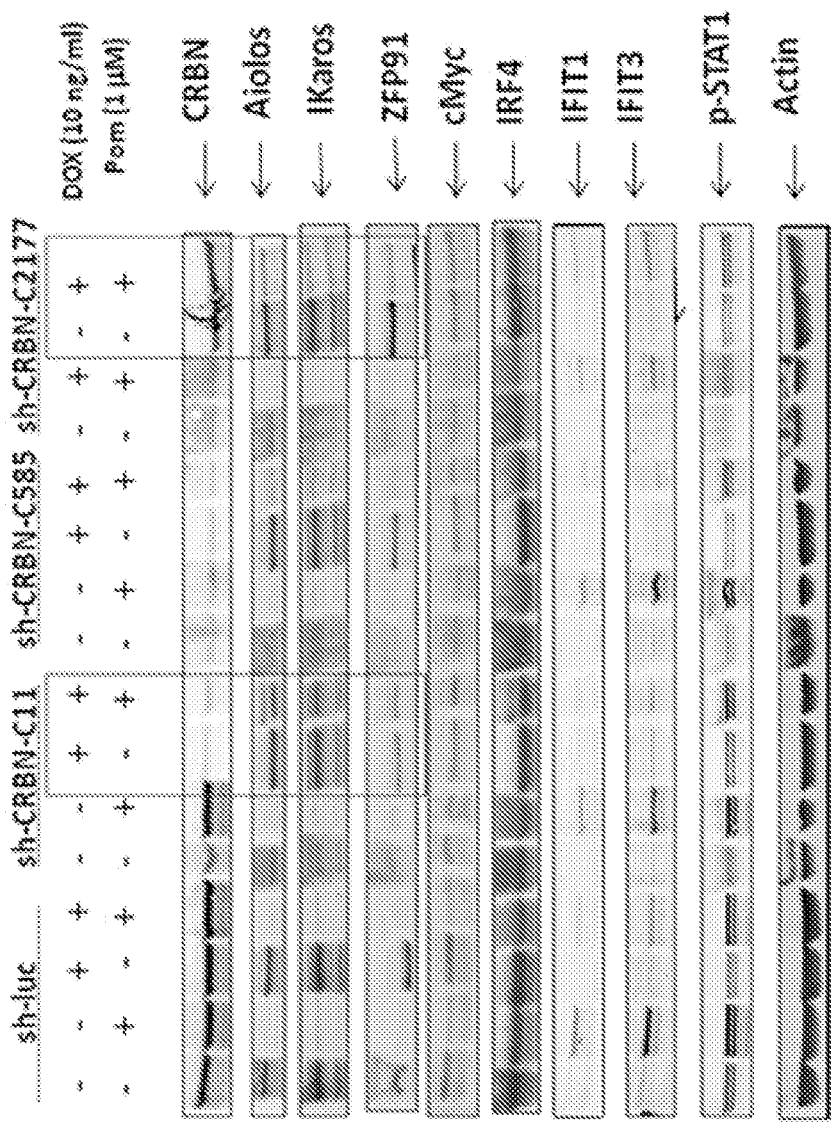
Figure 16B:
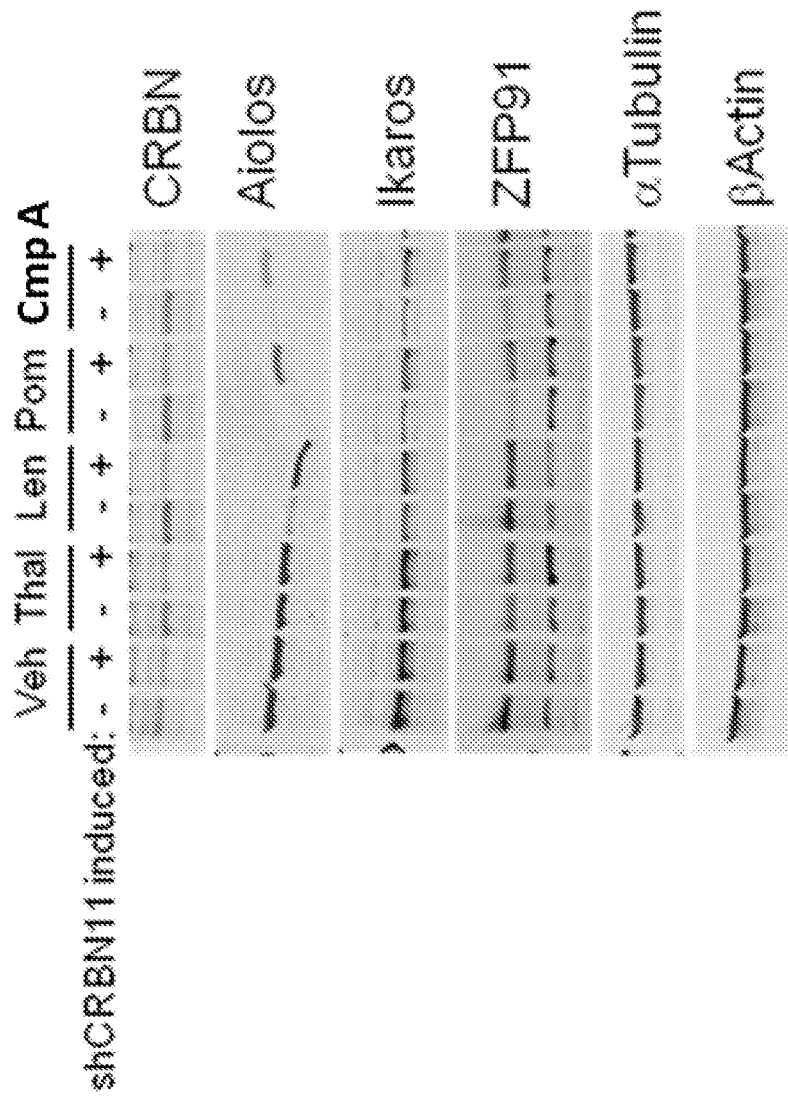
Figure 16C:
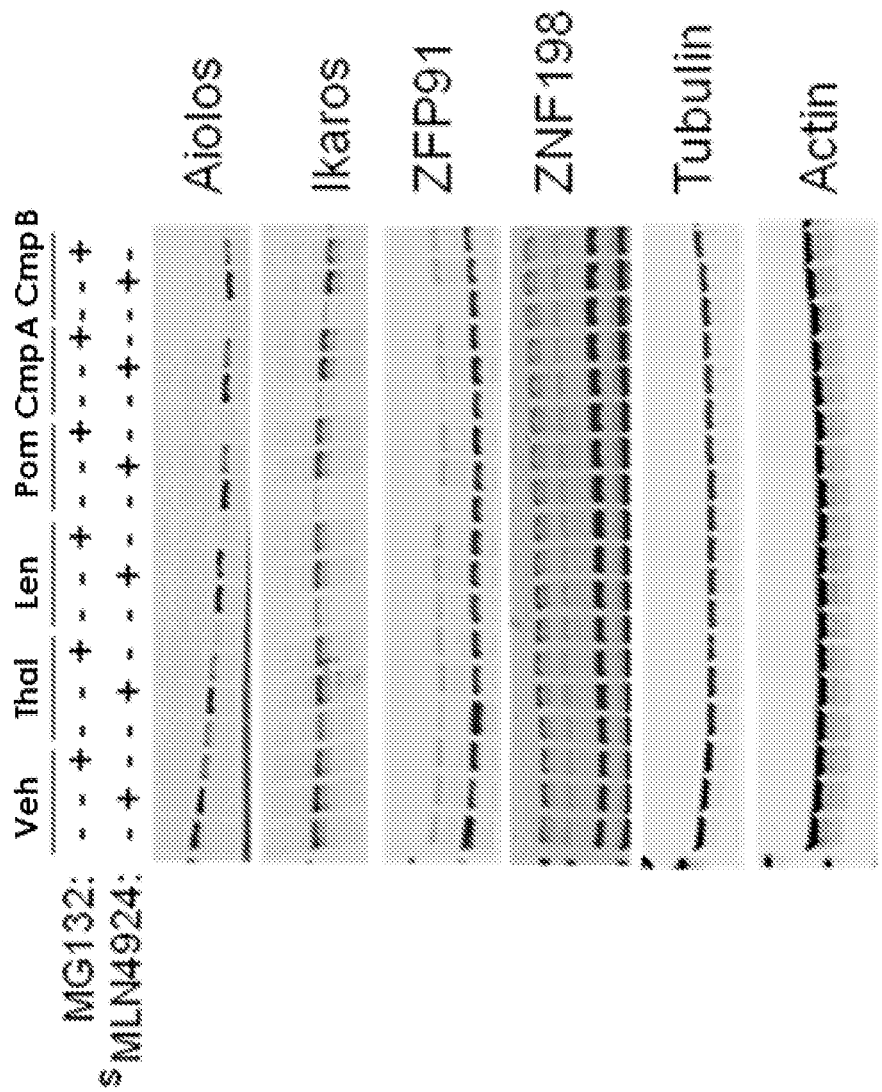

FIG. 16A-C show reduction of ZFP91 level induced by compounds is in a CRBN dependent pathway in U266 cells using western blot analysis. FIG. 16A shows pomalidomide induced ZFP91 degradation is CRBN dependent in U266 cells; FIG. 16B shows when CRBN was down regulated, reduction of Aiolos, Ikaros, and ZFP91 proteins induced by the compounds (thalidomide, lenalidomide, pomalidomide, or Compound A) was blocked; and FIG. 16C shows when NAE1 or proteasome inhibitors were used to treat the cells, reduction of Aiolos, Ikaros, and ZFP91 proteins induced by the compounds (thalidomide, lenalidomide, pomalidomide, or Compound A) was blocked.

Figure 17A:
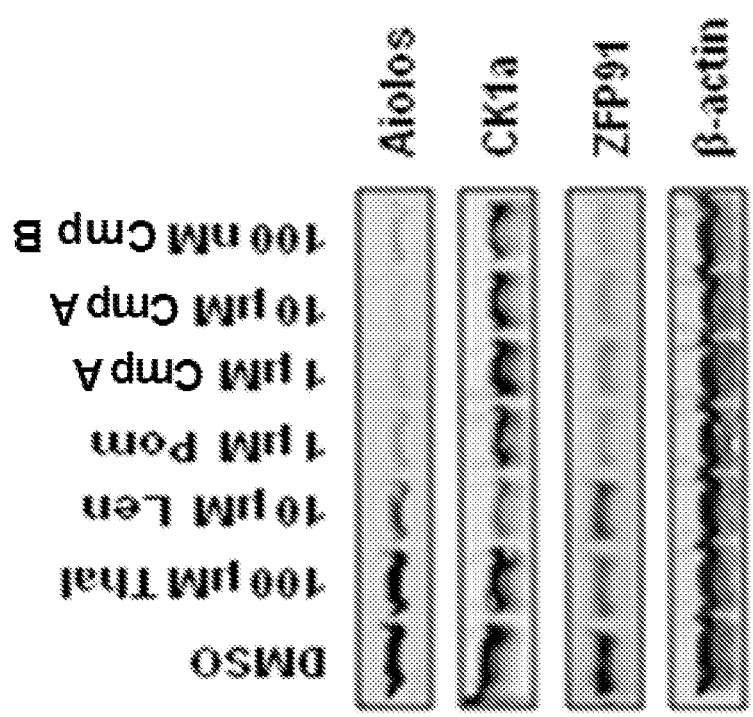
Figure 17B:
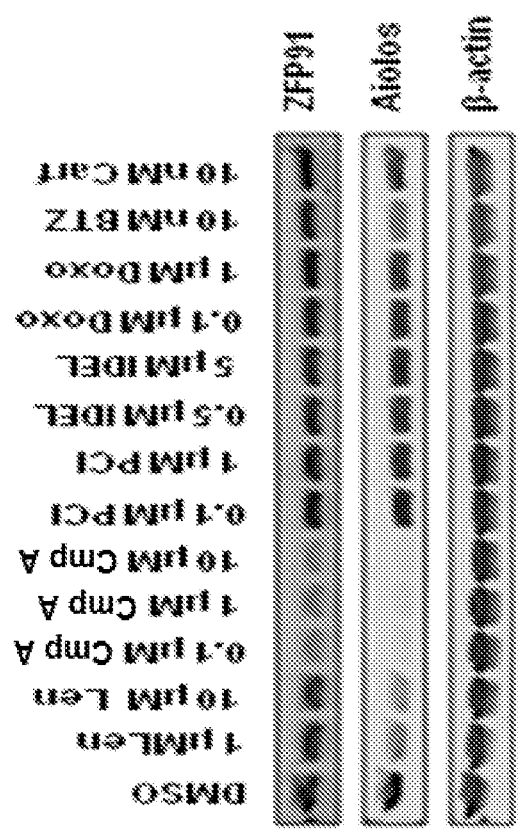
Figure 17C:
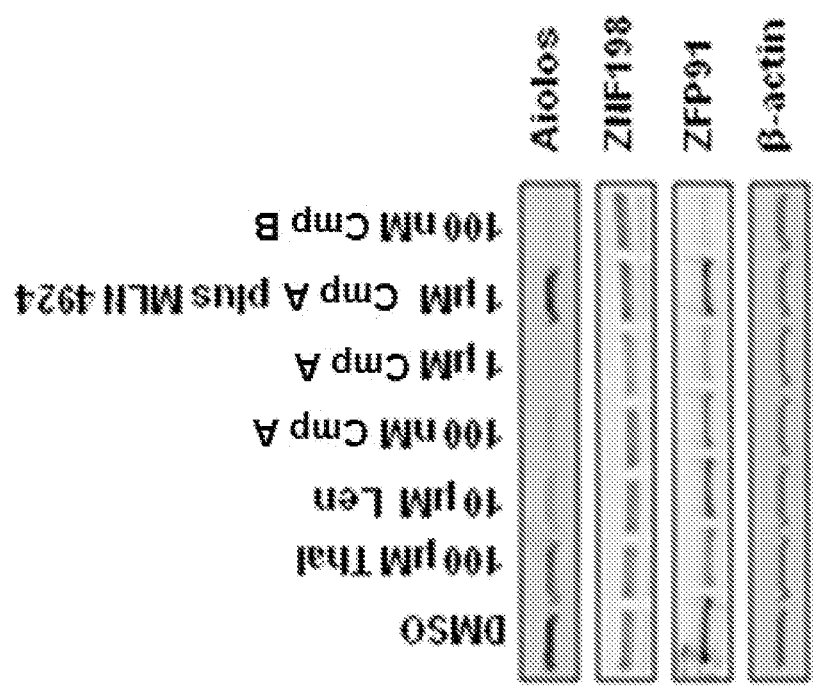
Figure 17D:
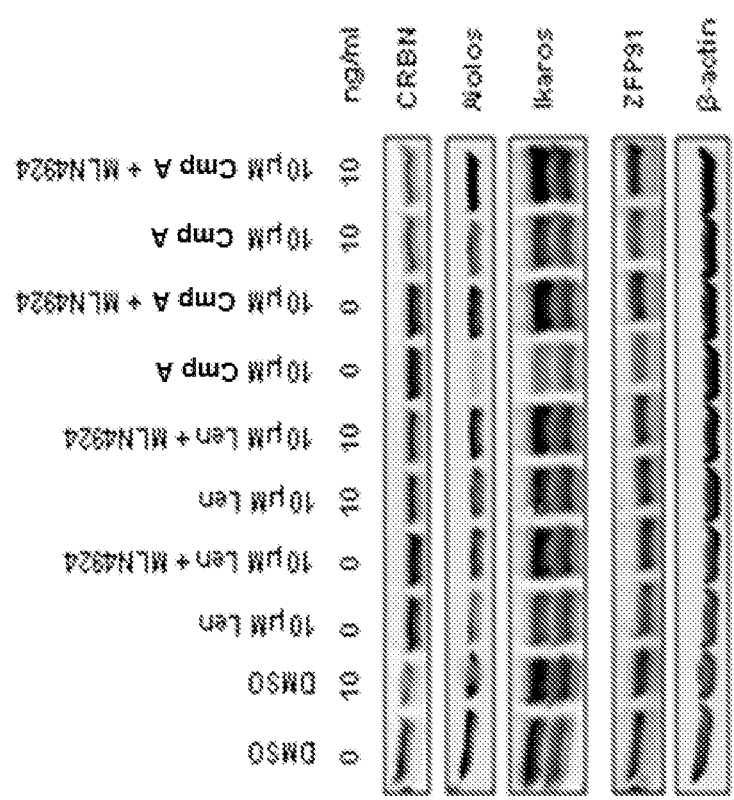

FIG. 17A-D shown reduction of ZFP91 level induced by compounds is in a CRBN dependent pathway in OCI-LY10 cells using western blot analysis. FIG. 17A shows that 100 mM thalidomide, 10 mM lenalidomide, 1 mM pomalidomide, 1 μM or 10 μM Compound A (Cmp A), or 100 nM Compound B (Cmp B) reduces the levels of ZFP91 and Aiolos in OCI-LY10 cells. FIG. 17B shows that 1 μM lenalidomide, 10 μM lenalidomide, 0.1 μM Compound A, 1 μM Compound A, or 10 μM Compound A reduces the levels of ZFP91 and Aiolos in OCI-LY10 cells. FIG. 17C-D show pre-treatment by MLN-4924 restores the level of both Aiolos and ZFP91 in OCI-LY10 cells treated with the compounds.

Figure 18:
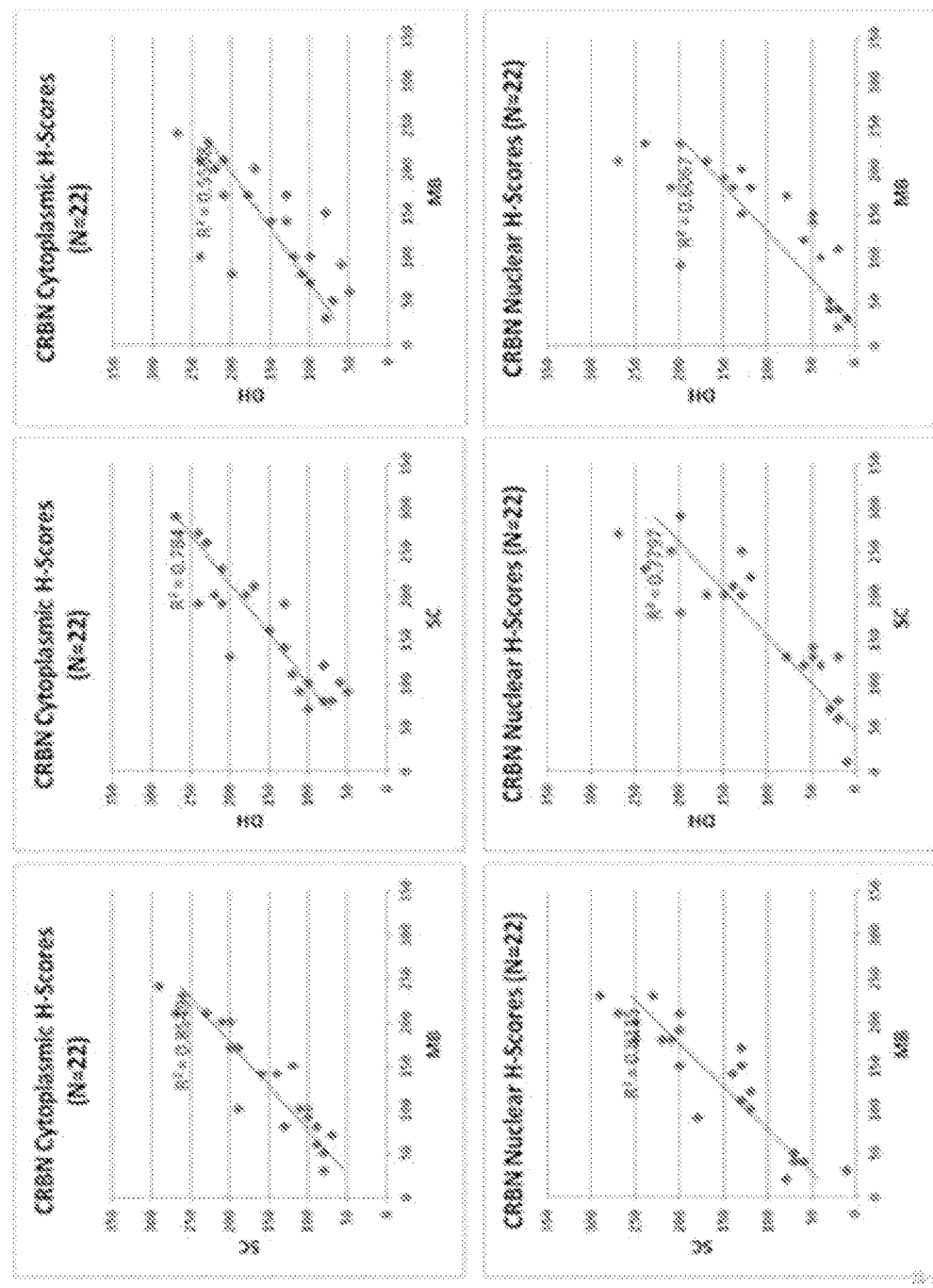

FIG. 18 shows pathologic evaluation of 22 MM samples using the dual assay and the H-score method.

Figure 19A:
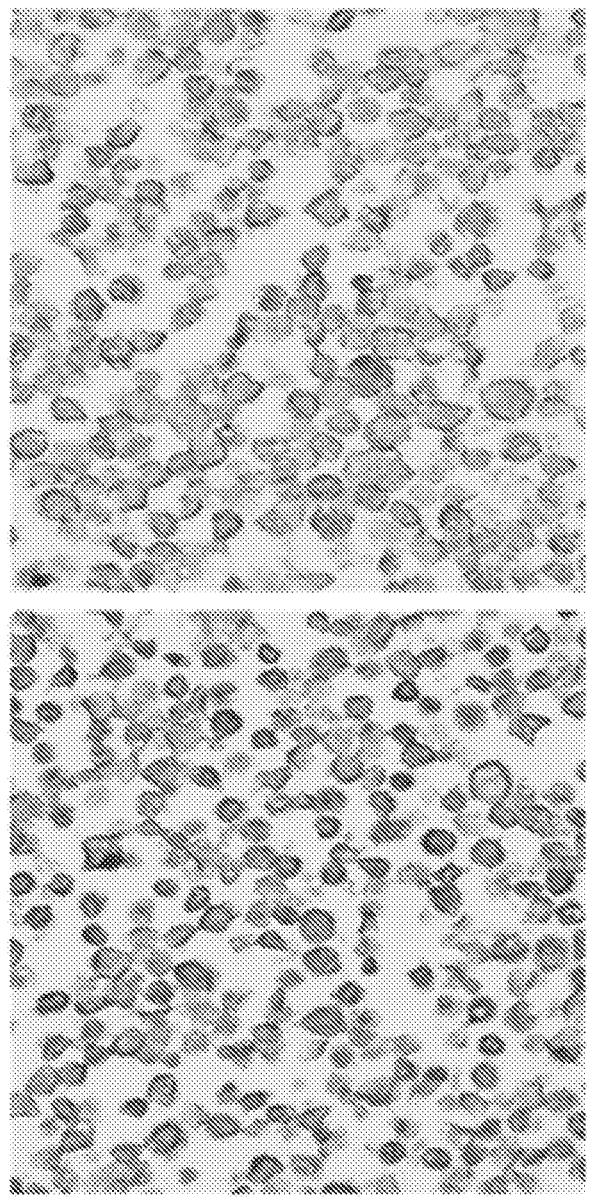
Figure 19B:
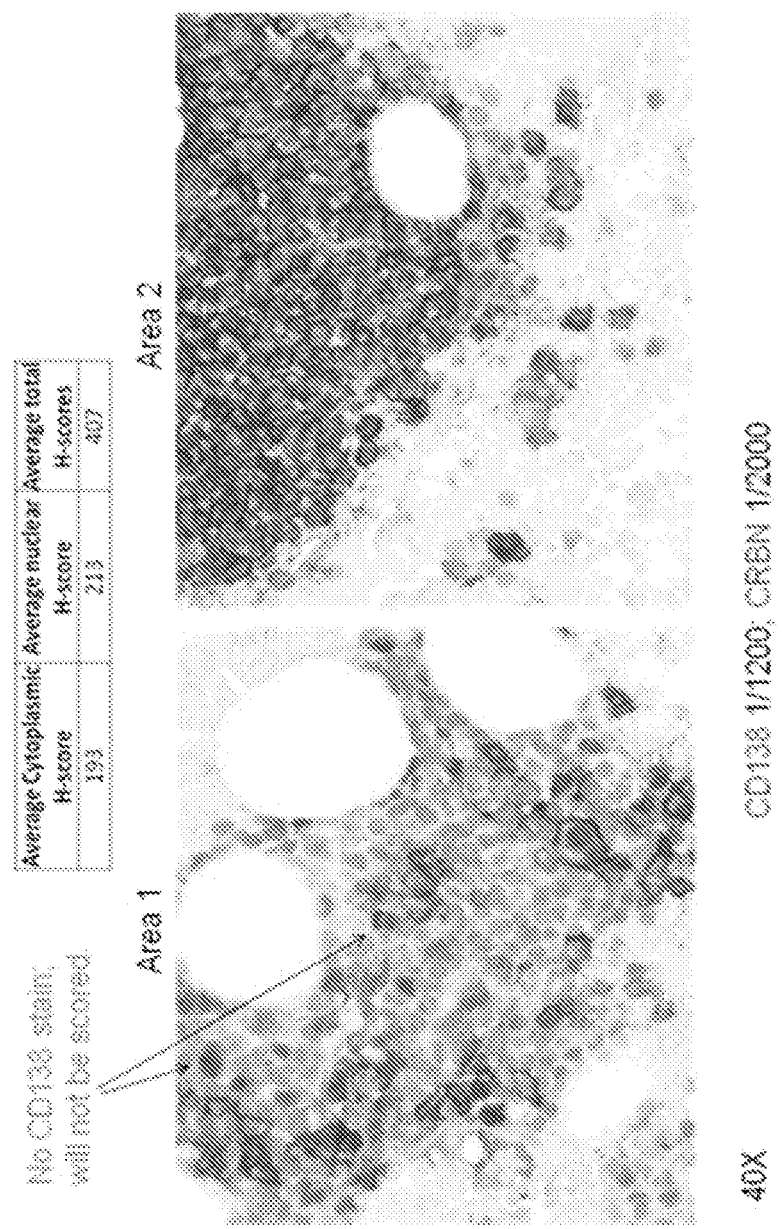
Figure 19C:
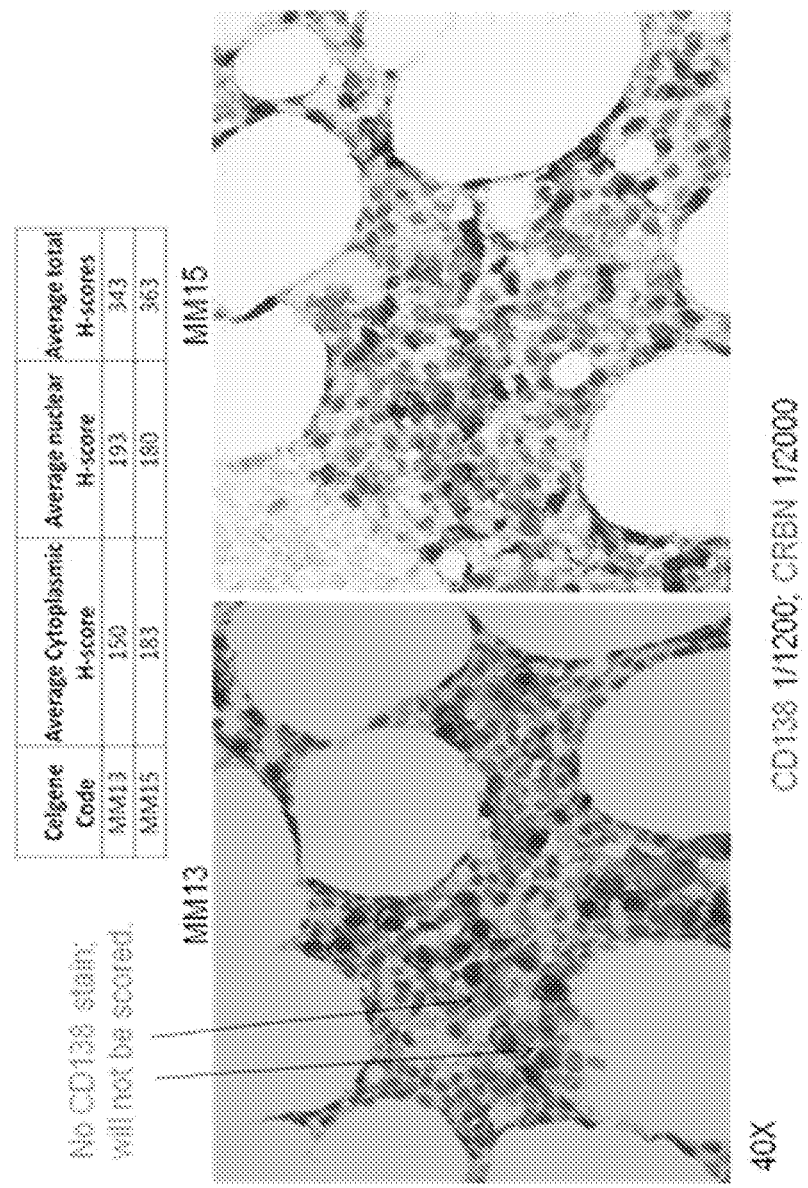

FIGS. 19A-C shows the results of a dual staining assay for CRBN. FIG. 19A shows that the dual staining assay differentiates high and low CRBN expression levels in multiple myeloma cell line DF15 and pomalidomide-resistant DF15R, respectively. FIG. 19B shows the CRBN staining results and H-score for Sample MM12. FIG. 19C shows the CRBN staining results and H-score for Samples MM13 and MM15.

Figure 20:
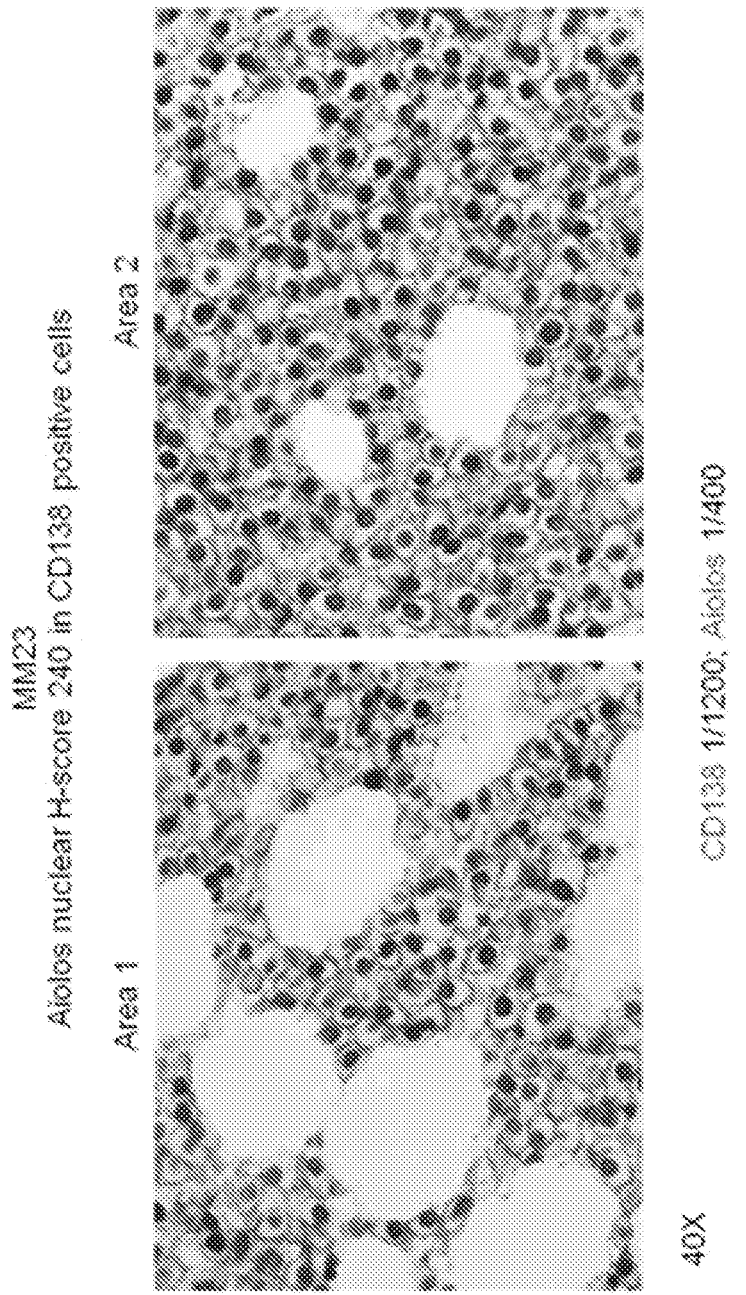

FIG. 20 shows the Aiolos staining and nuclear H-score in Sample MM23.

Figure 21:
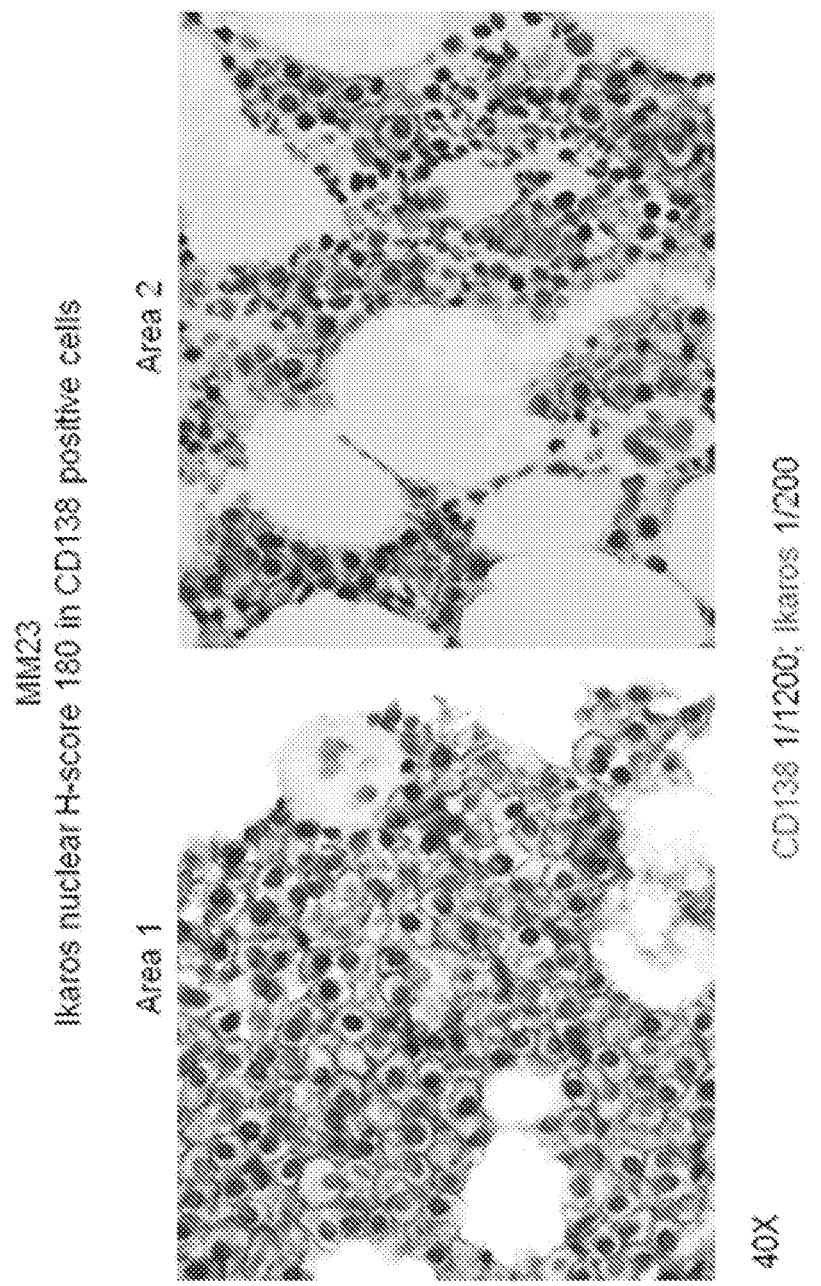

FIG. 21 shows the Ikaros staining and nuclear H-score in Sample MM23.

Figure 22A:
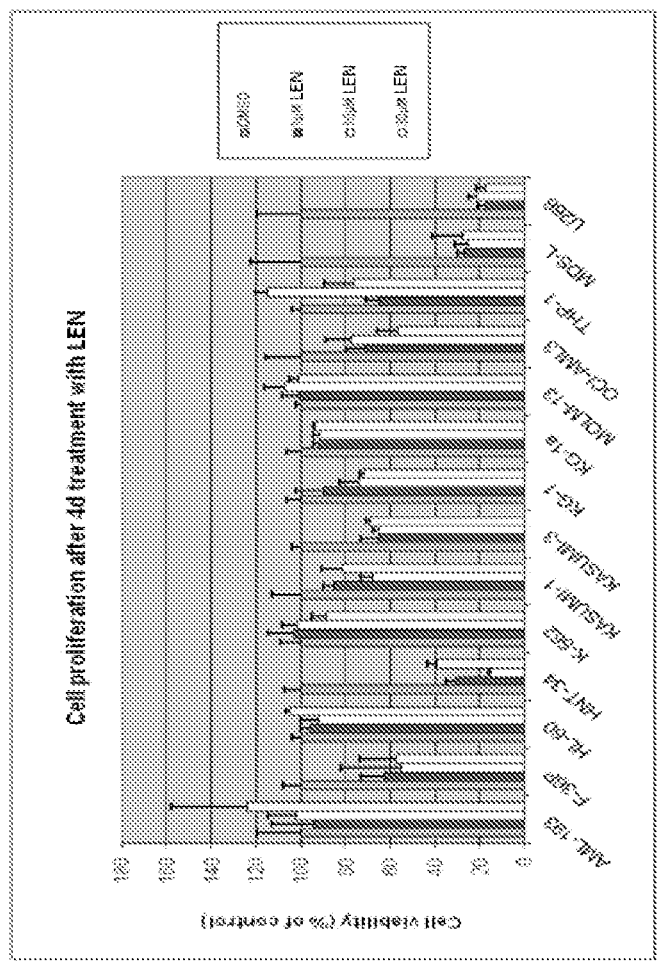
Figure 22B:
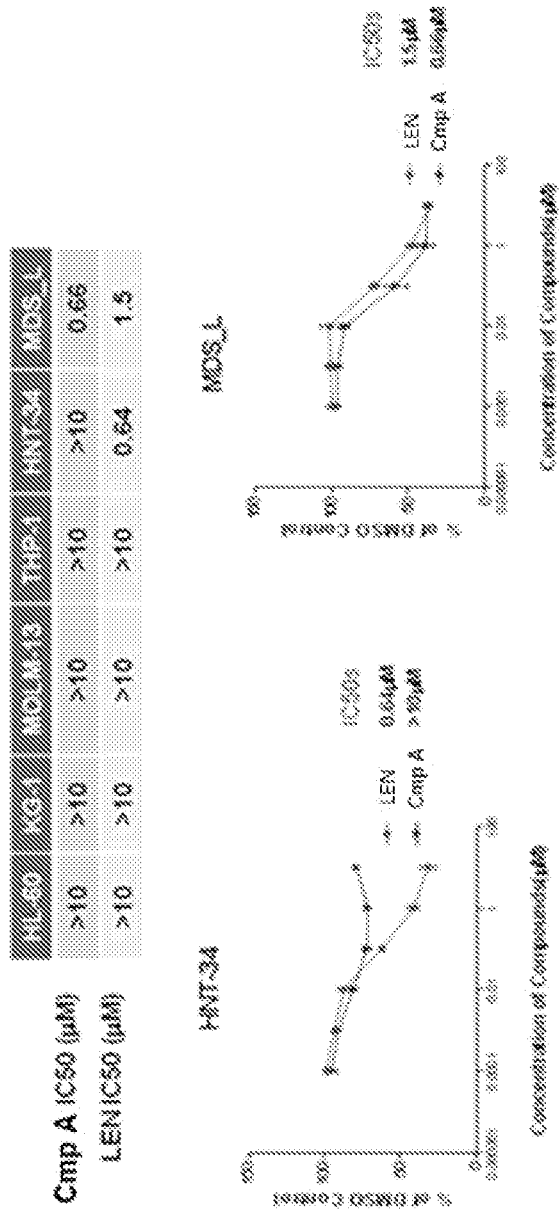
Figure 22D:
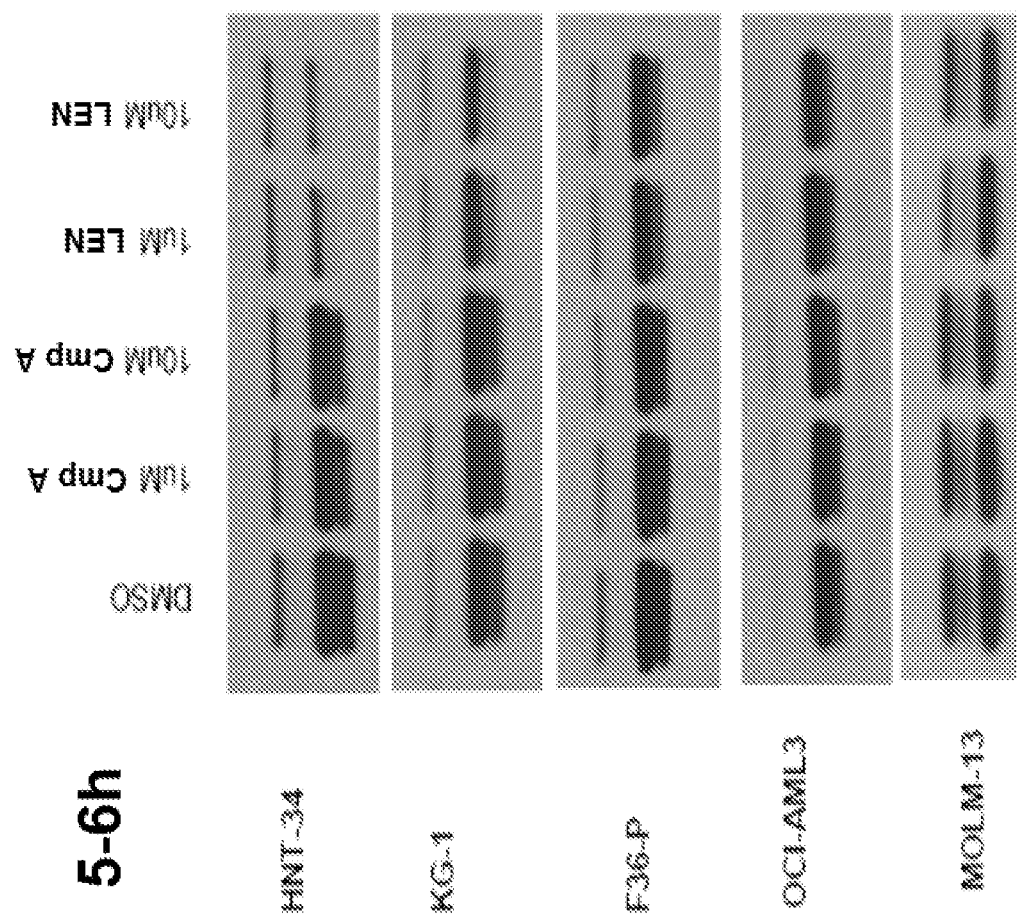
Figure 22E:
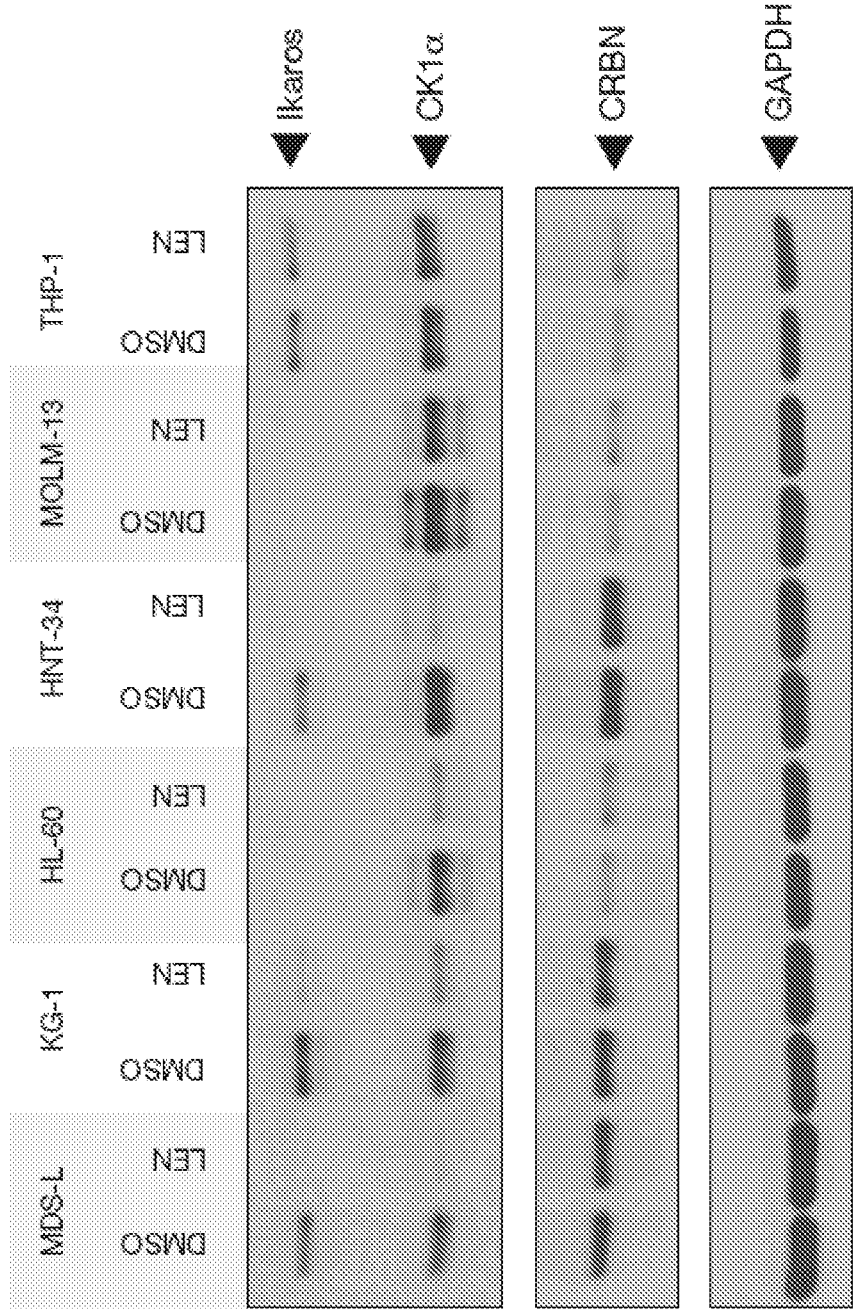

FIGS. 22A-E show sensitivity to lenalidomide treatment in a panel of myeloid cancer cell lines evaluated by tritiated thymidine and/or BrdU assays. FIG. 22A shows that 13 MDS/AML and 1 MM cell lines were evaluated for sensitivity to lenalidomide (LEN) in a 4 d BrdU cell assay, with HNT-34 and MDS-L cells showing the greatest sensitivity to lenalidomide. FIG. 22B shows both HNT-34 and MDS-L cells are sensitive to lenalidomide. FIG. 22C shows the sensitivity of myeloid cancer cell lines to lenalidomide (LEN) and Compound A. FIG. 22D shows that lenalidomide promotes the degradation of casein kinase 1, alpha 1(CSNK1A1; also interchangeably referred to as "CK1a" and "CK1α" herein) in the sensitive cell lines (HNT-34, MDS-L), but does not degrade CSNK1A1 in the insensitive cell lines (e.g., MOLM-13, THP-1). Lenalidomide also promoted degradation of CSNK1A1 in the insensitive cell lines KG-1 and HL-60. FIG. 22E shows a Western Blot analysis of CK1α, Ikaros, and CRBN protein levels in untreated and lenalidomide (LEN)-treated myeloid cancer cells.

Figure 23A:
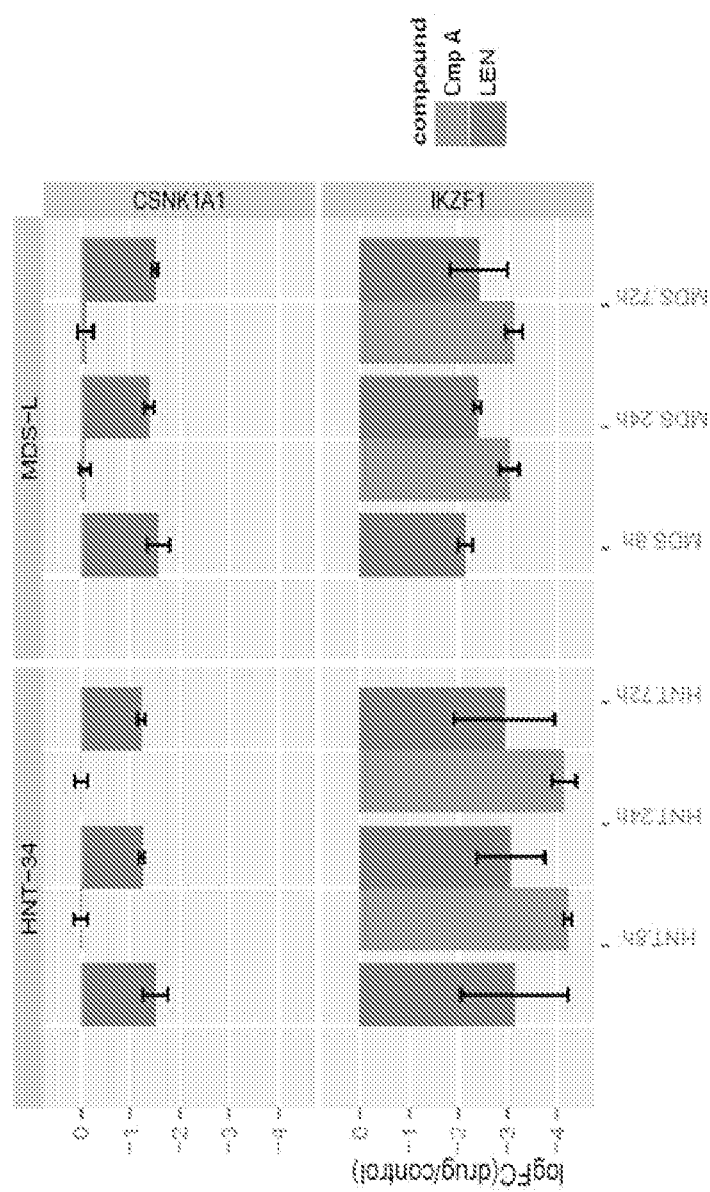
Figure 23C:
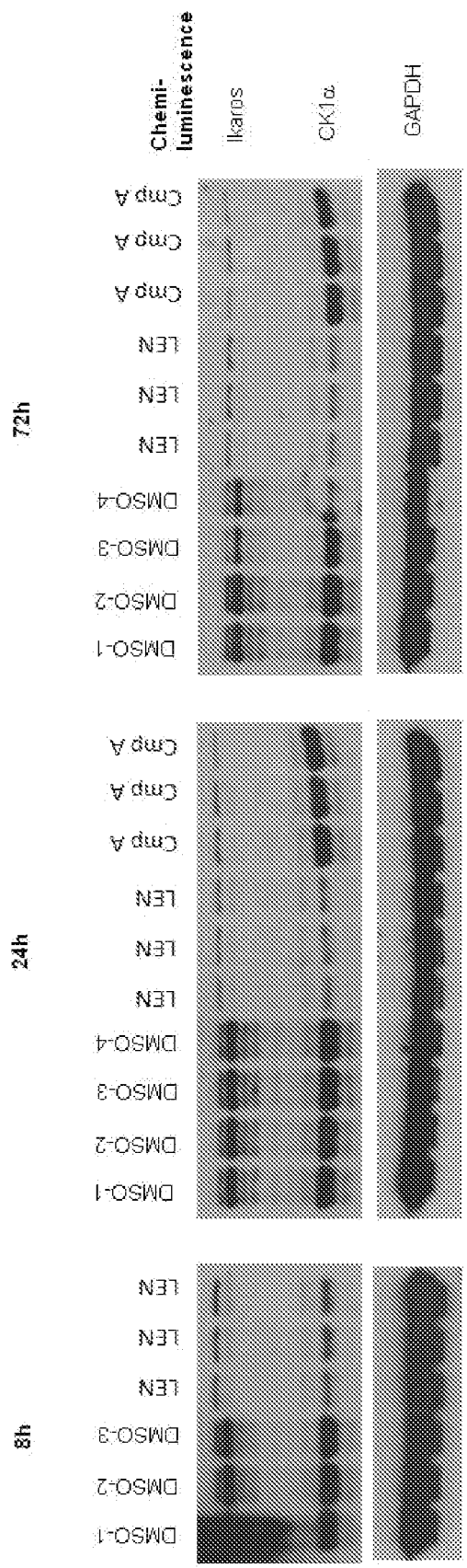
Figure 23D:
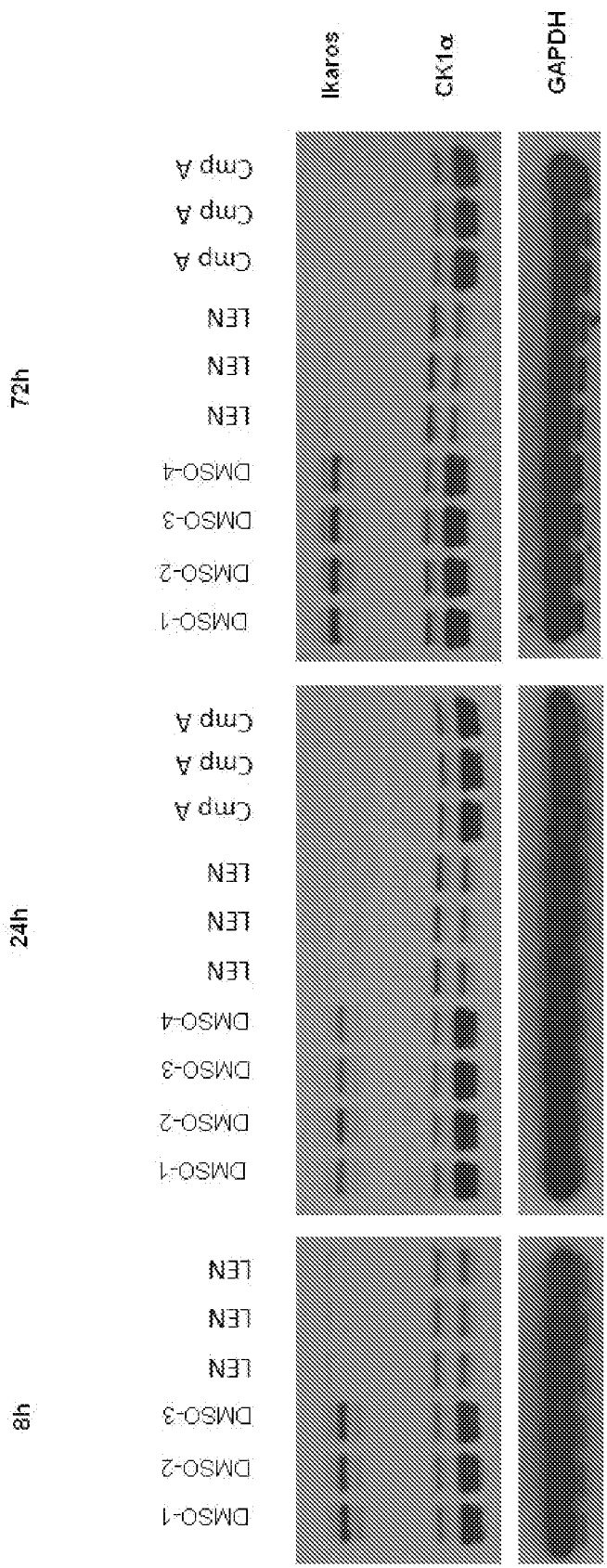

FIGS. 23A-D shows that lenalidomide decreases Ikaros and CSNK1A1 in a del(5q) MDS cell line (MDS-L) and an AML cell line (HNT-34). FIG. 23A and FIG. 23B show results of tandem-mass-tagged proteomics in a del(5q) MDS cell line (MDS-L) and an AML cell line (HNT-34), following treatment with vehicle or 10 uM lenalidomide for 8, 24 and 72 hours. FIG. 23C shows the decrease of Ikaros and CSNK1A1 proteins by lenalidomide are confirmed by Western blot analysis in MDS-L cells. FIG. 23D shows that the decrease of Ikaros and CSNK1A1 proteins by lenalidomide are confirmed by western blot analysis in HNT-34 cells.

Figure 24A:
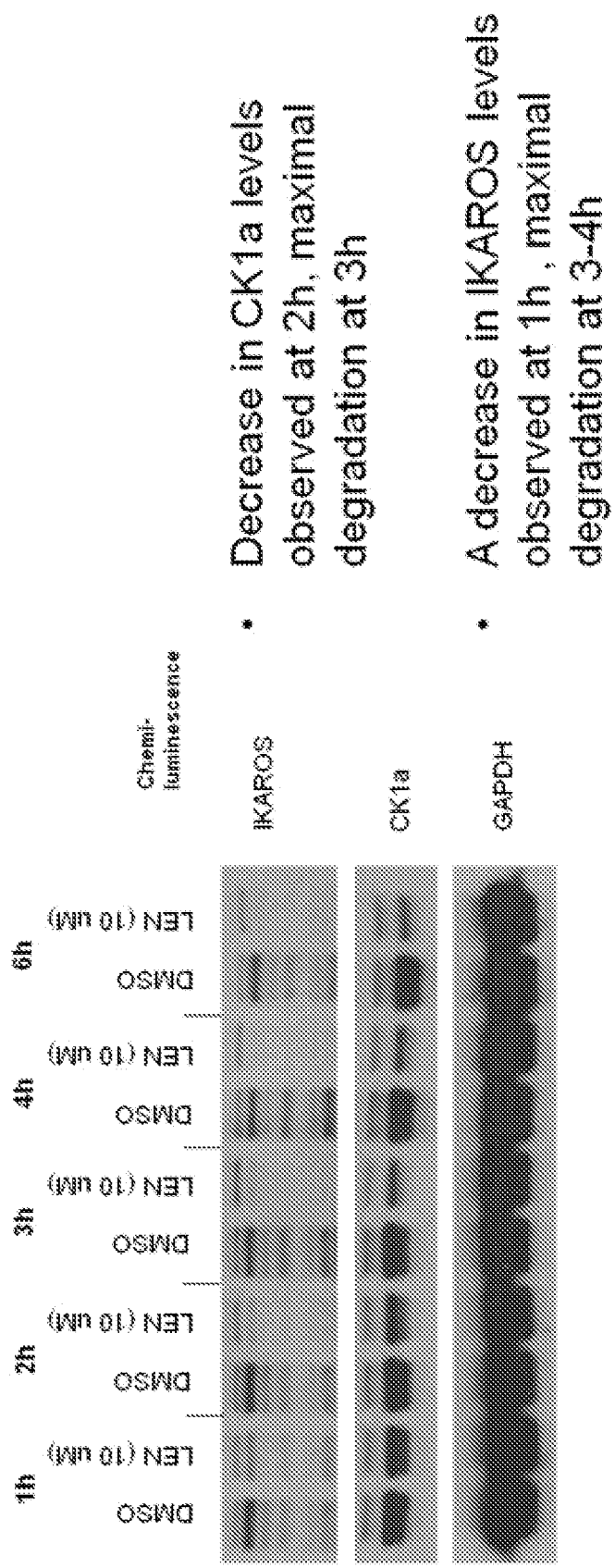
Figure 24B:
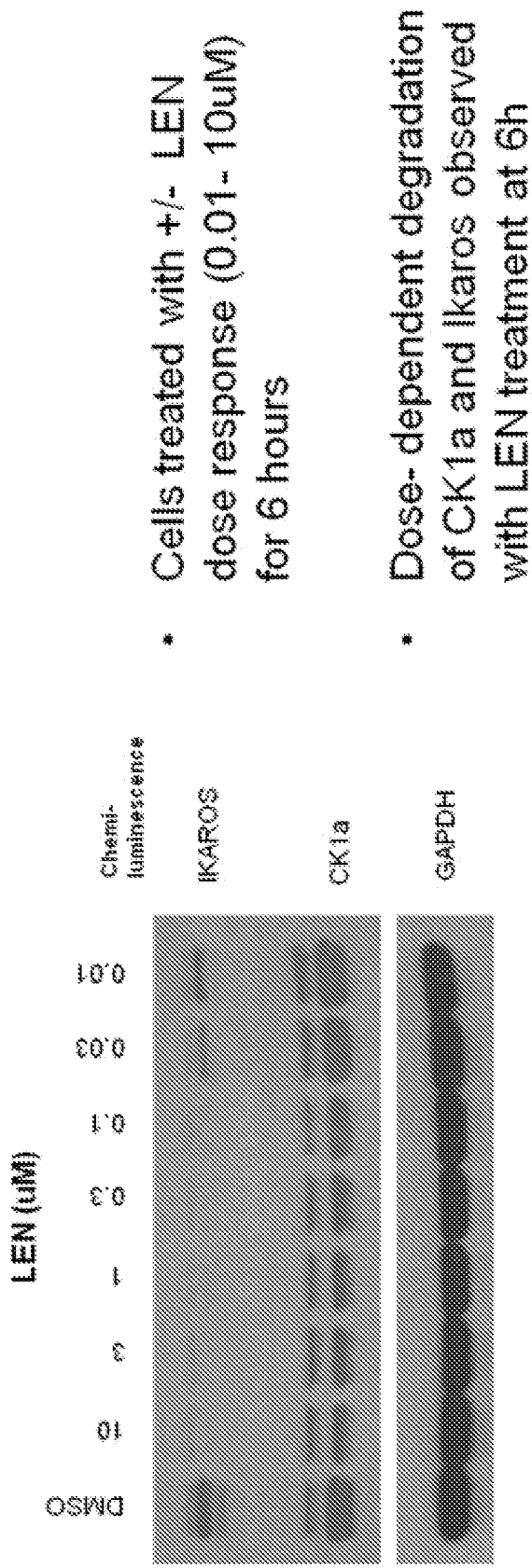

FIGS. 24A-B show degradations of CSNK1A1 and Ikaros in HNT-34 cells treated with lenalidomide are time and dose dependent. FIG. 24A shows degradations of CSNK1A1 and Ikaros in HNT-34 cells treated with lenalidomide are time-dependent. FIG. 24B shows degradations of CSNK1A1 and Ikaros in HNT-34 cells treated with lenalidomide are dose-dependent.

Figure 25A:
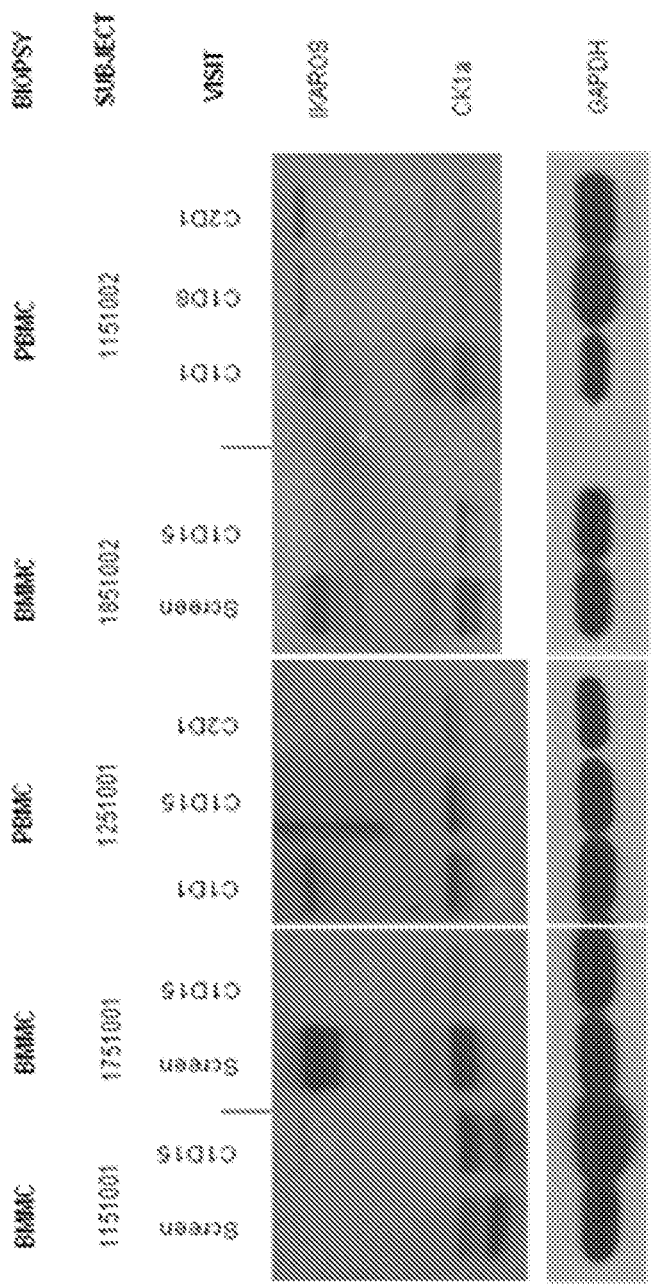

FIGS. 25A-B shows that lenalidomide treatment decreases CSNK1A1 and Ikaros levels in AML patients. FIG. 24A shows both CK1α and Ikaros were modulated (down-regulated) in 4 of 5 patients treated with lenalidomide. FIG. 25B shows that CK1α and Ikaros protein levels were reduced in bone marrow or peripheral blood of lenalidomide (LEN)-treated patients with AML in vivo.

Figure 26:
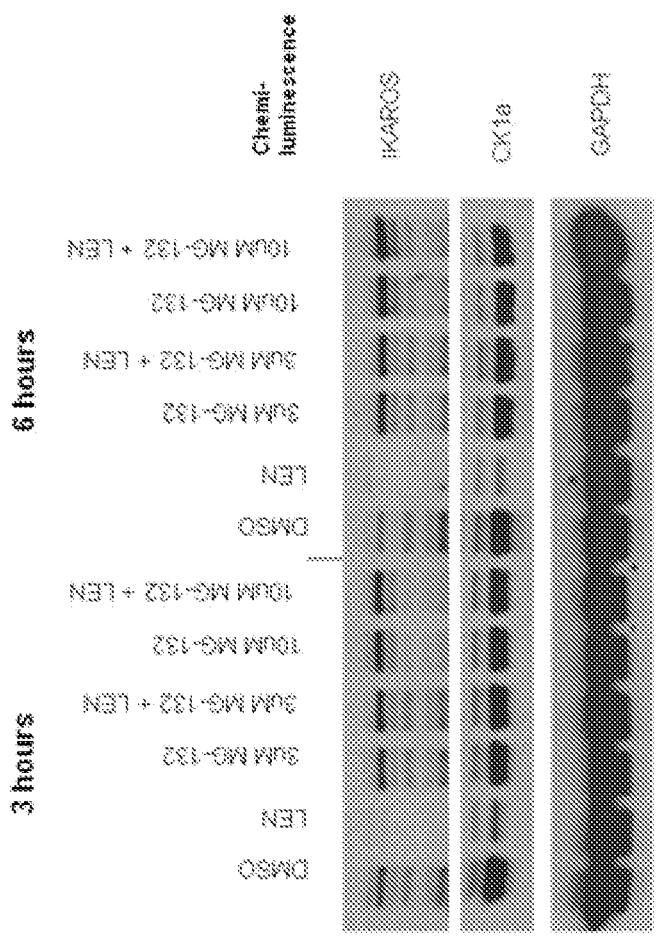

FIG. 26 shows that lenalidomide treatment decreases both CSNK1A1 and Ikaros proteins levels at 3 h or 6 h, and pre-treating HNT-34 cells with the proteasome inhibitor MG-132 stabilizes CSNK1A1 protein levels in the presence of lenalidomide.

Figure 27A:
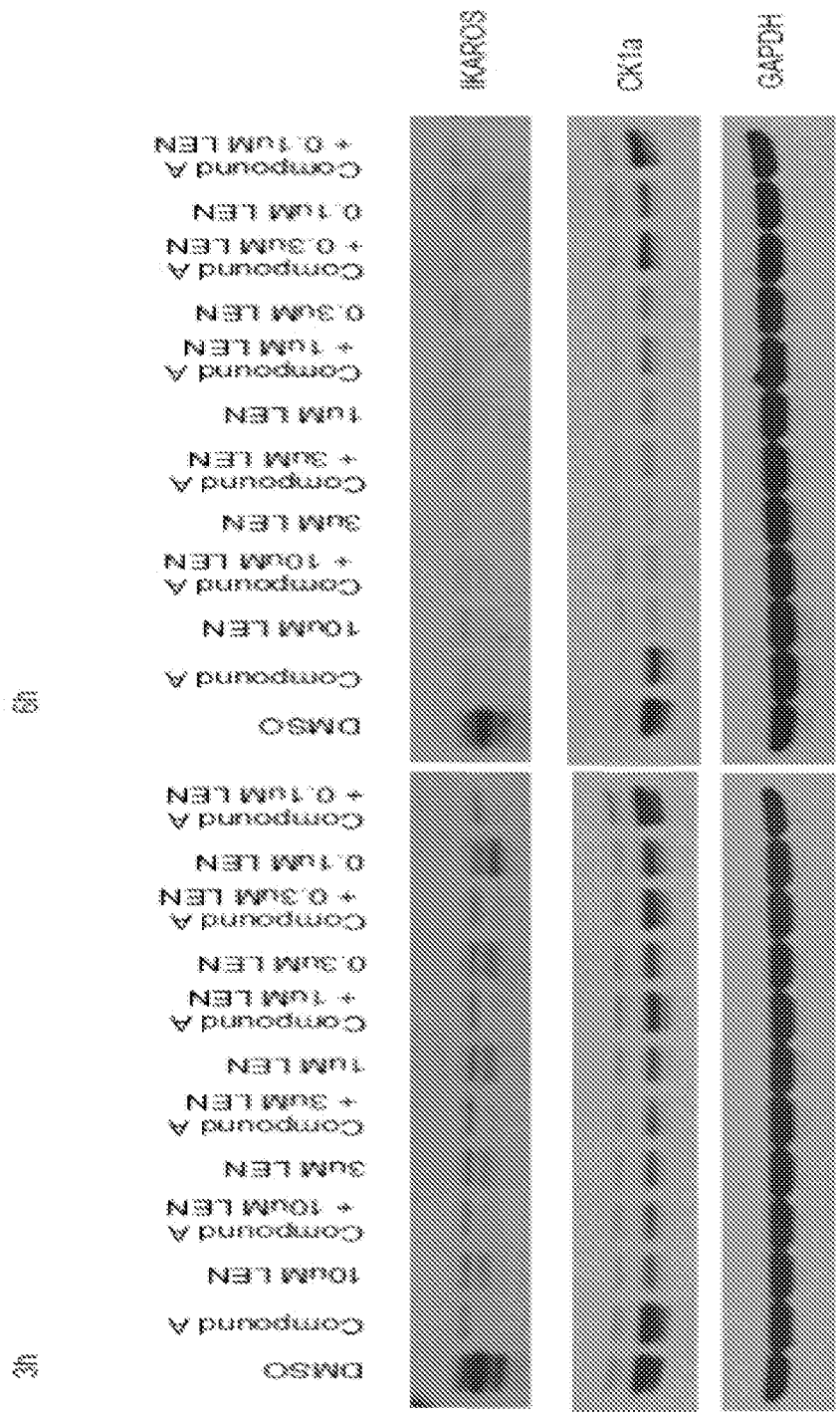
Figure 27B:
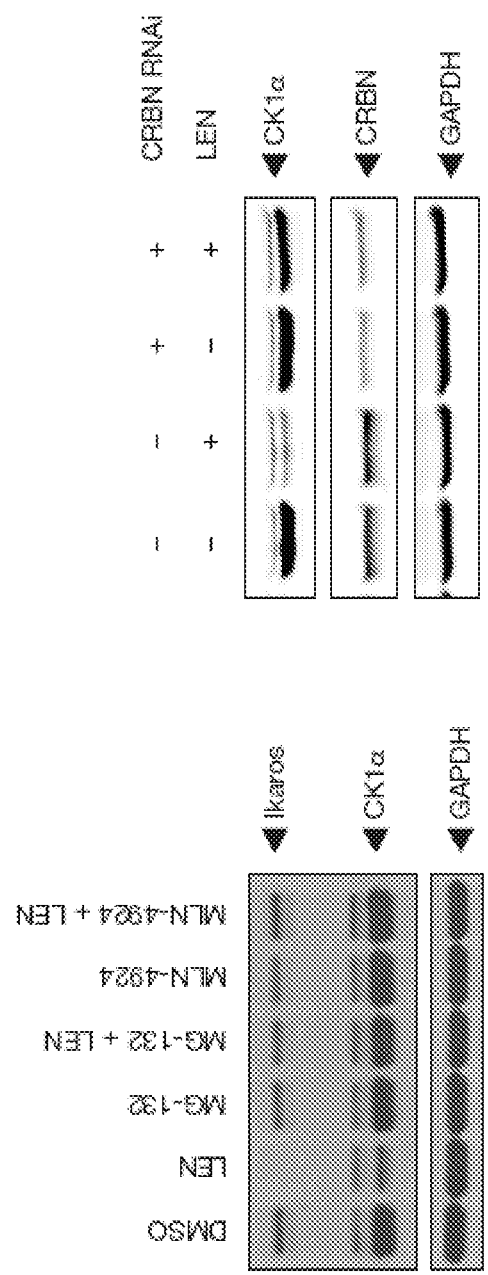

FIGS. 27A-B shows data for a mechanism of lenalidomide-mediated reduction of CK1α levels. FIG. 27A shows that pre-treating HNT-34 cells with Compound A blocks lenalidomide induced CSNK1A1 degradation. FIG. 27B shows that the LEN-mediated reduction of CK1α levels are cullin-dependent and CRBN-dependent. For example, pre-treatment with proteosome inhibitor (MG-132) and neddylation inhibitor (MLN-4924) abrogated LEN-mediated CK1α reduction in HNT-34 cells (FIG. 27B, left panel). In addition, pretreatment with CRBN RNAi inhibited LEN-mediated CK1a reduction in HNT-34 cells (FIG. 27B, right panel).

5 DETAILED DESCRIPTION OF THE INVENTION

The methods, arrays, probes, and kits provided herein are based, in part, on the finding that a changed level, e.g., an increased level and/or a decreased level, of certain molecules (e.g., mRNAs, cDNAs, or proteins) in a biological sample can be utilized as biomarkers to predict responsiveness of a subject having or suspected to have a cancer (e.g., DLBCL, MM, MDS or AML) to a treatment compound (e.g., thalidomide, lenalidomide, pomalidomide, Compound A, or Compound B, or a stereoisomer thereof, or a pharmaceutically acceptable salt, solvate, hydrate, co-crystal, clathrate, or a polymorph thereof).

5.1 Definitions

As used herein, and unless otherwise specified, the terms "treat," "treating" and "treatment" refer to an action that occurs while a patient is suffering from the specified cancer, which reduces the severity of the cancer, or retards or slows the progression of the cancer.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

As used herein, the terms "compound" and "treatment compound" are used interchangeably, and include immunomodulatory compound or immunomodulatory drug. As used herein, the term "immunomodulatory compound" or "immunomodulatory drug" refers generally to a molecule or agent capable of altering the immune response in some way. Non-limiting examples of immunomodulatory compounds include those disclosed in Section 5.7 below.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to a treatment refer to the degree of effectiveness of the treatment in lessening or decreasing the symptoms of a disease, e.g., DLBCL, MM, MDS or AML, being treated. For example, the term "increased responsiveness" when used in reference to a treatment of a cell or a subject refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," or "effective patient tumor response" refers to any increase in the therapeutic benefit to the patient. An "effective patient tumor response" can be, for example, a 5%, 10%, 15%, 20%, 25%, 30%, 40%, 50%, 60%, 70%, 80%, 90%, or 100% decrease in the rate of progress of the tumor. An "effective patient tumor response" can be, for example, a 5%, 10%, 15%, 20%, 25%, 30%, 40%, 50%, 60%, 70%, 80%, 90%, or 100% decrease in the physical symptoms of a cancer. An "effective patient tumor response" can be, for example, a 5%, 10%, 15%, 20%, 25%, 30%, 40%, 50%, 60%, 70%, 80%, 90%, or 100% decrease in the size of a tumor. An "effective patient tumor response" can be, for example, a 5%, 10%, 15%, 20%, 25%, 30%, 40%, 50%, 60%, 70%, 80%, 90%, or 100% decrease in the physical symptoms of a cancer. An "effective patient tumor response" can also be, for example, a 5%, 10%, 15%, 20%, 25%, 30%, 40%, 50%, 60%, 70%, 80%, 90%, 100%, 200%, or more increase in the response of the patient, as measured by any suitable means, such as gene expression, cell counts, assay results, etc.

An improvement in the cancer or cancer-related disease can be characterized as a complete or partial response. "Complete response" refers to an essential absence of clinically detectable disease with normalization of any previously abnormal radiographic studies, bone marrow, and cerebrospinal fluid (CSF) or abnormal monoclonal protein measurements. "Partial response" refers to at least about a 5%, 10%, 15%, 20%, 25%, 30%, 35%, 40%, 45%, 50%, 55%, 60%, 65%, 70%, 75%, 80%, 85% or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, the term "cereblon-associated protein" or "CAP" refers to a protein that interacts with or binds to CRBN, either directly or indirectly. For example, the term refers to any protein that directly bind to cereblon, as well as any protein that is an indirect downstream effector of cereblon pathways. In certain embodiments, a "cereblon-associated protein" or "CAP" is a substrate of CRBN, for example, a protein substrate of the E3 ubiquitin ligase complex involving CRBN, or the downstream substrates thereof. In one embodiment, the CAP provided herein is a substrate of CRBN such as IKZF3, also known as "Aiolos," and/or IKZF1, also known as "Ikaros." In certain embodiments, a "cereblon-associated protein" or "CAP" is a binding protein of CRBN. In yet other embodiments, the CAP is IFN. In other embodiments, the CAP is an IFN pathway protein listed in FIG. 12. In other embodiment, the IFN pathway protein is IFN-induced transmembrane protein 3 (IFITM3) and/or IFN regulatory factor 7 (IRF7). In yet other embodiments, the CAP is CSNK1A1. In yet other embodiments, the CAP is IFN-induced protein with IFIT3, DDX58, XAF1, IFIH1, OAS3, IFI27, IFIT1, or ISG15. In other embodiments, the CAP is an IRF. In one embodiment, the IRF is selected from a group consisting of IRF1, IRF3, IRF4, IRF7, and IRF9. In other embodiments, the CAP is TBK1 or TBK1-PO4. In other embodiments, the CAP is a STAT proteins or a phosphorylated STAT. In some embodiments, the CAP is ZNF198. Other exemplary CAPs are provided elsewhere herein.

The term "regulate" as used herein refers to controlling the activity of a molecule or biological function, such as enhancing or diminishing the activity or function.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors.

The term "refractory or resistant" refers to a circumstance where patients, even after intensive treatment, have residual cancer cells (e.g., leukemia or lymphoma cells) in their lymphatic system, blood and/or blood forming tissues (e.g., marrow).

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., a glycopolypeptide, glycoprotein, or glycopeptide; or a lipopolypeptide, lipoprotein, or lipopeptide.

The term "antibody" is used herein in the broadest sense and covers fully assembled antibodies, antibody fragments which retain the ability to specifically bind to the antigen (e.g., Fab, F(ab')$_2$, Fv, and other fragments), single chain antibodies, diabodies, antibody chimeras, hybrid antibodies, bispecific antibodies, humanized antibodies, and the like. The term "antibody" covers both polyclonal and monoclonal antibodies. The term "antibody" and "immunoglobulin" or "Ig" may be used interchangeably herein. The terms "antibodies that immunospecifically bind to a CRBN antigen," "antibodies that immunospecifically bind to a CRBN epitope," "CRBN antibodies," "anti-CRBN antibodies" and analogous terms are also used interchangeably herein and refer to antibodies and fragments thereof, that specifically bind to a CRBN polypeptide, such as a CRBN antigen or epitope (e.g., peptide 65-76 human CRBN). The antibodies, including both modified antibodies (i.e., antibodies that comprise a modified IgG (e.g., IgG1) constant domain and unmodified antibodies (i.e., antibodies that do not comprise a modified IgG (e.g., IgG1) constant domain that specifically bind to a CRBN polypeptide. An antibody or a fragment thereof that immunospecifically binds to a CRBN antigen may be cross-reactive with related antigens. In certain embodiments, an antibody or a fragment thereof that immunospecifically binds to a CRBN antigen does not cross-react with other antigens. An antibody or a fragment thereof that immunospecifically binds to a CRBN antigen can be identified, for example, by immunoassays, BIAcore, or other techniques known to those of skill in the art. An antibody or a fragment thereof binds specifically to a CRBN antigen when it binds to a CRBN antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab") fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to a CRBN antigen (e.g., one or more complementarity determining regions (CDRs) of an anti-CRBN antibody). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In some embodiments, the anti-CRBN antibodies are fully human, such as fully human monoclonal CRBN antibodies. In certain embodiments, antibodies provided herein are IgG antibodies, or a class (e.g., human IgG1 or IgG4) or subclass thereof.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the CDR). The antigen binding region can be derived from any animal species, such as rodents (e.g., rabbit, rat or hamster) and humans. In some embodiments, the antigen binding region will be of human origin.

The term "constant region" or "constant domain" of an antibody refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

The term "epitope" as used herein refers to a localized region on the surface of an antigen, such as CRBN polypeptide or CRBN polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits a antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen.

The terms "fully human antibody" or "human antibody" are used interchangeably herein and refer to an antibody that comprises a human variable region and, in some embodiments, a human constant region. In specific embodiments, the terms refer to an antibody that comprises a variable region and constant region of human origin. "Fully human" anti-CRBN antibodies, in certain embodiments, can also encompass antibodies which bind CRBN polypeptides and are encoded by nucleic acid sequences which are naturally occurring somatic variants of human germline immunoglobulin nucleic acid sequence. In a specific embodiment, the anti-CRBN antibodies provided herein are fully human antibodies. The term "fully human antibody" includes antibodies having variable and constant regions corresponding to human germline immunoglobulin sequences as described by Kabat et al., Sequences of Proteins of Immunological Interest, Fifth Edition, U.S. Department of Health and Human Services, NIH Publication No. 91-3242, 1991.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences. See Kabat, E. A. et al. (1991) Sequences of Proteins of Immunological Interest, Fifth Edition, U.S. Department of Health and Human Services, NIH Publication No. 91-3242. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. In some embodiments the heavy chain is a human heavy chain.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof. Kabat et al. (1971) Ann. any Acad. Sci. 190:382-391 and, Kabat et al. (1991) Sequences of Proteins of Immunological Interest, Fifth Edition, U.S. Department of Health and Human Services, NIH Publication No. 91-3242. For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3. Other numbering schemes will be readily understood by those skilled in the art.

The term "light chain" when used in reference to an antibody refers to two distinct types, called kappa (κ) of lambda (λ) based on the amino acid sequence of the constant domains. Light chain amino acid sequences are well known in the art. In certain embodiments, the light chain is a human light chain.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only a CRBN epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art. See, e.g., Chapter 11 in: Short Protocols in Molecular Biology, (2002) 5th Ed., Ausubel et al., eds., John Wiley and Sons, New York. Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art. See, e.g., Chapter 11 in: Short Protocols in Molecular Biology, (2002) 5th Ed., Ausubel et al., eds., John Wiley and Sons, New York.

The terms "cereblon" or "CRBN" and similar terms refers to the polypeptides ("polypeptides," "peptides" and "proteins" are used interchangeably herein) comprising the amino acid sequence any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and interspecies homologs, which, in certain embodiments, retain CRBN activity and/or are sufficient to generate an anti-CRBN immune response.

The term "CRBN antigen" refers to that portion of a CRBN polypeptide to which an antibody immunospecifically binds. A CRBN antigen also refers to an analog or derivative of a CRBN polypeptide or fragment thereof to which an antibody immunospecifically binds. A localized region on the surface of a CRBN antigen that is capable of eliciting an immune response is an CRBN "epitope." A region of a CRBN polypeptide contributing to an epitope may be contiguous amino acids of the polypeptide or the epitope may come together from two or more non-contiguous regions of the polypeptide. The epitope may or may not be a three-dimensional surface feature of the antigen.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the light and heavy chains are primarily responsible for the interaction of the antibody with antigen. Numbering of amino acid positions used herein is according to the EU Index, as in See Kabat, E. A. et al. (1991) Sequences of Proteins of Immunological Interest, Fifth Edition, U.S. Department of Health and Human Services, NIH Publication No. 91-3242. In some embodiments, the variable region is a human variable region.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

The term "level" refers to the amount, accumulation, or rate of a biomarker molecule. A level can be represented, for example, by the amount or the rate of synthesis of a massager RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or to a relative amount of the molecule, determined under steady-state or non-steady-state conditions.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, 10%, 20%, 30%, 40%, 50%, 60%, 70%, 90%, 100%, 200%, 300%, 500%, 600%, 700%, 800%, 900%, 1,000%, 1,500%, 2,000%, 2,500%, 3,00%, 3,500%, 4,000%, 4,500%, 5,000% or more of the comparative control mRNA level. Alternatively, an mRNA can be "downregulated", or expressed at a lower level, in response to administration of certain compounds or other agents. A downregulated mRNA can be, for example, present at a level of about 99%, 95%, 90%, 85%, 80%, 75%, 70%, 65%, 60%, 55%, 50%, 45%, 40%, 35%, 30%, 25%, 20%, 15%, 10%, 5%, 3%, 1% or less of the comparative control mRNA level.

Similarly, the level of a polypeptide or protein biomarker from a patient sample can be increased when treated with a drug, as compared to a non-treated control. This increase can be about 5%, 10%, 20%, 30%, 40%, 50%, 60%, 70%, 80%, 90%, 100%, 200%, 300%, 400%, 500%, 700%, 1,000%, 1,500%, 2,000%, 2,500%, 3,000%, 3,500%, 4,000%, 4,500%, 5,000% or more of the comparative control protein level. Alternatively, the level of a protein biomarker can be decreased in response to administration of certain compounds or other agents. This decrease can be, for example, present at a level of about 99%, 95%, 90%, 80%, 70%, 60%, 50%, 40%, 30%, 20%, 10%, 5%, 3%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

"Sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence. Another indication that nucleotide sequences are substantially identical is if two molecules hybridize to each other under stringent conditions.

The terms "isolated" and "purified" refer to isolation of a substance (such as mRNA, antibody or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 30%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "bound" can be used herein to indicate direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include but are not limited to whole blood, partially purified blood, PBMCs, tissue biopsies, and the like.

The term "analyte" as used herein, refers to a known or unknown component of a sample.

The term "capture agent," as used herein, refers to an agent that binds an mRNA or protein through an interaction that is sufficient to permit the agent to bind and concentrate the mRNA or protein from a homogeneous mixture.

The term "probe" as used herein, refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid probe" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term stringent assay conditions generally refers to the combination of hybridization and wash conditions.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The terms "polymerase chain reaction," or "PCR," as used herein generally refers to a procedure wherein small amounts of a nucleic acid, RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, N Y, 1989).

The term "cycle number" or "CT" when used herein in reference to PCR methods, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical cocrystals wherein the crystalline molecular complexes containin a therapeutic compound and one or more additional non-volatile compound(s) (referred to herein as counter-molecule(s)). A counter-molecule in a pharmaceutical cocrystal is typically a non-toxic pharmaceutically acceptable molecule, such as, for example, food additives, preservatives, pharmaceutical excipients, or other APIs. In some embodiments, pharmaceutical cocrystals enhance certain physicochemical properties of drug products (e.g., solubility, dissolution rate, bioavailability and/or stability). without compromising the chemical structural integrity of the active pharmaceutical ingredient (API). See, e.g., Jones et al., "Pharmaceutical Cocrystals: An Emerging Approach to Physical Property Enhancement," *MRS Bulletin*, 2006, 31, 875-879; Trask, "An Overview of Pharmaceutical Cocrystals as Intellectual Property," *Molecular Pharmaceutics*, 2007, 4(3), 301-309; Schultheiss & Newman, "Pharmaceutical Cocrystals and Their Physicochemical Properties," *Crystal Growth & Design*, 2009, 9(6), 2950-2967; Shan & Zaworotko, "The Role of Cocrystals in Pharmaceutical Science," *Drug Discovery Today*, 2008, 13(9/10), 440-446; and Vishweshwar et al., "Pharmaceutical Co-Crystals," *J. Pharm. Sci.*, 2006, 95(3), 499-516.

As used herein, the term "H-score" refers to a method of assessing the extent of immunoreactivity and the results thereof. A H-score is obtained by the formula: 3×percentage of strongly staining cells+2×percentage of moderately staining cells+1×percentage of weakly staining cells+0×percentage of negative staining cells, which gives a range of 0 to 300.

A biological marker or "biomarker" is a substance whose detection indicates a particular biological state, such as, for example, the presence of cancer. In some embodiments, biomarkers can either be determined individually, or several biomarkers can be measured simultaneously.

A "biomarker" can indicate a change in the level of mRNA expression that may correlate with the risk or progression of a disease, or with the susceptibility of the disease to a given treatment. The biomarker is a nucleic acid, such as a mRNA or cDNA.

A "biomarker" can indicate a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & SJ. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

5.2 Biomarkers and Methods of Use Thereof

The methods provided herein are based, in part, on the finding that detectable increase or decrease in certain biomarkers are observed in subjects with cancers (e.g., DLBCL, MM, MDS or AML), who are responsive to a given treatment (e.g., a compound, such as thalidomide, lenalidomide, pomlidomide, or a stereoisomer thereof, or a pharmaceutically acceptable salt, solvate, hydrate, co-crystal, clathrate, or a polymorph thereof), the levels of these biomarkers may be used for predicting the responsiveness of the subjects to the treatment.

A biological marker or "biomarker" is a substance, the change and/or the detection of which indicates a particular biological state. In some embodiments, the indication is the responsiveness of a disease, e.g., a cancer (e.g., DLBCL, MM, MDS or AML), to a given treatment (e.g., a compound, such as thalidomide, lenalidomide, pomlidomide, Compound A, or Compound B, or a stereoisomer thereof, or a pharmaceutically acceptable salt, solvate, hydrate, co-crystal, clathrate, or a polymorph thereof).

In specific embodiments of the various methods provided herein, the biomarker is a cereblon (CRBN)-associated protein (CAP).

In some embodiments, the biomarker comprises one CAP. In certain embodiments, the biomarker comprises two CAPs. In other embodiments, the biomarker comprises three CAPs. In certain embodiments, the biomarker comprises four CAPs. In some embodiments, the biomarker comprises five CAPs. In other embodiments, the biomarker comprises six CAPs. In another embodiment, the biomarker comprises seven CAPs. In certain embodiments, the biomarker comprises eights CAPs. In other embodiments, the biomarker comprises nine CAPs. In another embodiment, the biomarker comprises ten or more CAPs.

In one aspect, provided herein is a method of determining whether a compound is immunomodulatory, comprising:
  a. contacting a first cell (e.g., a cancer cell or an immune cell) with the compound;
  b. obtaining a first sample from the first cell from step (a);
  c. determining the level of a biomarker in the first sample, and
  d. comparing the level of the biomarker from step (c) to the level of the same protein obtained from a reference sample, wherein a change in the biomarker level as compared to the reference sample is indicative of the efficacy of the compound as an immunomodulatory compound.

In some embodiments, the cancer is diffuse large B-cell lymphoma (DLBCL). In other embodiments, the cancer is multiple myeloma (MM). In certain embodiments, the cancer is myelodysplastic syndrome (MDS) (e.g., a MDS with deletion of chromosome 5q (del(5q)). In certain embodiments, the cancer is acute myeloid leukemia (AML). In certain embodiments, the first cell is a cancer cell. In other embodiments, the cell is an immune cell.

In one embodiments, an increased level of the biomarker in the first sample as compared to the reference sample indicates that the compound is likely to be efficacious as an immunomodulatory compound. In another embodiment, a decreased level of the biomarker in the first sample as compared to the reference sample indicates that the compound is likely to be efficacious as an immunomodulatory compound. In other embodiments, provided herein is a method of treating a cancer, comprising a method of determining whether a compound is immunomodulatory provided herein, wherein the method further comprises (e) administering to the subject a therapeutically effective amount of the compound when the compound is indicated as likely to be efficacious as an immunomodulatory compound.

In other embodiments, an increased level of the biomarker in the first sample as compared to the reference sample indicates that the compound is unlikely to be efficacious as an immunomodulatory compound. In certain embodiments, a decreased level of the biomarker in the first sample as compared to the reference sample indicates that the compound is unlikely to be efficacious as an immunomodulatory compound. In other embodiments, provided herein is a method of treating a cancer, comprising a method of determining whether a compound is immunomodulatory provided herein, wherein the method further comprises (e) administering to the subject a therapeutically effective amount of a therapy other than the compound when the compound is indicated as unlikely to be efficacious as an immunomodulatory compound.

In another aspect, provided herein is a method of determining whether a compound is effective as an anti-tumor (or anti-cancer) agent, comprising:
  a. contacting a first cell (e.g., a cancer cell or an immune cell) with the compound;
  b. obtaining a first sample from the first cell from step (a);
  c. determining the level of a biomarker in the first sample; and
  d. comparing the level of the biomarker from step (c) to the level of the same protein(s) obtained from a reference sample, wherein a change in the biomarker level as compared to the reference sample is indicative of the efficacy of the compound as an anti-tumor (or anti-cancer) agent.

In some embodiments, the cancer is DLBCL. In other embodiments, the cancer is MM. In another embodiment, the cancer is MDS. In yet another embodiment, the cancer is AML. In certain embodiments, the first cell is a cancer cell. In other embodiments, the cell is an immune cell.

In one embodiment, an increased level of the biomarker in the first sample as compared to the reference sample indicates that the compound is likely to be efficacious as an anti-tumor agent. In another embodiments, a decreased level of the biomarker in the first sample as compared to the reference sample indicates that the compound is likely to be efficacious as an anti-tumor agent. In certain embodiments, provided herein is a method of treating a cancer, comprising the method of method of determining whether a compound is effective as an anti-tumor (or anti-cancer) agent provided herein, wherein the method further comprises (e) administering to the subject a therapeutically effective amount of the compound when the compound is indicated as likely to be efficacious as an anti-tumor agent.

In some embodiments, an increased level of the biomarker in the first sample as compared to the reference sample indicates that the compound is unlikely to be efficacious as an anti-tumor agent. In other embodiments, a decreased level of the biomarker in the first sample as compared to the reference sample indicates that the compound is unlikely to be efficacious as an anti-tumor agent. In some embodiments, provided herein is a method of treating a cancer, comprising the method of method of determining whether a compound is effective as an anti-tumor (or anti-cancer) agent provided herein, wherein the method further comprises (e) administering to the subject a therapeutically effective amount of a therapy other than the compound when the compound is indicated to be as unlikely to be efficacious as an anti-tumor agent.

In some embodiments of the methods provided herein, the contacting in step (a) is in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In one embodiment, the cells are obtained from a cell line. In other embodiments, the cells are obtained from a subject having (or suspected of having) the cancer.

In another aspect, provided herein is a method of assessing the efficacy of a compound in treating cancer, comprising:
  a. administering a compound to a subject having cancer;
  b. obtaining a first sample from the subject;
  c. determining the level of a biomarker in the first sample; and
  d. comparing the level of the biomarker from step (c) to the level of the same protein obtained from a reference sample, wherein a change in the biomarker level as compared to the reference sample is indicative of the efficacy of the compound in treating the cancer.

In some embodiments, the cancer is DLBCL. In other embodiments, the cancer is MM. In another embodiment, the cancer is MDS. In yet another embodiment, the cancer is AML.

In some embodiments, an increased level of the biomarker in the first sample as compared to the reference sample indicates that the compound is likely to be efficacious in treating the cancer. In other embodiments, a decreased level of the biomarker in the first sample as compared to the reference sample indicates that the compound is likely to be efficacious in treating the cancer. In certain embodiments, provided herein is a method of treating a cancer, comprising the method of assessing the efficacy of a compound in treating cancer provided herein, wherein the method further comprises (e) administering to the subject a therapeutically effective amount of the compound when the compound is indicated as likely to be efficacious in treating the cancer.

In one embodiments, an increased level of the biomarker in the first sample as compared to the reference sample indicates that the compound is unlikely to be efficacious in treating the cancer. In other embodiments, a decreased level of the biomarker in the first sample as compared to the reference sample indicates that the compound is unlikely to be efficacious in treating the cancer. In certain embodiments, provided herein is a method of treating a cancer, comprising the method of assessing the efficacy of a compound in treating cancer provided herein, wherein the method further comprises (e) administering to the subject a therapeutically effective amount of a therapy other than the compound when the compound is indicated as unlikely to be efficacious in treating the cancer.

In another aspect, provided herein is a method of selecting a group of cancer subjects for the purposes of predicting clinical response, monitoring clinical response, or monitoring patient compliance to dosing by a compound, comprising:
 a. administering a compound to a subject;
 b. obtaining a first sample from the subject;
 c. determining the level of a biomarker in the first sample; and
 d. diagnosing the subject as being likely to be responsive to the compound if the level of the biomarker in the first sample is different than the level in a reference sample.

In some embodiments, the cancer is DLBCL. In other embodiments, the cancer is MM. In another embodiment, the cancer is MDS. In yet another embodiment, the cancer is AML.

In some embodiments, the method is a method of selecting a group of cancer subjects for the purposes of predicting clinical response to dosing by a compound. In some embodiments, the method is a method of selecting a group of cancer subjects for the purposes of monitoring clinical response to dosing by a compound. In some embodiments, the method is a method of selecting a group of cancer subjects for the purposes of monitoring patient compliance to dosing by a compound.

In some embodiments, an increased level of the biomarker in the first sample as compared to the reference sample indicates that the subject is likely to be responsive to the compound. In other embodiments, a decreased level of the biomarker in the first sample as compared to the reference sample indicates that the subject is likely to be responsive to the compound. In certain embodiments, provided herein is a method of treating a cancer, comprising the method of selecting a group of cancer subjects for the purposes of predicting clinical response, monitoring clinical response, or monitoring patient compliance to dosing by a compound provided herein, wherein the method further comprises (e) administering to the subject a therapeutically effective amount of the compound when the subject is indicated as likely to be to be responsive to the compound.

In some embodiments, an increased level of the biomarker in the first sample as compared to the reference sample indicates that the subject is unlikely to be responsive to the compound. In other embodiments, a decreased level of the biomarker in the first sample as compared to the reference sample indicates that the subject is unlikely to be responsive to the compound. In certain embodiments, provided herein is a method of treating a cancer, comprising the method of selecting a group of cancer subjects for the purposes of predicting clinical response, monitoring clinical response, or monitoring patient compliance to dosing by a compound provided herein, wherein the method further comprises (e) administering to the subject a therapeutically effective amount of a therapy other than the compound when the subject is indicated as unlikely to be to be responsive to the compound.

In some embodiments, the first sample is obtained prior to administration of the compound to the subject. Accordingly, in certain embodiments, provided herein is a method of selecting a group of cancer subjects for the purposes of predicting clinical response to dosing by a compound, comprising: obtaining a first sample from the subject; determining the level of a biomarker in the first sample; and diagnosing the subject as being likely to be responsive to the compound if the level of the biomarker in the first sample is different than the level in a reference sample. In certain embodiments, provided herein is a method of treating a cancer, comprising the method of selecting a group of cancer subjects for the purposes of predicting clinical response to dosing by a compound provided herein, wherein the method further comprises administering to the subject a therapeutically effective amount of the compound when the subject is diagnosed as likely to be responsive to the treatment compound. In some embodiments, the cancer is DLBCL. In other embodiments, the cancer is MM. In another embodiment, the cancer is MDS. In yet another embodiment, the cancer is AML.

In some embodiments, of the various methods provided herein, the first sample is obtained from a tumor biopsy, node biopsy, or a biopsy from bone marrow, spleen, liver, brain or breast. In some embodiments, the reference sample is prepared by using a second sample not contacted with the compound. In an embodiment, the reference sample is prepared by using a second sample obtained from the subject prior to administration of the compound to the subject. In some embodiments, the reference is prepared by using a second sample obtained from a healthy subject not having the cancer. In one embodiment, the second sample is from the same source as the first sample.

In another aspect, provided herein is a method of identifying a subject having a cancer who is likely to be responsive to a treatment compound, comprising:
 a. administering the treatment compound to a subject having the cancer;
 b. obtaining a sample from the subject;
 c. determining the level of a biomarker in the sample from the subject; and
 d. diagnosing the subject as being likely to be responsive to the treatment compound if the level of the biomarker in the sample of the subject changes as compared to a level of the biomarker in a reference sample.

In some embodiments, the cancer is DLBCL. In other embodiments, the cancer is MM. In another embodiment, the cancer is MDS. In yet another embodiment, the cancer is AML.

In some embodiments, the subject is diagnosed as likely to be responsive to the treatment compound if the level of the biomarker in the sample of the subject is higher than a level of the biomarker in a reference sample. In other embodiments, the subject is diagnosed as likely to be responsive to the treatment compound if the level of the biomarker in the sample of the subject is lower than a level of the biomarker in a reference sample. In certain embodiments, provided herein is a method of treating a cancer, comprising the method of identifying a subject having a cancer who is likely to be responsive to a treatment compound provided herein, wherein the method further comprises (e) administering to the subject a therapeutically effective amount of the compound when the subject is diagnosed as likely to be responsive to the treatment compound.

In some embodiments, the subject is diagnosed as unlikely to be responsive to the treatment compound if the level of the biomarker in the sample of the subject is higher than a level of the biomarker in a reference sample. In other embodiments, the subject is diagnosed as unlikely to be responsive to the treatment compound if the level of the biomarker in the sample of the subject is lower than a level of the biomarker in a reference sample. In certain embodiments, provided herein is a method of treating a cancer, comprising the method of identifying a subject having a cancer who is likely to be responsive to a treatment compound provided herein, wherein the method further comprises (e) administering to the subject a therapeutically effective amount of a therapy other than the compound when the subject is diagnosed as unlikely to be responsive to the treatment compound.

In another aspect, provided herein is a method of predicting the responsiveness of a subject having or suspected of having a cancer to a treatment compound, comprising:
 a. administering the treatment compound to the subject;
 b. obtaining a sample from the subject;
 c. determining the level of a biomarker in the sample from the subject; and
 d. predicting or diagnosing the subject as being likely to be responsive to the treatment compound if the level of the biomarker in the sample changes as compared to the level of the biomarker obtained from a reference sample.

In some embodiments, the cancer is DLBCL. In other embodiments, the cancer is MM. In another embodiment, the cancer is MDS. In yet another embodiment, the cancer is AML.

In some embodiments, the subject is diagnosed as likely to be responsive to the treatment compound if the level of the biomarker in the sample of the subject is higher than the level of the biomarker in a reference sample. In other embodiments, the subject is diagnosed as likely to be responsive to the treatment compound if the level of the biomarker in the sample of the subject is lower than the level of the biomarker in a reference sample. In certain embodiments, provided herein is a method of treating a cancer, comprising the method of predicting the responsiveness of a subject having or suspected of having a cancer to a treatment compound provided herein, wherein the method further comprises (e) administering to the subject a therapeutically effective amount of the compound when the subject is diagnosed as likely to be responsive to the treatment compound.

In some embodiments, the subject is diagnosed as unlikely to be responsive to the treatment compound if the level of the biomarker in the sample of the subject is higher than the level of the biomarker in a reference sample. In other embodiments, the subject is diagnosed as unlikely to be responsive to the treatment compound if the level of the biomarker in the sample of the subject is lower than the level of the biomarker in a reference sample. In certain embodiments, provided herein is a method of treating a cancer, comprising the method of predicting the responsiveness of a subject having or suspected of having a cancer to a treatment compound provided herein, wherein the method further comprises (e) administering to the subject a therapeutically effective amount of a therapy other than the compound when the subject is diagnosed as unlikely to be responsive to the treatment compound.

In another aspect, provided herein is a method of monitoring the efficacy of a treatment of a cancer in a subject with a treatment compound, comprising:
 a. administering the treatment compound to a subject having cancer;
 b. obtaining a sample from the subject;
 c. determining the level of a biomarker in the sample from the subject; and
 d. comparing the level of the biomarker in the sample with the level of the biomarker obtained from a reference sample, wherein a change in the level as compared to the reference sample is indicative of the efficacy of the treatment compound in treating the cancer in the subject.

In some embodiments, the cancer is DLBCL. In other embodiments, the cancer is MM. In another embodiment, the cancer is MDS. In yet another embodiment, the cancer is AML.

In some embodiments, an increased level of the biomarker in the sample as compared to the of level of the biomarker in the reference sample is indicative of the efficacy of the treatment compound in treating the cancer in the subject. In other embodiments, a decreased level of the biomarker in the sample as compared to the of level of the biomarker in the reference sample is indicative of the efficacy of the treatment compound in treating the cancer in the subject. In certain embodiments, provided herein is a method of treating a cancer, comprising the method of monitoring the efficacy of a treatment of a cancer in a subject with a treatment compound provided herein, wherein the method further comprises (e) administering to the subject a therapeutically effective amount of the compound when the compound is indicated to be efficacious in treating the cancer in the subject.

In some embodiments, an increased level of the biomarker in the sample as compared to the of level of the biomarker in the reference sample is indicative of the lack of efficacy of the treatment compound in treating the cancer in the subject. In other embodiments, a decreased level of the biomarker in the sample as compared to the of level of the biomarker in the reference sample is indicative of the lack of efficacy of the treatment compound in treating the cancer in the subject. In certain embodiments, provided herein is a method of treating a cancer, comprising the method of monitoring the efficacy of a treatment of a cancer in a subject with a treatment compound provided herein, wherein the method further comprises (e) administering to the subject a therapeutically effective amount of a therapy other than the compound when the compound is indicated to have a lack of efficacy in treating the cancer in the subject.

In some embodiments of the various methods provided herein the sample from the subject is a biological sample. In certain embodiments, the from the subject sample is obtained from a tumor biopsy, node biopsy, or a biopsy from bone marrow, spleen, liver, brain or breast.

In some embodiments of the various methods provided herein the reference sample is a biological sample. In certain embodiments, the references sample is obtained from a tumor biopsy, node biopsy, or a biopsy from bone marrow, spleen, liver, brain or breast. In some embodiments, the reference sample is prepared by using a second sample not contacted with the compound. In other embodiments, the reference sample is prepared by using a second sample obtained from the subject prior to administration of the compound to the subject. In another embodiment, the reference sample is prepared by using a second sample obtained from a healthy subject not having the cancer. In other embodiments, the second sample is from the same source as the first sample.

In certain embodiments of the various methods provided herein, step (c) comprises: (i) contacting the proteins within the sample from step (b) with a first antibody that immunospecifically binds to the biomarker; (ii) contacting the proteins bound to the first antibody with a second antibody with a detectable label, wherein the second antibody immunospecifically binds to the biomarker, and wherein the second antibody immunospecifically binds to a different epitope on the biomarker than the first antibody; (iii) detecting the presence of second antibody bound to the biomarker; and (iv) determining the amount of the biomarker based on the amount of detectable label in the second antibody. In some embodiments of the various methods provided herein, step (c) comprises using immunohistochemistry to determine the level of the biomarker. In some embodiments, step (c) comprises: (i) contacting proteins within the first sample from step (b) with a first antibody that immunospecifically binds to a biomarker, the first antibody being coupled with a first detectable label; (ii) contacting the proteins within the first sample from step (b) with a second antibody that immunospecifically binds to a cancer biomarker, the second antibody being coupled with a second detectable label; (iii) detecting the presence of the first antibody and the second antibody bound to the proteins; and (iv) determining the level of the biomarker based on the amount of detectable label in the first antibody, and determining the level of the cancer biomarker based on the amount of detectable label in the second antibody. In some embodiments, the cancer biomarker is a DLBCL biomarker. In other embodiments, the cancer biomarker is a MM biomarker. In another embodiment, the cancer biomarker is a MDS biomarker. In yet another embodiment, the cancer biomarker is an AML biomarker. In certain embodiments, the cancer biomarker is CD138. In some embodiments, H-score is used to determine the level of the biomarker. In some embodiments, H-score is used to determine the level of the biomarker when the level of the cancer biomarker is higher than a reference level. In other embodiments of the various methods provided herein step (c) comprises: (i) contacting RNA within the first sample with a primer comprising a sequence specifically binding to the RNA to generate a first DNA molecule having a sequence complementary to the RNA; (ii) amplifying the DNA corresponding to a segment of a gene encoding the biomarker; and (iii) determining the RNA level of the biomarker based on the amount of the amplified DNA. While these embodiments reference step (c) of certain methods provided herein, it is understood that such embodiments can apply to the determination or measurement of a biomarker in any sample (e.g., a sample from a subject, a reference sample, or both a sample from a subject and a reference sample).

In another aspect, provided herein is a method of predicting patient response to compound treatment in a cancer patient, the method comprising:
 a. obtaining a sample comprising cells (e.g., cancer cells or immune cells) from the patient,
 b. culturing the cells in the presence or absence of the compound,
 c. purifying protein or nucleic acid (e.g., a RNA, such as mRNA, or DNA) from the cultured cells, and
 d. measuring the presence or absence of a biomarker.

In some embodiments, the cancer is DLBCL. In other embodiments, the cancer is MM. In another embodiment, the cancer is MDS. In yet another embodiment, the cancer is AML. In certain embodiments, the first cell is a cancer cell. In other embodiments, the cell is an immune cell.

In some embodiments, the presence of the biomarker indicates or is predictive of the likelihood of patient response to the compound treatment. In other embodiments, the absence of the biomarker indicates or is predictive of the likelihood of patient response to the compound treatment. In certain embodiments, provided herein is a method of treating a cancer, comprising the method of predicting patient response to compound treatment in a cancer patient provided herein, wherein the method further comprises (e) administering to the subject a therapeutically effective amount of the compound when a patient is predicted to have a response to the compound treatment.

In some embodiments, the presence of the biomarker indicates or is predictive of a decreased likelihood of patient response to the compound treatment. In other embodiments, the absence of the biomarker indicates or is predictive of a decreased likelihood of patient response to the compound treatment. In certain embodiments, provided herein is a method of treating a cancer, comprising the method of predicting patient response to compound treatment in a cancer patient provided herein, wherein the method further comprises (e) administering to the subject a therapeutically effective amount of a therapy other than the compound when a patient is not predicted to have a response to the compound treatment.

In some embodiments of the methods provided herein, the contacting in step (a) is in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In one embodiment, the cells are obtained from a cell line. In other embodiments, the cells are obtained from a subject having (or suspected of having) the cancer.

In another aspect, provided herein is a method of monitoring tumor response to compound treatment in a cancer patient, the method comprising
 a. obtaining a first sample from the patient,
 b. measuring the expression of a biomarker in the first sample,
 c. administering a compound to the patient,
 d. thereafter, obtaining a second sample from the patient,
 e. measuring biomarker expression in the second sample, and
 f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In some embodiments, an increased level of biomarker expression in the second sample after compound administration indicates the likelihood of an effective tumor response. In other embodiments, wherein a decreased level of biomarker expression in the second sample after compound administration indicates the likelihood of an effective tumor response. In certain embodiments, provided herein is a method of treating a cancer, comprising the method of monitoring tumor response to compound treatment in a cancer patient provided herein, wherein the method further comprises (g) administering to the subject a therapeutically effective amount of the compound when there is a likelihood of an effective tumor response.

In some embodiments, an increased level of biomarker expression in the second sample after compound administration indicates a decreased likelihood of an effective tumor response. In other embodiments, a decreased level of biomarker expression in the second sample after compound administration indicates a decreased likelihood of an effective tumor response. In certain embodiments, provided herein is a method of treating a cancer, comprising the method of monitoring tumor response to compound treatment in a cancer patient provided herein, wherein the method further comprises (g) administering to the subject a therapeutically effective amount of a therapy other than the compound when there is not a likelihood of an effective tumor response.

In another aspect, provided herein is a method of treating a subject with a compound, the method comprising
 a. obtaining a first sample from the patient,
 b. measuring the expression of a biomarker in the first sample,
 c. administering a compound to the patient,
 d. thereafter, obtaining a second sample from the patient,
 e. measuring biomarker expression in the second sample,
 f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In some embodiments, an increased level of biomarker expression in the second sample after compound administration indicates the likelihood of an effective tumor response. In other embodiments, a decreased level of biomarker expression in the second sample after compound administration indicates the likelihood of an effective tumor response. In certain embodiments, the method further comprises (g) administering to the subject a therapeutically effective amount of the compound when there is a likelihood of an effective tumor response.

In some embodiments, an increased level of biomarker expression in the second sample after compound administration indicates a decreased likelihood of an effective tumor response. In other embodiments, a decreased level of biomarker expression in the second sample after compound administration indicates a decreased likelihood of an effective tumor response. In certain embodiments, the method further comprises (g) administering to the subject a therapeutically effective amount of a therapy other than the compound when there is not a likelihood of an effective tumor response.

In another aspect, provided herein is a method of monitoring IFN therapy treatment response to compound treatment in a cancer patient, the method comprising
 a. obtaining a first sample from the patient,
 b. measuring the expression of a biomarker in the first sample,
 c. administering one or more compounds to the patient,
 d. thereafter, obtaining a second sample from the patient,
 e. measuring biomarker expression in the second sample, and
 f. comparing the levels of biomarker expression in the first and second samples.

In some embodiments, the cancer is DLBCL. In other embodiments, the cancer is MM. In another embodiment, the cancer is MDS. In yet another embodiment, the cancer is AML.

In some embodiments, an increased level of biomarker expression in the second sample after compound administration indicates the likelihood of an effective IFN therapy treatment response. In other embodiments, a decreased level of biomarker expression in the second sample after compound administration indicates the likelihood of an effective IFN therapy treatment response. In certain embodiments, provided herein is a method of treating a cancer, comprising the method of monitoring IFN therapy treatment response to compound treatment in a cancer patient provided herein, wherein the method further comprises (g) administering to the subject a therapeutically effective amount of the compound when there is a likelihood of an effective IFN therapy treatment response.

In some embodiments, an increased level of biomarker expression in the second sample after compound administration indicates a decreased likelihood of an effective IFN therapy treatment response. In other embodiments, a decreased level of biomarker expression in the second sample after compound administration indicates a decreased likelihood of an effective IFN therapy treatment response. In certain embodiments, provided herein is a method of treating a cancer, comprising the method of monitoring IFN therapy treatment response to compound treatment in a cancer patient provided herein, wherein the method further comprises (g) administering to the subject a therapeutically effective amount of a therapy other than the compound when there is not a likelihood of an effective IFN therapy treatment response.

In some embodiments of the various methods provided herein, the first sample is a biological sample. In certain embodiments, the first sample is obtained from a tumor biopsy, node biopsy, or a biopsy from bone marrow, spleen, liver, brain or breast. In some embodiments of the various methods provided herein, the second sample is a biological sample. In certain embodiments, the second sample is obtained from a tumor biopsy, node biopsy, or a biopsy from bone marrow, spleen, liver, brain or breast. In some embodiments, the second sample is from the same source as the first sample.

In one embodiment, the IFN therapy is to treat conyloma accuminata, chronic hepatitis B, chronic hepatitis C, relapsing-remitting multiple sclerosis, or chronic granulomatous disease.

In some embodiments of the various methods provided herein, the measuring step(s) comprises: (i) contacting proteins within the sample with a first antibody that immunospecifically binds to the biomarker; (ii) contacting the proteins bound to the first antibody with a second antibody with a detectable label, wherein the second antibody immunospecifically binds to the biomarker, and wherein the second antibody immunospecifically binds to a different epitope on the biomarker than the first antibody; (iii) detecting the presence of second antibody bound to the biomarker; and (iv) determining the amount of the biomarker based on the amount of detectable label in the second antibody. In some embodiments of the various methods provided herein the measuring step(s) comprises using immunohistochemistry to determine the level of the biomarker. In some embodiments of the various methods provided herein the measuring step(s) comprises: (i) contacting proteins within the sample with a first antibody that immunospecifically binds to a biomarker, the first antibody being coupled with a first detectable label; (ii) contacting the proteins within the sample with a second antibody that immunospecifically binds to a cancer biomarker, the second antibody being coupled with a second detectable label; (iii) detecting the presence of the first antibody and the second antibody bound to the biomarker; and (iv) determining the level of the biomarker based on the amount of detectable label in the first antibody, and determining the level of the cancer biomarker based on the amount of detectable label in the second antibody. In some embodiments, the cancer biomarker is a DLBCL biomarker. In other embodiments, the cancer biomarker is a MM biomarker. In another embodiment, the cancer biomarker is a MDS biomarker. In yet another embodiment, the cancer biomarker is an AML biomarker. In certain embodiments, the cancer biomarker is CD138. In some embodiments, wherein H-score is used to determine the level of the biomarker. In other embodiments, H-score is used to determine the level of the biomarker when the level of the cancer biomarker is higher than a reference level. In other embodiments of the various methods provided herein, the measuring step(s) comprises: (i) contacting the RNA within the sample with a primer comprising a sequence specifically binding to the RNA to generate a first DNA molecule having a sequence complementary to the RNA; (ii) amplifying the DNA corresponding to a segment of a gene encoding the biomarker; and (iii) determining the RNA level of the biomarker based on the amount of the amplified DNA.

In some embodiments, the measuring step(s) is measuring (or otherwise determining) of the expression (such as the level (e.g., protein or RNA level)) of the biomarker in a sample from the patient (e.g., a first sample, a second sample, or both a first and second sample). In other embodiments, the measuring step(s) is measuring (or otherwise determining) of the expression (such as the level (e.g., protein or RNA level)) of the biomarker in a reference sample.

In certain embodiments of the various methods provided herein, the cancer is diffuse large B-cell lymphoma (DLBCL). In certain embodiments of the various methods provided herein, the cancer is multiple myeloma (MM). In certain embodiments of the various methods provided herein, the cancer is myelodysplastic syndrome (MDS). In some embodiments, the MDS is a MDS with deletion of chromosome 5q (del(5q)). In certain embodiments of the various methods provided herein, the cancer is acute myeloid leukemia (AML). In some embodiments of the various methods provided herein, the cancer is mantle cell lymphoma (MCL). In other embodiments of the various methods provided herein, the cancer is follicular lymphoma (FL). In some embodiments of the various methods provided herein, the cancer is chronic lymphocytic leukemia (CLL). In other embodiments of the various methods provided herein, the cancer is non-Hodgkin's lymphoma (NHL). In certain embodiments of the various methods provided herein, the cancer is hairy cell leukemia. In some embodiments of the various methods provided herein, the cancer is chronic myelogenous leukemia (CML). In certain embodiments of the various methods provided herein, the cancer is AIDS-related Kaposi sarcoma. In other embodiments of the various methods provided herein, the cancer is a malignant melanoma.

In another aspect, provided herein is a method of monitoring IFN therapy treatment response to compound treatment in a patient having an IFN-associated disorder, the method comprising
a. obtaining a first sample from the patient,
b. measuring the expression of a biomarker in the first sample,
c. administering one or more compounds to the patient,
d. thereafter, obtaining a second sample from the patient,
e. measuring biomarker expression in the second sample, and
f. comparing the levels of biomarker expression in the first and second samples.

In some embodiments, an increased level of biomarker expression in the second sample after compound administration indicates the likelihood of an effective IFN therapy treatment response. In other embodiments, a decreased level of biomarker expression in the second sample after compound administration indicates the likelihood of an effective IFN therapy treatment response. In certain embodiments, provided herein is a method of treating an IFN-associated disorder, comprising the method of monitoring IFN therapy treatment response to compound treatment in a patient having an IFN-associated disorder, wherein the method further comprises (g) administering to the subject a therapeutically effective amount of the compound when there is a likelihood of an effective IFN therapy treatment response.

In some embodiments, an increased level of biomarker expression in the second sample after compound administration indicates a decreased likelihood of an effective IFN therapy treatment response. In another embodiment, a decreased level of biomarker expression in the second sample after compound administration indicates a decreased likelihood of an effective IFN therapy treatment response. In certain embodiments, provided herein is a method of treating an IFN-associated disorder, comprising the method of monitoring IFN therapy treatment response to compound treatment in a patient having an IFN-associated disorder, wherein the method further comprises (g) administering to the subject a therapeutically effective amount of a therapy other than the compound when there is not a likelihood of an effective IFN therapy treatment response.

In one embodiment, the IFN therapy is to treat conyloma accuminata, chronic hepatitis B, chronic hepatitis C, relapsing-remitting multiple sclerosis, or chronic granulomatous disease.

In some embodiments of the various methods provided herein, the first sample is a biological sample. In certain embodiments, the first sample is obtained from a tumor biopsy, node biopsy, or a biopsy from bone marrow, spleen, liver, brain or breast. In some embodiments of the various methods provided herein, the second sample is a biological sample. In certain embodiments, the second sample is obtained from a tumor biopsy, node biopsy, or a biopsy from bone marrow, spleen, liver, brain or breast. In some embodiments, the second sample is from the same source as the first sample.

In some embodiments, the measuring step(s) comprises: (i) contacting proteins within the sample with a first antibody that immunospecifically binds to the biomarker; (ii) contacting the proteins bound to the first antibody with a second antibody with a detectable label, wherein the second antibody immunospecifically binds to the biomarker, and wherein the second antibody immunospecifically binds to a different epitope on the biomarker than the first antibody; (iii) detecting the presence of second antibody bound to the biomarker; and (iv) determining the amount of the biomarker based on the amount of detectable label in the second antibody. In certain embodiments, the measuring step(s) comprises using immunohistochemistry to determine the level of the biomarker. In some embodiments, the measuring step(s) comprises: (i) contacting the RNA within the sample with a primer comprising a sequence specifically binding to the RNA to generate a first DNA molecule having a sequence complementary to the RNA; (ii) amplifying the DNA corresponding to a segment of a gene encoding the biomarker; and (iii) determining the RNA level of the biomarker based on the amount of the amplified DNA.

In some embodiments, the measuring step(s) is measuring (or otherwise determining) of the expression (such as the level (e.g., protein or RNA level)) of the biomarker in a sample from the patient (e.g., a first sample, a second sample, or both a first and second sample). In other embodiments, the measuring step(s) is measuring (or otherwise determining) of the expression (such as the level (e.g., protein or RNA level)) of the biomarker in a reference sample.

In certain embodiments, the IFN-associated disorder is conyloma accuminata. In some embodiments, the IFN-associated disorder is chronic hepatitis B. In other embodiments, the IFN-associated disorder is chronic hepatitis C. In certain embodiments, the IFN-associated disorder is relapsing-remitting multiple sclerosis. In some embodiments, the IFN-associated disorder is chronic granulomatous disease. In some embodiments, the IFN-associated disorder is a cancer.

In some embodiments of the various methods provided herein, the level (e.g., expression) of a biomarker is determined by measuring nucleic acids, e.g., RNA or DNA. In some embodiments, the level (e.g., expression) of a biomarker is determined by measuring protein. In certain embodiments, the nucleic acid (e.g., mRNA of cDNA) level (e.g., expression) of only one biomarker is monitored. In certain embodiments, the nucleic acid (e.g., mRNA or cDNA) levels (e.g., expression) of two or more biomarkers are monitored simultaneously or sequentially. In one embodiment, the RNA (e.g., mRNA) or protein is purified from the sample and the level of the biomarker is measured by gene or protein expression analysis. In certain embodiments, the level (e.g., expression) of the biomarker is measured by quantitative real-time PCR (QRT-PCR), microarray, flow cytometry or immunofluorescence. In other embodiments, the level (e.g., expression) of the biomarker is measured by enzyme-linked immunosorbent assay-based methodologies (ELISA) or other similar methods known in the art. In certain embodiments of the various methods provided herein, the level (e.g., expression) of the biomarker is measured by determining the mRNA level of the biomarker. In other embodiments of the various methods provided herein, the level (e.g., expression) of the biomarker is measured by determining the cDNA level of the biomarker. In yet other embodiments of the various methods provided herein, the level (e.g., expression) of the biomarker is measured by determining the protein level of the biomarker. In some embodiments, the biomarker is measured by a method comprising sequencing of the nucleic acid (e.g., mRNA). In some embodiments, the sequencing comprises next-generation sequencing. In certain embodiments, the protein level of only one biomarker is monitored. In certain embodiments, the protein levels of two or more biomarkers are monitored simultaneously or sequentially. Multiple biomarkers may be monitored simultaneously or sequentially.

In some embodiments of the various methods provided herein the sample (e.g., from the subject or a reference) is a biological sample. In some embodiments, the sample is obtained from a tumor biopsy, node biopsy, or a biopsy from bone marrow, spleen, liver, brain or breast. In some embodiments, the cells are cancer cells, and the cancer cells are obtained from a tumor biopsy, node biopsy, or a biopsy from bone marrow, spleen, liver, brain or breast.

In one embodiment of the various methods provided herein the reference is prepared by using a second cell (or other biological sample) not contacted with the compound. In another embodiment of the various methods provided herein, the reference is prepared by using a second sample obtained from the subject prior to administration of the compound to the subject; wherein the second sample is from the same source as the first sample. In other embodiments, the reference is prepared by using a second sample obtained from a healthy subject not having the disease or disorder; wherein the second sample is from the same source as the first sample.

In other embodiments of the various methods provided herein, the method comprises using immunohistochemistry to determine the level of the biomarker. In some embodiments, the method comprises using dual staining immunohistochemistry to determine the level of the biomarker.

In specific embodiments of the various methods provided herein, the biomarker is a cereblon (CRBN)-associated protein (CAP). In one embodiment, the compound decreases the level (e.g., protein or RNA level) of the CAP as compared to the reference. In another embodiment, the compound increases the level (e.g., protein or RNA level) of the CAP as compared to the reference.

In some embodiments, the biomarker comprises one CAP. In certain embodiments, the biomarker comprises two CAPs. In other embodiments, the biomarker comprises three CAPs. In certain embodiments, the biomarker comprises four CAPs. In some embodiments, the biomarker comprises five CAPs. In other embodiments, the biomarker comprises six CAPs. In another embodiment, the biomarker comprises seven CAPs. In certain embodiments, the biomarker comprises eights CAPs. In other embodiments, the biomarker comprises nine CAPs. In another embodiment, the biomarker comprises ten or more CAPs.

In certain embodiments, CAP is ABCE1, ACLY, ACTB, ALDOA, ARID1A, C7ORF42, COPS6, CPSF6, CSNK1A1, CSNK2A1, CTPS, CRBN, DDB1, DDIT4, DDX17, DDX21, DDX58, DDX58, DDX60, DDX60L, DHX9, DNAJC1, DUT, EEF1A1, EEF1AL3, EEF1G, EIF2S1, EIF2S2, EIF3J, EIF4A1, EWSR1, FASN, FBXO21, FERMT3, FUBP1, G3BP1, G3BP2, GBE1, GBP1, GNAS, GNB2L1, GNB3, H2AFJ, H2AFX, H2AFZ, HIST1H1A, HIST1H1B, HIST1H1C, HIST1H1D, HIST1H1E, HIST1H2AA, HNRNPA2B1, HNRNPC, HNRNPH2, HNRNPR, HSPA1A, HSPA1B, HSPA8, HSPA9, IFI16, IFI27, IFI27L2, IFI35, IFI44, IFI44L, IFI6, IFIH1, IFIT1, IFIT2, IFIT3, IFIT5, IFITM2, IFITM3, IFN, IFNA16, IFNA5, IFNG, IFNGR1, IGF2BP2, IKKE, IKZF1 (Ikaros), IKZF3 (Aiolos), ILF3, IPO5, IRF1, IRF2, IRF3, IRF4, IRF7, IRF8, IRF9, ISG15, ISG20, KCNAB2, MACF1, MCM2, MCM7, MX1, MX2, MYH10, NACA, NAP1L2, NCL, NEDD8, NUP88, OAS1, OAS2, OAS3, OASL, PABPC1, PABPC4, PCM1, PDXK, PPAT, PRKDC, PTPRC, PTRH2, RPL10A, RPL11, RPL12, RPL13A, RPL14, RPL15, RPL18A, RPL19, RPL21, RPL3, RPL30, RPL4, RPL7, RPL7A, RPL9, RPLP1, RPLP2, RPS13, RPS16, RPS19, RPS2, RPS6, SEC23B, SEC24A, SEC24C, SMC4, SND1, a STAT (e.g., STAT1, STAT2 or STAT3), a STAT-PO$_4$, STAT3, SYNCRIP, TBK1, TBK1-PO$_4$, TBL1XR1, TLR1, TLR3, TLR4, TLR7, TLR8, TPD52, TUBA1A, TUBA1B, TUBAIC, UAP1, UBA52, UBAP2L, UBB, UBE2O, UBE2Q1, USP15, VAPA, XAF1, XRCC6, YWHAE, ZFP91, ZNF198, or any combination thereof.

In some embodiments, the CAP is ARHGAP18, CASS4, CCNA2, CORO1B, CSNK1A1, CYTL1, DAB2, HSPB1, IKZF1, ITM2C, PPFIBP1, SERPINH1, YEATS2 or ZFP91, or any combination thereof.

In some embodiments, the CAP is ARHGAP18, CALM1, CASS4, CCNA2, CORO1B, CSNK1A1, DAB2, HSPB1, IKZF1, ITM2C, PPFIBP1, SERPINH1, or ZFP91, or any combination thereof.

In some embodiments, the biomarker is AHNAK, ALOX5, AMPD3, ANXA4, ANXA6, ATP2B4, BMF, BST2, C10orf76, C19orf66, CD36, CLN3, CNN3, CORO1B, CPNE2, CSRP2, CTNND1, CTSH, DAPK2, DDX58, DHX58, DLG2, DTX3L, EIF2AK2, EPB41L1, ETV6, EXTL2, F13A1, FAM65B, FCGR2B, FES, FMNL3, GBP1, GMFG, GMPR, HIP1, HLA-B, HLA-DMA, HPSE, ID3, IFI35, IFIH1, IFIT1, IFIT3, IFIT5, IFITM2, IL4I1, IRF7, IRF9, ISG15, ISG20, ITGB7, JAK3, LAP3, LGALS1, LGALS3BP, LIMD1, MAN2A2, MARCKS, MFI2, MGARP, MOV10, MPP7, MUC1, MX1, MX2, MYO1G, NCF2, NME3, NMI, NT5C3A, OAS1, OAS2, OAS3, PARP14, PARP9, PBXIP1, PLD4, PLEKHO1, PLSCR1, PLXNB2, POMP, PPFIBP1, PTMS, QPRT, RAB13, RCN1, RGCC, RNF213, S100A13, SAMD9L, SAMHD1, SERPINH1, SLFN11, SLFN13, SLFN5, SP110, SP140, SPN, SPR, STAP1, STAT1, STAT2, TAP1, TAX1BP3, THEMIS2, THTPA, TNFAIP8L2, TNFSF8, TP53I3, TREX1, TRIM22, TTC39C, TXNIP, UBA7, UBE2L6, USP41, VCL, VNN2, ZBTB38, ARHGAP19, ASNS, ASPM, B4GALT3, BANK1, BCDIN3D, BLZF1, CA2, CA8, CAMSAP3, CCDC69, CCNB1, CDC7, CDCA3, CENPF, CSNK1A1, DHPS, DLGAP5, DOK3, ECT2, EFCAB4B, EHMT1, EHMT2, EPCAM, ESRP1, FAM195A, FBRSL1, FHOD1, FIGNL1, GPT2, GRAMD1A, GRAMD1B, GRPEL2, HJURP, HMCES, HMMR, HOXC4, ICAM2, IKZF1, IKZF3, IRS2, KIF18B, KIF22, KIF2C, LIPG, LPXN, MINA, MIS18BP1, NEIL1, NFKBID, NPIPB5, OMA1, ORC6, PARVB, PBK, PDE6D, PKMYT1, PLK1, PODXL, PODXL2, POLE2, PRDM15, PRNP, PTAFR, PTTG1, PYROXD1, RASA4B, RASSF6, RGS1, RGS2, SEC14L1, SGOL1, SGOL2, SLCO3A1, SLCO4A1, TACC3, TIMM8B, TOP2A, TPX2, TRIB3, WIZ, WSB1, WWC1, ZFP91, ZMYM2, ZNF385B, ZNF581 or ZNF644, or any combination thereof.

In one embodiment, the biomarker is ADAM19, AIF1, ALDH1A1, ALDH2, ALOX5, AMPD3, APOBEC3G, APOE, APOH, ARHGAP10, ATP2B4, BST2, C4A, C4BPA, C4orf33, biomarkerN2, CASP4, CCR7, CD1D, CD63, CD86, CDR2, CORO1B, CPNE2, CYTH4, DAPK2, DDX58, DDX60, DDX60L, DHX58, DNASE1L3, DTX3L, EIF2AK2, ELOVL7, EPB41L1, F13A1, FAM129A, FBLN1, FCRLA, FERMT3, FGD6, FLNA, GALNT7, GBP1, GBP2, GBP4, GIPC1, GPD1, GPX3, HABP2, HBA1, HBD, HERC3, HERC6, HGF, HIGD1A, HMOX1, HSPA8, HSPB1, IFI35, IFI44, IFI44L, IFIH1, IFIT1, IFIT2, IFIT3, IFIT5, IFITM3, IL3RA, IRF7, IRF9, ISG15, ISG20, ITGA1, ITGB3, ITGB7, ITPKB, KIAA1618, L1TD1, LAP3, LDB3, LGALS1, LGALS3BP, LGALS9, LGALS9B, LMNA, LPIN1, MAP3K11, MCAM, MCM8, MGLL, MPP7, MUC1, MX1, MX2, MYL4, NCF4, NMI, NQO1, NUB, OAS1, OAS2, OAS3, OASL, ORMDL2, OTOF, P2RY6, PAPSS2, PARP14, PARP9, PBXIP1, PHF11, PHF15, PLG, PLSCR1, PREX1, PREX2, PRIC285, PRKCI, PSAP, PTMS, RAB13, RASSF4, RCN1, RGL1, RGS13, RNF213, RTN2, RTP4, RUNX3, S100A13, SAMD9, SAMD9L, SAMHD1, SERPINA7, SERPINF2, SERPINH1, SIPA1L3, SLAMF1, SLC1A3, SLC23A2, SLC27A3, SLFN5, SOD2, SPN, SPR, SRC, STAT1, STAT2, SYNJ2BP, TAX1BP3, TBC1D13, TDRD7, TGOLN2, TLR7, TMEM87A, TMOD2, TNFAIP2, TNFAIP8L2, TRANK1, TRIM14, TRPC4, TRPM4, TSPAN14, TSPAN3, UBA7, UBE2L6, USP18, USP41, VNN2, VTN, XAF1, ZCCHC2, ZER1, ZNF385A, ZNF480, ZNF770, 3-Sep, ADIPOR2, AHR, ALCAM, ALDOC, ALKBH6, ALPL, AP1S3, APBBIIP, ARHGAP24, ARHGAP27, ARNT, BCL11A, BCL2A1, BCL2L1, BCLAF1, BNIP3L, C19orf22, C9orf40, CANX, CD22, CD44, CD5, CDC42SE2, CENPJ, CEP97, CFLAR, CLDN23, CLEC17A, COX17, CROCC, CRYM, CSNK1A1, DBN1, DENND1C, DNM2, DOK3, DTWD1, EHD1, EIF4H, ENO2, EPHA4, EPHA7, EPHB 1, ERCC6, ETS1, EVI2B, EVL, FAR1, FCRL2, FCRL3, FCRL5, GABPB1, GAMT, GAPT, GAS7, GATM, GLRX, GNG2, GRPEL2, GYPC, GZMB, HK2, HLTF, HTRA3, IFNAR2, IKZF1, IKZF3, IL16, INF2, IQSEC1, IRF4, ISYNA1, ITGAL, ITGB2, KDM5B, KHK, L1CAM, LAT2, LBH, LNX1, LRRC25, LUC7L, LYSMD2, MEF2B, MEF2D, MICAL3, MYH11, NARF, NBR1, NEDD9, NEFL, OMA1, PARVB, PDK1, PFKFB4, PGM1, PIR, PLEKHG1, PMS2CL, PODXL2, POU2AF1, PPP1R2, PTPR, PTPRE, PTPRF, PTPRO, PTTG1, PVRL1, RAB33A, RANBP3, RASGRP3, RASSF6, RBBP5, RHOF, RPS29, RPS4Y2, SAMD1, SC5DL, SEC14L1, SEMA7A, SERPINB9, SETD8, SH2D3C, SIT1, SLAMF7, SLC16A3, SLC19A2, SNAP23, SNX11, SP140, SPIB, SPTAN1, SPTB, SSBIP1, STK17B, SYNCRIP, TCP11L1, TGM2, TJAP1, TNFAIP3, TNFRSF13B, TNFRSF1B, TOM1, TOR1AIP1, TP53111, TSTD1, TUBB2B, UBE2J1, VAT1, VIM, WIPF1, WIZ, ZBTB32, ZFP91, ZMYM2, ZNF316, ZNF644, ZNF805, or any combination thereof.

In some embodiments, the biomarker is ACSS1, ACY3, ADAM19, ADCY7, AIF1, ALDH2, AMPD3, ANK3, ANXA4, ANXA6, ANXA6, APOBEC3G, APOBR, B2M, BCL9L, BST2, C19orf66, CASP10, CCDC28B, CD40, CD59, CD83, CGN, CLSTN1, CMPK2, COL23A1, CORO1B, CORO1C, CTNND1, CTSH, CTTNBP2NL, CYTH1, CYTH4, DDX58, DDX60, DTX3L, EIF2AK2, ETHE1, F11R, FADS2, FAM76A, FDFT1, FGD4, FLNA, FLNB, FRRS1, FSCN1, GCH1, GMFG, GNB4, GNG2, H1F0, HECTD1, HELZ2, HGF, HGSNAT, HLA-A, HLA-B, HLA-G, HSPB1, HYI, IFI35, IFIT1, IFIT3, IFIT5, L4I1, IPCEF1, IRF9, ISG15, ISG20, JADE2, KIAA0101, LAT2, LGALS1, LGALS3BP, LGALS9, LGALS9B, LMCD1, LMNA, LY75, LYSMD2, MAGED4, MAPK10, MBD1, MEA1, MT2A, MX1, MX2, MYBPC2, NCOA7, NCOA7, NEXN, NT5C3A, OAS1, OAS2, OAS3, OSBPL10, PARP10, PARP14, PARP9, PCDHGC3, PLG, PLSCR1, PRCP, PTTGIIP, PYGO2, QPCT, S100A13, SAMHD1, SERPINH1, SIRPB1, SLC23A2, SLC25A33, SLC7A7, SLFN5, SOWAHD, SP110, SP140, SPR, STAT1, STAT2, STK3, SYBU, TAP1, TAP2, TDRD7, THEMIS2, TNFAIP8L2, TNFSF9, TRIM14, TRIM21, TRIM22, TYMP, UBE2L6, USP40, VPREB1, ADIPOR2, ATF5, BACH2, BANK1, BCDIN3D, CD320, CSNK1A1, DEPTOR, ETS1, GLIPRIL1, GNG7, GPT2, HSBP1, ICAM2, IKZF1, IKZF3, KRT1, KRT14, KRT2, KRT6B, KRT9, MED12L, NEIL1, NUGGC, OMA1, PDE6D, PDZRN3, PODXL, SYNGR3, SYTL1, WIZ, ZFP91 or ZMYM2, or any combination thereof.

In other embodiments, the biomarker is ADIPOR2, ATF5, BACH2, BANK1, BCDIN3D, CD320, CSNK1A1, DEPTOR, ETS1, GLIPRIL1, GNG7, GPT2, HSBP1, ICAM2, IKZF1, IKZF3, KRT1, KRT14, KRT2, KRT6B, KRT9, MED12L, NEIL1, NUGGC, OMA1, PDE6D, PDZRN3, PODXL, SYNGR3, SYTL1, WIZ, ZFP91 or ZMYM2, or any combination thereof.

In one embodiment, the CAP is ABCE1. In another embodiment, the CAP is ACLY.

In one embodiment, the CAP is ACTB. In another embodiment, the CAP is ALDOA. In some embodiments, the CAP is ARID1A. In one embodiment, the CAP is C7ORF42. In another embodiment, the CAP is COPS6. In some embodiments, the CAP is CPSF6. In one embodiment, the CAP is CSNK1A1. In another embodiment, the CAP is CSNK2A1. In some embodiments, the CAP is CTPS. In one embodiment, the CAP is CRBN. In another embodiment, the CAP is DDB1. In some embodiments, the CAP is DDIT4. In one embodiment, the CAP is DDX17. In another embodiment, the CAP is DDX21. In some embodiments, the CAP is DDX58. In one embodiment, the CAP is DDX58. In another embodiment, the CAP is DDX60. In some embodiments, the CAP is DDX60L. In one embodiment, the CAP is DHX9. In another embodiment, the CAP is DNAJC1. In some embodiments, the CAP is DUT. In one embodiment, the CAP is EEF1A1. In another embodiment, the CAP is EEF1AL3. In some embodiments, the CAP is EEF1G. In one embodiment, the CAP is EIF2S1. In another embodiment, the CAP is EIF2S2. In some embodiments, the CAP is EIF3J. In one embodiment, the CAP is EIF4A1. In another embodiment, the CAP is EWSR1. In some embodiments, the CAP is FASN. In one embodiment, the CAP is FBXO21. In another embodiment, the CAP is FERMT3. In some embodiments, the CAP is FUBP1. In one embodiment, the CAP is G3BP1. In another embodiment, the CAP is G3BP2. In some embodiments, the CAP is GBE1. In one embodiment, the CAP is GBP1. In another embodiment, the CAP is GNAS. In some embodiments, the CAP is GNB2L1. In one embodiment, the CAP is GNB3. In another embodiment, the CAP is H2AFJ. In some embodiments, the CAP is H2AFX. In some embodiments, the CAP is H2AFZ. In another embodiment, the CAP is HIST1H1A. In some embodiments, the CAP is HIST1H1B. In one embodiment, the CAP is HIST1H1C. In another embodiment, the CAP is HIST1H1D. In some embodiments, the CAP is HIST1H1E. In one embodiment, the CAP is HIST1H2AA. In another embodiment, the CAP is HNRNPA2B1. In some embodiments, the CAP is HNRNPC. In one embodiment, the CAP is HNRNPH2. In another embodiment, the CAP is HNRNPR. In some embodiments, the CAP is HSPA1A. In one embodiment, the CAP is HSPA1B. In another embodiment, the CAP is HSPA8. In some embodiments, the CAP is HSPA9. In one embodiment, the CAP is IFI16. In another embodiment, the CAP is IFI27. In some embodiments, the CAP is IFI27L2. In one embodiment, the CAP is IFI35. In another embodiment, the CAP is IFI44. In some embodiments, the CAP is IFI44L. In one embodiment, the CAP is IFI6. In another embodiment, the CAP is IFIH1. In some embodiments, the CAP is IFIT1. In one embodiment, the CAP is IFIT2. In another embodiment, the CAP is IFIT3. In some embodiments, the CAP is IFIT5. In one embodiment, the CAP is IFITM2. In another embodiment, the CAP is IFITM3. In some embodiments, the CAP is IFN. In one embodiment, the CAP is IFNA16. In another embodiment, the CAP is IFNA5. In some embodiments, the CAP is IFNG. In one embodiment, the CAP is IFNGR1. In another embodiment, the CAP is IGF2BP2. In some embodiments, the CAP is IKKE. In one embodiment, the CAP is IKZF1 (Ikaros). In another embodiment, the CAP is IKZF3 (Aiolos). In some embodiments, the CAP is ILF3. In one embodiment, the CAP is IPO5. In another embodiment, the CAP is IRF1. In some embodiments, the CAP is IRF2. In one embodiment, the CAP is IRF3. In another embodiment, the CAP is IRF4. In some embodiments, the CAP is IRF7. In one embodiment, the CAP is IRF8. In another embodiment, the CAP is IRF9. In some embodiments, the CAP is ISG15. In one embodiment, the CAP is ISG20. In another embodiment, the CAP is KCNAB2. In some embodiments, the CAP is MACF1. In one embodiment, the CAP is MCM2. In another embodiment, the CAP is MCM7. In some embodiments, the CAP is MX1. In one embodiment, the CAP is MX2. In another embodiment, the CAP is MYH10. In some embodiments, the CAP is NACA. In one embodiment, the CAP is NAP1L2. In another embodiment, the CAP is NCL. In some embodiments, the CAP is NEDD8. In one embodiment, the CAP is NUP88. In another embodiment, the CAP is OAS1. In some embodiments, the CAP is OAS2. In one embodiment, the CAP is OAS3. In another embodiment, the CAP is OASL. In some embodiments, the CAP is PABPC1. In one embodiment, the CAP is PABPC4. In another embodiment, the CAP is PCM1. In some embodiments, the CAP is PDXK. In one embodiment, the CAP is PPAT. In another embodiment, the CAP is PRKDC. In some embodiments, the CAP is PTPRC. In one embodiment, the CAP is PTRH2. In another embodiment, the CAP is RPL10A. In some embodiments, the CAP is RPL11. In one embodiment, the CAP is RPL12. In another embodiment, the CAP is RPL13A. In some embodiments, the CAP is RPL14. In one embodiment, the CAP is RPL15. In another embodiment, the CAP is RPL18A. In some embodiments, the CAP is RPL19. In one embodiment, the CAP is RPL21. In another embodiment, the CAP is RPL3. In some embodiments, the CAP is RPL30. In one embodiment, the CAP is RPL4. In another embodiment, the CAP is RPL7. In some embodiments, the CAP is RPL7A. In one embodiment, the CAP is RPL9. In another embodiment, the CAP is RPLP1. In some embodiments, the CAP is RPLP2. In one embodiment, the CAP is RPS13. In another embodiment, the CAP is RPS16. In some embodiments, the CAP is RPS19. In one embodiment, the CAP is RPS2. In another embodiment, the CAP is RPS6. In some embodiments, the CAP is SEC23B. In one embodiment, the CAP is SEC24A. In another embodiment, the CAP is SEC24C. In some embodiments, the CAP is SMC4. In one embodiment, the CAP is SND1. In another embodiment, the CAP is a STAT. In some embodiments, the CAP is a STAT-$PO_4$. In one embodiment, the CAP is STAT1. In some embodiments, the CAP is a STAT1-$PO_4$. In one embodiment, the CAP is STAT2. In one embodiment, the CAP is STAT3. In some embodiments, the CAP is a STAT3-$PO_4$. In another embodiment, the CAP is SYNCRIP. In some embodiments, the CAP is TBK1. In one embodiment, the CAP is TBK1-$PO_4$. In another embodiment, the CAP is TBL1XR1. In some embodiments, the CAP is TLR1. In one embodiment, the CAP is TLR3. In another embodiment, the CAP is TLR4. In some embodiments, the CAP is TLR7. In one embodiment, the CAP is TLR8. In another embodiment, the CAP is TPD52. In some embodiments, the CAP is TUBA1A. In one embodiment, the CAP is TUBA1B. In another embodiment, the CAP is TUBA1C. In some embodiments, the CAP is UAP1. In one embodiment, the CAP is UBA52. In another embodiment, the CAP is UBAP2L, UBB. In some embodiments, the CAP is UBE2O. In one embodiment, the CAP is UBE2Q1. In another embodiment, the CAP is USP15. In some embodiments, the CAP is VAPA. In one embodiment, the CAP is XAF1. In another embodiment, the CAP is XRCC6. In some embodiments, the CAP is YWHAE. In one embodiment, the CAP is ZFP91. In another embodiment the CAP is ZNF198.

In one embodiment ARHGAP18. In one embodiment, the CAP is CASS4. In one embodiment, the CAP is CCNA2. In one embodiment, the CAP is CORO1B. In one embodiment, the CAP is CYTL1. In one embodiment, the CAP is DAB2. In one embodiment, the CAP is HSPB1. In one embodiment, the CAP is ITM2C. In one embodiment, the CAP is PPFIBP1. In one embodiment, the CAP is SERPINH1.

In one embodiment, the CAP is YEATS2. In one embodiment, the CAP is CALM1. In one embodiment, the CAP is CASS4. In one embodiment, the CAP is CCNA2. In one embodiment, the CAP is DAB2. In one embodiment, the CAP is HSPB1. In one embodiment, the CAP is ITM2C. In one embodiment, the CAP is PPFIBP1. In one embodiment, the CAP is SERPINH1.

In one embodiment, the biomarker is the biomarker is AHNAK. In one embodiment, the biomarker is ALOX5. In certain embodiments, the biomarker is AMPD3. In one embodiment, the biomarker is ANXA4. In some embodiments, the biomarker is ANXA6. In one embodiment, the biomarker is ATP2B4. In certain embodiments, the biomarker is BMF. In one embodiment, the biomarker is BST2. In some embodiments, the biomarker is C10orf76. In one embodiment, the biomarker is C19orf66. In certain embodiments, the biomarker is CD36. In one embodiment, the biomarker is CLN3. In some embodiments, the biomarker is CNN3. In one embodiment, the biomarker is CORO1B. In certain embodiments, the biomarker is CPNE2. In one embodiment, the biomarker is CSRP2. In some embodiments, the biomarker is CTNND1. In one embodiment, the biomarker is CTSH. In certain embodiments, the biomarker is DAPK2. In one embodiment, the biomarker is DDX58. In some embodiments, the biomarker is DHX58. In one embodiment, the biomarker is DLG2. In certain embodiments, the biomarker is DTX3L. In one embodiment, the biomarker is EIF2AK2. In some embodiments, the biomarker is EPB41L1. In one embodiment, the biomarker is ETV6. In certain embodiments, the biomarker is EXTL2. In one embodiment, the biomarker is F13A1. In some embodiments, the biomarker is FAM65B. In one embodiment, the biomarker is FCGR2B. In certain embodiments, the biomarker is FES. In one embodiment, the biomarker is FMNL3. In some embodiments, the biomarker is GBP1. In one embodiment, the biomarker is GMFG. In certain embodiments, the biomarker is GMPR. In one embodiment, the biomarker is HIP1. In some embodiments, the biomarker is HLA-B. In one embodiment, the biomarker is HLA-DMA. In certain embodiments, the biomarker is HPSE. In one embodiment, the biomarker is ID3. In some embodiments, the biomarker is IFI35. In one embodiment, the biomarker is IFIH1. In certain embodiments, the biomarker is IFIT1. In one embodiment, the biomarker is IFIT3. In some embodiments, the biomarker is IFIT5. In one embodiment, the biomarker is IFITM2. In certain embodiments, the biomarker is IL4I1. In one embodiment, the biomarker is IRF7. In some embodiments, the biomarker is IRF9. In one embodiment, the biomarker is ISG15. In certain embodiments, the biomarker is ISG20. In one embodiment, the biomarker is ITGB7. In some embodiments, the biomarker is JAK3. In one embodiment, the biomarker is LAP3. In certain embodiments, the biomarker is LGALS1. In one embodiment, the biomarker is LGALS3BP. In some embodiments, the biomarker is LIMD1. In one embodiment, the biomarker is MAN2A2. In certain embodiments, the biomarker is MARCKS. In one embodiment, the biomarker is MFI2. In some embodiments, the biomarker is MGARP. In one embodiment, the biomarker is MOV10. In certain embodiments, the biomarker is MPP7. In one embodiment, the biomarker is MUC1. In some embodiments, the biomarker is MX1. In one embodiment, the biomarker is MX2. In certain embodiments, the biomarker is MYO1G. In one embodiment, the biomarker is NCF2. In some embodiments, the biomarker is NME3. In one embodiment, the biomarker is NMI. In certain embodiments, the biomarker is NT5C3A. In one embodiment, the biomarker is OAS1. In some embodiments, the biomarker is OAS2. In one embodiment, the biomarker is OAS3. In some embodiments, the biomarker is PARP14. In one embodiment, the biomarker is PARP9. In certain embodiments, the biomarker is PBXIP1. In one embodiment, the biomarker is PLD4. In some embodiments, the biomarker is PLEKHO1. In one embodiment, the biomarker is PLSCR1. In certain embodiments, the biomarker is PLXNB2. In one embodiment, the biomarker is POMP. In some embodiments, the biomarker is PPFIBP1. In some embodiments, the biomarker is PTMS. In certain embodiments, the biomarker is QPRT. In one embodiment, the biomarker is RAB13. In certain embodiments, the biomarker is RCN1. In one embodiment, the biomarker is RGCC. In an embodiment, the biomarker is RNF213. In some embodiments, the biomarker is S100A13. In one embodiment, the biomarker is SAMD9L. In certain embodiments, the biomarker is SAMHD1. In one embodiment, the biomarker is SERPINH1. In some embodiments, the biomarker is SLFN11. In an embodiment, the biomarker is SLFN13. In certain embodiments, the biomarker is SLFN5. In one embodiment, the biomarker is SP110. In some embodiments, the biomarker is SP140. In one embodiment, the biomarker is SPN. In certain embodiments, the biomarker is SPR. In an embodiment, the biomarker is STAP1. In some embodiments, the biomarker is STAT1. In one embodiment, the biomarker is STAT2. In certain embodiments, the biomarker is TAP1. In one embodiment, the biomarker is TAX1BP3. In some embodiments, the biomarker is THEMIS2. In an embodiment, the biomarker is THTPA. In certain embodiments, the biomarker is TNFAIP8L2. In one embodiment, the biomarker is TNFSF8. In some embodiments, the biomarker is TP53I3. In one embodiment, the biomarker is TREX1. In an embodiment, the biomarker is TRIM22. In certain embodiments, the biomarker is TTC39C. In one embodiment, the biomarker is TXNIP. In some embodiments, the biomarker is UBA7. In one embodiment, the biomarker is UBE2L6. In certain embodiments, the biomarker is USP41. In an embodiment, the biomarker is VCL. In some embodiments, the biomarker is VNN2. In one embodiment, the biomarker is ZBTB38. In certain embodiments, the biomarker is ARHGAP19. In one embodiment, the biomarker is ASNS. In some embodiments, the biomarker is ASPM. In an embodiment, the biomarker is B4GALT3. In certain embodiments, the biomarker is BANK1. In one embodiment, the biomarker is BCDIN3D. In some embodiments, the biomarker is BLZF1. In one embodiment, the biomarker is CA2. In certain embodiments, the biomarker is CA8. In an embodiment, the biomarker is CAMSAP3. In some embodiments, the biomarker is CCDC69. In one embodiment, the biomarker is CCNB1. In certain embodiments, the biomarker is CDC7. In an embodiment, the biomarker is CDCA3. In some embodiments, the biomarker is CENPF. In one embodiment, the biomarker is CSNK1A1. In certain embodiments, the biomarker is DHPS. In one embodiment, the biomarker is DLGAP5. In some embodiments, the biomarker is DOK3. In an embodiment, the biomarker is ECT2. In certain embodiments, the biomarker is EFCAB4B. In one embodiment, the biomarker is EHMT1. In some embodiments, the biomarker is EHMT2. In an embodiment, the biomarker is EPCAM. In certain embodiments, the biomarker is ESRP1. In one embodiment, the biomarker is FAM195A. In some embodiments, the biomarker is FBRSL1. In an embodiment, the biomarker is FHOD1. In certain embodiments, the biomarker is FIGNL1. In one embodiment, the biomarker is GPT2. In some embodiments, the biomarker is GRAMD1A. In an embodiment, the biomarker is GRAMD1B. In certain embodiments, the biomarker is GRPEL2. In one embodiment, the biomarker is HJURP. In an embodiment, the biomarker is HMCES. In some embodiments, the biomarker is HMMR. In one embodiment, the biomarker is HOXC4. In certain embodiments, the biomarker is ICAM2. In an embodiment, the biomarker is IKZF1. In some embodiments, the biomarker is IKZF3. In one embodiment, the biomarker is IRS2. In certain embodiments, the biomarker is KIF18B. In some embodiments, the biomarker is KIF22. In an embodiment, the biomarker is KIF2C. In one embodiment, the biomarker is LIPG. In an embodiment, the biomarker is LPXN. In one embodiment, the biomarker is MINA. In an embodiment, the biomarker is MIS18BP1. In one embodiment, the biomarker is NEIL1. In an embodiment, the biomarker is NFKBID. In one embodiment, the biomarker is NPIPB5. In an embodiment, the biomarker is OMA1. In one embodiment, the biomarker is ORC6. In an embodiment, the biomarker is PARVB. In one embodiment, the biomarker is PBK. In certain embodiments, the biomarker is PDE6D. In an embodiment, the biomarker is PKMYT1. In one embodiment, the biomarker is PLK1. In some embodiments, the biomarker is PODXL. In an embodiment, the biomarker is PODXL2. In certain embodiments, the biomarker is POLE2. In one embodiment, the biomarker is PRDM15. In some embodiments, the biomarker is PRNP. In an embodiment, the biomarker is PTAFR. In certain embodiments, the biomarker is PTTG1. In one embodiment, the biomarker is PYROXD1. In some embodiments, the biomarker is RASA4B. In an embodiment, the biomarker is RASSF6. In certain embodiments, the biomarker is RGS1. In one embodiment, the biomarker is RGS2. In some embodiments, the biomarker is SEC14L1. In an embodiment, the biomarker is SGOL1. In certain embodiments, the biomarker is SGOL2. In one embodiment, the biomarker is SLCO3A1. In some embodiments, the biomarker is SLCO4A1. In certain embodiments, the biomarker is TACC3. In an embodiment, the biomarker is TIMM8B. In some embodiments, the biomarker is TOP2A. In one embodiment, the biomarker is TPX2. In certain embodiments, the biomarker is TRIB3. In an embodiment, the biomarker is WIZ. In some embodiments, the biomarker is WSB1. In one embodiment, the biomarker is WWC1. In certain embodiments, the biomarker is ZFP91. In an embodiment, the biomarker is ZMYM2. In some embodiments, the biomarker is ZNF385B. In one embodiment, the biomarker is ZNF581. In certain embodiments, the biomarker is ZNF644.

In an embodiment, the biomarker is the biomarker is ADAM19. In some embodiments, the biomarker is AIF1. In one embodiment, the biomarker is ALDH1A1. In certain embodiments, the biomarker is ALDH2. In some embodiments, the biomarker is ALOX5. In an embodiment, the biomarker is AMPD3. In certain embodiments, the biomarker is APOBEC3G. In one embodiment, the biomarker is APOE. In some embodiments, the biomarker is APOH. In an embodiment, the biomarker is ARHGAP10. In certain embodiments, the biomarker is ATP2B4. In one embodiment, the biomarker is BST2. In some embodiments, the biomarker is C4A. In an embodiment, the biomarker is C4BPA. In certain embodiments, the biomarker is C4orf33. In one embodiment, the biomarker is biomarkerN2. In some embodiments, the biomarker is CASP4. In an embodiment, the biomarker is CCR7. In certain embodiments, the biomarker is CD1D. In one embodiment, the biomarker is CD63. In an embodiment, the biomarker is CD86. In some embodiments, the biomarker is CDR2. In one embodiment, the biomarker is CORO1B. In certain embodiments, the biomarker is CPNE2. In some embodiments, the biomarker is CYTH4. In certain embodiments, the biomarker is DAPK2. In an embodiment, the biomarker is DDX58. In one embodiment, the biomarker is DDX60. In some embodiments, the biomarker is DDX60L. In an embodiment, the biomarker is DHX58. In one embodiment, the biomarker is DNASE1L3. In certain embodiments, the biomarker is DTX3L. In an embodiment, the biomarker is EIF2AK2. In one embodiment, the biomarker is ELOVL7. In some embodiments, the biomarker is EPB41L1. In an embodiment, the biomarker is F13A1. In one embodiment, the biomarker is FAM129A. In certain embodiments, the biomarker is FBLN1. In an embodiment, the biomarker is FCRLA. In one embodiment, the biomarker is FERMT3. In some embodiments, the biomarker is FGD6. In an embodiment, the biomarker is FLNA. In one embodiment, the biomarker is GALNT7. In certain embodiments, the biomarker is GBP1. In an embodiment, the biomarker is GBP2. In one embodiment, the biomarker is GBP4. In some embodiments, the biomarker is GIPC1. In an embodiment, the biomarker is GPD1. In one embodiment, the biomarker is GPX3. In certain embodiments, the biomarker is HABP2. In an embodiment, the biomarker is HBA1. In one embodiment, the biomarker is HBD. In some embodiments, the biomarker is HERC3. In an embodiment, the biomarker is HERC6. In one embodiment, the biomarker is HGF. In certain embodiments, the biomarker is HIGD1A. In an embodiment, the biomarker is HMOX1. In one embodiment, the biomarker is HSPA8. In some embodiments, the biomarker is HSPB1. In an embodiment, the biomarker is IFI35. In one embodiment, the biomarker is IFI44. In certain embodiments, the biomarker is IFI44L. In an embodiment, the biomarker is IFIH1. In one embodiment, the biomarker is IFIT1. In some embodiments, the biomarker is IFIT2. In an embodiment, the biomarker is IFIT3. In one embodiment, the biomarker is IFIT5. In certain embodiments, the biomarker is IFITM3. In an embodiment, the biomarker is IL3RA. In one embodiment, the biomarker is IRF7. In some embodiments, the biomarker is IRF9. In an embodiment, the biomarker is ISG15. In one embodiment, the biomarker is ISG20. In certain embodiments, the biomarker is ITGA1. In an embodiment, the biomarker is ITGB3. In one embodiment, the biomarker is ITGB7. In some embodiments, the biomarker is ITPKB. In an embodiment, the biomarker is KIAA1618. In one embodiment, the biomarker is L1TD1. In certain embodiments, the biomarker is LAP3. In an embodiment, the biomarker is LDB3. In one embodiment, the biomarker is LGALS1. In some embodiments, the biomarker is LGALS3BP. In an embodiment, the biomarker is LGALS9. In one embodiment, the biomarker is LGALS9B. In certain embodiments, the biomarker is LMNA. In an embodiment, the biomarker is LPIN1. In one embodiment, the biomarker is MAP3K11. In some embodiments, the biomarker is MCAM. In an embodiment, the biomarker is MCM8. In one embodiment, the biomarker is MGLL. In certain embodiments, the biomarker is MPP7. In an embodiment, the biomarker is MUC1. In one embodiment, the biomarker is MX1. In some embodiments, the biomarker is MX2. In an embodiment, the biomarker is MYL4. In one embodiment, the biomarker is NCF4. In certain embodiments, the biomarker is NMI. In an embodiment, the biomarker is NQO1. In one embodiment, the biomarker is NUB1. In some embodiments, the biomarker is OAS1. In an embodiment, the biomarker is OAS2. In one embodiment, the biomarker is OAS3. In certain embodiments, the biomarker is OASL. In an embodiment, the biomarker is ORMDL2. In one embodiment, the biomarker is OTOF. In some embodiments, the biomarker is P2RY6. In an embodiment, the biomarker is PAPSS2. In one embodiment, the biomarker is PARP14. In certain embodiments, the biomarker is PARP9. In an embodiment, the biomarker is PBXIP1. In one embodiment, the biomarker is PHF11. In some embodiments, the biomarker is PHF15. In an embodiment, the biomarker is PLG. In certain embodiments, the biomarker is PLSCR1. In one embodiment, the biomarker is PREX1. In some embodiments, the biomarker is PREX2. In an embodiment, the biomarker is PRIC285. In one embodiment, the biomarker is PRKCI. In certain embodiments, the biomarker is PSAP. In an embodiment, the biomarker is PTMS. In one embodiment, the biomarker is RAB13. In some embodiments, the biomarker is RASSF4. In an embodiment, the biomarker is RCN1. In one embodiment, the biomarker is RGL1. In certain embodiments, the biomarker is RGS13. In an embodiment, the biomarker is RNF213. In one embodiment, the biomarker is RTN2. In some embodiments, the biomarker is RTP4. In an embodiment, the biomarker is RUNX3. In one embodiment, the biomarker is S100A13. In certain embodiments, the biomarker is SAMD9. In an embodiment, the biomarker is SAMD9L. In one embodiment, the biomarker is SAMHD1. In some embodiments, the biomarker is SERPINA7. In an embodiment, the biomarker is SERPINF2. In one embodiment, the biomarker is SERPINH1. In some embodiments, the biomarker is SIPA1L3. In an embodiment, the biomarker is SLAMF1. In one embodiment, the biomarker is SLC1A3. In certain embodiments, the biomarker is SLC23A2. In an embodiment, the biomarker is SLC27A3. In one embodiment, the biomarker is SLFN5. In some embodiments, the biomarker is SOD2. In an embodiment, the biomarker is SPN. In one embodiment, the biomarker is SPR. In certain embodiments, the biomarker is SRC. In an embodiment, the biomarker is STAT1. In one embodiment, the biomarker is STAT2. In some embodiments, the biomarker is SYNJ2BP. In an embodiment, the biomarker is TAX1BP3. In one embodiment, the biomarker is TBC1D13. In certain embodiments, the biomarker is TDRD7. In an embodiment, the biomarker is TGOLN2. In one embodiment, the biomarker is TLR7. In some embodiments, the biomarker is TMEM87A. In an embodiment, the biomarker is TMOD2. In one embodiment, the biomarker is TNFAIP2. In certain embodiments, the biomarker is TNFAIP8L2. In an embodiment, the biomarker is TRANK1. In one embodiment, the biomarker is TRIM14. In some embodiments, the biomarker is TRPC4. In an embodiment, the biomarker is TRPM4. In certain embodiments, the biomarker is TSPAN14. In one embodiment, the biomarker is TSPAN3. In an embodiment, the biomarker is UBA7. In some embodiments, the biomarker is UBE2L6. In one embodiment, the biomarker is USP18. In an embodiment, the biomarker is USP41. In certain embodiments, the biomarker is VNN2. In one embodiment, the biomarker is VTN. In an embodiment, the biomarker is XAF1. In some embodiments, the biomarker is ZCCHC2. In one embodiment, the biomarker is ZER1. In an embodiment, the biomarker is ZNF385A. In certain embodiments, the biomarker is ZNF480. In one embodiment, the biomarker is ZNF770. In an embodiment, the biomarker is 3-Sep. In some embodiments, the biomarker is ADIPOR2. In one embodiment, the biomarker is AHR. In an embodiment, the biomarker is ALCAM. In certain embodiments, the biomarker is ALDOC. In one embodiment, the biomarker is ALKBH6. In an embodiment, the biomarker is ALPL. In some embodiments, the biomarker is AP1S3. In one embodiment, the biomarker is APBB1IP. In an embodiment, the biomarker is ARHGAP24. In certain embodiments, the biomarker is ARHGAP27. In one embodiment, the biomarker is ARNT. In an embodiment, the biomarker is BCL11A. In some embodiments, the biomarker is BCL2A1. In one embodiment, the biomarker is BCL2L1. In an embodiment, the biomarker is BCLAF1. In certain embodiments, the biomarker is BNIP3L. In one embodiment, the biomarker is C19orf22. In an embodiment, the biomarker is C9orf40. In some embodiments, the biomarker is CANX. In one embodiment, the biomarker is CD22. In an embodiment, the biomarker is CD44. In some embodiments, the biomarker is CD5. In one embodiment, the biomarker is CDC42SE2. In an embodiment, the biomarker is CENPJ. In certain embodiments, the biomarker is CEP97. In one embodiment, the biomarker is CFLAR. In an embodiment, the biomarker is CLDN23. In some embodiments, the biomarker is CLEC17A. In one embodiment, the biomarker is COX17. In an embodiment, the biomarker is CROCC. In certain embodiments, the biomarker is CRYM. In one embodiment, the biomarker is CSNK1A1. In an embodiment, the biomarker is DBN1. In some embodiments, the biomarker is DENND1C. In one embodiment, the biomarker is DNM2. In an embodiment, the biomarker is DOK3. In certain embodiments, the biomarker is DTWD1. In one embodiment, the biomarker is EHD1. In an embodiment, the biomarker is EIF4H. In some embodiments, the biomarker is ENO2. In one embodiment, the biomarker is EPHA4. In an embodiment, the biomarker is EPHA7. In certain embodiments, the biomarker is EPHB 1. In one embodiment, the biomarker is ERCC6. In an embodiment, the biomarker is ETS1. In some embodiments, the biomarker is EVI2B. In one embodiment, the biomarker is EVL. In an embodiment, the biomarker is FAR1. In certain embodiments, the biomarker is FCRL2. In one embodiment, the biomarker is FCRL3. In an embodiment, the biomarker is FCRL5. In some embodiments, the biomarker is GABPB1. In one embodiment, the biomarker is GAMT. In certain embodiments, the biomarker is GAPT. In an embodiment, the biomarker is GAS7. In one embodiment, the biomarker is GATM. In some embodiments, the biomarker is GLRX. In an embodiment, the biomarker is GNG2. In one embodiment, the biomarker is GRPEL2. In certain embodiments, the biomarker is GYPC. In an embodiment, the biomarker is GZMB. In one embodiment, the biomarker is HK2. In some embodiments, the biomarker is HLTF. In an embodiment, the biomarker is HTRA3. In one embodiment, the biomarker is IFNAR2. In certain embodiments, the biomarker is IKZF1. In an embodiment, the biomarker is IKZF3. In one embodiment, the biomarker is IL16. In some embodiments, the biomarker is INF2. In an embodiment, the biomarker is IQSEC1. In one embodiment, the biomarker is IRF4. In certain embodiments, the biomarker is ISYNA1. In an embodiment, the biomarker is ITGAL. In one embodiment, the biomarker is ITGB2. In some embodiments, the biomarker is KDM5B. In an embodiment, the biomarker is KHK. In one embodiment, the biomarker is L1CAM. In certain embodiments, the biomarker is LAT2. In an embodiment, the biomarker is LBH. In one embodiment, the biomarker is LNX1. In some embodiments, the biomarker is LRRC25. In an embodiment, the biomarker is LUC7L. In one embodiment, the biomarker is LYSMD2. In certain embodiments, the biomarker is MEF2B. In an embodiment, the biomarker is MEF2D. In one embodiment, the biomarker is MICAL3. In some embodiments, the biomarker is MYH11. In an embodiment, the biomarker is NARF. In one embodiment, the biomarker is NBR1. In certain embodiments, the biomarker is NEDD9. In an embodiment, the biomarker is NEFL. In one embodiment, the biomarker is OMA1. In some embodiments, the biomarker is PARVB. In an embodiment, the biomarker is PDK1. In one embodiment, the biomarker is PFKFB4. In certain embodiments, the biomarker is PGM1. In an embodiment, the biomarker is PIR. In one embodiment, the biomarker is PLEKHG1. In some embodiments, the biomarker is PMS2CL. In an embodiment, the biomarker is PODXL2. In one embodiment, the biomarker is POU2AF1. In certain embodiments, the biomarker is PPP1R2. In an embodiment, the biomarker is PTPR. In one embodiment, the biomarker is PTPRE. In some embodiments, the biomarker is PTPRF. In an embodiment, the biomarker is PTPRO. In one embodiment, the biomarker is PTTG1. In some embodiments, the biomarker is PVRL1. In an embodiment, the biomarker is RAB33A. In one embodiment, the biomarker is RANBP3. In certain embodiments, the biomarker is RASGRP3. In an embodiment, the biomarker is RASSF6. In one embodiment, the biomarker is RBBP5. In some embodiments, the biomarker is RHOF. In an embodiment, the biomarker is RPS29. In one embodiment, the biomarker is RPS4Y2. In certain embodiments, the biomarker is SAMD1. In an embodiment, the biomarker is SC5DL. In one embodiment, the biomarker is SEC14L1. In some embodiments, the biomarker is SEMA7A. In an embodiment, the biomarker is SERPINB9. In one embodiment, the biomarker is SETD8. In certain embodiments, the biomarker is SH2D3C. In an embodiment, the biomarker is SIT1. In one embodiment, the biomarker is SLAMF7. In some embodiments, the biomarker is SLC16A3. In an embodiment, the biomarker is SLC19A2. In one embodiment, the biomarker is SNAP23. In certain embodiments, the biomarker is SNX11. In an embodiment, the biomarker is SP140. In one embodiment, the biomarker is SPIB. In some embodiments, the biomarker is SPTAN1. In an embodiment, the biomarker is SPTB. In one embodiment, the biomarker is SSBIP1. In certain embodiments, the biomarker is STK17B. In an embodiment, the biomarker is SYNCRIP. In one embodiment, the biomarker is TCP11L1. In an embodiment, the biomarker is TGM2. In one embodiment, the biomarker is TJAP1. In some embodiments, the biomarker is TNFAIP3. In an embodiment, the biomarker is TNFRSF13B. In one embodiment, the biomarker is TNFRSF1B. In certain embodiments, the biomarker is TOM1. In an embodiment, the biomarker is TOR1AIP1. In one embodiment, the biomarker is TP53I11. In some embodiments, the biomarker is TSTD1. In an embodiment, the biomarker is TUBB2B. In one embodiment, the biomarker is UBE2J1. In certain embodiments, the biomarker is VAT1. In an embodiment, the biomarker is VIM. In one embodiment, the biomarker is WIPF1. In some embodiments, the biomarker is WIZ. In an embodiment, the biomarker is ZBTB32. In one embodiment, the biomarker is ZFP91. In certain embodiments, the biomarker is ZMYM2. In an embodiment, the biomarker is ZNF316. In one embodiment, the biomarker is ZNF644. In an embodiment, the biomarker is ZNF805.

In one embodiment, the biomarker is the biomarker is ACSS1. In one embodiment, the biomarker is ACY3. In another embodiment, the biomarker is ADAM19. In one embodiment, the biomarker is ADCY7. In one embodiment, the biomarker is AIF1. In another embodiment, the biomarker is ALDH2. In one embodiment, the biomarker is AMPD3. In one embodiment, the biomarker is ANK3. In another embodiment, the biomarker is ANXA4. In one embodiment, the biomarker is ANXA6. In one embodiment, the biomarker is ANXA6. In another embodiment, the biomarker is APOBEC3G. In one embodiment, the biomarker is APOBR. In one embodiment, the biomarker is B2M. In another embodiment, the biomarker is BCL9L. In one embodiment, the biomarker is BST2. In one embodiment, the biomarker is C19orf66. In another embodiment, the biomarker is CASP10. In one embodiment, the biomarker is CCDC28B. In one embodiment, the biomarker is CD40. In another embodiment, the biomarker is CD59. In one embodiment, the biomarker is CD83. In one embodiment, the biomarker is CGN. In another embodiment, the biomarker is CLSTN1. In one embodiment, the biomarker is CMPK2. In one embodiment, the biomarker is COL23A1. In another embodiment, the biomarker is CORO1B. In one embodiment, the biomarker is CORO1C. In one embodiment, the biomarker is CTNND1. In another embodiment, the biomarker is CTSH. In one embodiment, the biomarker is CTTNBP2NL. In one embodiment, the biomarker is CYTH1. In another embodiment, the biomarker is CYTH4. In one embodiment, the biomarker is DDX58. In one embodiment, the biomarker is DDX60. In another embodiment, the biomarker is DTX3L. In one embodiment, the biomarker is EIF2AK2. In another embodiment, the biomarker is ETHE1. In one embodiment, the biomarker is F11R. In one embodiment, the biomarker is FADS2. In another embodiment, the biomarker is FAM76A. In one embodiment, the biomarker is FDFT1. In one embodiment, the biomarker is FGD4. In another embodiment, the biomarker is FLNA. In one embodiment, the biomarker is FLNB. In one embodiment, the biomarker is FRRS1. In another embodiment, the biomarker is FSCN1. In one embodiment, the biomarker is GCH1. In one embodiment, the biomarker is GMFG. In another embodiment, the biomarker is GNB4. In one embodiment, the biomarker is GNG2. In one embodiment, the biomarker is H1F0. In another embodiment, the biomarker is HECTD1. In one embodiment, the biomarker is HELZ2. In one embodiment, the biomarker is HGF. In another embodiment, the biomarker is HGSNAT. In one embodiment, the biomarker is HLA-A. In one embodiment, the biomarker is HLA-B. In another embodiment, the biomarker is HLA-G. In one embodiment, the biomarker is HSPB1. In one embodiment, the biomarker is HYI. In another embodiment, the biomarker is IFI35. In one embodiment, the biomarker is IFIT1. In one embodiment, the biomarker is IFIT3. In another embodiment, the biomarker is IFIT5. In one embodiment, the biomarker is IL4I1. In one embodiment, the biomarker is IPCEF1. In another embodiment, the biomarker is IRF9. In one embodiment, the biomarker is ISG15. In one embodiment, the biomarker is ISG20. In another embodiment, the biomarker is JADE2. In one embodiment, the biomarker is KIAA0101. In one embodiment, the biomarker is LAT2. In another embodiment, the biomarker is LGALS1. In one embodiment, the biomarker is LGALS3BP. In one embodiment, the biomarker is LGALS9. In another embodiment, the biomarker is LGALS9B. In one embodiment, the biomarker is LMCD1. In one embodiment, the biomarker is LMNA. In another embodiment, the biomarker is LY75. In one embodiment, the biomarker is LYSMD2. In one embodiment, the biomarker is MAGED4. In another embodiment, the biomarker is MAPK10. In one embodiment, the biomarker is MBD1. In one embodiment, the biomarker is MEA1. In another embodiment, the biomarker is MT2A. In one embodiment, the biomarker is MX1. In one embodiment, the biomarker is MX2. In another embodiment, the biomarker is MYBPC2. In one embodiment, the biomarker is NCOA7. In one embodiment, the biomarker is NCOA7. In another embodiment, the biomarker is NEXN. In one embodiment, the biomarker is NT5C3A. In one embodiment, the biomarker is OAS1. In another embodiment, the biomarker is OAS2. In one embodiment, the biomarker is OAS3. In one embodiment, the biomarker is OSBPL10. In another embodiment, the biomarker is PARP10. In one embodiment, the biomarker is PARP14. In one embodiment, the biomarker is PARP9. In another embodiment, the biomarker is PCDHGC3. In one embodiment, the biomarker is PLG. In one embodiment, the biomarker is PLSCR1. In another embodiment, the biomarker is PRCP. In another embodiment, the biomarker is PTTGIIP. In one embodiment, the biomarker is PYGO2. In another embodiment, the biomarker is QPCT. In one embodiment, the biomarker is S100A13. In one embodiment, the biomarker is SAMHD1. In another embodiment, the biomarker is SERPINH1. In one embodiment, the biomarker is SIRPB1. In another embodiment, the biomarker is SLC23A2. In one embodiment, the biomarker is SLC25A33. In one embodiment, the biomarker is SLC7A7. In another embodiment, the biomarker is SLFN5. In one embodiment, the biomarker is SOWAHD. In one embodiment, the biomarker is SP110. In another embodiment, the biomarker is SP140. In one embodiment, the biomarker is SPR. In one embodiment, the biomarker is STAT1. In another embodiment, the biomarker is STAT2. In one embodiment, the biomarker is STK3. In one embodiment, the biomarker is SYBU. In another embodiment, the biomarker is TAP1. In one embodiment, the biomarker is TAP2. In one embodiment, the biomarker is TDRD7. In another embodiment, the biomarker is THEMIS2. In one embodiment, the biomarker is TNFAIP8L2. In one embodiment, the biomarker is TNFSF9. In another embodiment, the biomarker is TRIM14. In one embodiment, the biomarker is TRIM21. In one embodiment, the biomarker is TRIM22. In another embodiment, the biomarker is TYMP. In one embodiment, the biomarker is UBE2L6. In one embodiment, the biomarker is USP40. In another embodiment, the biomarker is VPREB1. In one embodiment, the biomarker is ADIPOR2. In one embodiment, the biomarker is ATF5. In another embodiment, the biomarker is BACH2. In one embodiment, the biomarker is BANK1. In one embodiment, the biomarker is BCDIN3D. In another embodiment, the biomarker is CD320. In one embodiment, the biomarker is CSNK1A1. In one embodiment, the biomarker is DEPTOR. In another embodiment, the biomarker is ETS1. In one embodiment, the biomarker is GLIPRIL1. In one embodiment, the biomarker is GNG7. In another embodiment, the biomarker is GPT2. In one embodiment, the biomarker is HSBP1. In one embodiment, the biomarker is ICAM2. In another embodiment, the biomarker is IKZF1. In one embodiment, the biomarker is IKZF3. In one embodiment, the biomarker is KRT1. In another embodiment, the biomarker is KRT14. In one embodiment, the biomarker is KRT2. In one embodiment, the biomarker is KRT6B. In another embodiment, the biomarker is KRT9. In one embodiment, the biomarker is MED12L. In one embodiment, the biomarker is NEIL1. In another embodiment, the biomarker is NUGGC. In one embodiment, the biomarker is OMA1. In one embodiment, the biomarker is PDE6D. In another embodiment, the biomarker is PDZRN3. In one embodiment, the biomarker is PODXL. In one embodiment, the biomarker is SYNGR3. In another embodiment, the biomarker is SYTL1. In one embodiment, the biomarker is WIZ. In one embodiment, the biomarker is ZFP91. In another embodiment, the biomarker is ZMYM2.

In other embodiments. In one embodiment, the biomarker is the biomarker is ADIPOR2. In one embodiment, the biomarker is ATF5. In another embodiment, the biomarker is BACH2. In one embodiment, the biomarker is BANK1. In one embodiment, the biomarker is BCDIN3D. In another embodiment, the biomarker is CD320. In one embodiment, the biomarker is CSNK1A1. In one embodiment, the biomarker is DEPTOR. In another embodiment, the biomarker is ETS1. In one embodiment, the biomarker is GLIPRIL1. In one embodiment, the biomarker is GNG7. In another embodiment, the biomarker is GPT2. In one embodiment, the biomarker is HSBP1. In one embodiment, the biomarker is ICAM2. In another embodiment, the biomarker is IKZF1. In one embodiment, the biomarker is IKZF3. In one embodiment, the biomarker is KRT1. In another embodiment, the biomarker is KRT14. In one embodiment, the biomarker is KRT2. In one embodiment, the biomarker is KRT6B. In another embodiment, the biomarker is KRT9. In one embodiment, the biomarker is MED12L. In one embodiment, the biomarker is NEIL1. In another embodiment, the biomarker is NUGGC. In one embodiment, the biomarker is OMA1. In one embodiment, the biomarker is PDE6D. In another embodiment, the biomarker is PDZRN3. In one embodiment, the biomarker is PODXL. In one embodiment, the biomarker is SYNGR3. In another embodiment, the biomarker is SYTL1. In one embodiment, the biomarker is WIZ. In one embodiment, the biomarker is ZFP91. In another embodiment, the biomarker is ZMYM2.

Combinations of two, three, four, five, six, seven, eight, nine, 10, eleven, twelve, thirteen, fourteen, fifteen, sixteen, seventeen, eighteen, nineteen, twenty, twenty-five, thirty, thirty-five, forth, forty-five, fifty or up to all of the above-referenced CAPs are also contemplated.

Without being limited by a particular theory, it was found that certain compounds provided herein (e.g., lenalidomide, pomalidomide and Compound A), activate an IFN pathway(s).

Accordingly, in certain embodiments, the CAP is an IFN. In some embodiments, embodiments, the CAP is IFN, and the level of IFN increases as compared to the reference. In other embodiments, the CAP is an IFN pathway protein, and the level of the protein increases as compared to the reference. In some embodiments, the CAP is IFN and another or more IFN pathway proteins, and the levels of both the IFN protein and IFN pathway proteins increase as compared to the reference. In some embodiments, the CAP is ZFP91, and the level of ZFP91 protein decreases as compared to the reference. In various embodiments of the methods provided herein, the compounds provided herein up-regulate IFN expression (e.g., protein or gene expression). In certain embodiments, the compounds provided herein increase IFN protein levels. In another embodiment, the compound is lenalidomide and IFN expression (e.g., protein or gene expression) is up-regulated. In another embodiment, the compound is Compound A and IFN (e.g., protein or gene expression) is up-regulated. In specific embodiments, the IFN protein levels increase. In other embodiments, the compounds provided herein up-regulate the expression (e.g., protein or gene expression) of an IFN pathway protein. In certain embodiments, the compounds provided herein increase the protein levels. In another embodiment, the compound is lenalidomide and the expression (e.g., protein or gene expression) of an IFN pathway protein is up-regulated. In another embodiment, the compound is Compound A and the expression (e.g., protein or gene expression) of an IFN pathway protein is up-regulated. In certain embodiments, the IFN pathway protein is IFN-induced transmembrane protein 3 (IFITM3) and/or IFN regulatory factor 7 (IRF7). In some embodiments, the biomarker is an IFN, and the level of IFN increases as compared to the reference. In other embodiments, the CAP is an IFN pathway protein, and the level of the IFN pathway protein increases as compared to the reference. In some embodiments, the IFN pathway protein is IFN (IFN). In certain embodiments, the IFN pathway protein is an IFN Regulatory Factor (IRF), In some embodiments, the IRF is selected from a group consisting of IRF1, IRF2, IRF3, IRF4, IRF7, IRF8, IRF9, or any combination thereof. In some embodiments, the IRF is selected from a group consisting of IRF1, IRF3, IRF4, IRF7, and IRF9, or any combination thereof. In some embodiments, the IFN pathway protein is DDX58, IFI27, IFIH1, IFIT1, IFIT3, IFITM3, IFN, ISG15, OAS3, a STAT, a STAT-$PO_4$, TBK1, TBK1-$PO_4$, XAF1, or any combination thereof. In other embodiments, the IFN pathway protein is IFITM3 and/or IRF7. In some embodiments, the IFN pathway protein is DDX58, IFI27, IFIH1, IFIT1, IFIT3, IKKE, ISG15, OAS3, XAF1, or any combination thereof. In certain embodiments, the IFN pathway protein is a protein provided in FIG. 12. In other embodiments, the IFN pathway protein is DDX58, DDX60, DDX60L, GBP1, IFI16, IFI27, IFI27L2, IFI35, IFI44, IFI44L, IFI6, IFIH1, IFIT1, IFIT2, IFIT3, IFIT5, IFITM2, IFNA16, IFNA5, IFNG, IFNGR1, IRF1, IRF2, IRF4, IRF7, IRF8, ISG15, ISG20, MX1, MX2, OAS1, OAS2, OAS3, OASL, TLR1, TLR3, TLR4, TLR7, TLR8, or any combination thereof. In some embodiments, the CAP is IFN and one or more IFN pathway proteins, and the levels of both the IFN protein and IFN pathway proteins increase as compared to the reference. In various embodiments of the methods provided herein, the compounds provided herein up-regulate the expression of IFN or IFN pathway proteins (e.g., protein or gene expression). In certain embodiments, the compounds provided herein increase IFN levels.

In some embodiments, the CAP is IFIT1, IFIT3, DDX58, XAF1, IFIH1, or OAS3, and the level of the protein increases as compared to the reference. In some embodiments, the levels of two or more of IFIT1, IFIT3, DDX58, XAF1, IFIH1, and OAS3 increase as compared to the reference. In some embodiments, the CAP is DDX58, IFI27, IFIT1, IFIT3, DDX58, or XAF1, and the level of the protein increases as compared with the reference. In some embodiments, the levels of two or more of DDX58, IFI27, IFIT1, IFIT3, DDX58, and XAF1 increase compared with the reference. In some embodiments, the CAP is ISG15 or OAS3, and the level of the protein increases as compared with the reference. In some embodiments, level of both ISG15 and OAS3 increase as compared with the reference. In some embodiments, CAP is an IRF, and the levels of IRFs change as compared with the reference. In some embodiments, CAP is IFIT1, IFIT3, TBK1, TBK1-$PO_4$, or IKKE, and the level of the protein change as compared with reference. In one embodiment, the levels of IFIT1, IFIT3, and TBK1-$PO_4$ increase as compared with the reference. In one embodiment, the level of IKKE decreases as compared with the reference. In one embodiment, the levels of IFIT1, IFIT3, and TBK1-$PO_4$ increase as compared with the reference, and the level of IKKE decreases as compared with the reference. In certain embodiments, the CAP is IFN, and the level of IFN increases as compared to the reference. In other embodiments, the CAP is an IFN pathway protein, and the level of the protein increases as compared to the reference. In some embodiments, the CAP is IFN and one or more IFN pathway proteins, and the levels of both the IFN and IFN pathway protein(s) increase as compared to the reference.

In some embodiments, the CAP is IKZF1 (Ikaros). In some embodiments, the biomarker is Ikaros, wherein the level of Ikaros decreases as compared to a reference. In some embodiments, the CAP further comprises Ikaros.

Aiolos (IKZF3) is a member of the Ikaros family of zinc-finger proteins. IKZF3 is a hematopoietic-specific transcription factor involved in the regulation of lymphocyte development (e.g., B lymphocyte proliferation and differentiation). The DNA-binding domain of IKZF3 recognizes the core motif of GGGA. IKZF3 was shown to participates in chromatin remodeling, regulates Bcl family members, binds to HDACs, mSin3, Mi-2 in T cells and acts as a transcriptional repressor. Aiolos-Foxp3 interaction has been shown to silence IL-2 expression in human T cells.

In certain embodiments, the CAP IKZF3 (Aiolos). In some embodiments, the Aiolos has a protein molecular weight of 42 kDa. In some embodiments, the Aiolos has a protein molecular weight of 58 kDa. In some embodiments, the biomarker is Aiolos, wherein the level of Aiolos decreases as compared to a reference. In other embodiments, the CAP further comprise Aiolos. In certain embodiments, the CAP is Ikaros and Aiolos. In some embodiments, the biomarker is Ikaros and Aiolos, wherein the levels of both Ikaros and Aiolos decrease as compared to a reference. In some embodiments, the CAP is CRBN. In some embodiments, the biomarker is CRBN, wherein the level of CRBN increases as compared to a reference. In other embodiments, the CAP further comprises CRBN. In some embodiments, the CAP is not (or does not comprise) Ikaros. In other embodiments, the CAP is not (or does not comprise) Aiolos. In some embodiments, the CAP is not (or does not comprise) CRBN.

In certain embodiments, the CAP is Ikaros, and the level of Ikaros protein decreases as compared to the reference. In other embodiments, the CAP is Aiolos, and the level of Aiolos protein decreases as compared to the reference. In some embodiments, the CAP is Ikaros and Aiolos, and the levels of both the Ikaros protein and Aiolos protein decrease as compared to the reference.

In another embodiment, the compounds provided herein down-regulate Aiolos expression (e.g., protein or gene expression). In another embodiment, the compound is lenalidomide and Aiolos expression (e.g., protein or gene expression) is down-regulated. In another embodiment, the compound is Compound A and Aiolos expression (e.g., protein or gene expression) is down-regulated. In specific embodiments, the Aiolos protein levels decrease.

In various embodiments of the methods provided herein, the compounds provided herein down-regulate Ikaros expression (e.g., protein or gene expression). In certain embodiments, the compounds provided herein decrease Ikaros protein levels. In another embodiment, the compound is lenalidomide and Ikaros expression (e.g., protein or gene expression) is down-regulated. In another embodiment, the compound is Compound A and Ikaros expression (e.g., protein or gene expression) is down-regulated. In specific embodiments, the Ikaros protein levels decrease. In some embodiments, the Aiolos protein levels decrease, and the Ikaros protein levels decrease.

In certain embodiments, the compound is immunomodulatory if the level (e.g., protein or RNA level) of Ikaros as compared to the reference decreases. In certain embodiments, the compound is immunomodulatory if the level (e.g., protein or RNA level) of Ikaros as compared to the reference increases. In one embodiment, the reference is prepared by using a second cell (e.g., a cancer cell or an immune cell) not contacted with the compound. In some embodiments, the compound is lenalidomide, and both the Ikaros protein level decreases as compared to the reference, and the Aiolos protein level decreases as compared to the reference. In some embodiments, the compound is Compound A, and both the Ikaros protein level decreases as compared to the reference, and the Aiolos protein level decreases as compared to the reference.

In certain embodiments, the compound is immunomodulatory if the level (e.g., protein or RNA level) of Aiolos decreases as compared to the reference. In certain embodiments, the compound is immunomodulatory if the level (e.g., protein or RNA level) of Aiolos increases as compared to the reference. In one embodiment, the reference is prepared by using a second DLBCL cell not contacted with the compound. In some embodiments, the compound is lenalidomide and the Aiolos protein level decreases as compared to the reference. In some embodiments, the compound is Compound A and the Aiolos protein level decreases as compared to the reference.

In some embodiments, the immunomodulatory compounds provided herein up-regulate CRBN expression (e.g., protein expression) as compared to the reference. In some embodiments, IMiDs provided herein up-regulate CRBN expression (e.g., protein or gene expression) as compared to the reference. In one embodiment, 3-(5-amino-2-methyl-4-oxo-4H-quinazolin-3-yl)-piperidine-2,6-dione up-regulates CRBN expression (e.g., protein or gene expression) as compared to the reference. In another embodiment, lenalidomide up-regulates CRBN expression (e.g., protein or gene expression) as compared to the reference. In another embodiment, Compound A up-regulates CRBN expression (e.g., protein or gene expression) as compared to the reference. In some embodiments, the CRBN protein levels are increased as compared to the reference. In some embodiments, CRBN levels do not decrease as compared to the reference.

In some embodiments, the CAP is a STAT. In one embodiment, the CAP is a STAT protein, and the level of the protein changes as compared with the reference. In one embodiment, the compound changes the level of a STAT protein and/or its phosphorylated form.

In certain embodiments, the CAP is CSNK1A1. In some embodiments, the biomarker is CSNK1A1, and the level of CSNK1A1 decreases as compared to a reference. In some embodiments, the CAP is CSNK1A1 and IFN. In one embodiment, the CAP is CSNK1A1, and the level of CSNK1A1 changes as compared with the reference. In certain embodiments, the change is an increase. In other embodiments, the change is a decrease. In various embodiments of the methods provided herein, the compounds provided herein up-regulate CSNK1A1 expression (e.g., protein or gene expression). In certain embodiments, the compounds provided herein increase CSNK1A1 protein levels. In specific embodiments, the CSNK1A1 protein levels increase. In various embodiments of the methods provided herein, the compounds provided herein down-regulate CSNK1A1 expression (e.g., protein or gene expression). In certain embodiments, the compounds provided herein decrease CSNK1A1 protein levels. In another embodiment, the compound is lenalidomide and CSNK1A1 expression (e.g., protein or gene expression) is down-regulated.

In certain embodiments, the compound is efficacious anti-tumor compound if the level (e.g., protein or RNA level) of IFN or IFN pathway protein increases as compared to the reference. In certain embodiments, the compound is efficacious antitumor compound if the level (e.g., protein or RNA level) of IFN or IFN pathway protein increases as compared to the reference. In one embodiment, the reference is prepared by using a second DLBCL cell not contacted with the compound. In some embodiments, the compound is lenalidomide and the IFN or IFN pathway protein level increases as compared to the reference. In some embodiments, the compound is Compound A and the IFN or IFN pathway protein level increases as compared to the reference.

In certain embodiments, the compound is immunomodulatory if the level (e.g., protein or RNA level) of CSNK1A1 as compared to the reference increases. In certain embodiments, the compound is immunomodulatory if the level (e.g., protein or RNA level) of CSNK1A1 as compared to the reference decreases. In one embodiment, the reference is prepared by using a second cell (e.g., a cancer cell or an immune cell) not contacted with the compound. In some embodiments, the compound is lenalidomide and the CSNK1A1 protein level decreases as compared to the reference. In some embodiments, the compound is lenalidomide and the CSNK1A1 protein level decreases as compared to the reference.

In some embodiments, the CAP is ZFP91. In some embodiments, the biomarker is ZFP91, and the level of ZFP91 decreases as compared to a reference. In some embodiments, the CAP is Ikaros, Aiolos and ZFP91, and the levels of each of Ikaros protein, Aiolos protein and ZFP91 protein decrease as compared to the reference. In some embodiments, the decrease in the level ZFP91 protein is the result of protein degradation. In various embodiments of the methods provided herein, the compounds provided herein down-regulate ZFP91 expression (e.g., protein or gene expression). In one embodiment, the compound is lenalidomide, and ZFP91 is down-regulated. In one embodiment, the compound is pomalidomide, and ZFP91 is down-regulated. In one embodiment, the compound is Compound A, and ZFP91 is down-regulated. In one embodiment, the compound is thalidomide, and ZFP91 is down-regulated. In one embodiment, the compound is Compound B, and ZFP91 is down-regulated.

In specific embodiments of the methods provided herein, the CAP is ZFP91. In one embodiment, the ZFP91 protein has a protein molecular weight of 63.4 kDa. In some embodiments, the compounds provided herein down-regulate ZFP91 expression (e.g., protein or gene expression). In one embodiment, the compound is lenalidomide, and ZFP91 is down-regulated. In one embodiment, the compound is pomalidomide, and ZFP91 is down-regulated. In one embodiment, the compound is Compound A, and ZFP91 is down-regulated. In one embodiment, the compound is thalidomide, and ZFP91 is down-regulated. In one embodiment, the compound is Compound B, and ZFP91 is down-regulated.

In certain embodiments, the compound is immunomodulatory if the level (e.g., protein or RNA level) of ZFP91 decreases as compared to the reference. In one embodiment, the reference is prepared by using a second cell (e.g., a cancer cell or an immune cell) not contacted with the compound. In some embodiments, the compound is lenalidomide and the ZFP91 protein level decreases as compared to the reference. In some embodiments, the compound is Compound A and the ZFP91 protein level decreases as compared to the reference. In some embodiments, the compound is pomalidomide, and the ZFP91 protein level decreases as compared to the reference. In some embodiments, the compound is thalidomide, and the ZFP91 protein level decreases as compared to the reference. In some embodiments, the compound is Compound B, and the ZFP91 protein level decreases as compared to the reference.

In some embodiments of the various methods provided herein, the biomarkers are one or more proteins listed in Table 1 or 3-8. In other embodiments of the various methods provided herein, the biomarkers are one or more proteins listed in Table 1 and/or Table 3 and/or Table 4 and/or Table 5 and/or Table 6 and/or Table 7 and/or Table 8.

In some embodiments of the various methods provided herein, the compounds provided herein down-regulate one or more of ABCE1, ACLY, ACTB, ALDOA, ARID A, C7ORF42, COPS6, CPSF6, CSNK2A1, CTPS, DDB1, DDIT4, DDX17, DDX21, DHX9, DNAJC1, DUT, EEF1A1, EEF1AL3, EEF1G, EIF2S1, EIF2S2, EIF3J, EIF4A1, EWSR1, FASN, FBXO21, FERMT3, FUBP1, G3BP1, G3BP2, GBE1, GNAS, GNB2L1, GNB3, H2AFJ, H2AFX, H2AFZ, HIST1H1A, HIST1H1B, HIST1H1C, HIST1H1D, HIST1H1E, HIST1H2AA, HNRNPA2B1, HNRNPC, HNRNPH2, HNRNPR, HSPA1A, HSPA1B, HSPA8, HSPA9, IFI16, IGF2BP2, ILF3, IPO5, KCNAB2, MACF1, MCM2, MCM7, MYH10, NACA, NAP1L2, NCL, NEDD8, NUP88, PABPC1, PABPC4, PCM1, PDXK, PPAT, PRKDC, PTPRC, PTRH2, RPL10A, RPL11, RPL12, RPL13A, RPL14, RPL15, RPL18A, RPL19, RPL21, RPL3, RPL30, RPL4, RPL7, RPL7A, RPL9, RPLP1, RPLP2, RPS13, RPS16, RPS19, RPS2, RPS6, SEC23B, SEC24A, SEC24C, SMC4, SND1, STAT3, SYNCRIP, TBL1XR1, TPD52, TUBA1A, TUBA1B, TUBA1C, UAP1, UBA52, UBAP2L, UBB, UBE2O, UBE2Q1, USP15, VAPA, XRCC6 or YWHAE expression (e.g., protein or gene expression). In other embodiments of the various methods provided herein, the compounds provided herein up-regulate one or more of ABCE1, ACLY, ACTB, ALDOA, ARID1A, C7ORF42, COPS6, CPSF6, CSNK2A1, CTPS, DDB1, DDIT4, DDX17, DDX21, DHX9, DNAJC1, DUT, EEF1A1, EEF1AL3, EEF1 G, EIF2S1, EIF2S2, EIF3J, EIF4A1, EWSR1, FASN, FBXO21, FERMT3, FUBP1, G3BP1, G3BP2, GBE1, GNAS, GNB2L1, GNB3, H2AFJ, H2AFX, H2AFZ, HIST1H1A, HIST1H1B, HIST1H1C, HIST1H1D, HIST1H1E, HIST1H2AA, HNRNPA2B1, HNRNPC, HNRNPH2, HNRNPR, HSPA1A, HSPA1B, HSPA8, HSPA9, IFI16, IGF2BP2, ILF3, IPO5, KCNAB2, MACF1, MCM2, MCM7, MYH10, NACA, NAP1L2, NCL, NEDD8, NUP88, PABPC1, PABPC4, PCM1, PDXK, PPAT, PRKDC, PTPRC, PTRH2, RPL10A, RPL11, RPL12, RPL13A, RPL14, RPL15, RPL18A, RPL19, RPL21, RPL3, RPL30, RPL4, RPL7, RPL7A, RPL9, RPLP1, RPLP2, RPS13, RPS16, RPS19, RPS2, RPS6, SEC23B, SEC24A, SEC24C, SMC4, SND1, STAT3, SYNCRIP, TBL1XR1, TPD52, TUBA1A, TUBA1B, TUBA1C, UAP1, UBA52, UBAP2L, UBB, UBE2O, UBE2Q1, USP15, VAPA, XRCC6 or YWHAE expression (e.g., protein or gene expression). In some embodiments, these CAPs are evaluated in combination with other CAPs provided herein, such as CRBN, Ikaros, Aiolos, IFN, an IFN pathway protein, CSNK1A1, and/or ZFP91.

In some embodiments, the biomarker is selected from Table 1. In some embodiments, the treatment compound is Compound A, and the biomarker is selected from Table 1. In some embodiments, the level of the biomarker increases as compared to a reference, e.g., the biomarkers upregulated in Table 1. In other embodiments, the level of the biomarker decreases as compared to a reference, e.g., the biomarkers downregulated in Table 1.

In some embodiments of the various methods provided herein, the biomarker is a protein listed in Tables 3-8. In other embodiments of the various methods provided herein, the biomarker is one or more proteins listed in Table 3 and/or Table 4 and/or Table 5 and/or Table 6 and/or Table 7 and/or Table 8 As shown in the Examples and Tables 3-8, the amount of certain proteins listed in the tables increases in response to the treatment compound; while the amount of certain proteins listed in the tables decreases in response to the treatment compound. Thus, in some embodiments, the level of the biomarker increases as compared to a reference. In other embodiments, the level of the biomarker decreases as compared to a reference.

In some embodiments of the various methods provided herein, the level (e.g., expression) of only one biomarker is determined. In other embodiments of the various methods provided herein, the levels (e.g., expression) of two, three, four, five or more biomarkers are determined.

In certain embodiments, provided herein are methods for the treatment or management of a cancer with a compound using biomarkers, such as Ikaros, Aiolos, IFN, an IFN pathway protein, CSNK1A1, and/or ZFP91, as a predictive or prognostic factor for the compounds provided herein.

In other embodiments, provided herein are methods for screening or identifying cancer patients, e.g., MM, DLBCL, mantle cell lymphoma, follicular lymphoma, acute myeloblastic leukemia, chronic lymphocytic leukemia, MDS patients, non-Hodgkin lymphoma, hairy cell leukemia, chronic myelogenous leukemia, AIDS-related Kaposi sarcoma, melanoma, malignant melanoma, MDS for treatment with a compound using a biomarker, such as Ikaros, Aiolos, IFN, an IFN pathway protein, CSNK1A1 and/or ZFP91, levels as a predictive or prognostic factor Also provided herein, in certain embodiments, are methods for the treatment or management of a disease using a biomarker, such as Ikaros, Aiolos, IFN, an IFN pathway protein, CSNK1A1, and/or ZFP91, as a predictive or prognostic factor for the compounds provided herein.

In other embodiments, provided herein are methods for screening or identifying patients, e.g., conyloma accuminata, chronic hepatitis B, chronic hepatitis C, relapsing-remitting multiple sclerosis, or chronic granulomatous disease for treatment with a compound using a biomarker, such as Ikaros, Aiolos, IFN, an IFN pathway protein, CSNK1A1 and/or ZFP91 levels as a predictive or prognostic factor.

In some embodiments, provided herein are methods for selecting patients having a higher response rate to therapy with a compound provided herein, using CRBN and/or a CAP, such as Ikaros, Aiolos, IFN, an IFN pathway protein, CSNK1A1, and/or ZFP91, levels as a predictive or prognostic factor.

In another embodiment, provided herein is a method of predicting patient response to treatment of cancer with a compound provided herein, the method comprising obtaining biological material from the patient, and measuring the presence or absence of a biomarker, e.g., Ikaros, Aiolos, IFN, an IFN pathway protein, CSNK1A1, and/or ZFP91.

In another embodiment, provided herein is a method of predicting patient response to treatment in a cancer patient, the method comprising obtaining cells (e.g., a cancer cell or an immune cell) from the patient, culturing the cells in the presence or absence of a compound provided herein, purifying protein or RNA from the cultured cells, and measuring the presence or absence of a biomarker by, e.g., protein or gene expression analysis. In one embodiment, the cells are cancer cells. In another embodiment, the cells are immune cells. The expression monitored may be, for example, mRNA expression or protein expression. In one embodiment, the cancer patient is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS, hairy cell leukemia, chronic myelogenous leukemia, AIDS-related Kaposi sarcoma, melanoma, malignant melanoma patient.

In another embodiment, provided herein is a method of predicting patient response to treatment in a patient, the method comprising obtaining cells from the patient, culturing the cells in the presence or absence of a compound provided herein, purifying protein or RNA from the cultured cells, and measuring the presence or absence of a biomarker by, e.g., protein or gene expression analysis. The expression monitored may be, for example, mRNA expression or protein expression. In one embodiment, the patient is a conyloma accuminata, chronic hepatitis B, chronic hepatitis C, relapsing-remitting multiple sclerosis, or chronic granulomatous disease patient.

In another embodiment, provided herein is a method of monitoring tumor response to compound (e.g., drug) treatment in a cancer patient. The method comprises obtaining a biological sample from the patient, measuring the expression of a biomarker in the biological sample, administering one or more compounds to the patient, thereafter obtaining a second biological sample from the patient, measuring biomarker expression in the second biological sample, and comparing the levels of expression, where an increased level of biomarker expression after treatment indicates the likelihood of an effective tumor response. In one embodiment, the cancer patient is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma patient.

In certain embodiments, CRBN protein levels are not down-regulated or decreased, whereas Ikaros protein levels and/or Aiolos protein levels are down-regulated or decreased. In some embodiments, such a phenotype indicates the patient has, or may be developing, an acquired resistance to the compound. In certain embodiments, the biomarker is c-Myc. In certain embodiments, c-Myc levels are decreased. In other embodiments, the biomarker is CD44. In certain embodiments, CD44 levels are increased.

In other embodiments, a decrease in the level of Ikaros, Aiolos and/or ZFP91 protein levels indicates an effective treatment with the compound. In other embodiments, an increase of IFN pathway protein level indicates an effective treatment of the compound.

In one embodiment, a decreased level of biomarker expression after treatment indicates the likelihood of effective tumor response. The biomarker expression monitored can be, for example, mRNA expression or protein expression.

In one embodiment, the tumor is a lymphoma, leukemia, MM, solid tumor, non-Hodgkin's lymphoma, DLBCL, melanoma, hairy cell leukemia, chronic myelogenous leukemia, AIDS-related Kaposi sarcoma, follicular lymphoma, melanoma, malignant melanoma, or MDS.

In specific embodiments of the various methods provided herein the compound is a CRBN-binding compound (CBC). In some embodiments of the various methods provided herein, the compound is an IMiD® immunomodulatory drug (from Celgene Corporation). In some embodiments, the compound is lenalidomide, pomalidomide, thalidomide, 3-(5-amino-2-methyl-4-oxo-4H-quinazolin-3-yl)-piperidine-2,6-dione (Compound A), or 3-(4-((4-(morpholinomethyl)benzyl)oxy)-1-oxoisoindolin-2-yl)piperidine-2,6-dione (Compound B).

Various combinations of one or more compound (e.g., one or more CRBN-binding compound) and one or more biomarkers (e.g., one or more CAP) are contemplated for use in the various methods provided herein.

In one embodiment, the compound is lenalidomide. In some embodiments, the compound is a stereoisomer of lenalidomide, or a pharmaceutically acceptable salt, solvate, hydrate, co-crystal, clathrate, or polymorph of lenalidomide.

In one embodiment, the compound is pomalidomide. In other embodiments, the compound is a stereoisomer of pomalidomide, or a pharmaceutically acceptable salt, solvate, hydrate, co-crystal, clathrate, or polymorph of pomalidomide.

In another embodiment, the compound is thalidomide. In certain embodiments, the compound is a stereoisomer of thalidomide, or a pharmaceutically acceptable salt, solvate, hydrate, co-crystal, clathrate, or polymorph of thalidomide. In some embodiments, the compound is Compound A. In other embodiments, the compound is a stereoisomer of Compound A, or a pharmaceutically acceptable salt, solvate, hydrate, co-crystal, clathrate, or polymorph of Compound A. In some embodiments, the compound is Compound B. In other embodiments, the compound is a stereoisomer of Compound B, or a pharmaceutically acceptable salt, solvate, hydrate, co-crystal, clathrate, or polymorph of Compound B.

In certain embodiments of the various methods provided herein, the cancer is DLBCL, MM, MDS (e.g., a MDS with deletion of chromosome 5q (del(5q)), AML, MCL, FL, CLL, NHL, CML, or a malignant melanoma. In certain embodiments, the cancer is a tumor. In specific embodiments, the cancer is DLBCL, MM, MDS or AML.

In a specific embodiment of the various methods provided herein, the cancer is DLBCL and the compound is lenalidomide. In another embodiment of the various methods provided herein, the cancer is DLBCL and the compound is a stereoisomer of lenalidomide, or a pharmaceutically acceptable salt, solvate, hydrate, co-crystal, clathrate, or polymorph of lenalidomide. In one specific embodiment of the various methods provided herein, the cancer is DLBCL and the compound is pomalidomide. In another embodiment of the various methods provided herein, the cancer is DLBCL and the compound is a stereoisomer of pomalidomide, or a pharmaceutically acceptable salt, solvate, hydrate, co-crystal, clathrate, or polymorph of pomalidomide. In another specific embodiment of the various methods provided herein, the cancer is DLBCL and the compound is thalidomide. In another embodiment of the various methods provided herein, the cancer is DLBCL and the compound is a stereoisomer of thalidomide, or a pharmaceutically acceptable salt, solvate, hydrate, co-crystal, clathrate, or polymorph of thalidomide. In a yet another embodiment of the various methods provided herein, the cancer is DLBCL and the compound is Compound A. In another embodiment of the various methods provided herein, the cancer is DLBCL and the compound is a stereoisomer of Compound A, or a pharmaceutically acceptable salt, solvate, hydrate, co-crystal, clathrate, or polymorph of Compound A. In yet other specific embodiments of the various methods provided herein, the cancer is DLBCL and the compound is Compound B. In another embodiment of the various methods provided herein, the cancer is DLBCL and the compound is a stereoisomer of Compound B, or a pharmaceutically acceptable salt, solvate, hydrate, co-crystal, clathrate, or polymorph of Compound B. In certain embodiments, the biomarker is a CAP. In certain embodiments, the compound is likely efficacious in treating DLBCL if the level (e.g., protein or RNA level) of the CAP as compared to the reference decreases. In certain embodiments, the compound is likely efficacious in treating DLBCL if the level (e.g., protein or RNA level) of the CAP as compared to the reference increases. In some embodiments, the biomarker is Aiolos, Ikaros, IFN, an IFN pathway protein, an IRF, a STAT, CSNK1A1, or ZFP91. In certain embodiments, the biomarker is CRBN. In some embodiments, the biomarker is CRBN, and the level of the CRBN increases as compared to a reference. In certain embodiments, the biomarker is Aiolos. In some embodiments, the biomarker is Aiolos, and the level of the Aiolos decreases as compared to a reference. In certain embodiments, the biomarker is Ikaros. In some embodiments, the biomarker is Ikaros, and the level of Ikaros decreases as compared to a reference. In other embodiments, the biomarker is an IFN pathway protein. In some embodiments, the biomarker is an IFN pathway protein, and the level of the IFN pathway protein increases as compared to a reference. In some embodiments, the biomarker is an IFN. In some embodiments, the biomarker is an IFN, and the level of the IFN increases as compared to a reference. In some embodiments, the biomarker is an IRF. In some embodiments, the biomarker is an IRF, and the level of the IRF increases as compared to a reference In some embodiments, the biomarker is a STAT. In yet other embodiments, the is CSNK1A1. In some embodiments, the biomarker is CSNK1A1 and the level of the CSNK1A1 decreases as compared to a reference. In other embodiments, the biomarker is ZFP91. In some embodiments, the biomarker is ZFP91, and the level of the ZFP91 decreases as compared to a reference. Combinations of 2, 3, 4, 5, 6, 7, 8 or more of the above-referenced biomarkers (or other biomarkers provided herein, are also contemplated.

In a specific embodiment of the various methods provided herein, the biomarker is an IFN or an IFN pathway protein. Thus, in some embodiments, the method provided herein comprises selecting a group of subjects having DLBCL based on the level of IFN or an IFN pathway protein, or the levels of IFN or an IFN pathway protein expression within the DLBCL, for the purposes of predicting clinical response, monitoring clinical response, or monitoring patient compliance to dosing by a compound. As shown in Examples, IFN or IFN pathway protein level changes in response to treatment with the treatment compound (or compound) provided herein. Thus, a changed level of IFN or an IFN pathway protein can be used to identify subjects who are likely to be responsive to treatment with the treatment compound provided herein and/or to predict if further treatment with the treatment compound will receive responsiveness from the subject.

In one embodiment, the cancer is DLBCL, and the biomarker is IFN. In one embodiment, the cancer is DLBCL, the biomarker is IFN, and the compound is lenalidomide. In one embodiment, the cancer is DLBCL, the biomarker is IFN, and the compound is pomalidomide. In one embodiment, the cancer is DLBCL, the biomarker is IFN, and the compound is thalidomide. In one embodiment, the cancer is DLBCL, the biomarker is IFN, and the compound is Compound A. In one embodiment, the cancer is DLBCL, the biomarker is IFN, and the compound is Compound B. In one embodiment, the cancer is DLBCL, and the biomarker is an IFN pathway protein. In one embodiment, the cancer is DLBCL, the biomarker is an IFN pathway protein, and the compound is lenalidomide. In one embodiment, the cancer is DLBCL, the biomarker is an IFN pathway protein, and the compound is pomalidomide. In one embodiment, the cancer is DLBCL, the biomarker is an IFN pathway protein, and the compound is thalidomide. In one embodiment, the cancer is DLBCL, the biomarker is an IFN pathway protein, and the compound is Compound A. In one embodiment, the cancer is DLBCL, the biomarker is an IFN pathway protein, and the compound is Compound B.

In another specific embodiment of the various methods provided herein, the biomarker is CSNK1A1. Thus, in some embodiments, the method provided herein comprises selecting a group of subjects having DLBCL based on the level of CSNK1A1, or the levels of CSNK1A1 expression within the DLBCL, for the purposes of predicting clinical response, monitoring clinical response, or monitoring patient compliance to dosing by a compound. In one embodiment, the cancer is DLBCL, and the biomarker is CSNK1A1. In one embodiment, the cancer is DLBCL, the biomarker is CSNK1A1, and the compound is lenalidomide. In one embodiment, the cancer is DLBCL, the biomarker is CSNK1A1, and the compound is pomalidomide. In one embodiment, the cancer is DLBCL, the biomarker is CSNK1A1, and the compound is thalidomide. In one embodiment, the cancer is DLBCL, the biomarker is CSNK1A1, and the compound is Compound A. In one embodiment, the cancer is DLBCL, the biomarker is CSNK1A1, and the compound is Compound B.

In another specific embodiment of the various methods provided herein, the biomarker is ZFP91. Thus, in some embodiments, the method provided herein comprises selecting a group of subjects having DLBCL based on the level of ZFP91, or the levels of ZFP91 expression within the DLBCL, for the purposes of predicting clinical response, monitoring clinical response, or monitoring patient compliance to dosing by a compound. In one embodiment, the cancer is DLBCL, and the biomarker is ZFP91. In one embodiment, the cancer is DLBCL, the biomarker is ZFP91, and the compound is lenalidomide. In one embodiment, the cancer is DLBCL, the biomarker is ZFP91, and the compound is pomalidomide. In one embodiment, the cancer is DLBCL, the biomarker is ZFP91, and the compound is thalidomide. In one embodiment, the cancer is DLBCL, the biomarker is ZFP91, and the compound is Compound A. In one embodiment, the cancer is DLBCL, the biomarker is ZFP91, and the compound is Compound B.

In one specific embodiment of the various methods provided herein, the cancer is MM and the compound is pomalidomide. In another embodiment of the various methods provided herein, the cancer is MM and the compound is a stereoisomer of pomalidomide, or a pharmaceutically acceptable salt, solvate, hydrate, co-crystal, clathrate, or polymorph of pomalidomide. In another specific embodiment of the various methods provided herein, the cancer is MM and the compound is thalidomide. In another embodiment of the various methods provided herein, the cancer is MM and the compound is a stereoisomer of thalidomide, or a pharmaceutically acceptable salt, solvate, hydrate, co-crystal, clathrate, or polymorph of thalidomide. In a yet another embodiment of the various methods provided herein, the cancer is MM and the compound is Compound A. In another embodiment of the various methods provided herein, the cancer is MM and the compound is a stereoisomer of Compound A, or a pharmaceutically acceptable salt, solvate, hydrate, co-crystal, clathrate, or polymorph of Compound A. In yet other specific embodiments of the various methods provided herein, the cancer is MM and the compound is Compound B. In another embodiment of the various methods provided herein, the cancer is MM and the compound is a stereoisomer of Compound B, or a pharmaceutically acceptable salt, solvate, hydrate, co-crystal, clathrate, or polymorph of Compound B. In certain embodiments, the biomarker is a CAP. In certain embodiments, the compound is likely efficacious in treating MM if the level (e.g., protein or RNA level) of the CAP as compared to the reference decreases. In certain embodiments, the compound is likely efficacious in treating MM if the level (e.g., protein or RNA level) of the CAP as compared to the reference increases. In certain embodiments, the biomarker is a CAP. In some embodiments, the biomarker is Aiolos, Ikaros, IFN, an IFN pathway protein, an IRF, a STAT, CSNK1A1, or ZFP91. In certain embodiments, the biomarker is CRBN. In some embodiments, the biomarker is CRBN, and the level of the CRBN increases as compared to a reference. In certain embodiments, the biomarker is Aiolos. In some embodiments, the biomarker is Aiolos, and the level of the Aiolos decreases as compared to a reference. In certain embodiments, the biomarker is Ikaros. In some embodiments, the biomarker is Ikaros, and the level of Ikaros decreases as compared to a reference. In other embodiments, the biomarker is an IFN pathway protein. In some embodiments, the biomarker is an IFN pathway protein, and the level of the IFN pathway protein increases as compared to a reference. In some embodiments, the biomarker is an IFN. In some embodiments, the biomarker is an IFN, and the level of the IFN increases as compared to a reference. In some embodiments, the biomarker is an IRF. In some embodiments, the biomarker is an IRF, and the level of the IRF increases as compared to a reference In some embodiments, the biomarker is a STAT. In yet other embodiments, the is CSNK1A1. In some embodiments, the biomarker is CSNK1A1 and the level of the CSNK1A1 decreases as compared to a reference. In other embodiments, the biomarker is ZFP91. In some embodiments, the biomarker is ZFP91, and the level of the ZFP91 decreases as compared to a reference. Combinations of 2, 3, 4, 5, 6, 7, 8 or more of the above-referenced biomarkers (or other biomarkers provided herein, are also contemplated.

In a specific embodiment of the various methods provided herein, the biomarker is an IFN or an IFN pathway protein. Thus, in some embodiments, the method provided herein comprises selecting a group of subjects having MM based on the level of IFN or an IFN pathway protein, or the levels of IFN or an IFN pathway protein expression within the MM, for the purposes of predicting clinical response, monitoring clinical response, or monitoring patient compliance to dosing by a compound. As shown in Examples, IFN or IFN pathway protein level changes in response to treatment with the treatment compound (or compound) provided herein. Thus, a changed level of IFN or an IFN pathway protein can be used to identify subjects who are likely to be responsive to treatment with the treatment compound provided herein and/or to predict if further treatment with the treatment compound will receive responsiveness from the subject.

In one embodiment, the cancer is MM, and the biomarker is IFN. In one embodiment, the cancer is MM, the biomarker is IFN, and the compound is lenalidomide. In one embodiment, the cancer is MM, the biomarker is IFN, and the compound is pomalidomide. In one embodiment, the cancer is MM, the biomarker is IFN, and the compound is thalidomide. In one embodiment, the cancer is MM, the biomarker is IFN, and the compound is Compound A. In one embodiment, the cancer is MM, the biomarker is IFN, and the compound is Compound B.

In one embodiment, the cancer is MM, and the biomarker is an IFN pathway protein. In one embodiment, the cancer is MM, the biomarker is an IFN pathway protein, and the compound is lenalidomide. In one embodiment, the cancer is MM, the biomarker is an IFN pathway protein, and the compound is pomalidomide. In one embodiment, the cancer is MM, the biomarker is an IFN pathway protein, and the compound is thalidomide. In one embodiment, the cancer is MM, the biomarker is an IFN pathway protein, and the compound is Compound A. In one embodiment, the cancer is MM, the biomarker is an IFN pathway protein, and the compound is Compound B.

In another specific embodiment of the various methods provided herein, the biomarker is CSNK1A1. Thus, in some embodiments, the method provided herein comprises selecting a group of subjects having MM based on the level of CSNK1A1, or the levels of CSNK1A1 expression within the MM, for the purposes of predicting clinical response, monitoring clinical response, or monitoring patient compliance to dosing by a compound. In one embodiment, the cancer is MM, and the biomarker is CSNK1A1. In one embodiment, the cancer is MM, the biomarker is CSNK1A1, and the compound is lenalidomide. In one embodiment, the cancer is MM, the biomarker is CSNK1A1, and the compound is pomalidomide. In one embodiment, the cancer is MM, the biomarker is CSNK1A1, and the compound is thalidomide. In one embodiment, the cancer is MM, the biomarker is CSNK1A1, and the compound is Compound A. In one embodiment, the cancer is MM, the biomarker is CSNK1A1, and the compound is Compound B.

In another specific embodiment of the various methods provided herein, the biomarker is ZFP91. Thus, in some embodiments, the method provided herein comprises selecting a group of subjects having MM based on the level of ZFP91, or the levels of ZFP91 expression within the MM, for the purposes of predicting clinical response, monitoring clinical response, or monitoring patient compliance to dosing by a compound. In one embodiment, the cancer is MM, and the biomarker is ZFP91. In one embodiment, the cancer is MM, the biomarker is ZFP91, and the compound is lenalidomide. In one embodiment, the cancer is MM, the biomarker is ZFP91, and the compound is pomalidomide. In one embodiment, the cancer is MM, the biomarker is ZFP91, and the compound is thalidomide. In one embodiment, the cancer is MM, the biomarker is ZFP91, and the compound is Compound A. In one embodiment, the cancer is MM, the biomarker is ZFP91, and the compound is Compound B.

In one specific embodiment of the various methods provided herein, the cancer is MDS and the compound is pomalidomide. In another embodiment of the various methods provided herein, the cancer is MDS and the compound is a stereoisomer of pomalidomide, or a pharmaceutically acceptable salt, solvate, hydrate, co-crystal, clathrate, or polymorph of pomalidomide. In another specific embodiment of the various methods provided herein, the cancer is MDS and the compound is thalidomide. In another embodiment of the various methods provided herein, the cancer is MDS and the compound is a stereoisomer of thalidomide, or a pharmaceutically acceptable salt, solvate, hydrate, co-crystal, clathrate, or polymorph of thalidomide. In a yet another embodiment of the various methods provided herein, the cancer is MDS and the compound is Compound A. In another embodiment of the various methods provided herein, the cancer is MDS and the compound is a stereoisomer of Compound A, or a pharmaceutically acceptable salt, solvate, hydrate, co-crystal, clathrate, or polymorph of Compound A. In yet other specific embodiments of the various methods provided herein, the cancer is MDS and the compound is Compound B. In another embodiment of the various methods provided herein, the cancer is MDS and the compound is a stereoisomer of Compound B, or a pharmaceutically acceptable salt, solvate, hydrate, co-crystal, clathrate, or polymorph of Compound B. In certain embodiments, the MDS is a MDS with deletion of chromosome 5q (del(5q)). In certain embodiments, the biomarker is a CAP. In certain embodiments, the compound is likely efficacious in treating MDS if the level (e.g., protein or RNA level) of the CAP as compared to the reference decreases. In certain embodiments, the compound is likely efficacious in treating MDS if the level (e.g., protein or RNA level) of the CAP as compared to the reference increases. In certain embodiments, the biomarker is a CAP. In some embodiments, the biomarker is Aiolos, Ikaros, IFN, an IFN pathway protein, an IRF, a STAT, CSNK1A1, or ZFP91. In certain embodiments, the biomarker is CRBN. In some embodiments, the biomarker is CRBN, and the level of the CRBN increases as compared to a reference. In certain embodiments, the biomarker is Aiolos. In some embodiments, the biomarker is Aiolos, and the level of the Aiolos decreases as compared to a reference. In certain embodiments, the biomarker is Ikaros. In some embodiments, the biomarker is Ikaros, and the level of Ikaros decreases as compared to a reference. In other embodiments, the biomarker is an IFN pathway protein. In some embodiments, the biomarker is an IFN pathway protein, and the level of the IFN pathway protein increases as compared to a reference. In some embodiments, the biomarker is an IFN. In some embodiments, the biomarker is an IFN, and the level of the IFN increases as compared to a reference. In some embodiments, the biomarker is an IRF. In some embodiments, the biomarker is an IRF, and the level of the IRF increases as compared to a reference In some embodiments, the biomarker is a STAT. In yet other embodiments, the is CSNK1A1. In some embodiments, the biomarker is CSNK1A1 and the level of the CSNK1A1 decreases as compared to a reference. In other embodiments, the biomarker is ZFP91. In some embodiments, the biomarker is ZFP91, and the level of the ZFP91 decreases as compared to a reference. Combinations of 2, 3, 4, 5, 6, 7, 8 or more of the above-referenced biomarkers (or other biomarkers provided herein, are also contemplated.

The present disclosure is also based, in part, on the finding that casein kinase 1A1 (CSNK1A1, also known as CK1α) is down-regulated in MDS cell lines in response to a treatment with treatment compounds provided herein (e.g., lenalidomide). Thus, in a specific embodiment, the biomarker is CSNK1A1. CSNK1A1 is a member of CSNK1 kinase family. This kinase family is involved in many cellular processes such as gene transcription, DNA repair, cell division, nuclear localization, and membrane transport. In particular, CSNK1A1 has been shown to be involved in signaling pathways, and has been shown to be a tumor suppressor.

In one embodiment, the cancer is MDS, and the biomarker is CSNK1A1. In one embodiment, the cancer is MDS, the biomarker is CSNK1A1, and the compound is lenalidomide. In one embodiment, the cancer is MDS, the biomarker is CSNK1A1, and the compound is pomalidomide. In one embodiment, the cancer is MDS, the biomarker is CSNK1A1, and the compound is thalidomide. In one embodiment, the cancer is MDS, the biomarker is CSNK1A1, and the compound is Compound A. In one embodiment, the cancer is MDS, the biomarker is CSNK1A1, and the compound is Compound B. In some embodiments, the biomarker is CSNK1A1, and wherein the level of CSNK1A1 decreases as compared to a reference.

In one specific embodiment of the various methods provided herein, the cancer is AML and the compound is pomalidomide. In another embodiment of the various methods provided herein, the cancer is AML and the compound is a stereoisomer of pomalidomide, or a pharmaceutically acceptable salt, solvate, hydrate, co-crystal, clathrate, or polymorph of pomalidomide. In another specific embodiment of the various methods provided herein, the cancer is AML and the compound is thalidomide. In another embodiment of the various methods provided herein, the cancer is AML and the compound is a stereoisomer of thalidomide, or a pharmaceutically acceptable salt, solvate, hydrate, co-crystal, clathrate, or polymorph of thalidomide. In a yet another embodiment of the various methods provided herein, the cancer is AML and the compound is Compound A. In another embodiment of the various methods provided herein, the cancer is AML and the compound is a stereoisomer of Compound A, or a pharmaceutically acceptable salt, solvate, hydrate, co-crystal, clathrate, or polymorph of Compound A. In yet other specific embodiments of the various methods provided herein, the cancer is AML and the compound is Compound B. In another embodiment of the various methods provided herein, the cancer is AML and the compound is a stereoisomer of Compound B, or a pharmaceutically acceptable salt, solvate, hydrate, co-crystal, clathrate, or polymorph of Compound B. In certain embodiments, the biomarker is a CAP. In certain embodiments, the compound is likely efficacious in treating AML if the level (e.g., protein or RNA level) of the CAP as compared to the reference decreases. In certain embodiments, the compound is likely efficacious in treating AML if the level (e.g., protein or RNA level) of the CAP as compared to the reference increases. In certain embodiments, the biomarker is a CAP. In some embodiments, the biomarker is Aiolos, Ikaros, IFN, an IFN pathway protein, an IRF, a STAT, CSNK1A1, or ZFP91. In certain embodiments, the biomarker is CRBN. In some embodiments, the biomarker is CRBN, and the level of the CRBN increases as compared to a reference. In certain embodiments, the biomarker is Aiolos. In some embodiments, the biomarker is Aiolos, and the level of the Aiolos decreases as compared to a reference. In certain embodiments, the biomarker is Ikaros. In some embodiments, the biomarker is Ikaros, and the level of Ikaros decreases as compared to a reference. In other embodiments, the biomarker is an IFN pathway protein. In some embodiments, the biomarker is an IFN pathway protein, and the level of the IFN pathway protein increases as compared to a reference. In some embodiments, the biomarker is an IFN. In some embodiments, the biomarker is an IFN, and the level of the IFN increases as compared to a reference. In some embodiments, the biomarker is an IRF. In some embodiments, the biomarker is an IRF, and the level of the IRF increases as compared to a reference In some embodiments, the biomarker is a STAT. In yet other embodiments, the is CSNK1A1. In some embodiments, the biomarker is CSNK1A1 and the level of the CSNK1A1 decreases as compared to a reference. In other embodiments, the biomarker is ZFP91. In some embodiments, the biomarker is ZFP91, and the level of the ZFP91 decreases as compared to a reference. Combinations of 2, 3, 4, 5, 6, 7, 8 or more of the above-referenced biomarkers (or other biomarkers provided herein, are also contemplated.

The present disclosure is also based, in part, on the finding that CSNK1A1 is down-regulated in AML cell lines in response to a treatment with treatment compounds provided herein (e.g., lenalidomide). Thus, in a specific embodiment, the biomarker is CSNK1A1.

In one embodiment, the cancer is AML, and the biomarker is CSNK1A1. In one embodiment, the cancer is AML, the biomarker is CSNK1A1, and the compound is lenalidomide. In one embodiment, the cancer is AML, the biomarker is CSNK1A1, and the compound is pomalidomide. In one embodiment, the cancer is AML, the biomarker is CSNK1A1, and the compound is thalidomide. In one embodiment, the cancer is AML, the biomarker is CSNK1A1, and the compound is Compound A. In one embodiment, the cancer is AML, the biomarker is CSNK1A1, and the compound is Compound B. In some embodiments, the biomarker is CSNK1A1, and wherein the level of CSNK1A1 decreases as compared to a reference.

In certain embodiments, the level of the biomarker is the nucleic acid expression level of the biomarker (e.g., DNA or RNA, such as mRNA)). In some embodiments, the level of the biomarker is the protein expression level of the biomarker. In certain embodiments, the level of the biomarker decreases as a result of down-regulation of the gene. In other embodiments, the level of the biomarker increases as a result of up-regulation of a gene. In some embodiments, the level of the biomarker increases as a result of an increase in mRNA level of the biomarker. In other embodiments, the level of the biomarker decreases as a result of a decrease in mRNA level of the biomarker (e.g., by degradation). In some embodiments, the level of the biomarker increases as a result of an increase in protein level of the biomarker. In other embodiments, the level of the biomarker decreases as a result of a decrease in protein level of the biomarker (e.g., by degradation, such as following ubiquitination. Exemplary methods of measuring or otherwise determining such levels are provided elsewhere herein. In some embodiments, a biomarker (e.g., protein or gene expression) is up-regulated. In specific embodiments, the biomarker levels increase. In certain embodiments, the compounds provided herein increase levels of the biomarker. In some embodiments, a biomarker (e.g., protein or gene expression) is down-regulated. In specific embodiments, the biomarker levels decrease. In certain embodiments, the compounds provided herein decrease levels of the biomarker.

In some embodiments, the level of the biomarker provided herein correlates with or is indicative of the responsiveness of a disease (e.g., DLBCL, MM, MDS or AML) to a treatment, (e.g., thalidomide, lenalidomide, pomalidomide, Compound A, and Compound B).

In some embodiments, the biomarker is a protein. When a biomarker is a polypeptide, protein, or peptide, the level of the biomarker can be measured by determining the protein level, or the enzymatic activity of the biomarker. In other embodiments, the biomarker is mRNA. In yet other embodiments, the biomarker is a cDNA. The level of the biomarker can be determined using the methods provided herein.

In some embodiments, the level of a biomarker is determined by measuring nucleic acids, e.g., RNA or DNA. In some embodiments, the level of a biomarker is determined by measuring protein. In one embodiment, the RNA (e.g., mRNA) or protein is purified from the sample and the level of the biomarker is measured by gene or protein expression analysis. In certain embodiments, the level of the biomarker is measured by quantitative real-time PCR (QRT-PCR), microarray, flow cytometry or immunofluorescence. In other embodiments, the level of the biomarker is measured by enzyme-linked immunosorbent assay-based methodologies (ELISA) or other similar methods known in the art. In certain embodiments of the various methods provided herein, the level of the biomarker is measured by determining the mRNA level of the biomarker. In other embodiments of the various methods provided herein, the level of the biomarker is measured by determining the cDNA level of the biomarker. In yet other embodiments of the various methods provided herein, the level of the biomarker is measured by determining the protein level of the biomarker.

In one embodiment, the mRNA or protein is purified from the tumor (or other sample) and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art. Biomarkers associated with, e.g., non-Hodgkin's lymphomas are described, for example, in U.S. Patent Publication No. 2011/0223157, the entirety of which is incorporated by reference in its entirety.

In some embodiments of the various methods provided herein the sample is a biological sample.

In some embodiments, the sample (e.g., a biological sample) is obtained from a tumor biopsy, node biopsy, or a biopsy from bone marrow, spleen, liver, brain or breast. In some embodiments, the cancer cells are obtained from a tumor biopsy, node biopsy, or a biopsy from bone marrow, spleen, liver, brain or breast.

In one embodiment of the various methods provided herein the reference is prepared by using a second cell (or other biological sample) not contacted with the compound. In another embodiment of the various methods provided herein, the reference is prepared by using a second sample obtained from the subject prior to administration of the compound to the subject; wherein the second sample is from the same source as the first sample. In other embodiments, the reference is prepared by using a second sample obtained from a healthy subject not having the disease or disorder; wherein the second sample is from the same source as the first sample.

In other embodiments of the various methods provided herein, the method comprises using immunohistochemistry to determine the level of the biomarker. In some embodiments, the method comprises using dual staining immunohistochemistry to determine the level of the biomarker.

The reference level can be determined by a plurality of methods. In some embodiments, the reference level is one that a treatment decision is made based on whether a subject having or suspected of having a disease, such as a cancer (e.g., DLBCL, MM, MDS or AML) has the level of the biomarker above the reference level. Subjects who have a level of the biomarker higher than the reference level have a different probability of responsiveness to the treatment than subjects who have a level of the biomarker lower than the reference level. In certain embodiments, the reference level is measured simultaneously with the biological sample from the subject. In some embodiments, the reference level is predetermined.

In some embodiments, the reference level is determined from a sample from the same subject that contains no disease cells, such as a cancer (e.g., DLBCL, MM, MDS or AML) cells. In other embodiments, the reference level is determined from a sample from a group of subjects that contains no disease cells, such as a cancer (e.g., DLBCL, MM, MDS or AML) cells. In yet other embodiments, the reference level is determined from a sample from a group of subjects who do not have the disease, such as a cancer (e.g., DLBCL, MM, MDS or AML). An increased level or a decreased level of the biomarker correlates positively with increased responsiveness of the subject to a treatment by a treatment compound (e.g., thalidomide, lenalidomide, pomalidomide, Compound A, or Compound B, or a stereoisomer thereof, or a pharmaceutically acceptable salt, solvate, hydrate, co-crystal, clathrate, or a polymorph thereof).

In some embodiments, the control sample is a sample containing no disease cells, such as a cancer (e.g., DLBCL, MM, MDS or AML) cells from the same subject. In other embodiments, the control sample is a sample containing no disease cells, such as a cancer (e.g., DLBCL, MM, MDS or AML) cells from a group of subjects. In yet other embodiments, the control sample is a sample from a subject having no disease, such as a cancer (e.g., DLBCL, MM, MDS or AML). In yet other embodiments, the control sample is a sample from a group of subjects having no disease, such as a cancer (e.g., DLBCL, MM, MDS or AML). An increased or a decreased level of the one or more biomarkers as compared with the level of the control sample correlates positively with increased responsiveness of the subject to a treatment by a treatment compound.

In some embodiments, the reference is prepared by using a second tumor cell not treated with the compound. In other embodiments, the reference is prepared by using a second sample obtained from the subject prior to administration of the treatment compound to the patient; and wherein the second sample is from the same source as the sample. In yet other embodiments, the reference is prepared by using a second sample obtained from a healthy subject not having a disease, such as a cancer (e.g., DLBCL, MM, MDS or AML); and wherein the second sample is from the same source as the sample.

In some embodiments, the biomarkers provided herein are determined individually. In other embodiments, two or more of the biomarkers provided herein are determined simultaneously.

In some embodiments, the level of a biomarker nucleic acid or polypeptide provided herein is measured in a biological sample from a subject, such as a cancer (e.g., DLBCL, MM, MDS or AML) cell containing-sample from the subject. In other embodiments, an affinity binding assay is used to measure the level of the biomarker polypeptide. The affinity binding assays that are applicable for use in the methods provided herein include both soluble and solid phase assays.

An example of a soluble phase affinity binding assay is immunoprecipitation using a biomarker binding agent, e.g., an antibody reactive with the biomarker polypeptide. Examples of solid phase affinity binding assays include immunohistochemical binding assays and immunoaffinity binding assays. Examples of immunoaffinity binding assays include, but are not limited to, immunohistochemistry methods, immunoblot methods, ELISA and radioimmunoassay (RIA).

An antibody useful in the methods provided herein includes a polyclonal and monoclonal antibodies. An antibody useful in the methods provided herein includes naturally occurring antibodies as well as non-naturally occurring antibodies, e.g., single chain antibodies, chimeric antibodies, bifunctional antibodies, humanized antibodies, and antigen-binding fragments thereof.

The biological sample can be liver tissue or a fluid such as blood, serum, or urine. In certain embodiments, the sample of cells from a subject is obtained via biopsy. Once a level of a biomarker is determined, this value can be correlated with clinical data on the subject from whom the sample is derived, e.g., the responsiveness of a subject to a given treatment.

In some embodiments, the sample of cells from a subject is obtained via biopsy.

In some embodiments, the level of only one of the biomarkers is monitored. In other embodiments, the levels of two or more of the biomarkers are monitored simultaneously. In certain embodiments, the level of only one of the mRNA biomarkers is monitored. In certain embodiments, the levels of two or more of the mRNA biomarkers are monitored simultaneously.

In some embodiments, the level of biomarker in the sample is less than 90% of the level of biomarker of a reference. In some embodiments, the level of biomarker in the sample is less than 80% of the level of biomarker of a reference. In other embodiments, the level of biomarker in the sample is less than 70% of the level of biomarker of a reference. In other embodiments, the level of biomarker in the sample is less than 60% of the level of biomarker of a reference. In other embodiments, the level of biomarker in the sample is less than 50% of the level of biomarker of a reference. In other embodiments, the level of biomarker in the sample is less than 40% of the level of biomarker of a reference. In yet other embodiments, the level of biomarker in the sample is less than 30% of the level of biomarker of a reference. In yet other embodiments, the level of biomarker in the sample is less than 20% of the level of biomarker of a reference. In yet other embodiments, the level of biomarker in the sample is less than 10% of the level of biomarker of a reference.

In other embodiments, the level of biomarker in the sample is 10% higher than the level of biomarker of a reference. In yet other embodiments, the level of biomarker in the sample is 20% higher than the level of biomarker of a reference. In yet other embodiments, the level of biomarker in the sample is 30% higher than the level of biomarker of a reference. In yet other embodiments, the level of biomarker in the sample is 40% higher than the level of biomarker of a reference. In yet other embodiments, the level of biomarker in the sample is 50% higher than the level of biomarker of a reference. In yet other embodiments, the level of biomarker in the sample is 60% higher than the level of biomarker of a reference. In yet other embodiments, the level of biomarker in the sample is 70% higher than the level of biomarker of a reference. In yet other embodiments, the level of biomarker in the sample is 80% higher than the level of biomarker of a reference. In yet other embodiments, the level of biomarker in the sample is 90% higher than the level of biomarker of a reference. In some embodiments, the level of biomarker in the sample is 1.5-100-fold of the level of biomarker of a reference. In some embodiments, the level of biomarker in the sample is 1.5-fold of the level of biomarker of a reference. In other embodiments, the level of biomarker in the sample is 2-fold of the level of biomarker of a reference. In yet other embodiments, the level of biomarker in the sample is 5-fold of the level of biomarker of a reference. In yet other embodiments, the level of biomarker in the sample is 10-fold of the level of biomarker of a reference.

In certain embodiments, the change in the level of a biomarker may be evaluated by a statistical hypothesis test, for example, against a null hypothesis of no difference between two levels (e.g., sample vs. reference) at a predetermined level of significance. For example, the p value might, in certain embodiments, be less than 0.01, less than 0.0.001, less than $10^{-4}$, less than $10^{-5}$, less than $10^{-6}$, less than $10^{-7}$, less than $10^{-8}$ and so forth. Such exemplary methods are provided in Section 6, infra.

In some embodiments, the protein level of biomarker is measured. For example, in some embodiments, the method provided herein comprises contacting proteins within the sample with a first antibody that immunospecifically binds to biomarker protein. In some embodiments, the method provided herein further includes (i) contacting the proteins bound to the first antibody with a second antibody with a detectable label, wherein the second antibody immunospecifically binds to biomarker, and wherein the second antibody immunospecifically binds to a different epitope on biomarker protein than the first antibody; (ii) detecting the presence of second antibody bound to the proteins; and (iii) determining the amount of biomarker protein based on the amount of detectable label in the second antibody. In other embodiments, the method provided herein further comprises (i) contacting the proteins bound to the first antibody with a second antibody with a detectable label, wherein the second antibody immunospecifically binds to the first antibody; (ii) detecting the presence of second antibody bound to the proteins; and (iii) determining the amount of biomarker protein based on the amount of detectable label in the second antibody.

Therapeutically effective amounts of the treatment compounds depend on the recipient of the treatment, the disorder being treated and the severity thereof, the composition containing the treatment compound, the time of administration, the route of administration, the duration of treatment, the compound potency, its rate of clearance and whether or not another drug is co-administered. In some embodiments, the amount of a treatment compound provided herein used to make a composition to be administered daily to a subject in a single dose or in divided doses is from about 0.03 to about 200 mg/kg body weight. Single dose compositions contain these amounts or a combination of submultiples thereof. In some embodiments, 1 mg/day to 100 mg/day treatment compounds are administered to the subject having DLBCL or MM. Exemplary daily dose includes 1, 5, 10, 15, 20, 25, 30, 35, 40, 50, 60, 70, 80, 90 or 100 mg. In some embodiments, treatment compounds are administered for 1 to 40 days.

The methods provided herein are also based, in part, on the finding that CRBN is associated with the anti-proliferative activities of certain drugs, such as the compounds provided herein. CRBN or a CAP (e.g., Ikaros, Aiolos, IFN, an IFN pathway protein, CSNK1A1, ZFP91 or a combination thereof) can be utilized as a biomarker(s) to indicate the effectiveness or progress of a disease treatment with a compound provided herein. Thus, in certain embodiments, the methods provided herein are useful for characterizing a disease or disorder (e.g., a cancer, such as DLBCL, MM, MDS or AML) in a subject, prior to, during or after the subject receiving a treatment of an immunomodulatory compound (e.g., a compound provided in Section 5.7 below).

Without being bound to a particular theory, CRBN binding may contribute to or even be required for anti-proliferative or other activities of certain compounds, such as the compounds provided herein. In certain embodiments, the compounds provided herein target CRBN or one or more CAPs. In one embodiment, the compounds provided herein bind directly to CRBN-DDB1 and/or the CRBN E3 ubiquitin-ligase complex. Mutations in CRBN could be associated with resistance to the compounds provided herein.

For example, the levels of Aiolos and Ikaros were significantly lower in the lenalidomide-resistant cells lines WSU-DLCL2 and TMD8 and the 3-(5-amino-2-methyl-4-oxo-4H-quinazolin-3-yl)-piperidine-2,6-dione cell line WSU-DLCL2 compared to the matched parental lines. Thus, in certain embodiments, the sensitivity of a cancer (e.g., DLBCL, MM, MDS or AML) or a patient having a cancer a cancer (e.g., DLBCL, MM, MDS or AML), to therapy with a compound provided herein is related to Aiolos and/or Ikaros levels.

IRF4 inhibition by lenalidomide caused downregulation of B cell receptor (BCR)-dependent NF-κB activation. While IRF4-specific siRNA mimicked effects of lenalidomide reducing NF-κB activation, IRF4 overexpression enhanced NF-κB activation and conferred resistance to lenalidomide. Furthermore, lenalidomide-induced IRF4 downregulation required the expression of CRBN. Without being bound to a particular theory, these data show that lenalidomide may have direct antitumor activity against DLBCL cells, preferentially ABC-DLBCL cells, by blocking IRF4 expression and the BCR—NF-κB signaling pathway in a CRBN-dependent manner.

It has been proposed that CRBN protein functions as a substrate receptor for Cul4-E3-ligase complexes through its interaction with DDB1. In H929 cells, compounds provided herein decrease total K48-linked polyubiquitination but not K-63-linked ubiquitination after 30 minutes treatment. At present, nearly two dozen proteins are reported to be degraded by a Cul4-DDB1 ligase2. Several studies have shown Cul4/DDB1-dependent ubiquitination of core histones, DNA repair proteins, cell cycle regulators and key signaling pathways molecules. mTORC 1 signaling requires proteasomal function and the involvement of CUL4-DDB1 ubiquitin E3 ligase. Using CST Ubiscan technology, 162 unique ubiquitin-peptides were identified which were significantly modulated by the compounds provided herein after short treatments (1-4 h). The corresponding proteins participate in nucleosome and chromatin function, protein-DNA assembly and histone H2A. The relevance of this early modification in the mode of action of compounds provided herein, and the relationship with CRBN and CUL4/DDB1 activities are under investigation.

The embodiments reflected in examples provided in Section 6 below show, among other things: (i) Aiolos and Ikaros are substrates of consequence for lenalidomide and Compound A in DLBCL, and Aiolos and Ikaros are degraded in a lenalidomide and Compound A dependent mechanism in both ABC and GCB DLBCL; (ii) Aiolos is a driver of proliferation in DLBCL, and Aiolos shRNA results in decreased c-myc levels and reduced proliferative capacity; (iii) CRBN, Aiolos and Ikaros are shown to be useful as predictive biomarkers of response in DLBCL, and a dynamic range or expression of CRBN, Aiolos and Ikaros can be useful as a patient stratification strategy for lenalidomide and/or Compound A clinical trials; (iv) mechanism(s) of resistance for lenalidomide and Compound A in DLBCL, and cell lines resistant to lenalidomide and Compound A downregulate levels of Aiolos, Ikaros and c-myc, potentially as a resistance mechanism; (v) differentiation of lenalidomide and Compound A mechanism of Action in DLBCL, and ABC DLBCL cell lines are sensitive to lenalidomide and Compound A, while GCB cell lines are less sensitive to lenalidomide; (vi) IFN and CSNK1A1 are substrates of consequence for lenalidomide and/or Compound A in DLBCL, and Compound A induces IFN response in both ABC and GCB DLBCL; (vii) the level of ZFP91 decreases in response to lenalidomide, pomalidomide, Compound A, thalidomide, or Compound B treatment; and (viii) the level of ZFP91 decreases in response to treatment using compounds provided herein through a CRBN-dependent pathway.

In certain embodiments, the methods provided herein are useful for assessing the clinical sensitivity and patient response to treatment an immunomodulatory compound (e.g., a compound provided in Section 5.7 below). In one embodiment, the immunomodulatory compound provided herein regulate (e.g., down-regulate or decrease) CRBN or one or more CAPs (e.g., Ikaros, Aiolos, ZFP91 or a combination thereof). In one embodiment, the compound provided herein regulate (e.g., up-regulate or down-regulate) CRBN or one or more CAPs (e.g., IFN, an IFN pathway protein, CSNK1A1, or a combination thereof). In another embodiment, the immunomodulatory compound provided herein provided herein binds directly to CRBN-DDB 1.

In certain embodiments, Ikaros and Aiolos are evaluated. In other embodiments, Ikaros, Aiolos and CRBN are evaluated, or any combination thereof. In certain embodiments, IFN and IFN pathway protein are evaluated. In other embodiments, IFN, IFN pathway protein, and CRBN are evaluated, or any combination thereof. In certain embodiments, ZFP91 is evaluated. In certain embodiments, ZFP91 and CRBN are evaluated. In some embodiments, ZFP91 and Ikaros are evaluated. In some embodiments, ZFP91 and Aiolos are evaluated. In some embodiments, ZFP91, CRBN, Ikaros, and Aiolos are all evaluated.

In one embodiment, the cancer is DLBCL, the biomarker is Ikaros, and the compound is lenalidomide. In some embodiments, the Ikaros level decreases as compared to the reference level. In certain embodiments, the decrease in Ikaros is the result of protein degradation. In one embodiment, the cancer is DLBCL, the biomarker is Aiolos and the compound is lenalidomide. In some embodiments, the Aiolos level decreases as compared to the reference level. In certain embodiments, the decrease in Aioos is the result of protein degradation. In one embodiment, the cancer is DLBCL, the biomarker is Ikaros and Aiolos and the compound is lenalidomide. In some embodiments, the Ikaros and Aiolos level decreases as compared to the reference level. In certain embodiments, the decrease in Ikaros and Aiolos is the result of protein degradation.

In one embodiment, the cancer is DLBCL, the biomarker is Ikaros and the compound is Compound A. In some embodiments, the Ikaros level decreases as compared to the reference level. In certain embodiments, the decrease in Ikaros is the result of protein degradation. In one embodiment, the cancer is DLBCL, the biomarker is Aiolos and the compound is Compound A. In some embodiments, the Aiolos level decreases as compared to the reference level. In certain embodiments, the decrease in Aiolos is the result of protein degradation. In one embodiment, the cancer is DLBCL, the biomarker is Ikaros and Aiolos and the compound is Compound A. In some embodiments, the Ikaros and Aiolos level decreases as compared to the reference level. In certain embodiments, the decrease in Ikaros and Aiolos is the result of protein degradation.

In one embodiment, the cancer is DLBCL, the biomarker is IFN, and the compound is Compound A. In some embodiments, the IFN level increases as compared to the reference level. In certain embodiments, the increase in the IFN is the result of up-regulation of gene expression. In some embodiments, the increase in the IFN is the result of up-regulation of protein expression. In other embodiments, the increase in the IFN is a result of reduced degradation of the protein.

In one embodiment, the cancer is DLBCL, the biomarker is IFN, and the compound is Compound A. In some embodiments, the IRF7 level increases as compared to the reference level. In certain embodiments, the increase in the IRF7 is the result of up-regulation of gene expression. In some embodiments, the increase in the IRF7 is the result of up-regulation of protein expression. In other embodiments, the increase in the IRF7 is a result of reduced degradation of the protein.

In one embodiment, the cancer is DLBCL, the biomarker is CSNK1A1, and the compound is lenalidomide. In some embodiments, the CSNK1A1 level decreases as compared to the reference level. In certain embodiments, the decrease in the CSNK1A1 is the result of protein degradation.

In one embodiment, the cancer is DLBCL, the biomarker is IFN, and the compound is Compound A. In some embodiments, the IRF7 level increases as compared to the reference level. In certain embodiments, the increase in the IRF7 is the result of up-regulation of gene expression. In some embodiments, the increase in the IRF7 is the result of up-regulation of protein expression. In other embodiments, the increase in the IRF7 is a result of reduced degradation of the protein.

In one embodiment, the biomarker is an IFN pathway protein, and the compound is lenalidomide. In one embodiment, the biomarker is an IFN pathway protein, and the compound is pomalidomide. In one embodiment, the biomarker is an IFN pathway protein, and the compound is Compound A. In some embodiments, the IFN pathway protein level increases as compared to the reference level. In certain embodiments, the increase in the IFN pathway protein is the result of up-regulation of gene expression. In some embodiments, the increase in the IFN pathway protein is the result of up-regulation of protein expression. In other embodiments, the increase in the IFN pathway protein is a result of reduced degradation of the protein. In certain embodiments, the cancer is a MM.

In one embodiment, the biomarker is an IFN pathway protein is one or more selected from the group consisting of IFIT1, IFIT3, DDX58, XAF1, IFIH1, and OAS3, and the compound is lenalidomide. In one embodiment, the biomarker is an IFN pathway protein is one or more selected from the group consisting of IFIT1, IFIT3, DDX58, XAF1, IFIH1, and OAS3, and the compound is pomalidomide. In one embodiment, the biomarker is an IFN pathway protein is one or more selected from the group consisting of IFIT1, IFIT3, DDX58, XAF1, IFIH1, and OAS3, and the compound is Compound A. In some embodiments, the IFN pathway protein level(s) increases as compared to the reference level. In certain embodiments, the increase in the IFN pathway protein(s) is the result of up-regulation of gene expression. In some embodiments, the increase in the IFN pathway protein(s) is the result of up-regulation of protein expression. In other embodiments, the increase in the IFN pathway protein(s) is a result of reduced degradation of the protein. In certain embodiments, the cancer is a MM.

In one embodiment, the biomarker is an IFN pathway protein is one or more selected from the group consisting of DDX58, IFI27, IFIT1, IFIT3, DDX58, and XAF1, and the compound is lenalidomide. In one embodiment, the biomarker is an IFN pathway protein is one or more selected from the group consisting of DDX58, IFI27, IFIT1, IFIT3, DDX58, and XAF1, and the compound is pomalidomide. In one embodiment, the biomarker is an IFN pathway protein is one or more selected from the group consisting of DDX58, IFI27, IFIT1, IFIT3, DDX58, and XAF1, and the compound is Compound A. In some embodiments, the IFN pathway protein level(s) increases as compared to the reference level. In certain embodiments, the increase in the IFN pathway protein(s) is the result of up-regulation of gene expression. In some embodiments, the increase in the IFN pathway protein(s) is the result of up-regulation of protein expression. In other embodiments, the increase in the IFN pathway protein(s) is a result of reduced degradation of the protein. In certain embodiments, the cancer is a MM.

In one embodiment, the biomarker is ISG15 and/or OAS3, and the compound is lenalidomide. In one embodiment, the biomarker is ISG15 and/or OAS3, and the compound is pomalidomide. In one embodiment, the biomarker is ISG15 and/or OAS3, and the compound is Compound A. In some embodiments, the ISG15 and/or OAS3 protein level(s) increases as compared to the reference level. In certain embodiments, the increase in the ISG15 and/or OAS3 level(s) is the result of up-regulation of gene expression. In some embodiments, the increase in the ISG15 and/or OAS3 level(s) is the result of up-regulation of protein expression. In other embodiments, the increase in the ISG15 and/or OAS3 level(s) is a result of reduced degradation of the protein. In certain embodiments, the cancer is a MM.

In one embodiment, the biomarker is IFIT1 and/or IFIT3, and the compound is lenalidomide. In one embodiment, the biomarker is IFIT1 and/or IFIT3, and the compound is pomalidomide. In one embodiment, the biomarker is IFIT1 and/or IFIT3, and the compound is Compound A. In some embodiments, the IFIT1 and/or IFIT3 protein level(s) increases as compared to the reference level. In certain embodiments, the increase in the IFIT1 and/or IFIT3 level(s) is the result of up-regulation of gene expression. In some embodiments, the increase in the IFIT1 and/or IFIT3 level(s) is the result of up-regulation of protein expression. In other embodiments, the increase in the IFIT1 and/or IFIT3 level(s) is a result of reduced degradation of the protein. In certain embodiments, the cancer is a MM.

In one embodiment, the biomarker is one or more of STAT1, STAT1-$PO_4$, STAT2 or STAT3-$PO_4$, and the compound is lenalidomide. In one embodiment, the biomarker is one or more of STAT1, STAT1-$PO_4$, STAT2 or STAT3-$PO_4$, and the compound is pomalidomide. In one embodiment, the biomarker is one or more of STAT1, STAT1-$PO_4$, STAT2 or STAT3-$PO_4$, and the compound is Compound A. In some embodiments, the is one or more of STAT1, STAT1-$PO_4$, STAT2 or STAT3-$PO_4$ protein level(s) increases as compared to the reference level. In certain embodiments, the increase in the is one or more of STAT1, STAT1-$PO_4$, STAT2 or STAT3-$PO_4$ level(s) is the result of up-regulation of gene expression. In some embodiments, the increase in the is one or more of STAT1, STAT1-$PO_4$, STAT2 or STAT3-$PO_4$ level(s) is the result of up-regulation of protein expression. In other embodiments, the increase in the is one or more of STAT1, STAT1-$PO_4$, STAT2 or STAT3-$PO_4$ level(s) is a result of reduced degradation of the protein. In some embodiments, the increase in STAT1-$PO_4$ or STAT3-$PO_4$ is the result of increased phosphorylation of the STAT1 or STAT3, respectively. In certain embodiments, the cancer is a MM.

In one embodiment, the biomarker is IKKE, and the compound is lenalidomide. In one embodiment, the biomarker is IKKE, and the compound is pomalidomide. In one embodiment, the biomarker is IKKE, and the compound is Compound A. In some embodiments, the IKKE level decreases as compared to the reference level. In certain embodiments, the decrease in the IKKE is the result of protein degradation. In certain embodiments, the cancer is a MM.

In one embodiment, the biomarker is TBK1-$PO_4$, and the compound is lenalidomide. In one embodiment, the biomarker is TBK1-$PO_4$, and the compound is pomalidomide. In one embodiment, the biomarker is TBK1-$PO_4$, and the compound is Compound A. In some embodiments, the TBK1-$PO_4$ level increases as compared to the reference level. In certain embodiments, the increase in the TBK1-$PO_4$ is the result of up-regulation of gene expression. In some embodiments, the increase in the TBK1-$PO_4$ is the result of up-regulation of protein expression. In other embodiments, the increase in the TBK1-$PO_4$ is a result of reduced degradation of the protein. In some embodiments, the increase TBK1-$PO_4$ is the result of increased phosphorylation of TBK1. In certain embodiments, the cancer is a MM.

In some embodiments, the cancer is DLBCL, the biomarker is ZFP91, and the compound is Compound A. In some embodiments, the ZFP91 level decreases as compared to the reference level. In certain embodiments, the decrease in the ZFP91 is the result of protein degradation.

In some embodiments, the cancer is DLBCL, the biomarker is Aiolos and ZFP91, and the compound is Compound A. In some embodiments, the cancer is DLBCL, the biomarker is Aiolos and ZFP91, and the compound is Compound B. In some embodiments, the cancer is DLBCL, the biomarker is Aiolos and ZFP91, and the compound is lenalidomide. In some embodiments, the cancer is DLBCL, the biomarker is Aiolos and ZFP91, and the compound is pomalidomide. In some embodiments, the cancer is DLBCL, the biomarker is Aiolos and ZFP91, and the compound is thalidomide. In some embodiments, both the Aiolos and ZFP91 levels decreases as compared to the reference level. In certain embodiments, the decrease in the Aiolos and ZFP91 is the result of protein degradation.

In some embodiments, the cancer is MM, the biomarker is Aiolos, Ikaros and ZFP91, and the compound is pomalidomide. In some embodiments, the cancer is MM, the biomarker is Aiolos, Ikaros and ZFP91, and the compound is Compound A. In some embodiments, the cancer is MM, the biomarker is Aiolos, Ikaros and ZFP91, and the compound is Compound B. In some embodiments, the cancer is MM, the biomarker is Aiolos, Ikaros and ZFP91, and the compound is lenalidomide. In some embodiments, the cancer is MM, the biomarker is Aiolos, Ikaros and ZFP91, and the compound is thalidomide. In some embodiments, the biomarker further comprises CRBN. In some embodiments, the biomarker further comprises ZNF198. In other embodiments, the biomarker further comprises IRF4, IFIT1, IFIT3 and/or P-STAT1. In some embodiments, the Aiolos, Ikaros and ZFP91 level decreases as compared to the reference level. In certain embodiments, the decrease in the Aiolos, Ikaros and ZFP91 is the result of protein degradation.

In some embodiments, the cancer is MM, the biomarker is In some embodiments, the cancer is MM, the biomarker is ZFP91, and the compound is Compound A. In other embodiments, the cancer is MM, the biomarker is ZFP91, and the compound is Compound B. In certain embodiments, the cancer is MM, the biomarker is ZFP91, and the compound is thalidomide. In some embodiments, the cancer is MM, the biomarker is ZFP91, and the compound is lenalidomide. In other embodiments, the ZFP91 level decreases as compared to the reference level. In certain embodiments, the decrease in the ZFP91 is the result of protein degradation.

In some embodiments, the cancer is MM, the biomarker is Aiolos, ZNF198 and ZFP91, and the compound is pomalidomide. In some embodiments, the cancer is MM, the biomarker is Aiolos, ZNF198 and ZFP91, and the compound is Compound A. In some embodiments, the cancer is MM, the biomarker is Aiolos, ZNF198 and ZFP91, and the compound is Compound B. In some embodiments, the cancer is MM, the biomarker is Aiolos, ZNF198 and ZFP91, and the compound is lenalidomide. In some embodiments, the cancer is MM, the biomarker is Aiolos, ZNF198 and ZFP91, and the compound is thalidomide. In some embodiments, the Aiolos, ZNF198 and ZFP91 level decreases as compared to the reference level. In certain embodiments, the decrease in the Aiolos, ZNF198 and ZFP91 is the result of protein degradation.

In some embodiments, the biomarker is AHNAK, ALOX5, AMPD3, ANXA4, ANXA6, ATP2B4, BMF, BST2, C10orf76, C19orf66, CD36, CLN3, CNN3, CORO1B, CPNE2, CSRP2, CTNND1, CTSH, DAPK2, DDX58, DHX58, DLG2, DTX3L, EIF2AK2, EPB41L1, ETV6, EXTL2, F13A1, FAM65B, FCGR2B, FES, FMNL3, GBP1, GMFG, GMPR, HIP1, HLA-B, HLA-DMA, HPSE, ID3, IFI35, IFIH1, IFIT1, IFIT3, IFIT5, IFITM2, IL4I1, IRF7, IRF9, ISG15, ISG20, ITGB7, JAK3, LAP3, LGALS1, LGALS3BP, LIMD1, MAN2A2, MARCKS, MFI2, MGARP, MOV10, MPP7, MUC1, MX1, MX2, MYO1G, NCF2, NME3, NMI, NT5C3A, OAS1, OAS2, OAS3, PARP14, PARP9, PBXIP1, PLD4, PLEKHO1, PLSCR1, PLXNB2, POMP, PPFIBP1, PTMS, QPRT, RAB13, RCN1, RGCC, RNF213, S100A13, SAMD9L, SAMHD1, SERPINH1, SLFN11, SLFN13, SLFN5, SP110, SP140, SPN, SPR, STAP1, STAT1, STAT2, TAP1, TAX1BP3, THEMIS2, THTPA, TNFAIP8L2, TNFSF8, TP53I3, TREX1, TRIM22, TTC39C, TXNIP, UBA7, UBE2L6, USP41, VCL, VNN2, ZBTB38, ARHGAP19, ASNS, ASPM, B4GALT3, BANK1, BCDIN3D, BLZF1, CA2, CA8, CAMSAP3, CCDC69, CCNB1, CDC7, CDCA3, CENPF, CSNK1A1, DHPS, DLGAP5, DOK3, ECT2, EFCAB4B, EHMT1, EHMT2, EPCAM, ESRP1, FAM195A, FBRSL1, FHOD1, FIGNL1, GPT2, GRAMD1A, GRAMD1B, GRPEL2, HJURP, HMCES, HMMR, HOXC4, ICAM2, IKZF1, IKZF3, IRS2, KIF18B, KIF22, KIF2C, LIPG, LPXN, MINA, MIS18BP1, NEIL1, NFKBID, NPIPB5, OMA1, ORC6, PARVB, PBK, PDE6D, PKMYT1, PLK1, PODXL, PODXL2, POLE2, PRDM15, PRNP, PTAFR, PTTG1, PYROXD1, RASA4B, RASSF6, RGS1, RGS2, SEC14L1, SGOL1, SGOL2, SLCO3A1, SLCO4A1, TACC3, TIMM8B, TOP2A, TPX2, TRIB3, WIZ, WSB1, WWC1, ZFP91, ZMYM2, ZNF385B, ZNF581 or ZNF644, or any combination thereof. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the compound is Compound B. In other embodiments, the compound is lenalidomide. In other embodiments, the compound is pomalidomide. In yet other embodiments, the compound is thalidomide.

In some embodiments, the biomarker is AHNAK, ALOX5, AMPD3, ANXA4, ANXA6, ATP2B4, BMF, BST2, C10orf76, C19orf66, CD36, CLN3, CNN3, CORO1B, CPNE2, CSRP2, CTNND1, CTSH, DAPK2, DDX58, DHX58, DLG2, DTX3L, EIF2AK2, EPB41L1, ETV6, EXTL2, F13A1, FAM65B, FCGR2B, FES, FMNL3, GBP1, GMFG, GMPR, HIP1, HLA-B, HLA-DMA, HPSE, ID3, IFI35, IFIH1, IFIT1, IFIT3, IFIT5, IFITM2, IL4I1, IRF7, IRF9, ISG15, ISG20, ITGB7, JAK3, LAP3, LGALS1, LGALS3BP, LIMD1, MAN2A2, MARCKS, MFI2, MGARP, MOV10, MPP7, MUC1, MX1, MX2, MYO1G, NCF2, NME3, NMI, NT5C3A, OAS1, OAS2, OAS3, PARP14, PARP9, PBXIP1, PLD4, PLEKHO1, PLSCR1, PLXNB2, POMP, PPFIBP1, PTMS, QPRT, RAB13, RCN1, RGCC, RNF213, S100A13, SAMD9L, SAMHD1, SERPINH1, SLFN11, SLFN13, SLFN5, SP110, SP140, SPN, SPR, STAP1, STAT1, STAT2, TAP1, TAX1BP3, THEMIS2, THTPA, TNFAIP8L2, TNFSF8, TP53I3, TREX1, TRIM22, TTC39C, TXNIP, UBA7, UBE2L6, USP41, VCL, VNN2 or ZBTB38, or any combination thereof. In specific embodiments, the level of the biomarker increases as compared to the reference level. In certain embodiments, the increase in the biomarker level is the result of up-regulation of gene expression. In some embodiments, the increase in the biomarker level is the result of up-regulation of protein expression. In other embodiments, the increase in the biomarker level is a result of reduced degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is AHNAK, ALOX5, AMPD3, ANXA4, ANXA6, ATP2B4, BMF, BST2, C10orf76, C19orf66, CD36, CLN3, CNN3, CORO1B, CPNE2, CSRP2, CTNND1, CTSH, DAPK2, DDX58, DHX58, DLG2, DTX3L, EIF2AK2, EPB41L1, ETV6, EXTL2, F13A1, FAM65B, FCGR2B, FES, FMNL3, GBP1, GMFG, GMPR, HIP1, HLA-B, HLA-DMA, HPSE, ID3, IFI35, IFIH1, IFIT1, IFIT3, IFIT5, IFITM2, IL4I1, IRF7, IRF9, ISG15, ISG20, ITGB7, JAK3, LAP3, LGALS1, LGALS3BP, LIMD1, MAN2A2, MARCKS, MFI2, MGARP, MOV10, MPP7, MUC1, MX1, MX2, MYO1G, NCF2, NME3, NMI, NT5C3A, OAS1, OAS2, OAS3, PARP14, PARP9, PBXIP1, PLD4, PLEKHO1, PLSCR1, PLXNB2, POMP, PPFIBP1, PTMS, QPRT, RAB13, RCN1, RGCC, RNF213, S100A13, SAMD9L, SAMHD1, SERPINH1, SLFN11, SLFN13, SLFN5, SP110, SP140, SPN, SPR, STAP1, STAT1, STAT2, TAP1, TAX1BP3, THEMIS2, THTPA, TNFAIP8L2, TNFSF8, TP53I3, TREX1, TRIM22, TTC39C, TXNIP, UBA7, UBE2L6, USP41, VCL, VNN2 or ZBTB38, or any combination thereof. In further embodiments, the level of the biomarker increases as compared to the reference level.

In some embodiments, the biomarker is ARHGAP19, ASNS, ASPM, B4GALT3, BANK1, BCDIN3D, BLZF1, CA2, CA8, CAMSAP3, CCDC69, CCNB1, CDC7, CDCA3, CENPF, CSNK1A1, DHPS, DLGAP5, DOK3, ECT2, EFCAB4B, EHMT1, EHMT2, EPCAM, ESRP1, FAM195A, FBRSL1, FHOD1, FIGNL1, GPT2, GRAMD1A, GRAMD1B, GRPEL2, HJURP, HMCES, HMMR, HOXC4, ICAM2, IKZF1, IKZF3, IRS2, KIF18B, KIF22, KIF2C, LIPG, LPXN, MINA, MIS18BP1, NEIL1, NFKBID, NPIPB5, OMA1, ORC6, PARVB, PBK, PDE6D, PKMYT1, PLK1, PODXL, PODXL2, POLE2, PRDM15, PRNP, PTAFR, PTTG1, PYROXD1, RASA4B, RASSF6, RGS1, RGS2, SEC14L1, SGOL1, SGOL2, SLCO3A1, SLCO4A1, TACC3, TIMM8B, TOP2A, TPX2, TRIB3, WIZ, WSB1, WWC1, ZFP91, ZMYM2, ZNF385B, ZNF581 or ZNF644, or any combination thereof. In specific embodiments, the level of the biomarker decreases as compared to the reference level. In certain embodiments, the decrease in the biomarker level is the result of down-regulation of gene expression. In some embodiments, the decrease in the biomarker level is the result of down-regulation of protein expression. In other embodiments, the decrease in the biomarker level is a result of increased degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is ARHGAP19, ASNS, ASPM, B4GALT3, BANK1, BCDIN3D, BLZF1, CA2, CA8, CAMSAP3, CCDC69, CCNB1, CDC7, CDCA3, CENPF, CSNK1A1, DHPS, DLGAP5, DOK3, ECT2, EFCAB4B, EHMT1, EHMT2, EPCAM, ESRP1, FAM195A, FBRSL1, FHOD1, FIGNL1, GPT2, GRAMD1A, GRAMD1B, GRPEL2, HJURP, HMCES, HMMR, HOXC4, ICAM2, IKZF1, IKZF3, IRS2, KIF18B, KIF22, KIF2C, LIPG, LPXN, MINA, MIS18BP1, NEIL1, NFKBID, NPIPB5, OMA1, ORC6, PARVB, PBK, PDE6D, PKMYT1, PLK1, PODXL, PODXL2, POLE2, PRDM15, PRNP, PTAFR, PTTG1, PYROXD1, RASA4B, RASSF6, RGS1, RGS2, SEC14L1, SGOL1, SGOL2, SLCO3A1, SLCO4A1, TACC3, TIMM8B, TOP2A, TPX2, TRIB3, WIZ, WSB1, WWC1, ZFP91, ZMYM2, ZNF385B, ZNF581 or ZNF644, or any combination thereof. In further embodiments, the level of the biomarker decreases as compared to the reference level.

In one embodiment, the biomarker is ADAM19, AIF1, ALDH1A1, ALDH2, ALOX5, AMPD3, APOBEC3G, APOE, APOH, ARHGAP10, ATP2B4, BST2, C4A, C4BPA, C4orf33, biomarkerN2, CASP4, CCR7, CD1D, CD63, CD86, CDR2, CORO1B, CPNE2, CYTH4, DAPK2, DDX58, DDX60, DDX60L, DHX58, DNASE1L3, DTX3L, EIF2AK2, ELOVL7, EPB41L1, F13A1, FAM129A, FBLN1, FCRLA, FERMT3, FGD6, FLNA, GALNT7, GBP1, GBP2, GBP4, GIPC1, GPD1, GPX3, HABP2, HBA1, HBD, HERC3, HERC6, HGF, HIGD1A, HMOX1, HSPA8, HSPB1, IFI35, IFI44, IFI44L, IFIH1, IFIT1, IFIT2, IFIT3, IFIT5, IFITM3, IL3RA, IRF7, IRF9, ISG15, ISG20, ITGA1, ITGB3, ITGB7, ITPKB, KIAA1618, L1TD1, LAP3, LDB3, LGALS1, LGALS3BP, LGALS9, LGALS9B, LMNA, LPIN1, MAP3K11, MCAM, MCM8, MGLL, MPP7, MUC1, MX1, MX2, MYL4, NCF4, NMI, NQO1, NUB1, OAS1, OAS2, OAS3, OASL, ORMDL2, OTOF, P2RY6, PAPSS2, PARP14, PARP9, PBXIP1, PHF11, PHF15, PLG, PLSCR1, PREX1, PREX2, PRIC285, PRKCI, PSAP, PTMS, RAB13, RASSF4, RCN1, RGL1, RGS13, RNF213, RTN2, RTP4, RUNX3, S100A13, SAMD9, SAMD9L, SAMHD1, SERPINA7, SERPINF2, SERPINH1, SIPA1L3, SLAMF1, SLC1A3, SLC23A2, SLC27A3, SLFN5, SOD2, SPN, SPR, SRC, STAT1, STAT2, SYNJ2BP, TAX1BP3, TBC1D13, TDRD7, TGOLN2, TLR7, TMEM87A, TMOD2, TNFAIP2, TNFAIP8L2, TRANK1, TRIM14, TRPC4, TRPM4, TSPAN14, TSPAN3, UBA7, UBE2L6, USP18, USP41, VNN2, VTN, XAF1, ZCCHC2, ZER1, ZNF385A, ZNF480, ZNF770, 3-Sep, ADIPOR2, AHR, ALCAM, ALDOC, ALKBH6, ALPL, AP1S3, APBB1IP, ARHGAP24, ARHGAP27, ARNT, BCL11A, BCL2A1, BCL2L1, BCLAF1, BNIP3L, C19orf22, C9orf40, CANX, CD22, CD44, CD5, CDC42SE2, CENPJ, CEP97, CFLAR, CLDN23, CLEC17A, COX17, CROCC, CRYM, CSNK1A1, DBN1, DENND1C, DNM2, DOK3, DTWD1, EHD1, EIF4H, ENO2, EPHA4, EPHA7, EPHB 1, ERCC6, ETS1, EVI2B, EVL, FAR1, FCRL2, FCRL3, FCRL5, GABPB1, GAMT, GAPT, GAS7, GATM, GLRX, GNG2, GRPEL2, GYPC, GZMB, HK2, HLTF, HTRA3, IFNAR2, IKZF1, IKZF3, IL16, INF2, IQSEC1, IRF4, ISYNA1, ITGAL, ITGB2, KDM5B, KHK, L1CAM, LAT2, LBH, LNX1, LRRC25, LUC7L, LYSMD2, MEF2B, MEF2D, MICAL3, MYH11, NARF, NBR1, NEDD9, NEFL, OMA1, PARVB, PDK1, PFKFB4, PGM1, PIR, PLEKHG1, PMS2CL, PODXL2, POU2AF1, PPP1R2, PTPR, PTPRE, PTPRF, PTPRO, PTTG1, PVRL1, RAB33A, RANBP3, RASGRP3, RASSF6, RBBP5, RHOF, RPS29, RPS4Y2, SAMD1, SC5DL, SEC14L1, SEMA7A, SERPINB9, SETD8, SH2D3C, SIT1, SLAMF7, SLC16A3, SLC19A2, SNAP23, SNX11, SP140, SPIB, SPTAN1, SPTB, SSBIP1, STK17B, SYNCRIP, TCP11L1, TGM2, TJAP1, TNFAIP3, TNFRSF13B, TNFRSF1B, TOM1, TOR1AIP1, TP53111, TSTD1, TUBB2B, UBE2J1, VAT1, VIM, WIPF1, WIZ, ZBTB32, ZFP91, ZMYM2, ZNF316, ZNF644, ZNF805, or any combination thereof. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the compound is Compound B. In other embodiments, the compound is lenalidomide. In other embodiments, the compound is pomalidomide. In yet other embodiments, the compound is thalidomide.

In one embodiment, the biomarker is ADAM19, AIF1, ALDH1A1, ALDH2, ALOX5, AMPD3, APOBEC3G, APOE, APOH, ARHGAP10, ATP2B4, BST2, C4A, C4BPA, C4orf33, biomarkerN2, CASP4, CCR7, CD1D, CD63, CD86, CDR2, CORO1B, CPNE2, CYTH4, DAPK2, DDX58, DDX60, DDX60L, DHX58, DNASE1L3, DTX3L, EIF2AK2, ELOVL7, EPB41L1, F13A1, FAM129A, FBLN1, FCRLA, FERMT3, FGD6, FLNA, GALNT7, GBP1, GBP2, GBP4, GIPC1, GPD1, GPX3, HABP2, HBA1, HBD, HERC3, HERC6, HGF, HIGD1A, HMOX1, HSPA8, HSPB1, IFI35, IFI44, IFI44L, IFIH1, IFIT1, IFIT2, IFIT3, IFIT5, IFITM3, IL3RA, IRF7, IRF9, ISG15, ISG20, ITGA1, ITGB3, ITGB7, ITPKB, KIAA1618, L1TD1, LAP3, LDB3, LGALS1, LGALS3BP, LGALS9, LGALS9B, LMNA, LPIN1, MAP3K11, MCAM, MCM8, MGLL, MPP7, MUC1, MX1, MX2, MYL4, NCF4, NMI, NQO1, NUB1, OAS1, OAS2, OAS3, OASL, ORMDL2, OTOF, P2RY6, PAPSS2, PARP14, PARP9, PBXIP1, PHF11, PHF15, PLG, PLSCR1, PREX1, PREX2, PRIC285, PRKCI, PSAP, PTMS, RAB13, RASSF4, RCN1, RGL1, RGS13, RNF213, RTN2, RTP4, RUNX3, S100A13, SAMD9, SAMD9L, SAMHD1, SERPINA7, SERPINF2, SERPINH1, SIPA1L3, SLAMF1, SLC1A3, SLC23A2, SLC27A3, SLFN5, SOD2, SPN, SPR, SRC, STAT1, STAT2, SYNJ2BP, TAX1BP3, TBC1D13, TDRD7, TGOLN2, TLR7, TMEM87A, TMOD2, TNFAIP2, TNFAIP8L2, TRANK1, TRIM14, TRPC4, TRPM4, TSPAN14, TSPAN3, UBA7, UBE2L6, USP18, USP41, VNN2, VTN, XAF1, ZCCHC2, ZER1, ZNF385A, ZNF480 or ZNF770, or any combination thereof. In specific embodiments, the level of the biomarker increases as compared to the reference level. In certain embodiments, the increase in the biomarker level is the result of up-regulation of gene expression. In some embodiments, the increase in the biomarker level is the result of up-regulation of protein expression. In other embodiments, the increase in the biomarker level is a result of reduced degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is ADAM19, AIF1, ALDH1A1, ALDH2, ALOX5, AMPD3, APOBEC3G, APOE, APOH, ARHGAP10, ATP2B4, BST2, C4A, C4BPA, C4orf33, biomarkerN2, CASP4, CCR7, CD1D, CD63, CD86, CDR2, CORO1B, CPNE2, CYTH4, DAPK2, DDX58, DDX60, DDX60L, DHX58, DNASE1L3, DTX3L, EIF2AK2, ELOVL7, EPB41L1, F13A1, FAM129A, FBLN1, FCRLA, FERMT3, FGD6, FLNA, GALNT7, GBP1, GBP2, GBP4, GIPC1, GPD1, GPX3, HABP2, HBA1, HBD, HERC3, HERC6, HGF, HIGD1A, HMOX1, HSPA8, HSPB1, IFI35, IFI44, IFI44L, IFIH1, IFIT1, IFIT2, IFIT3, IFIT5, IFITM3, IL3RA, IRF7, IRF9, ISG15, ISG20, ITGA1, ITGB3, ITGB7, ITPKB, KIAA1618, L1TD1, LAP3, LDB3, LGALS1, LGALS3BP, LGALS9, LGALS9B, LMNA, LPIN1, MAP3K11, MCAM, MCM8, MGLL, MPP7, MUC1, MX1, MX2, MYL4, NCF4, NMI, NQO1, NUB1, OAS1, OAS2, OAS3, OASL, ORMDL2, OTOF, P2RY6, PAPSS2, PARP14, PARP9, PBXIP1, PHF11, PHF15, PLG, PLSCR1, PREX1, PREX2, PRIC285, PRKCI, PSAP, PTMS, RAB13, RASSF4, RCN1, RGL1, RGS13, RNF213, RTN2, RTP4, RUNX3, S100A13, SAMD9, SAMD9L, SAMHD1, SERPINA7, SERPINF2, SERPINH1, SIPA1L3, SLAMF1, SLC1A3, SLC23A2, SLC27A3, SLFN5, SOD2, SPN, SPR, SRC, STAT1, STAT2, SYNJ2BP, TAX1BP3, TBC1D13, TDRD7, TGOLN2, TLR7, TMEM87A, TMOD2, TNFAIP2, TNFAIP8L2, TRANK1, TRIM14, TRPC4 TRPM4, TSPAN14, TSPAN3, UBA7, UBE2L6, USP18, USP41, VNN2, VTN, XAF1, ZCCHC2, ZER1, ZNF385A, ZNF480 or ZNF770, or any combination thereof. In further embodiments, the level of the biomarker increases as compared to the reference level.

In another embodiment, the biomarker is 3-Sep, ADIPOR2, AHR, ALCAM, ALDOC, ALKBH6, ALPL, AP1S3, APBBIIP, ARHGAP24, ARHGAP27, ARNT, BCL11A, BCL2A1, BCL2L1, BCLAF1, BNIP3L, C19orf22, C9orf40, CANX, CD22, CD44, CD5, CDC42SE2, CENPJ, CEP97, CFLAR, CLDN23, CLEC17A, COX17, CROCC, CRYM, CSNK1A1, DBN1, DENND1C, DNM2, DOK3, DTWD1, EHD1, EIF4H, ENO2, EPHA4, EPHA7, EPHB 1, ERCC6, ETS1, EVI2B, EVL, FAR1, FCRL2, FCRL3, FCRL5, GABPB1, GAMT, GAPT, GAS7, GATM, GLRX, GNG2, GRPEL2, GYPC, GZMB, HK2, HLTF, HTRA3, IFNAR2, IKZF1, IKZF3, IL16, INF2, IQSEC1, IRF4, ISYNA1, ITGAL, ITGB2, KDM5B, KHK, L1CAM, LAT2, LBH, LNX1, LRRC25, LUC7L, LYSMD2, MEF2B, MEF2D, MICAL3, MYH11, NARF, NBR1, NEDD9, NEFL, OMA1, PARVB, PDK1, PFKFB4, PGM1, PIR, PLEKHG1, PMS2CL, PODXL2, POU2AF1, PPP1R2, PTPR, PTPRE, PTPRF, PTPRO, PTTG1, PVRL1, RAB33A, RANBP3, RASGRP3, RASSF6, RBBP5, RHOF, RPS29, RPS4Y2, SAMD1, SC5DL, SEC14L1, SEMA7A, SERPINB9, SETD8, SH2D3C, SIT1, SLAMF7, SLC16A3, SLC19A2, SNAP23, SNX11, SP140, SPIB, SPTAN1, SPTB, SSBIP1, STK17B, SYNCRIP, TCP11L1, TGM2, TJAP1, TNFAIP3, TNFRSF13B, TNFRSF1B, TOM1, TOR1AIP1, TP53111, TSTD1, TUBB2B, UBE2J1, VAT1, VIM, WIPF1, WIZ, ZBTB32, ZFP91, ZMYM2, ZNF316, ZNF644, ZNF805, or any combination thereof. In specific embodiments, the level of the biomarker decreases as compared to the reference level. In certain embodiments, the decrease in the biomarker level is the result of down-regulation of gene expression. In some embodiments, the decrease in the biomarker level is the result of down-regulation of protein expression. In other embodiments, the decrease in the biomarker level is a result of increased degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is 3-Sep, ADIPOR2, AHR, ALCAM, ALDOC, ALKBH6, ALPL, AP1S3, APBB IIP, ARHGAP24, ARHGAP27, ARNT, BCL11A, BCL2A1, BCL2L1, BCLAF1, BNIP3L, C19orf22, C9orf40, CANX, CD22, CD44, CD5, CDC42SE2, CENPJ, CEP97, CFLAR, CLDN23, CLEC17A, COX17, CROCC, CRYM, CSNK1A1, DBN1, DENND1C, DNM2, DOK3, DTWD1, EHD1, EIF4H, ENO2, EPHA4, EPHA7, EPHB 1, ERCC6, ETS1, EVI2B, EVL, FAR1, FCRL2, FCRL3, FCRL5, GABPB1, GAMT, GAPT, GAS7, GATM, GLRX, GNG2, GRPEL2, GYPC, GZMB, HK2, HLTF, HTRA3, IFNAR2, IKZF1, IKZF3, IL16, INF2, IQSEC1, IRF4, ISYNA1, ITGAL, ITGB2, KDM5B, KHK, L1CAM, LAT2, LBH, LNX1, LRRC25, LUC7L, LYSMD2, MEF2B, MEF2D, MICAL3, MYH11, NARF, NBR1, NEDD9, NEFL, OMA1, PARVB, PDK1, PFKFB4, PGM1, PIR, PLEKHG1, PMS2CL, PODXL2, POU2AF1, PPP1R2, PTPR, PTPRE, PTPRF, PTPRO, PTTG1, PVRL1, RAB33A, RANBP3, RASGRP3, RASSF6, RBBP5, RHOF, RPS29, RPS4Y2, SAMD1, SC5DL, SEC14L1, SEMA7A, SERPINB9, SETD8, SH2D3C, SIT1, SLAMF7, SLC16A3, SLC19A2, SNAP23, SNX11, SP140, SPIB, SPTAN1, SPTB, SSBIP1, STK17B, SYNCRIP, TCP11L1, TGM2, TJAP1, TNFAIP3, TNFRSF13B, TNFRSF1B, TOM1, TOR1AIP1, TP53111, TSTD1, TUBB2B, UBE2J1, VAT1, VIM, WIPF1, WIZ, ZBTB32, ZFP91, ZMYM2, ZNF316, ZNF644, ZNF805, or any combination thereof. In further embodiments, the level of the biomarker decreases as compared to the reference level.

In some embodiments, the biomarker is ACSS1, ACY3, ADAM19, ADCY7, AIF1, ALDH2, AMPD3, ANK3, ANXA4, ANXA6, ANXA6, APOBEC3G, APOBR, B2M, BCL9L, BST2, C19orf66, CASP10, CCDC28B, CD40, CD59, CD83, CGN, CLSTN1, CMPK2, COL23A1, CORO1B, CORO1C, CTNND1, CTSH, CTTNBP2NL, CYTH1, CYTH4, DDX58, DDX60, DTX3L, EIF2AK2, ETHE1, F11R, FADS2, FAM76A, FDFT1, FGD4, FLNA, FLNB, FRRS1, FSCN1, GCH1, GMFG, GNB4, GNG2, H1F0, HECTD1, HELZ2, HGF, HGSNAT, HLA-A, HLA-B, HLA-G, HSPB1, HYI, IFI35, IFIT1, IFIT3, IFIT5, IL4I1, IPCEF1, IRF9, ISG15, ISG20, JADE2, KIAA0101, LAT2, LGALS1, LGALS3BP, LGALS9, LGALS9B, LMCD1, LMNA, LY75, LYSMD2, MAGED4, MAPK10, MBD1, MEA1, MT2A, MX1, MX2, MYBPC2, NCOA7, NCOA7, NEXN, NT5C3A, OAS1, OAS2, OAS3, OSBPL10, PARP10, PARP14, PARP9, PCDHGC3, PLG, PLSCR1, PRCP, PTTGIIP, PYGO2, QPCT, S100A13, SAMHD1, SERPINH1, SIRPB1, SLC23A2, SLC25A33, SLC7A7, SLFN5, SOWAHD, SP110, SP140, SPR, STAT1, STAT2, STK3, SYBU, TAP1, TAP2, TDRD7, THEMIS2, TNFAIP8L2, TNFSF9, TRIM14, TRIM21, TRIM22, TYMP, UBE2L6, USP40, VPREB1, ADIPOR2, ATF5, BACH2, BANK1, BCDIN3D, CD320, CSNK1A1, DEPTOR, ETS1, GLIPRIL1, GNG7, GPT2, HSBP1, ICAM2, IKZF1, IKZF3, KRT1, KRT14, KRT2, KRT6B, KRT9, MED12L, NEIL1, NUGGC, OMA1, PDE6D, PDZRN3, PODXL, SYNGR3, SYTL1, WIZ, ZFP91 or ZMYM2, or any combination thereof. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the compound is Compound B. In other embodiments, the compound is lenalidomide. In other embodiments, the compound is pomalidomide. In yet other embodiments, the compound is thalidomide.

In some embodiments, the biomarker is ACSS1, ACY3, ADAM19, ADCY7, AIF1, ALDH2, AMPD3, ANK3, ANXA4, ANXA6, ANXA6, APOBEC3G, APOBR, B2M, BCL9L, BST2, C19orf66, CASP10, CCDC28B, CD40, CD59, CD83, CGN, CLSTN1, CMPK2, COL23A1, CORO1B, CORO1C, CTNND1, CTSH, CTTNBP2NL, CYTH1, CYTH4, DDX58, DDX60, DTX3L, EIF2AK2, ETHE1, F11R, FADS2, FAM76A, FDFT1, FGD4, FLNA, FLNB, FRRS1, FSCN1, GCH1, GMFG, GNB4, GNG2, H1F0, HECTD1, HELZ2, HGF, HGSNAT, HLA-A, HLA-B, HLA-G, HSPB1, HYI, IFI35, IFIT1, IFIT3, IFIT5, IL4I11, IPCEF1, IRF9, ISG15, ISG20, JADE2, KIAA0101, LAT2, LGALS1, LGALS3BP, LGALS9, LGALS9B, LMCD1, LMNA, LY75, LYSMD2, MAGED4, MAPK10, MBD1, MEA1, MT2A, MX1, MX2, MYBPC2, NCOA7, NCOA7, NEXN, NT5C3A, OAS1, OAS2, OAS3, OSBPL10, PARP10, PARP14, PARP9, PCDHGC3, PLG, PLSCR1, PRCP, PTTG1IP, PYGO2, QPCT, S100A13, SAMHD1, SERPINH1, SIRPB1, SLC23A2, SLC25A33, SLC7A7, SLFN5, SOWAHD, SP110, SP140, SPR, STAT1, STAT2, STK3, SYBU, TAP1, TAP2, TDRD7, THEMIS2, TNFAIP8L2, TNFSF9, TRIM14, TRIM21, TRIM22, TYMP, UBE2L6, USP40 or VPREB1, or any combination thereof. In specific embodiments, the level of the biomarker increases as compared to the reference level. In certain embodiments, the increase in the biomarker level is the result of up-regulation of gene expression. In some embodiments, the increase in the biomarker level is the result of up-regulation of protein expression. In other embodiments, the increase in the biomarker level is a result of reduced degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is ACSS1, ACY3, ADAM19, ADCY7, AIF1, ALDH2, AMPD3, ANK3, ANXA4, ANXA6, ANXA6, APOBEC3G, APOBR, B2M, BCL9L, BST2, C19orf66, CASP10, CCDC28B, CD40, CD59, CD83, CGN, CLSTN1, CMPK2, COL23A1, CORO1B, CORO1C, CTNND1, CTSH, CTTNBP2NL, CYTH1, CYTH4, DDX58, DDX60, DTX3L, EIF2AK2, ETHE1, F11R, FADS2, FAM76A, FDFT1, FGD4, FLNA, FLNB, FRRS1, FSCN1, GCH1, GMFG, GNB4, GNG2, H1F0, HECTD1, HELZ2, HGF, HGSNAT, HLA-A, HLA-B, HLA-G, HSPB1, HYI, IFI35, IFIT1, IFIT3, IFIT5, IL4I11, IPCEF1, IRF9, ISG15, ISG20, JADE2, KIAA0101, LAT2, LGALS1, LGALS3BP, LGALS9, LGALS9B, LMCD1, LMNA, LY75, LYSMD2, MAGED4, MAPK10, MBD1, MEA1, MT2A, MX1, MX2, MYBPC2, NCOA7, NCOA7, NEXN, NT5C3A, OAS1, OAS2, OAS3, OSBPL10, PARP10, PARP14, PARP9, PCDHGC3, PLG, PLSCR1, PRCP, PTTG1IP, PYGO2, QPCT, S100A13, SAMHD1, SERPINH1, SIRPB1, SLC23A2, SLC25A33, SLC7A7, SLFN5, SOWAHD, SP110, SP140, SPR, STAT1, STAT2, STK3, SYBU, TAP1, TAP2, TDRD7, THEMIS2, TNFAIP8L2, TNFSF9, TRIM14, TRIM21, TRIM22, TYMP, UBE2L6, USP40 or VPREB1, or any combination thereof. In further embodiments, the level of the biomarker increases as compared to the reference level.

In other embodiments, the biomarker is ADIPOR2, ATF5, BACH2, BANK1, BCDIN3D, CD320, CSNK1A1, DEPTOR, ETS1, GLIPR1L1, GNG7, GPT2, HSBP1, ICAM2, IKZF1, IKZF3, KRT1, KRT14, KRT2, KRT6B, KRT9, MED12L, NEIL1, NUGGC, OMA1, PDE6D, PDZRN3, PODXL, SYNGR3, SYTL1, WIZ, ZFP91 or ZMYM2, or any combination thereof. In specific embodiments, the level of the biomarker decreases as compared to the reference level. In certain embodiments, the decrease in the biomarker level is the result of down-regulation of gene expression. In some embodiments, the decrease in the biomarker level is the result of down-regulation of protein expression. In other embodiments, the decrease in the biomarker level is a result of increased degradation of the protein. In a specific embodiment, the cancer is DLBCL. In one embodiment, the DLBCL is ABC DLBCL. In another embodiment, the DLBCL is GBC DLBCL. In certain embodiments, the compound is Compound A. In some embodiments, the cancer is DLBCL, the compound is Compound A, and the biomarker is ADIPOR2, ATF5, BACH2, BANK1, BCDIN3D, CD320, CSNK1A1, DEPTOR, ETS1, GLIPR1L1, GNG7, GPT2, HSBP1, ICAM2, IKZF1, IKZF3, KRT1, KRT14, KRT2, KRT6B, KRT9, MED12L, NEIL1, NUGGC, OMA1, PDE6D, PDZRN3, PODXL, SYNGR3, SYTL1, WIZ, ZFP91 or ZMYM2, or any combination thereof. In further embodiments, the level of the biomarker decreases as compared to the reference level.

In some embodiments, the cancer is MDS, the compound is lenalidomide, and the biomarker is CSNK1A1. In specific embodiments, the level of the CSNK1A1 decreases as compared to the reference level. In certain embodiments, the decrease in the CSNK1A1 level is the result of down-regulation of gene expression. In some embodiments, the decrease in the CSNK1A1 level is the result of down-regulation of protein expression. In other embodiments, the decrease in the CSNK1A1 level is a result of increased degradation of the protein.

In some embodiments, the cancer is MDS, the compound is lenalidomide, and the biomarker is ARHGAP18, CASS4, CORO1B, CSNK1A1, DAB2, HSPB1, IKZF1, ITM2C, PPFIBP1, SERPINH1, or ZFP91, or any combination thereof. In specific embodiments, the level of the biomarker decreases as compared to the reference level. In certain embodiments, the decrease in the biomarker level is the result of down-regulation of gene expression. In some embodiments, the decrease in the biomarker level is the result of down-regulation of protein expression. In other embodiments, the decrease in the biomarker level is a result of increased degradation of the protein.

In some embodiments, the cancer is MDS, the biomarker is ARHGAP18, CASS4, CCNA2, CORO1B, CSNK1A1, CYTL1, DAB2, HSPB1, IKZF1, ITM2C, PPFIBP1, SERPINH1, YEATS2 or ZFP91, or any combination thereof, and the compound is lenalidomide. In some embodiments, the cancer is MDS, the biomarker is ARHGAP18, CASS4, CCNA2, CORO1B, CSNKiA1, CYTL1, DAB2, HSPB1, IKZF1, ITM2C, PPFIBP1, SERPINH1, YEATS2 or ZFP91, or any combination thereof, and the compound is Compound A.

In some embodiments, the cancer is AML, the biomarker is ARHGAP18, CALM1, CASS4, CCNA2, CORO1B, CSNK1A1, DAB2, HSPB1, IKZF1, ITM2C, PPFIBP1, SERPINH1, or ZFP91, or any combination thereof, and the compound is lenalidomide. In some embodiments, the cancer is MDS, the biomarker is ARHGAP18, CASS4, CCNA2, CORO1B, CSNK1A1, CYTL1, DAB2, HSPB1, IKZF1, ITM2C, PPFIBP1, SERPINH1, YEATS2 or ZFP91, or any combination thereof, and the compound is Compound A.

In specific embodiments of the methods provided herein, the CAP is CRBN. In some embodiments, the immunomodulatory compounds provided herein up-regulate CRBN expression (e.g., protein expression). In some embodiments, IMiDs provided herein up-regulate CRBN expression (e.g., protein or gene expression). In one embodiment, 3-(5-amino-2-methyl-4-oxo-4H-quinazolin-3-yl)-piperidine-2,6-dione up-regulates CRBN expression (e.g., protein or gene expression). In another embodiment, lenalidomide up-regulates CRBN expression (e.g., protein or gene expression). In another embodiment, Compound A up-regulates CRBN expression (e.g., protein or gene expression). In some embodiments, the CRBN protein levels are increased.

In another embodiment, the immunomodulatory compounds provided herein down-regulate IL-2 expression. In another embodiment, IMiDs provided herein down-regulate Aiolos expression (e.g., protein or gene expression). In another embodiment, 3-(5-amino-2-methyl-4-oxo-4H-quinazolin-3-yl)-piperidine-2,6-dione down-regulates Aiolos expression (e.g., protein or gene expression). In another embodiment, lenalidomide down-regulates Aiolos expression (e.g., protein or gene expression). In another embodiment, Compound A down-regulates Aiolos expression (e.g., protein or gene expression). In some embodiments, the Aiolos protein levels are decreased. In specific embodiments, the Aiolos levels are decreased as a result of Aiolos protein degradation, e.g., following ubiquitination.

5.3. Methods of Detecting and Quantifying CRBN or CRBN-Associated Proteins

In certain embodiments, provided herein are methods of detecting and quantifying the protein level of biomarker, such as CRBN or a CAP, from a biological sample, comprising: (a) contacting the sample with a first antibody that immunospecifically binds to the biomarker; (b) contacting the sample bound to the first antibody with a second antibody with a detectable label, wherein the second antibody immunospecifically binds to the biomarker, and wherein the second antibody immunospecifically binds to a different epitope on the biomarker than the first antibody; (c) detecting the presence of second antibody bound to the sample; and (d) determining the protein level of the biomarker based on the amount of detectable label in the second antibody.

In some embodiments of the various methods provided herein, the method comprises using dual staining immunohistochemistry to determine the level of a biomarker, such as CRBN or a CAP. In a dual staining immunohistochemistry assay, a CAP and another cancer biomarker are simultaneously detected using a first labeled antibody targeting a CAP and a second labeled antibody targeting a cancer biomarker. Such assay can improve the specificity, accuracy and sensitivity for detecting and measuring a CAP. In some embodiments, the cancer biomarker is a DLBCL biomarker. In some embodiments, the cancer biomarker is a MM biomarker. In some embodiments, the cancer biomarker is a MDS biomarker. In some embodiments, the cancer biomarker is an AML biomarker. In some embodiments, the cancer biomarker is CD138. CD138 is a plasma cell and multiple myeloma biomarker. In addition, because the assay can simultaneously detect CD138 and a CAP in the same cell sample, the assay can detect tumor samples (containing CD138 positive cells) that express no or fewer CAPs. Thus, the dual staining immunohistochemistry method provided herein provides, among various advantages, a more sensitive measurement of a change of a CAP in a sample. In some embodiments, the level of a CAP is measured using H-score. The H-score method takes consideration of the tumor cells in the whole specimen that are CD138 positive, either with or without a CAP.

Thus, in some embodiments, the method provided herein comprises (i) contacting proteins within a sample with a first antibody that immunospecifically binds to a CAP, the first antibody being coupled with a first detectable label; (ii) contacting the proteins within the sample with a second antibody that immunospecifically binds to a cancer biomarker, the second antibody being coupled with a second detectable label; (iii) detecting the presence of the first antibody and the second antibody bound to the proteins; and (iv) determining the level of the CAP based on the amount of detectable label in the first antibody, and determining the level of the cancer biomarker based on the amount of detectable label in the second antibody. In some embodiments, the cancer biomarker is a DLBCL biomarker. In some embodiments, the cancer biomarker is a MM biomarker. In some embodiments, the cancer biomarker is a MDS biomarker. In some embodiments, the cancer biomarker is an AML biomarker. In some embodiments, the cancer biomarker is CD138. In some embodiments, H-score is used to determine the level of the CAP. In some embodiments, H-score is used to determine the level of the CAP when the level of the cancer biomarker is higher than a reference level.

In certain embodiments, provided herein are methods of detecting and quantifying the RNA (e.g., mRNA) level of a biomarker, such as CRBN or a CAP, from a biological sample, comprising: (a) obtaining RNA from the sample; (b) contacting the RNA with a primer comprising a sequence specifically binding to a sequence in the RNA to generate a first DNA molecule having a sequence complementary to said RNA; (c) amplifying the DNA corresponding to a segment of a gene encoding the biomarker; and (d) determining the RNA level of the biomarker based on the amount of the amplified DNA.

In some embodiments, the biomarker(s) are evaluated in combination with other biomarker(s) provided herein, such as Ikaros, Aiolos, IFN, an IFN pathway protein, CSNK1A1 and/or ZFP91.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of a biomarker, such as CRBN or a CAP (e.g., Ikaros, Aiolos, IFN, an IFN pathway protein, CSNK1A1, ZFP91, or a combination thereof) are immunoassays, such as western blot analysis, and an enzyme-linked immunosorbent assay (ELISA) (e.g., a sandwich ELISA). An exemplary assay provided herein for the methods of detecting and quantifying the RNA level of a biomarker, such as CRBN or a CAP (e.g., Ikaros, Aiolos, IFN, an IFN pathway protein, CSNK1A1, ZFP91, or a combination thereof) is reverse transcription polymerase chain reaction (RT-PCR), e.g., quantitative PCR or qPCR.

5.4. Subjects, Samples and Types of Cells

Subjects and Samples

In certain embodiments, the various methods provided herein use samples (e.g., biological samples) from subjects or individuals (e.g., patients). The subject can be a patient, such as, a patient with a cancer (e.g., DLBCL, MM, MDS or AML). The subject can be a mammal, for example, a human. The subject can be male or female, and can be an adult, child or infant. Samples can be analyzed at a time during an active phase of a cancer (e.g., DLBCL, MM, MDS or AML), or when the cancer (e.g., DLBCL, MM, MDS or AML) is inactive. In certain embodiments, more than one sample from a subject can be obtained.

In certain embodiments, the sample used in the methods provided herein comprises body fluids from a subject. Non-limiting examples of body fluids include blood (e.g., peripheral whole blood, peripheral blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In some embodiments, the sample is a blood sample. The blood sample can be obtained using conventional techniques as described in, e.g． Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Subpopulations of white blood cells, e.g. mononuclear cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., a compound provided in Section 5.7 below) to the subject.

Types of Cells:

In certain embodiments, the sample used in the methods provided herein comprises a plurality of cells, such as cancer (e.g., DLBCL, MM, MDS or AML) cells. Such cells can include any type of cells, e.g., stem cells, blood cells (e.g., peripheral blood mononuclear cells), lymphocytes, B cells, T cells, monocytes, granulocytes, immune cells, or tumor or cancer cells. The tumor or cancer cells or a tumor tissue, such as a tumor biopsy or a tumor explants.

The number of cells, such as cancer (e.g., DLBCL, MM, MDS, or AML) cells used in the methods can range from a single cell to about $10^9$ cells. B cells (B lymphocytes) include, for example, plasma B cells, memory B cells, B1 cells, B2 cells, marginal-zone B cells, and follicular B cells. B cells can express immunoglobulins (antibodies, B cell receptor). In one embodiment, the cells used in the methods provided herein are Karpas 422, TMD8, WSU-DLCL2, OCI-LY10, Karpas 1106P, HT, SUDHL-10, Riva, OCI-LY19, SUDHL-4, SUDHL-6, OCI-LY3, Farage, U266, DF15, or RPMI, e.g., as detected by flow cytometry.

Specific cell populations can be obtained using a combination of commercially available antibodies (e.g., Quest Diagnostic (San Juan Capistrano, Calif.); Dako (Denmark)).

The cells in the methods provided herein can be obtained from a cell line. In certain embodiments, the cell line is lenalidomide-resistant WSU-DLCL2 or TMD8 cell line. In certain embodiments, the cell line is a DLBCL cell line. In certain embodiments, the cell line is a ABC-DLBCL (activated B cell-like DLBCL) cell line, for example, TMD8, OCI-LY10, Riva, or OCI-LY3 cell line. In certain embodiments, the cell line is a GCB-DLBCL (germinal center B cell-like DLBCL) cell line, for example, Karpas 422, WSU-DLCL2, Karpas 1106P, HT, SUDHL-10, OCI-LY19, SUDHL-4, or SUDHL-6 cell line. In some embodiments, the MM cells in the methods provided herein can be obtained from a cell line. In some embodiments, the cell line is U266 cell line. In certain embodiments, the cell line is a DF15 cell line. In some embodiments, the cell line is a RPMI cell line. In some embodiments, the myeloid cancer cells in the method provided herein can be obtained from a cell line. In some embodiments, the cell line is a MDS-L cell line. In some embodiments, the cell line is a HNT-34 cell line.

It is understood that results provided in the examples herein can, in certain embodiments, be extrapolated to cancer cells from wider patient populations.

In certain embodiments, the sample used in the methods provided herein is from a diseased tissue, e.g., from an individual having cancer (e.g., DLBCL, MM, MDS or AML). In certain embodiments, the methods provided herein are useful for detecting gene rearrangement in cells from a healthy individual. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

In one embodiment, the RNA (e.g., mRNA) or protein is purified from the tumor and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

5.5. Methods of Detecting mRNA Levels in a Sample

Several methods of detecting or quantitating mRNA levels are known in the art. Exemplary methods include but are not limited to northern blots, ribonuclease protection assays, PCR-based methods, and the like. The mRNA sequence (e.g., the mRNA of a biomarker, such as CRBN or a CAP, or a fragment thereof), can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA that has altered expression during an immunomodulatory treatment in a patient, such as the mRNA of a biomarker (e.g., CRBN or a CAP). The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

In some embodiments, the mRNA sequences comprise at least one mRNA of a biomarker provided herein. In one embodiment, the biomarker is selected from the group consisting of the mRNA of DDB1, PABPC1, HNRNPR, RPL19, SYNCRIP, H2AFX, HSPA8, ALDOA, HIST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IP05, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPS6, GNAS, UBE2Q1, FERMT3, NAP1L2, TPD52, VAPA, EEF1AL3, DDIT4, NEDD8, HIST1H1A, HIST1H1B, PCM1, IKZF1, IKZF3, IFITM3, or CSNK1A1, or a fragment thereof. In one embodiment, the mRNA is Ikaros mRNA. In another embodiment, the mRNA is Aiolos mRNA. In another embodiment, the mRNA is IFITM3 mRNA. In another embodiment, the mRNA is CSNK1A1 mRNA. In other embodiments, the mRNA is IFIT3 mRNA. In one embodiment, the mRNA is DDX58 mRNA. In one embodiment, the mRNA is XAF1 mRNA. In one embodiment, the mRNA is IFIH1 mRNA. In one embodiment, the mRNA is IF127 mRNA. In one embodiment, the mRNA is IFIT1 mRNA. In one embodiment, the mRNA is ISG15 mRNA. In other embodiments, the mRNA is an IRF mRNA. In one embodiment, the mRNA is ZFP91 mRNA. The nucleic acids may be present in specific, addressable locations on a solid support; each corresponding to at least a portion of mRNA sequences that are differentially expressed upon treatment of an immunomodulatory compound in a cell or a patient.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of CRBN or CRB-associated proteins. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (qRT-PCR) can be used for both the detection and quantification of RNA targets (Bustin, et al., 2005, *Clin. Sci.*, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TaqMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

Techniques known to one skilled in the art may be used to measure the amount of an RNA transcript(s). In some embodiments, the amount of one, two, three, four, five or more RNA transcripts is measured using deep sequencing, such as ILLUMINA® RNASeq, ILLUMINA® next generation sequencing (NGS), ION TORREN™ RNA next generation sequencing, 454™ pyrosequencing, or Sequencing by Oligo Ligation Detection (SOLID™). In other embodiments, the amount of multiple RNA transcripts is measured using a microarray and/or gene chip, such as described in Section 6, infra. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art. Other examples of assays to measure RNA transcripts are described elsewhere herein.

In some embodiments, a statistical analysis or other analysis is performed on data from the assay utilized to measure an RNA transcript or protein. In certain specific embodiments, p value of those RNA transcripts or proteins differentially expressed is 0.1, 0.5, 0.4, 0.3, 0.2, 0.01, 0.05, 0.001, 0.005, or 0.0001. In specific embodiments, a false discovery rate (FDR) of 10%, 9%, 8%, 7%, 6%, 5%, 4%, 3%, 2%, 1% or less is selected.

5.6. Methods of Detecting Polypeptide or Protein Levels in a Sample

Several protein detection and quantitation methods can be used to measure the level of a biomarker, such as CRBN or a CAP. Any suitable protein quantitation method can be used. In some embodiments, antibody-based methods are used. Exemplary methods that can be used include but are not limited to immunoblotting (Western blot), enzyme-linked immunosorbent assay (ELISA), immunohistochemistry, flow cytometry, cytometric bead array, mass spectroscopy, and the like. In certain embodiments, a biomarker protein is detected using mass spectroscopy. Exemplary mass spectroscopy methods that can be used are provided in Section 6, infra. Several types of ELISA are commonly used, including direct ELISA, indirect ELISA, and sandwich ELISA. In certain embodiments, the biomarker is a CAP. In one embodiment, the CAP is Ikaros. In another embodiment, the CAP is Aiolos. In another embodiment, the CAP is CSNK1A1. In other embodiments, the CAP is IFN-induced protein with IFIT3, DDX58, XAF1, IFIH1, OAS3, IFI27, IFIT1, or ISG15, or a combination thereof. In other embodiments, the CAP is an IRF. In one embodiment, the IRF is selected from a group consisting of IRF1, IRF3, IRF4, IRF7, and IRF9. In other embodiments, the CAP is TBK1 or TBK1-$PO_4$. In another embodiment, the CAP is CSNK1A1. In another embodiment, the CAP is ZFP91.

5.7. Compounds

Compounds for the methods provided herein include, but are not limited to, the immunomodulatory compounds, including compounds known as "IMiDs®" (Celgene Corporation), a group of compounds that can be useful to treat several types of human diseases, including certain cancers.

As used herein and unless otherwise indicated, the term "immunomodulatory compound" can encompass certain small organic molecules that inhibit LPS induced monocyte TNF-α, IL-1β, IL-12, IL-6, MIP-1α, MCP-1, GM-CSF, G-CSF, and COX-2 production. These compounds can be prepared synthetically, or can be obtained commercially.

Exemplary immunomodulating compounds include but are not limited to N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (−)-3-(3,4-Dimethoxy-phenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-propionamide; (−)-{2-[1-(3-ethoxy-4-methoxy-phenyl)-2-methylsulfonylethyl]-4-acetylaminoisoindoline-1,3-dione}; (+)-{2-[1-(3-ethoxy-4-methoxyphenyl)-2-methylsulfonylethyl]-4-acetylaminoi soindoline-1,3-dione}; Difluoro-methoxy SelCIDs; 1-phthalimido-1-(3,4-diethoxy-phenyl)ethane; 3-(3,4-dimethoxyphenyl)-3-(3,5-dimethoxy-phenyl)acrylo nitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; Cyclopropyl-N-{2-[(1S)-1-(3-ethoxy-4-methoxyphenyl)-2-(methylsulfonyl)ethyl]-3-oxoisoindoline-4-yl}carboxamide; Substituted 2-(3-hydroxy-2,6-dioxopiperidin-5-yl) isoindoline; N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3 S)-3-methyl-2,6-dioxo-piperidin-3-yl]-1,3-dioxo-2,3-dihydro-1H-isoindol-5-ylmethyl]-amide; (S)—N-((2-(3-methyl-2,6-dioxopiperidin-3-yl)-1,3-dioxoisoindolin-5-yl)methyl)-4-(trifluoromethyl)benzamide; 3-(2,5-dimethyl-4-oxo-4H-quinazolin-3-yl)-piperidine-2,6-dione, 3-[4-(4-morpholin-4-ylmethyl-benzyloxy)-1-oxo-1,3-dihydro-isoindol-2-yl]-piperidine-2,6-dione, and the like.

The inflammatory cytokine TNF-α, which is produced by macrophages and monocytes during acute inflammation, causes a diverse range of signaling events within cells. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA.

Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperdin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. Publication No. 2003/0045552 published on Mar. 6, 2003, U.S. Publication No. 2003/0096841 published on May 22, 2003, and International Application No. PCT/US01/50401 (International Publication No. WO 02/059106). U.S. Publication No. 2006/0205787 describes 4-amino-2-(3-methyl-2,6-dioxopiperidin-3-yl)-isoindole-1,3-dione compositions. U.S. Publication No. 2007/0049618 describes isoindole-imide compounds. The entireties of each of the patents and patent applications identified herein are incorporated by reference. In one embodiment, immunomodulatory compounds do not include thalidomide.

Various immunomodulatory compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

Immunomodulatory compounds provided herein include, but are not limited to, 1-oxo- and 1,3 dioxo-2-(2,6-dioxopiperdin-3-yl) isoindolines substituted with amino in the benzo ring as described in U.S. Pat. No. 5,635,517 which is incorporated herein by reference.

These compounds have the structure I:

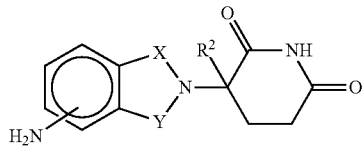

in which one of X and Y is C=O, the other of X and Y is C=O or CH$_2$, and R$^2$ is hydrogen or lower alkyl, in particular methyl. Specific immunomodulatory compounds include, but are not limited to:

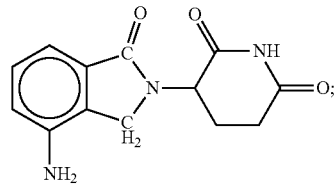

1-oxo-2-(2,6-dioxopiperidin-3-yl)-4-aminoisoindoline

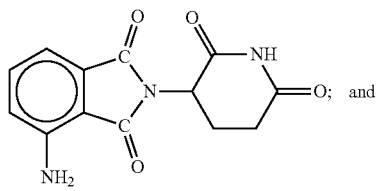

1,3-dioxo-2-(2,6-dioxopiperidin-3-yl)-4-aminoisoindoline

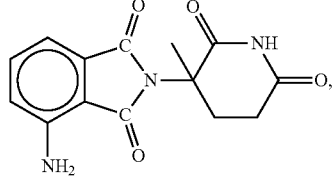

1,3-dioxo-2-(3-methyl-2,6-dioxopiperidin-3-yl)-4-aminoisoindoline and optically pure isomers thereof.

The compounds can be obtained via standard, synthetic methods (see e.g., U.S. Pat. No. 5,635,517, incorporated herein by reference). The compounds are also available from Celgene Corporation, Warren, N.J.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

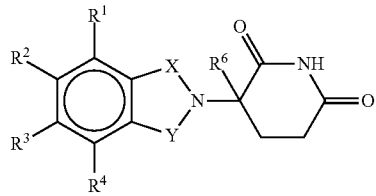

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

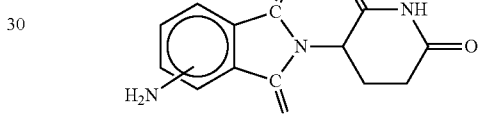

and

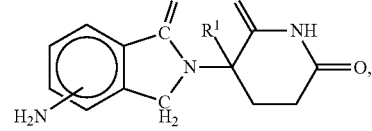

wherein R$^1$ is hydrogen or methyl. In a separate embodiment, provided herein is the use of enantiomerically pure forms (e.g. optically pure (R) or (S) enantiomers) of these compounds.

Still other specific immunomodulatory compounds disclosed herein belong to a class of isoindole-imides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula II:

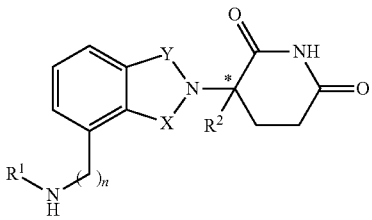

and pharmaceutically acceptable salts, hydrates, solvates, clathrates, enantiomers, diastereomers, racemates, and mixtures of stereoisomers thereof, wherein:

one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_5$)alkyl-N(R$^6$)$_2$, (C$_1$-C$_5$)alkyl-OR$^5$, (C$_1$-C$_5$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_5$)alkyl-O(CO)R$^5$;

R$^2$ is H, F, benzyl, (C$_1$-C$_5$)alkyl, (C$_2$-C$_5$)alkenyl, or (C$_2$-C$_5$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C0-C$_8$)alkyl-N(R$^6$)$_2$, (C$_1$-C$_8$)alkyl-OR$^5$, (C$_1$-C$_8$)alkyl-C(O)OR$^5$, (C$_1$-C$_5$)alkyl-O(CO)R$^5$, or C(O)OR$^5$;

R$^4$ is (C$_1$-C$_5$)alkyl, (C$_2$-C$_5$)alkenyl, (C$_2$-C$_5$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;

n is 0 or 1; and

* represents a chiral-carbon center.

In specific compounds of formula II, when n is 0 then R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(S)NHR$^3$, or (C$_1$-C$_8$)alkyl-O(CO)R$^5$;

R$^2$ is H or (C$_1$-C$_8$)alkyl; and

R$^3$ is (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_5$-C$_8$)alkyl-N(R$^6$)$_2$; (C$_0$-C$_8$)alkyl-NH—C(O)O—R$^5$; (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;

and the other variables have the same definitions.

In other specific compounds of formula II, R$^2$ is H or (C$_1$-C$_4$)alkyl.

In other specific compounds of formula II, R$^1$ is (C$_1$-C$_5$) alkyl or benzyl. CH$_2$CH$_2$OCH3, or

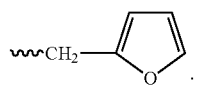

In another embodiment of the compounds of formula II, R$^1$ is

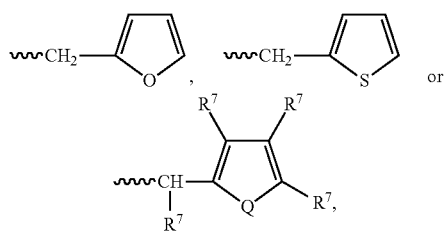

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In other specific compounds of formula II, R$^1$ is C(O)R$^3$.

In other specific compounds of formula II, R$^3$ is (C$_0$-C$_4$) alkyl-(C$_2$-C$_5$)heteroaryl, (C$_1$-C$_8$)alkyl, aryl, or (C$_0$-C$_4$)alkyl-OR$^5$.

In other specific compounds of formula II, heteroaryl is pyridyl, furyl, or thienyl.

In other specific compounds of formula II, R$^1$ is C(O) OR$^4$.

In other specific compounds of formula II, the H of C(O)NHC(O) can be replaced with (C$_1$-C$_4$)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds disclosed herein belong to a class of isoindole-imides disclosed in U.S. Patent Application Publication Nos. 2002/0045643, International Publication No. WO 98/54170, and U.S. Pat. No. 6,395,754, each of which is incorporated herein by reference. Representative compounds are of formula III:

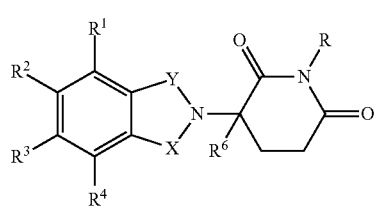

and pharmaceutically acceptable salts, hydrates, solvates, clathrates, enantiomers, diastereomers, racemates, and mixtures of stereoisomers thereof, wherein:

one of X and Y is C=O and the other is CH$_2$ or C=O;

R is H or CH$_2$OCOR';

(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, or R$^4$ is nitro or —NHR$^5$ and the remaining of R$^1$, R$^2$, R$^3$, or R$^4$ are hydrogen;

R$^5$ is hydrogen or alkyl of 1 to 8 carbons

R$^6$ hydrogen, alkyl of 1 to 8 carbon atoms, benzo, chloro, or fluoro;

R' is R$^7$—CHR$^{10}$—N(R$^8$R$^9$);

R$^7$ is m-phenylene or p-phenylene or —(CnH2n)- in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S—, or —NH—;

R$^{10}$ is hydrogen, alkyl of to 8 carbon atoms, or phenyl; and

* represents a chiral-carbon center.

Other representative compounds are of formula:

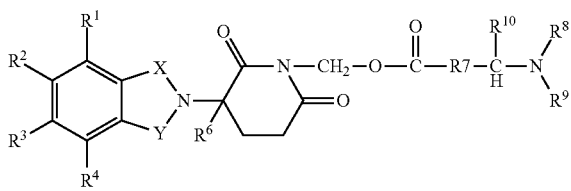

wherein:

one of X and Y is C=O and the other of X and Y is C=O or CH$_2$;

(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzo, chloro, or fluoro;

R$^7$ is m-phenylene or p-phenylene or —(CnH2n)- in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$ X$^1$CH$_2$CH$_2$— in which X$^1$ is —O—, —S—, or —NH—; and R$^{10}$ is hydrogen, alkyl of to 8 carbon atoms, or phenyl.

Other representative compounds are of formula:

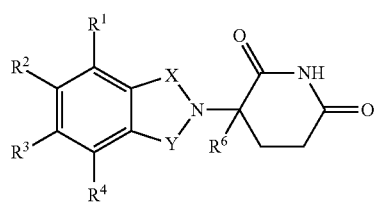

in which one of X and Y is C=O and the other of X and Y is C=O or CH$_2$;

each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and R$^6$ is hydrogen, alkyl of 1 to 8 carbon atoms, benzo, chloro, or fluoro.

Other representative compounds are of formula:

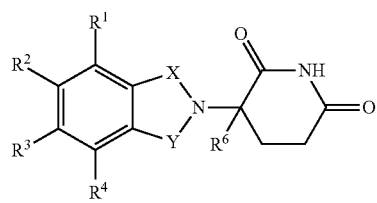

in which:

one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and R$^6$ is alkyl of 1 to 8 carbon atoms, benzo, chloro, or fluoro.

Specific examples of the compounds are of formula:

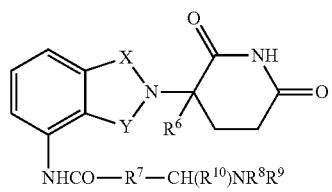

in which:

one of X and Y is C=O and the other of X and Y is C=O or CH$_2$;

R$^6$ is hydrogen, alkyl of 1 to 8 carbon atoms, benzyl, chloro, or fluoro;

R$^7$ is m-phenylene, p-phenylene or —(CnH2n)- in which n has a value of 0 to 4; each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and R$^{10}$ is hydrogen, alkyl of 1 to 8 carbon atoms, or phenyl.

Other specific immunomodulatory compounds are 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

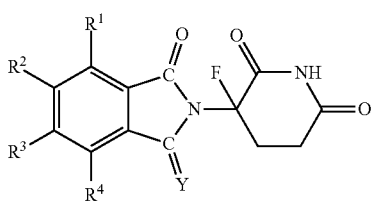

wherein:

Y is oxygen or $H_2$ and each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds are the tetra substituted 2-(2,6-dioxopiperdin-3-yl)-1-oxoisoindolines described in U.S. Pat. No. 5,798,368, which is incorporated herein by reference. Representative compounds are of formula:

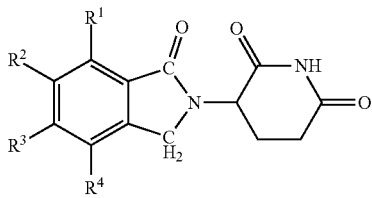

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl) isoindolines disclosed in U.S. Pat. No. 6,403,613, which is incorporated herein by reference. Representative compounds are of formula:

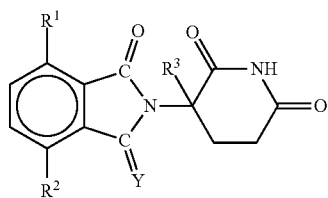

in which

Y is oxygen or $H_2$, a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

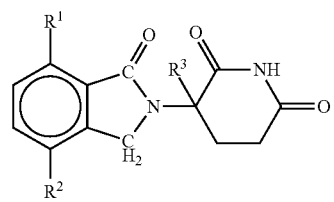

wherein
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

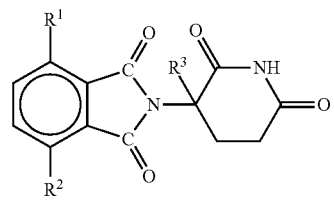

wherein:
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl.

Other specific immunomodulatory compounds disclosed herein are 1-oxo and 1,3-dioxoisoindolines substituted in the 4- or 5-position of the indoline ring described in U.S. Pat. Nos. 6,380,239 and 7,244,759, both of which are incorporated herein by reference. Representative compounds are of formula:

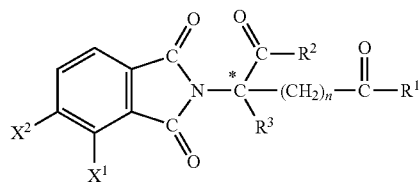

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

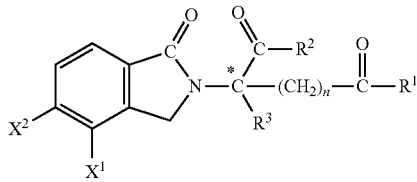

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

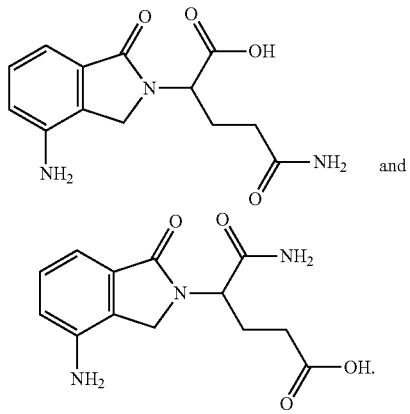

Other representative compounds are of formula:

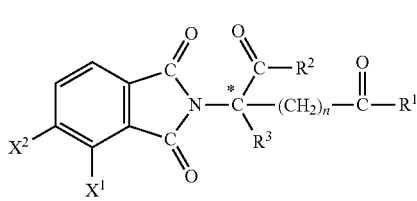

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

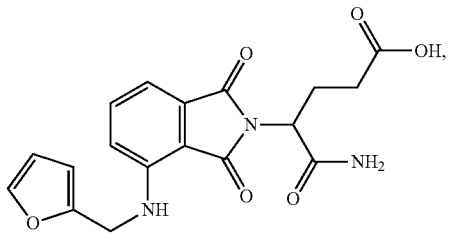

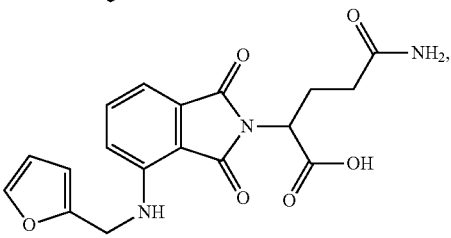

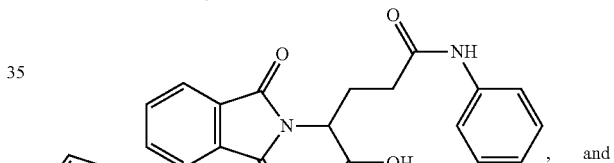

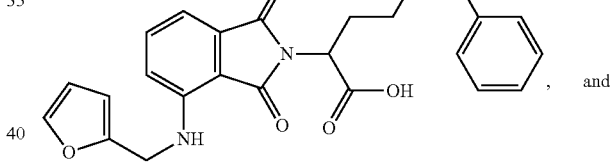

, and

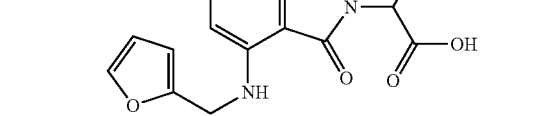

Other specific examples of the compounds are of formula:

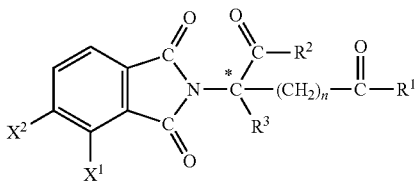

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;

R³ is alkyl of one to six carbons, halo, or hydrogen;

Z is hydrogen, phenyl, an acyl of one to six carbons, or an alkyl of one to six carbons; and n has a value of 0, 1, or 2; and if —COR² and —(CH₂)ₙCOR¹ are different, the carbon atom designated C* constitutes a center of chirality.

Other representative compounds are of formula:

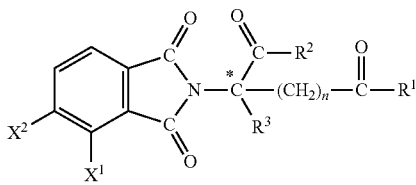

wherein:

one of X¹ and X² is alkyl of one to six carbons;

each of R¹ and R², independent of the other, is hydroxy or NH—Z;

R³ is alkyl of one to six carbons, halo, or hydrogen;

Z is hydrogen, phenyl, an acyl of one to six carbons, or an alkyl of one to six carbons; and n has a value of 0, 1, or 2; and if —COR² and —(CH₂)ₙCOR¹ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

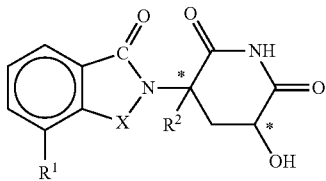

wherein:

the carbon atoms designated * constitute centers of chirality;

X is —C(O)— or —CH₂—;

R¹ is alkyl of 1 to 8 carbon atoms or —NHR³;

R² is hydrogen, alkyl of 1 to 8 carbon atoms, or halogen; and

R³ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —COR⁴ in which R⁴ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

Other specific compounds provided herein are of formula:

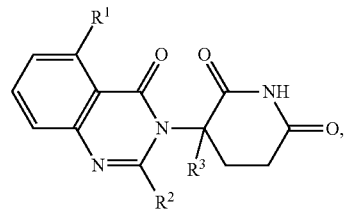

and pharmaceutically acceptable salts, solvates, and stereoisomers thereof, wherein:

R¹ is: hydrogen; halo; —(CH₂)ₙOH; (C₁-C₆)alkyl, optionally substituted with one or more halo;

(C₁-C₆)alkoxy, optionally substituted with one or more halo; or

—(CH₂)ₙNHRᵃ, wherein Rᵃ is:

hydrogen;

(C₁-C₆)alkyl, optionally substituted with one or more halo;

(CH₂)ₙ-(6 to 10 membered aryl);

—C(O)—(CH₂)ₙ-(6 to 10 membered aryl) or —C(O)—(CH₂)ₙ-(6 to 10 membered heteroaryl), wherein the aryl or heteroaryl is optionally substituted with one or more of: halo; —SCF₃; (C₁-C₆)alkyl, itself optionally substituted with one or more halo; or (C₁-C₆)alkoxy, itself optionally substituted with one or more halo;

—C(O)—(C₁-C₅)alkyl, wherein the alkyl is optionally substituted with one or more halo;

—C(O)—(CH₂)ₙ—(C₃-C₁₀-cycloalkyl);

—C(O)—(CH₂)ₙ—NRᵇRᶜ, wherein Rᵇ and Rᶜ are each independently:

hydrogen;

(C₁-C₆)alkyl, optionally substituted with one or more halo;

(C₁-C₆)alkoxy, optionally substituted with one or more halo; or 6 to 10 membered aryl, optionally substituted with one or more of: halo;

(C₁-C₆)alkyl, itself optionally substituted with one or more halo; or (C₁-C₆)alkoxy, itself optionally substituted with one or more halo;

—C(O)—(CH₂)ₙ—O—(C₁-C₆)alkyl; or

—C(O)—(CH₂)ₙ—O—(CH₂)ₙ-(6 to 10 membered aryl);

R² is: hydrogen; —(CH₂)ₙOH; phenyl; —O—(C₁-C₆)alkyl; or (C₁-C₆)alkyl, optionally substituted with one or more halo;

R³ is: hydrogen; or (C₁-C₆)alkyl, optionally substituted with one or more halo; and n is 0, 1, or 2.

Specific examples include, but are not limited to, 3-(5-amino-2-methyl-4-oxo-4H-quinazolin-3-yl)-piperidine-2,6-dione ("Compound A"), which has the following structure:

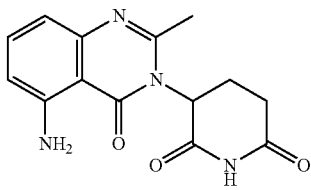

A or an enantiomer or a mixture of enantiomers thereof; or a pharmaceutically acceptable salt, solvate, hydrate, co-crystal, clathrate, or polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional Pat. App. No. 61/451,995, filed Mar. 11, 2011, which is incorporated herein by reference in its entirety.

Specific examples include, but are not limited to lenalidomide, which has the following structure:

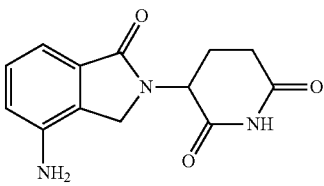 [SMILES: Nc1cccc2c1CN(C1CCC(=O)NC1=O)C2=O]

or an enantiomer or a mixture of enantiomers thereof; or a pharmaceutically acceptable salt, solvate, hydrate, co-crystal, clathrate, or polymorph thereof.

Lenalidomide can be prepared as described in WO2012/149299, the disclosure of which is incorporated herein by reference in its entirety. The compound can be also synthesized according to other methods apparent to those of skill in the art based upon the teaching herein.

Specific examples include, but are not limited to 3-[4-(4-morpholin-4-ylmethyl-benzyloxy)-1-oxo-1,3-dihydro-isoindol-2-yl]-piperidine-2,6-dione (Compound B), which has the following structure:

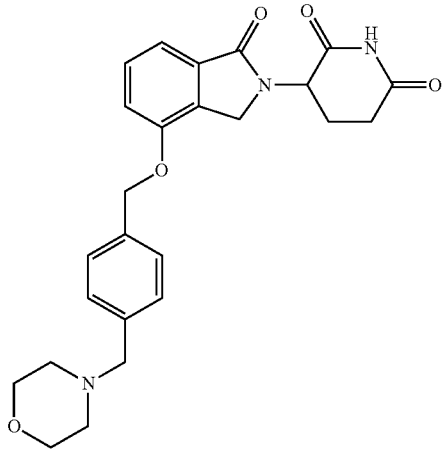

B or an enantiomer or a mixture of enantiomers thereof; or a pharmaceutically acceptable salt, solvate, hydrate, co-crystal, clathrate, or polymorph thereof.

Other specific compounds provided herein are of formula:

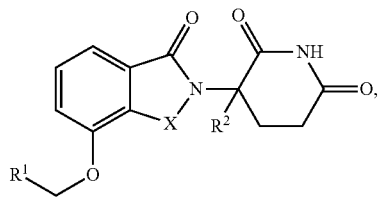

or a pharmaceutically acceptable salt, solvate or stereoisomer thereof, wherein:

X is C=O or $CH_2$;

$R^1$ is —Y—$R^3$;

$R^2$ is H or ($C_1$-$C_6$)alkyl;

Y is: 6 to 10 membered aryl, heteroaryl or heterocycle, each of which may be optionally substituted with one or more halogen; or a bond;

$R^3$ is: —$(CH_2)_n$-aryl, —O—$(CH_2)_n$-aryl or —$(CH_2)_n$—O-aryl, wherein the aryl is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen;

$(CH_2)_n$-heterocycle, —O—$(CH_2)_n$-heterocycle or —$(CH_2)_n$—O-heterocycle, wherein the heterocycle is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen;

$(CH_2)_n$-heteroaryl, —O—$(CH_2)_n$-heteroaryl or —$(CH_2)_n$—O-heteroaryl, wherein the heteroaryl is optionally substituted with one or more: $(C_1-C_6)$alkyl, itself optionally substituted with one or more halogen; $(C_1-C_6)$alkoxy, itself substituted with one or more halogen; oxo; amino; carboxyl; cyano; hydroxyl; halogen; deuterium; 6 to 10 membered aryl or heteroaryl, optionally substituted with one or more $(C_1-C_6)$alkyl, $(C_1-C_6)$alkoxy or halogen; —CONH$_2$; or —COO—$(C_1-C_6)$alkyl, wherein the alkyl may be optionally substituted with one or more halogen; and n is 0, 1, 2 or 3.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. 2006/0188475, 2006/0205787, and 2007/0049618, each of which is incorporated by reference herein in its entirety.

The compounds may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.8. Kits

Kits and compositions for carrying out the methods provided herein are also contemplated. In certain embodiments, provided herein are kits useful for determining the efficacy of an immunomodulatory compound. In certain embodiments, provided herein are kits useful for determining whether a compound is immunomodulatory. In certain embodiments, provided herein are kits useful for assessing the efficacy of a compound in treating a disease or disorder. In some embodiments, provided herein are kits useful for determining the effect of an immunomodulatory compound. In certain embodiments, provided herein are kits useful for predicting the likelihood of an effective DLBCL, MM, MDS, or AML or for monitoring the effectiveness of a treatment with one or more compounds (e.g., drugs). The kit comprises a solid support, and a means for detecting the protein expression of at least one biomarker in a biological sample.

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, RT-qPCR, deep sequencing or a microarray. In some embodiments, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein In another specific embodiment, the pharmaceutical or assay kit comprises, in a container, a compound or a pharmaceutical composition, and further comprises, in one or more containers, components for conducting flow cytometry or an ELISA.

In another aspect, provided herein are kits for measuring biomarkers providing the materials necessary to measure the abundance of one or more of the gene products of the genes or a subset of genes (e.g., one, two, three, four, five or more genes) of the biomarkers provided herein. Such kits may comprise materials and reagents required for measuring RNA or protein. In some embodiments, such kits include microarrays, wherein the microarray is comprised of oligonucleotides and/or DNA and/or RNA fragments which hybridize to one or more of the products of one or more of the genes or a subset of genes of the biomarkers provided herein, or any combination thereof. In some embodiments, such kits may include primers for PCR of either the RNA product or the cDNA copy of the RNA product of the genes or subset of genes, or both. In some embodiments, such kits may include primers for PCR as well as probes for Quantitative PCR. In some embodiments, such kits may include multiple primers and multiple probes wherein some of said probes have different fluorophores so as to permit multiplexing of multiple products of a gene product or multiple gene products. In some embodiments, such kits may further include materials and reagents for creating cDNA from RNA. In some embodiments, such kits may include antibodies specific for the protein products of a gene or subset of genes of the biomarkers provided herein. Such kits may additionally comprise materials and reagents for isolating RNA and/or proteins from a biological sample. In addition such kits may include materials and reagents for synthesizing cDNA from RNA isolated from a biological sample. In some embodiments, such kits may include, a computer program product embedded on computer readable media for predicting whether a patient is clinically sensitive to a compound. In some embodiments, the kits may include a computer program product embedded on a computer readable media along with instructions.

In some embodiments, kits for measuring the expression of one or more nucleic acid sequences of a gene or a subset of genes of the biomarkers provided herein. In a specific embodiment, such kits measure the expression of one or more nucleic acid sequences associated with a gene or a subset of genes of the biomarkers provided herein. In accordance with this embodiment, the kits may comprise materials and reagents that are necessary for measuring the expression of particular nucleic acid sequence products of genes or a subset of genes of the biomarkers provided herein. For example, a microarray or RT-PCR kit may be produced for a specific condition and contain only those reagents and materials necessary for measuring the levels of specific RNA transcript products of the genes or a subset of genes of the biomarkers provided herein to predict whether a hematological cancer in a patient is clinically sensitive to a compound. Alternatively, in some embodiments, the kits can comprise materials and reagents that are not limited to those required to measure the expression of particular nucleic acid sequences of any particular gene of the biomarkers provided herein. For example, in certain embodiments, the kits comprise materials and reagents necessary for measuring the levels of expression of 1, 2, 3, 4, 5, 6, 7, 8, 9, 10, 15, 20, 25, 30, 35, 40, 45, 50 or more of the genes of the biomarkers provided herein, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than those of the biomarkers provided herein. In other embodiments, the kits contain reagents and materials necessary for measuring the levels of expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more of the genes of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are genes not of the biomarkers provided herein, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are genes not of the biomarkers provided herein.

For nucleic acid microarray kits, the kits generally comprise probes attached to a solid support surface. In one such embodiment, probes can be either oligonucleotides or longer length probes including probes ranging from 150 nucleotides in length to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from the performance of the assay. In a specific embodiment, the kits comprise instructions for predicting whether a hematological cancer in a patient is clinically sensitive to a compound. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

In certain embodiments, a nucleic acid microarray kit comprises materials and reagents necessary for measuring the levels of expression of 1, 2, 3, 4, 5, 6, 7, 8, 9, 10, 15, 20, 25, 30, 35, 40, 45, 50 or more of the genes identified of the biomarkers provided herein, or a combination thereof, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than those of the biomarkers provided herein. In other embodiments, a nucleic acid microarray kit contains reagents and materials necessary for measuring the levels of expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not of the biomarkers provided herein.

For Quantitative PCR, the kits generally comprise preselected primers specific for particular nucleic acid sequences. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for the nucleic acid sequences associated with or indicative of a condition. The probes may or may not be labeled with a fluorophore. The probes may or may not be labeled with a quencher molecule. In some embodiments the Quantitative PCR kits also comprise components suitable for reverse-transcribing RNA including enzymes (e.g., reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the assay and methods for interpreting and analyzing the data resulting from the performance of the assay. In a specific embodiment, the kits contain instructions for predicting whether a hematological cancer in a patient is clinically sensitive to a compound.

For antibody based kits, the kit can comprise, for example: (1) a first antibody (which may or may not be attached to a solid support) which binds to a peptide, polypeptide or protein of interest; and, optionally, (2) a second, different antibody which binds to either the peptide, polypeptide or protein, or the first antibody and is conjugated to a detectable label (e.g., a fluorescent label, radioactive isotope or enzyme). In a specific embodiment, the peptide, polypeptide or protein of interest is associated with or indicative of a condition (e.g., a disease). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for predicting whether a hematological cancer in a patient is clinically sensitive to a compound.

In one embodiment a kit provided herein comprises a compound provided herein, or a pharmaceutically acceptable salt, solvate or hydrate thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support and the like, are also contemplated in relation to any of the various methods and/or kits provided and the like, are also contemplated in relation to any of the various methods and/or kits provided herein.

Certain embodiments of the invention are illustrated by the following non-limiting examples.

6 EXAMPLES

The examples show, among other things: (i) Aiolos and Ikaros are substrates of consequence for lenalidomide and Compound A in DLBCL, and Aiolos and Ikaros are degraded in a lenalidomide and Compound A dependent mechanism in both ABC and GCB DLBCL; (ii) Aiolos is a driver of proliferation in DLBCL, and Aiolos shRNA results in decreased c-myc levels and reduced proliferative capacity; (iii) CRBN, Aiolos and Ikaros are shown to be useful as predictive biomarkers of response in DLBCL, and a dynamic range or expression of CRBN, Aiolos and Ikaros can be useful as a patient stratification strategy for lenalidomide and/or Compound A clinical trials; (iv) mechanism(s) of resistance for lenalidomide and Compound A in DLBCL, and cell lines resistant to lenalidomide and Compound A downregulate levels of Aiolos, Ikaros and c-myc, potentially as a resistance mechanism; (v) differentiation of lenalidomide and Compound A mechanism of action in DLBCL, and ABC DLBCL cell lines are sensitive to lenalidomide and Compound A, while GCB cell lines are less sensitive to lenalidomide; (vi) IFN and CSNK1A1 are substrates of consequence for lenalidomide and/or Compound A in DLBCL, and Compound A induces IFN response in both ABC and GCB DLBCL; (vii) the level of ZFP91 decreases in response to lenalidomide, pomalidomide, Compound A, thalidomide, or Compound B treatment; (viii) the level of ZFP91 decreases in response to treatment using compounds provided herein through a CRBN-dependent pathway; (ix) lenalidomide promotes degradation of Casein Kinase 1α (CK1α(CSNK1A1)) in MDS and AML cells; and (x) MG-132 or Compound A pre-treatment blocks lenalidomide-induced degradation of CK1α and Ikaros in HNT-34 Cells.

6.1 Preparation of 3-(4-amino-1-oxo-1,3-dihydro-isoindol-2-yl)-piperidine-2,6-dione (lenalidomide)

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$ (aq) 7.27 min(98.92%); Anal. Calcd for C$_9$H$_8$NO$_4$Br: C, 39.44; H, 2.94; N, 5.1 1; Br, 29.15. Found: C, 39.46; H, 3.00; N, 5.00; Br, 29.1 1.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL)

and dried. The solvent was removed in vacuo and the residue was purified by flash chromatography (3% $CH_3OH$ in methylene chloride) to afford 2.84 g (60%) of crude product which was used directly in the next reaction: 1H NMR ($CDCl_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 $CH_3CN/0.1\%$ $H_3PO_4$ (aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR ($DMSO-d_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 and 10.4 Hz, 1H), 2.34-2.10 (m, 4H); $^{13}C$ NMR ($DMSO-d_6$) δ 173.03, 171.88, 165.96, 143.35, 137.49, 134.77, 130.10, 129.61, 126.95, 53.65, 48.13, 31.50, 24.69; Anal. Calcd for $C_{13}H_{13}N_3O_6$: C, 50.82; H, 4.26; N, 13.68. Found: C, 50.53; H. 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 1 1.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR ($DMSO-d_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}C$ NMR ($DMSO-d_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 $CH_3CN/0.1\%$ $H_3PO_4$ (aq) 3.67 min(100%); Anal. Calcd for $C_{13}H_nN_3O_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2, 6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1H$ NMR ($DMSO-d_6$) δ 11.01 (s, 1H). 7.19 (t, J=7.6 Hz, 1H). 6.90 (d. J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}C$ NMR ($DMSO-d_6$) δ 172.85, 171.19, 168.84, 143.58, 132.22. 128.79, 125.56, 1 16.37, 1 10.39, 51.48, 45.49, 31.20, 22.74; HPLC. Waters Nova-Pak/C18, 3.9×150 mm, 4 micron, 1 mL/min, 240 nm, 10/90 $CH_3CN/0.1\%$ $H_3PO_4$ (aq) 0.96 min(100%); Chiral analysis, Daicel Chiral Pak AD, 40/60 Hexane/IPA, 6.60 min(99.42%); Anal. Calcd for $C_{13}H_{13}N_3O_3$: C, 60.23; H, 5.05; N, 16.21. Found: C, 59.96; H. 4.98; N, 15.84.

3-(4-Amino-1-oxo-1,3-dihydro-isoindol-2-yl)-piperidine-2,6-dione may also be prepared by methods known in the art, for example, as provided in *Drugs of the Future,* 2003, 28(5): 425-431, the entirety of which is incorporated by reference.

6.2 Preparation of 3-(5-amino-2-methyl-4-oxo-4H-quinazolin-3-yl)-piperidine-2,6-dione (Compound A)

To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): 1H NMR ($DMSO-d_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}C$ NMR ($DMSO-d_6$) δ 125.33, 129.15, 130.25, 132.54, 136.72, 147.03, 165.90, 167.31.

To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry C18, 5 μm, 3.9×150 mm, 1 mL/min, 240 nm, $CH_3CN/0.1\%$ $H_3PO_4$, 5% grad to 95% over 5 min, 5.83 min (85%); $^1H$ NMR ($DMSO-d_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, $NH_2$); $^{13}C$ NMR ($DMSO-d_6$) δ 105.58, 110.14, 120.07, 131.74, 149.80, 151.36, 166.30; LCMS: MH=183.

A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry C18, 5 μm, 3.9×150 mm, 1 mL/min, 240 nm, $CH_3CN/0.1\%$ $H_3PO_4$, 5% grad 95% in 5 min, 5.36 min (92%); $^1H$ NMR ($DMSO-d_6$) δ 2.42 (s, 3H, $CH_3$), 7.79 (dd, J=1, 8 Hz, 1H, Ar), 7.93 (dd, J=1, 8 Hz, 1H, Ar), 8.06 (t, J=8 Hz, 1H, Ar); $^{13}C$ NMR ($DMSO-d_6$) δ 20.87, 107.79, 121.54, 128.87, 137.19, 147.12, 148.46, 155.18, 161.78; LCMS: MH=207.

Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry C$_{18}$, 5 m, 3.9×150 mm, 1 mL/min, 240 nm, 10/90 CH$_3$CN/0.1% H$_3$PO$_4$, 3.52 min (99.9%); mp: 293-295° C.; $^1$H NMR (DMSO-d$_6$) δ 2.10-2.17 (m, 1H, CHH), 2.53 (s, 3H, CH$_3$), 2.59-2.69 (m, 2H, CH$_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, NH$_2$), 7.36 (t, J=8 Hz, 1H, Ar), 10.98 (s, 1H, NH); $^{13}$C NMR (DMSO-d$_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for C$_{14}$H$_{14}$N$_4$O$_3$+0.3H$_2$O: C, 57.65; H, 5.05; N, 19.21. Found: C, 57.50; H, 4.73; N, 19.00.

6.3 Preparation of 3-[4-(4-morpholin-4-ylmethyl-benzyloxy)-1-oxo-1,3-dihydro-isoindol-2-yl]-piperidine-2,6-dione (Compound B)

Procedure 1:

Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the THF solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated NaHCO$_3$ (25 mL). The mixture was extracted with EtOAc (2×50 mL). The organic layer was washed with water (30 mL), brine (30 mL), dried over MgSO$_4$ and concentrated. To the resulting solid was added EtOAc (10 mL) followed by hexane (10 mL) under stirring. The suspension was filtered to give 3-[4-(4-morpholin-4-ylmethyl-benzyloxy)-1-oxo-1,3-dihydro-isoindol-2-yl]-piperidine-2,6-dione as white solid (1.5 g, 73% yield). HPLC: Waters Symmetry C18, 5 μm, 3.9×150 mm, 1 mL/min, 240 nm, gradient to 95/5 acetonitrile/0.1% H$_3$PO$_4$ in 5 min: tR=4.78 min (97.5%); mp: 210-212° C.; $^1$H NMR (DMSO-d$_6$) δ 1.86-2.09 (m, 1H, CHH), 2.29-2.38 (m, 4H, CH$_2$, CH$_2$), 2.44 (dd, J=4.3, 13.0 Hz, 1H, CHH), 2.53-2.64 (m, 1H, CHH), 2.82-2.99 (m, 1H, CHH), 3.46 (s, 2H, CH$_2$), 3.52-3.61 (m, 4H, CH$_2$, CH$_2$), 4.18-4.51 (m, 2H, CH$_2$), 5.11 (dd, J=5.0, 13.3 Hz, 1H, NCH), 5.22 (s, 2H, CH$_2$), 7.27-7.38 (m, 5H, Ar), 7.40-7.53 (m, 3H, Ar), 10.98 (s, 1H, NH) $^{13}$C NMR (DMSO-d$_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for C$_{25}$H$_{27}$N$_3$O$_5$+0.86H$_2$O: C, 64.58; H, 6.23; N, 9.04; Found: C, 64.77; H, 6.24; N, 8.88.

Procedure 2

Step 1: To a 2-L round bottom flask, were charged methyl 5-amino-4-(4-hydroxy-1-oxoisoindolin-2-yl)-5-oxopentanoate (30 g, 103 mmol), 1,4-bis(bromomethyl)benzene (81 g, 308 mmol) and potassium carbonate (14.19 g, 103 mmol) and acetonitrile (1.2 L). The mixture was stirred at room temperature for 10 minutes and heated to 50° C. for 12 hours. The reaction mixture was allowed to cool to room temperature. The mixture was filtered and the filtrate was concentrated on rota-vap. The resulting solid was dissolved in CH$_2$Cl$_2$ and loaded on 2 silica gel columns (330 g each) and eluted using CH$_2$C$_{12}$/MeOH to give 4-[4-(4-bromomethyl-benzyloxy)-1-oxo-1,3-dihydro-isoindol-2-yl]-4-carbamoyl-butyric acid methyl ester as white solid (40 g, 82% yield): $^1$H NMR (DMSO-d$_6$) δ 1.98-2.13 (m, 1H, CHH), 2.14-2.23 (m, 1H, CHH), 2.23-2.32 (m, 2H, CHH, CHH), 3.50 (s, 3H, CH$_3$), 4.34-4.63 (m, 2H, CH$_2$), 4.67-4.80 (m, 3H, CH$_2$, NCH), 5.25 (s, 4H, CH$_2$), 7.19 (s, 1H, NHH), 7.24-7.34 (m, 2H, Ar), 7.41-7.54 (m, 5H, Ar), 7.58 (br. s., 1H, NHH).

Step 2: To the CH$_2$Cl$_2$ solution of methyl 5-amino-4-(4-(4-(bromomethyl)benzyloxy)-1-oxoisoindolin-2-yl)-5-oxopentanoate (36.5 g, 77 mmol), was added morpholine (14.72 ml, 169 mmol) at room temperature. The mixture was stirred at room temperature for 1 hour. The resulting suspension was filtered, and the filtrate was concentrated on rota-vap. The resulting oil was dissolved in 350 mL of EtOAc and washed with water (50 mL×3). The organic layer was concentrated on rota-vap to give 4-carbamoyl-4-[4-(4-morpholin-4-ylmethyl-benzyloxy)-1-oxo-1,3-dihydro-isoindol-2-yl]-butyric acid methyl ester as a foamy solid (39 g, 100% yield): $^1$H NMR (DMSO-d$_6$) δ 2.00-2.12 (m, 1H, CHH), 2.14-2.22 (m, 1H, CHH), 2.22-2.29 (m, 2H, CHH, CHH), 2.30-2.39 (m, 4H, CH$_2$, CH$_2$), 3.46 (s, 2H, CH$_2$), 3.50 (s, 3H, CH$_3$), 3.53-3.63 (m, 4H, CH$_2$, CH$_2$), 4.28-4.59 (m, 2H, CH$_2$), 4.73 (dd, J=4.7, 10.2 Hz, 1H, NCH), 5.22 (s, 2H, CH$_2$), 7.14-7.23 (m, 1H, NHH), 7.26-7.39 (m, 4H, Ar), 7.41-7.51 (m, 3H, Ar), 7.58 (s, 1H, NHH).

Step 3: To the THF solution of methyl 5-amino-4-(4-(4-(morpholinomethyl)benzyloxy)-1-oxoisoindolin-2-yl)-5-oxopentanoate (40 g, 83 mmol), was added potassium 2-methylpropan-2-olate (9.80 g, 87 mmol) portion wise at 0° C. The mixture was stirred at this temperature for 30 minutes. To the reaction mixture, was added 45 mL of 1N HCl solution, followed by 200 mL of saturated NaHCO$_3$ solution. The mixture was diluted with 500 mL of EtOAc at 0° C., stirred for 5 minutes and separated. The organic layer was washed with water (50 mL×3) and brine (100 mL), and concentrated on rota-vap to give a white solid, which was stirred in diethyl ether (300 mL) to give a suspension. The suspension was filtered to give 3-[4-(4-morpholin-4-ylmethyl-benzyloxy)-1-oxo-1,3-dihydro-isoindol-2-yl]-piperidine-2,6-dione as white solid (28.5 g, 72% yield): HPLC: Waters Symmetry $C_{18}$, 5 µm, 3.9×150 mm, 1 mL/min, 240 nm, gradient to 95/5 acetonitrile/0.1% $H_3PO_4$ in 5 min: tR=4.78 min (98.5%); mp: 209-211° C.; $^1$H NMR (DMSO-$d_6$) δ 1.86-2.09 (m, 1H, CHH), 2.29-2.38 (m, 4H, $CH_2$, $CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$, $CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH); $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86$H_2O$: C, 64.63; H, 6.22; N, 9.04; Found: C, 64.39; H, 6.11; N, 8.89; $H_2O$, 3.24.

6.4 Cell Culture and Generation of Stable Cell Lines

Cell Culture of DLBCL Cell Lines

Diffuse Large B-Cell Lymphoma (OCI-LY10, OCI-LY3, SUDHL-10, WSU-DLCL2, SUDHL-6, KARPAS-422, TMD8, HT, RIVA, KARPAS-1106P, OCI-LY19 and SUDHL-4) cultured in RPMI-1640 containing 10% fetal bovine serum and 1% Penicillin/Streptomycin.

Generation of Compound-Resistant Cell Lines

Generation of WSU-DLCL2 and TMD8 cells resistant to either Lenalidomide or Compound A was achieved through chronic exposure of compound in an escalating manner.

Gene silencing with shRNA

WSU-DLCL2, and OCI-LY10 cells were transduced with lentivirus encoding shRNA targeting Aiolos and c-myc. 24 hours post-transduction, cells were cultured with 1 µg/ml of puromycin for stable cell selection.

6.5 Western Blotting

Immunoblots were probed with antibodies recognizing: Aiolos, Ikaros, Cereblon, IRF4, c-myc, CD44, EZH2, EBF 1, PU. 1, and β-actin. Signals were detected with a LI-COR imager 6.6 Cell Proliferation Assays 2×10e4 cells were plated per well in media containing either DMSO or increasing concentrations of Lenalidomide, Compound A or Compound C. Cells were then cultured for 3 days at 37° C. Tritiated thymidine was applied to the cell culture for the final 6 hours and cells were then harvested onto filter plates. After the plates have dried, scintillation fluid was added to the plates and read on a Top-count reader.

6.7 Current Paradigms in DLBCL

DLBCL is currently subgrouped into three clinical diseases: germinal center B cell (GBC), activated B cell (ABC) and primary mediastinal B cell lymphoma. Historically, patients diagnosed with ABC phenotype have a worse overall prognosis, and lenalidomide has a greater efficacy in ABC phenotype compared to a GCB phenotype. This is shown by greater overall survival in relapsed/refractory ABC patients treated with lenalidomide.

6.8 Aiolos and Ikaros are CRBN Substrates in ABC and GCB

Lenalidomide and Compound A were tested for their activity and effect on various diffuse large B-cell lymphoma (DLBCL) cell lines. The following DLBCL cell lines were evaluated for sensitivity to lenalidomide and Compound A: OCI-Ly10 (ABC), OCI-Ly-3 (ABC), RIVA (ABC), OCI-Ly-19 (GCB), WSU-DLCL2 (GCB), Karpas-1106P (GCB), HT (GCB), SUDHL-10 (GCB), SUDHL-4 (GCB), SUDHL-6 (GCB), Karpas 422 (GCB), and TMD8 (ABC).

The following steps can be performed to harvest cells in preparation for Western Blot analysis. The steps are performed on ice and any centrifugation is performed in a 4° C. refrigerated centrifuge. RIPA lysis buffer (Pierce, cat #89900) is first prepared by adding 10 L proteinase inhibitors (Pierce, cat #78443) to 1 mL of RIPA buffer. Subsequently, cells are washed once in ice-cold phosphate buffered saline (PBS). The cells are then lysed with 0.25 mL RIPA lysis buffer. The PBMCs are placed on ice for 30 minutes and vortexed every 10 minutes. Lysates are frozen and stored at −80° C. prior to further processing.

Lysates are placed in a QIAshredder® tube (QIAGEN, cat #79656) and spun down 30 sec, top speed (13200 rpm) in an Eppendorf benchtop centrifuge (Model 5415 R). The lysate is then transferred to a 1.5 mL clear Eppendorf tube and spun down 10 min at top speed. The supernatant is collected without disturbing the cell debris pellet. The supernatent is dry ice frozen and stored at −80° C. prior to analysis.

The protein concentration in supernatent is measured using BCA assay and the expected protein yield is about 0.5-5 µg/µL, or 125-1250 µg total. Approximately ≥10 µg protein per lane is loaded for western blotting (IRF4, IKZF3, etc.) using antibodies against the human proteins.

Membranes are immunoblotted with anti-Aiolos (Santa Cruz Biotechnology, Dallas, Tex.), anti-Ikaros (Millipore, Billerica, Mass.) and anti-Actin (Sigma, St. Louis, Mo.; or LI-COR Biosciences, Lincoln, Nebr.) and secondary antibodies (LI-COR Biosciences, Lincoln, Nebr.). The blots are analyzed on Odyssey imager (LI-COR Biosciences, Lincoln, Nebr.).

FIG. 1 shows that Aiolos and Ikaros are CRBN substrates in ABC and GCB DLBCL. DLBCL cells were treated with DMSO, Lenalidomide or Compound A for 1, 6, 12 or 72 hours and then levels of Aiolos, Ikaros, IRF4 or β-actin were assessed.

Figure 1A:
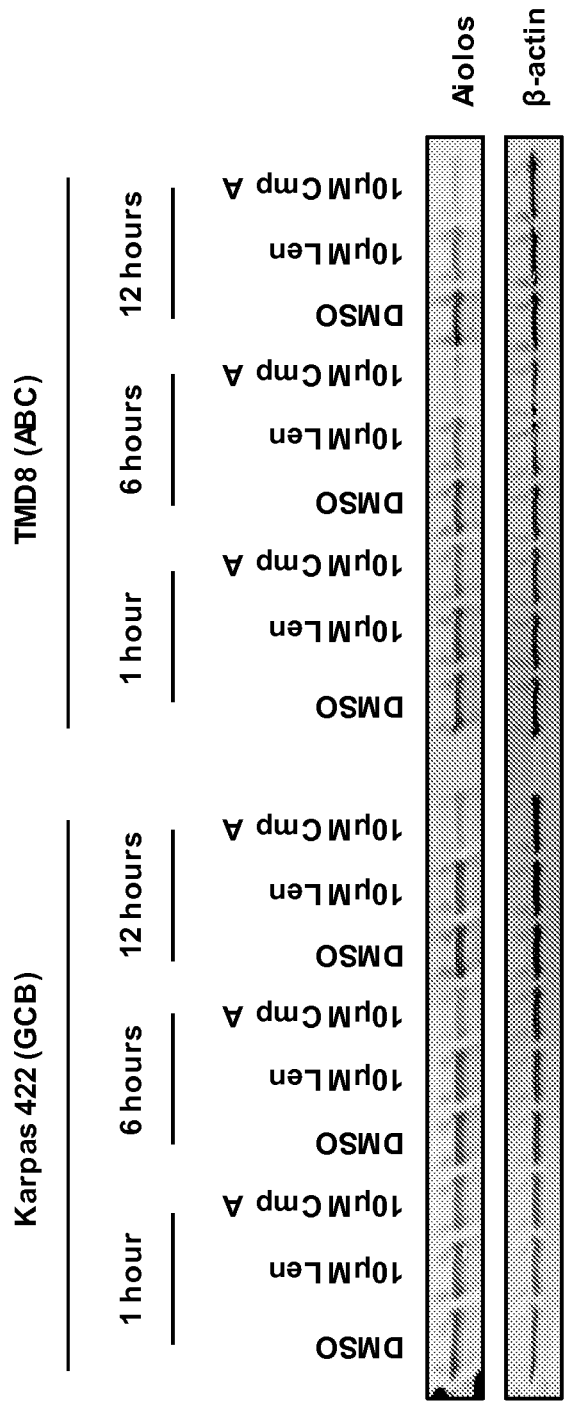

Karpas 422 (GCB) and TMD8 (ABC) cells were contacted with DMSO (control) or 10 µM lenalidomide or 10 µM Compound A. Aiolos or β-actin (control) levels were evaluated by Western blotting 1 hour, 6 hours or 12 hours later. FIG. 1A shows that lenalidomide and Compound A are biochemically active in both GCB and ABC DLBCL subsets, and Aiolos levels decrease following contact with lenalidomide and Compound A, but not the DMSO control compound.

Figure 1B:
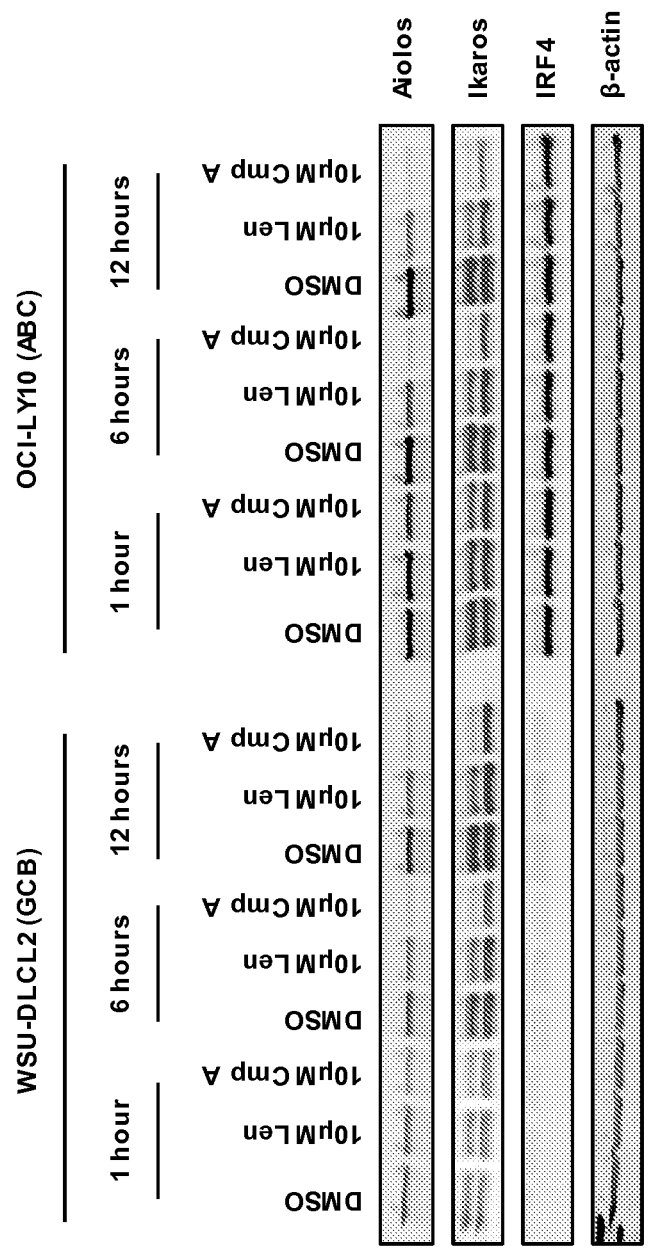

WSU-DLCL2 (GCB) and OCI-LY10 (ABC) cells were also contacted with DMSO (control) or 10 µM lenalidomide or 10 µM Compound A. Aiolos, Ikaros, IRF4 or β-actin (control) levels were evaluated 1 hour, 6 hours or 12 hours later. FIG. 1B shows that Lenalidomide and Compound A are biochemically active in both GCB and ABC DLBCL subsets, with both Aiolos and Ikaros levels decreasing following contact with lenalidomide and Compound A, but not the DMSO control compound.

Figure 1C:
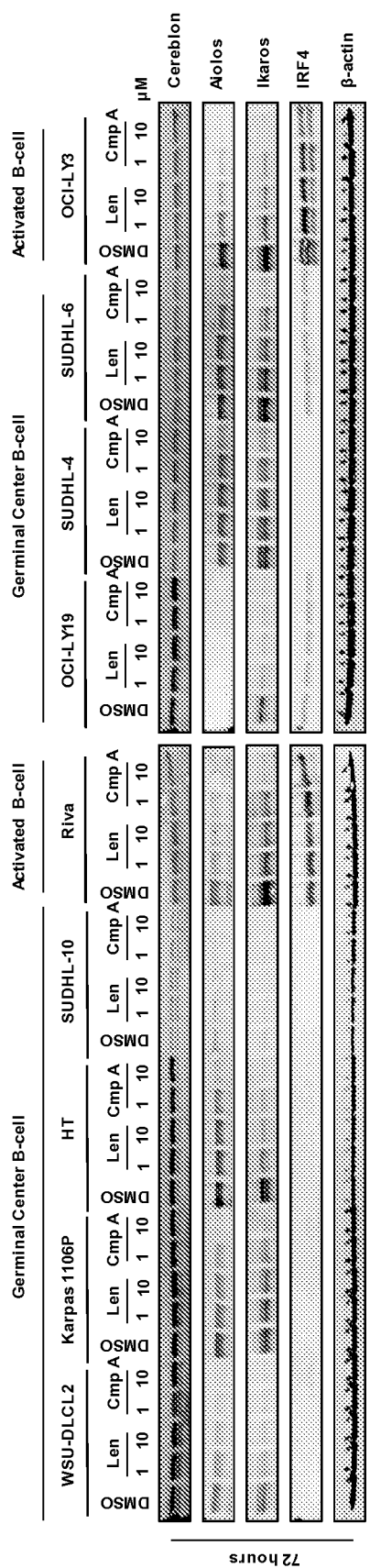

WSU-DLCL2 (GCB), Karpas-1106P (GCB), HT (GCB), SUDHL-10 (GCB), RIVA (ABC), OCI-Ly-19 (GCB), SUDHL-4 (GCB), SUDHL-6 (GCB) and OCI-Ly-3 (ABC) cells were also contacted with DMSO (control) or 1 µM or 10 µM lenalidomide, or 1 µM or 10 µM Compound A. Cereblon, Aiolos, Ikaros, IRF4 or β-actin (control) levels were evaluated 72 hours later. FIG. 1C shows that Lenalidomide and Compound A are biochemically active in both GCB and ABC DLBCL subsets, with both Aiolos and Ikaros levels decreasing following contact with lenalidomide and Compound A, but not the DMSO control compound. CRBN levels remained constant. Aiolos and Ikaros are substrates of the CRBN complex in DLBCL; and lenalidomide and Compound A reduce IRF4 levels within 72 hours.

6.9 Aiolos and Ikaros are CRL4$^{CRBN}$ Substrates In Vivo

WSU-DLCL2 xenograft SCID mice can be prepared using methods known in the art. In brief, female CB17 severe combined immunodeficiency (SCID) mice (6-12 weeks old) are obtained from the Charles River Laboratory (Wilmington, Mass.) and maintained in microisolator cages under sterile conditions. A total of $10 \times 10^6$ WSU-DLCL2 DLBCL cells in 100% Matrigel® (Becton Dickinson, San Jose, Calif.) are injected subcutaneously into the right flank of mice. Mice are monitored 2 or 3 times a week for the appearance of tumors. Once the tumors reach an average size of 100-150 mg, mice in each group are treated with either vehicle (e.g., 0.5% carboxymethyl cellulose: 0.25% Tween 80 in deionized $H_2O$) or a dose of lenalidomide (e.g., 30 mg/kg qd).

WSU-DLCL2 xenograft SCID mice (a human tumor xenograft model) were treated with either vehicle or 30 mg/kg Compound A q.d. Tumor samples were harvested at 1 hour, 6 hours, or 24 hours after the last dose.

Immunohistochemistry was performed using standard methods. For example, immunohistochemistry is performed on the Bond-Max™ automated slide stainer (Leica Microsystems) using the associated Bond™ Polymer Refine Detection Kit. Four micron thick FFPE sections are deparaffinized on the instrument. Antigen retrieval is performed with Epitope Retrieval™ 2 (pH 9.0) for 20 minutes at 100° C. The slides are blocked for endogenous peroxidase activity with Peroxide Block for 5 minutes at room temperature. Sections are then incubated with rabbit polyclonal antibody to Aiolos (Santa Cruz, sc-101982) or Ikaros at a 1/1000 dilution for 15 minutes at room temperature, followed by incubation with HRP labeled Polymer for 8 minutes at room temperature. Enzymatic detection of anti-Aiolos or anti-Ikaros antibody is accomplished with hydrogen peroxide substrate and diaminobenzidine tetrahydrochloride (DAB) chromogen at room temperature for 10 minutes. Slides are counterstained with Hematoxylin for 5 minutes at room temperature.

Figure 2A:
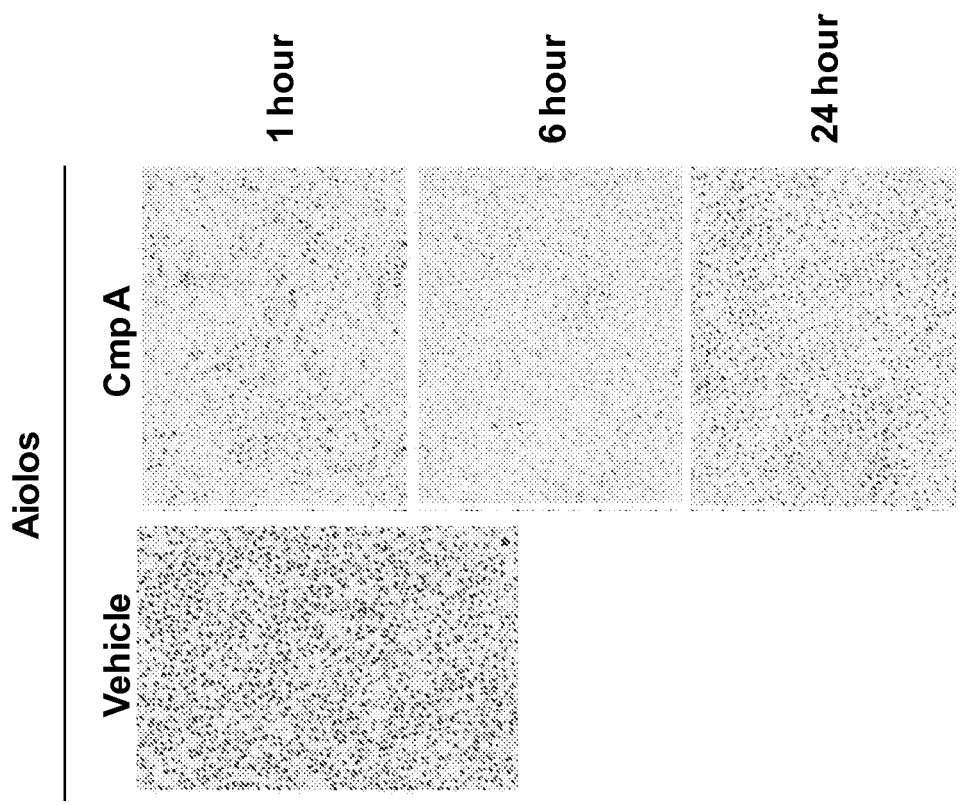
Figure 2B:
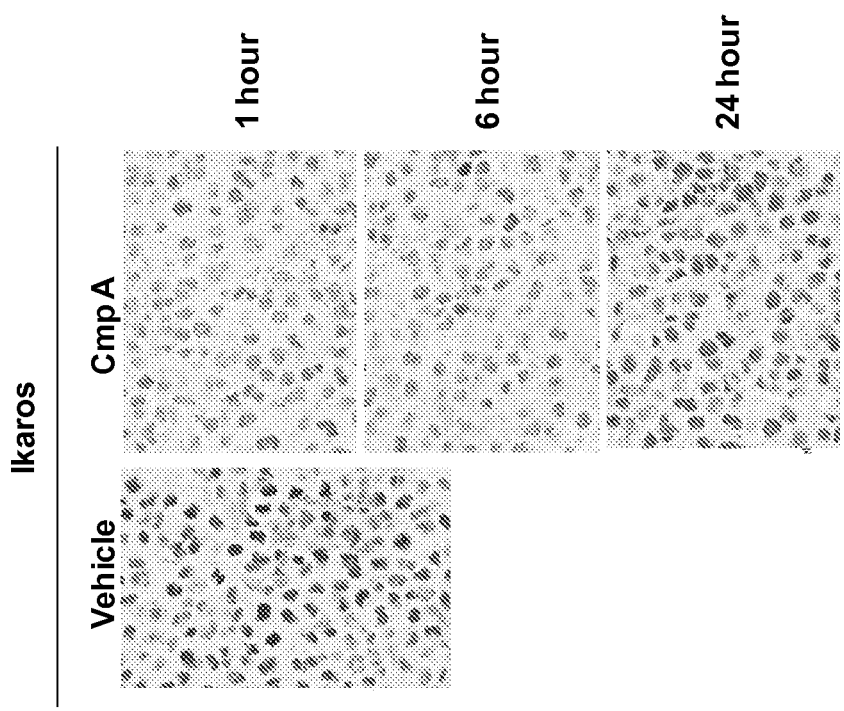

As shown in FIG. 2, Aiolos and Ikaros are CRL4CRBN substrates in vivo. WSU-DLCL2 xenograft SCID mice were treated with either vehicle or 30 mg/kg Compound A qd. Tumor samples were harvested at indicated time points after last dose. Tissues were then subjected to formalin-fixed, paraffin-embedded (FFPE) immunohistochemistry (IHC) for Aiolos, and Ikaros. Compound A induces Aiolos and Ikaros degradation within 6 hours of treatment in the WSU-DLCL2 xenograft SCID mice.

6.10 Aiolos is a Driver of Lymphoma Proliferation and Regulates c-Myc

WSU-DLCL2 (GCB) and OCI-LY10 (ABC) cells were transfected with negative control siRNA (luciferase) or Aiolos specific siRNA at a concentration of 0, 10 or 100 ng/ml. After 72 hours, Aiolos, IRF4, c-myc and β-actin (control) were measured by Western blot, essentially as described in Section 6.8. Alternatively, after 3 or 5 days, the cells were analyzed for proliferation using a $^3$H-thymidine incorporation assay.

Figure 3A:
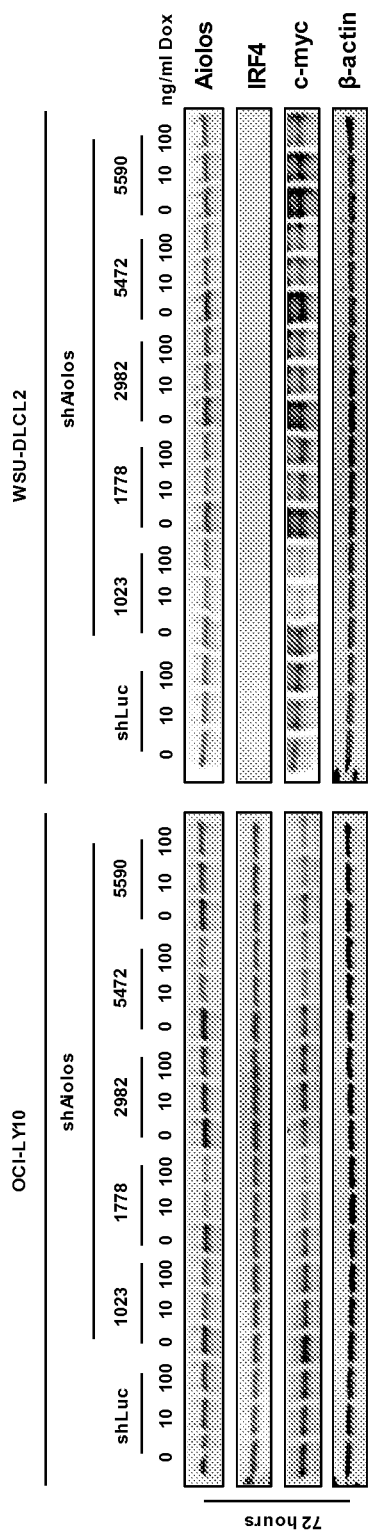
Figure 3B:
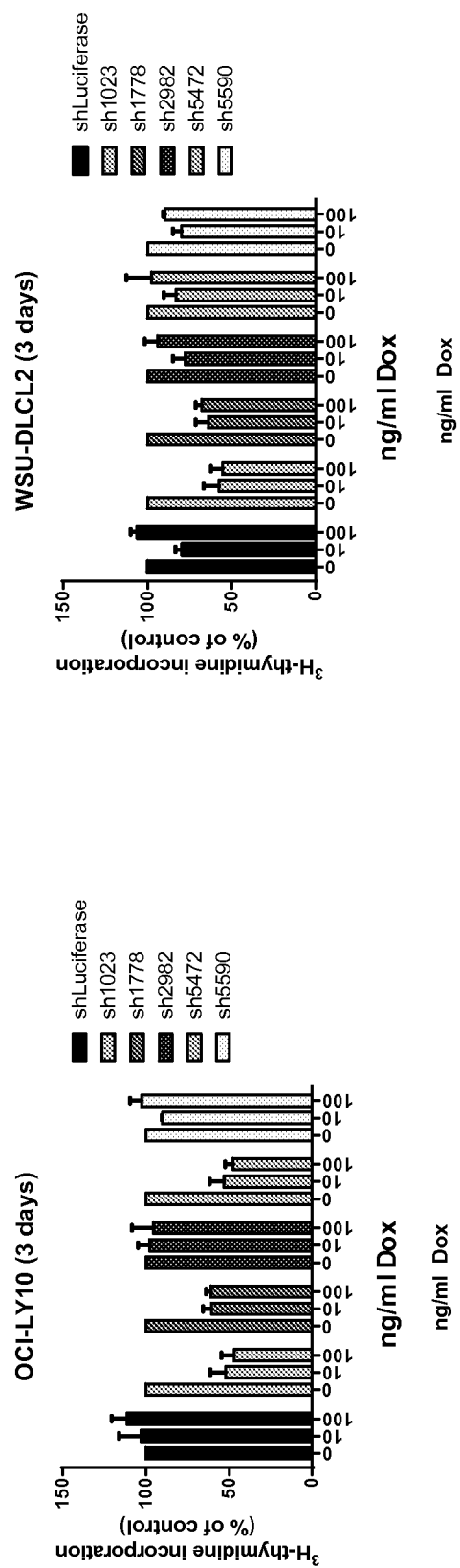
Figure 3C:
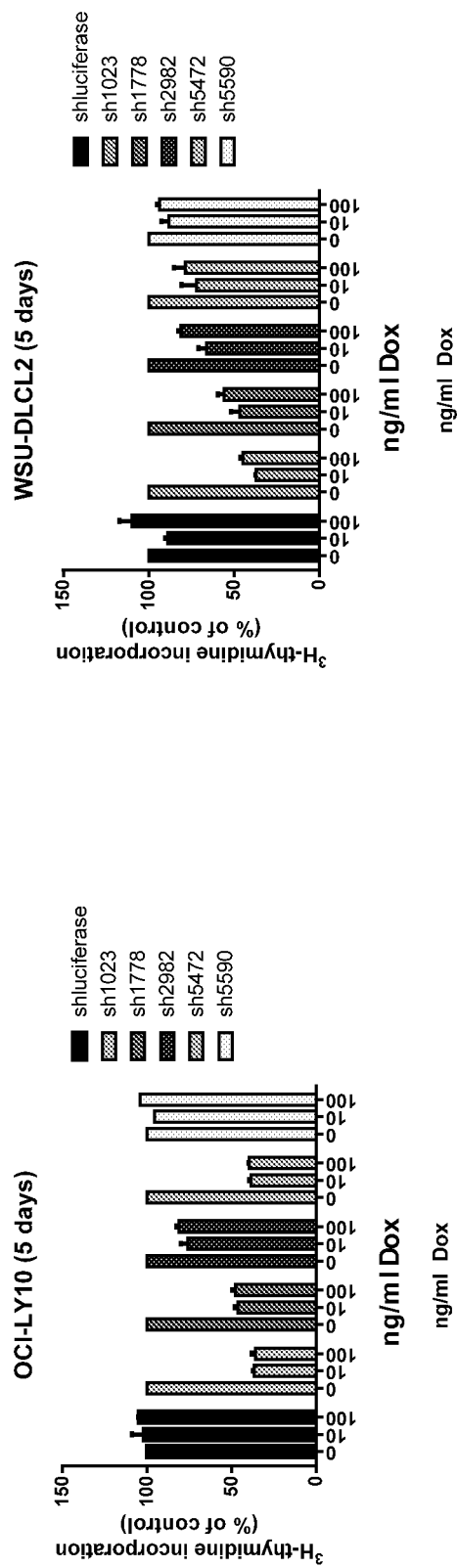

FIG. 3 shows Aiolos is a driver of lymphoma proliferation and regulates c-Myc. Inducible Aiolos shRNA cell lines were treated with 0-100 ng/ml of doxycycline for 72 hours and Aiolos, c-myc, IRF4 or β-actin protein levels were assessed. As shown in FIG. 3, at least three out of five Aiolos shRNAs (sh1778, sh2982 and sh5472) resulted in a dose-dependent decrease in Aiolos and c-myc protein levels (FIG. 3A), and also showed a corresponding decrease in proliferation in both DLBCL subsets (FIGS. 3B and 3C). Aiolos shRNA results in the significant decrease of c-myc but not IRF4. Proliferation assays indicate that shRNA targeting Aiolos inhibit proliferation of cells at 3 and 5 days post-doxycycline treatment.

6.11 Generation of DLBCL Cell Lines Resistant to Lenalidomide and Compound A

WSU-DLCL2 (GCB) or TMD8 (ABC) were cultured and cell-passaged long-term in lenalidomide or Compound A. Resistance to each compound was assessed using $^3$H-thymidine incorporation proliferation assays.

Figure 4A:
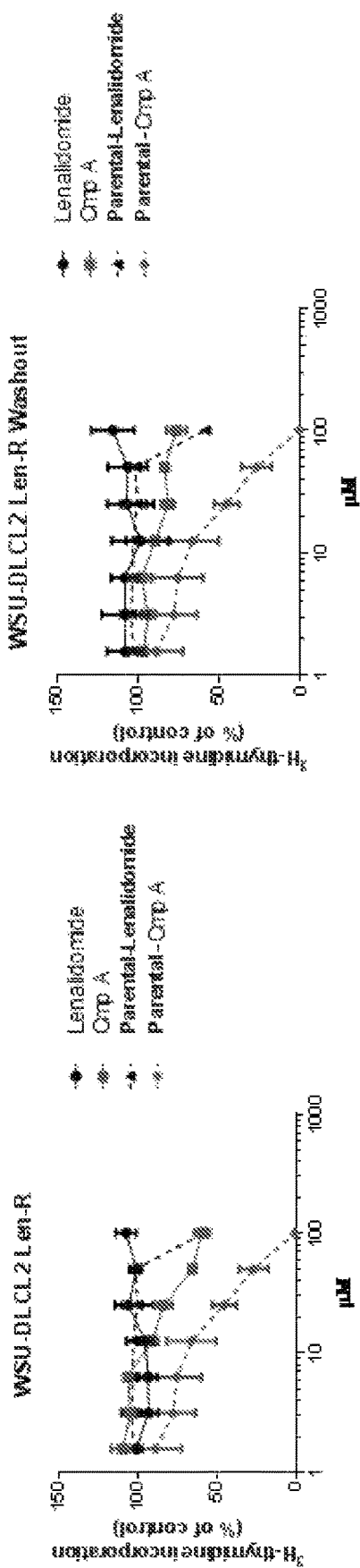
Figure 4B:
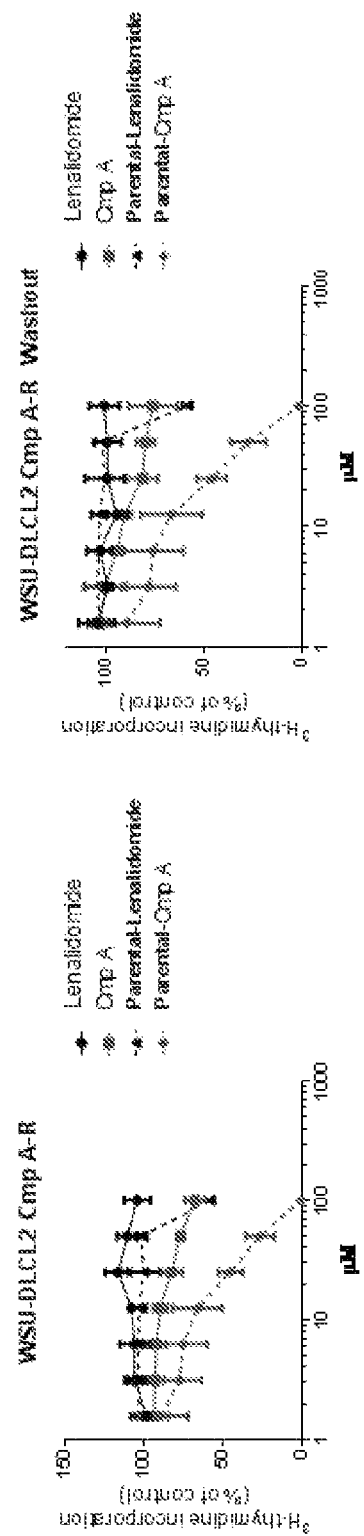
Figure 4C:
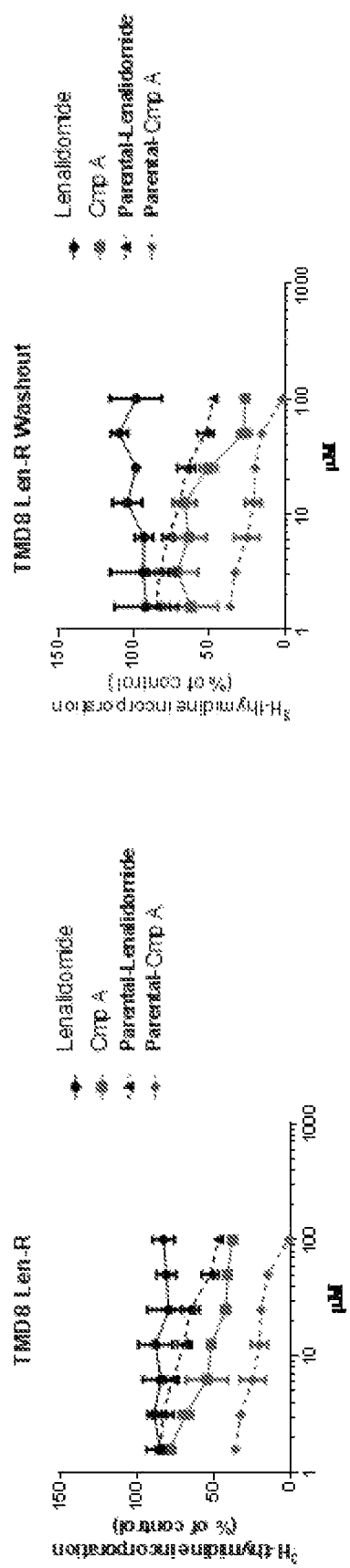

FIG. 4 shows the generation of DLBCL cell lines resistant to lenalidomide and Compound A. Cell lines were made resistant to Lenalidomide and Compound A through chronic exposure to both compounds. Proliferation of resistant and parental cells were assessed through tritiated thymidine incorporation assays. As shown in FIG. 4, each of the cell lines demonstrated resistance to lenalidomide (Len-R) or Compound A (CmpA-R), as compared to parental cells, after a 10 day washout period, which indicated that resistance was now an inherent trait in the resistant cells.

6.12 Resistance to Lenalidomide and Compound a Mechanism of Action

FIG. 5 depicts the resistance to lenalidomide and Compound A mechanism of action.

WSU-DLCL2 (GCB) or TMD8 (ABC) were cultured and cell-passaged long-term in lenalidomide or Compound A as described in Section 6.10. Levels of CRBN, Aiolos, Ikaros, IRF4, c-myc, CD44, EZH2, EBF 1, PU1 and β-actin (control) were assessed using Western blotting, essentially as described above in Section 6.8.

Figure 5A:
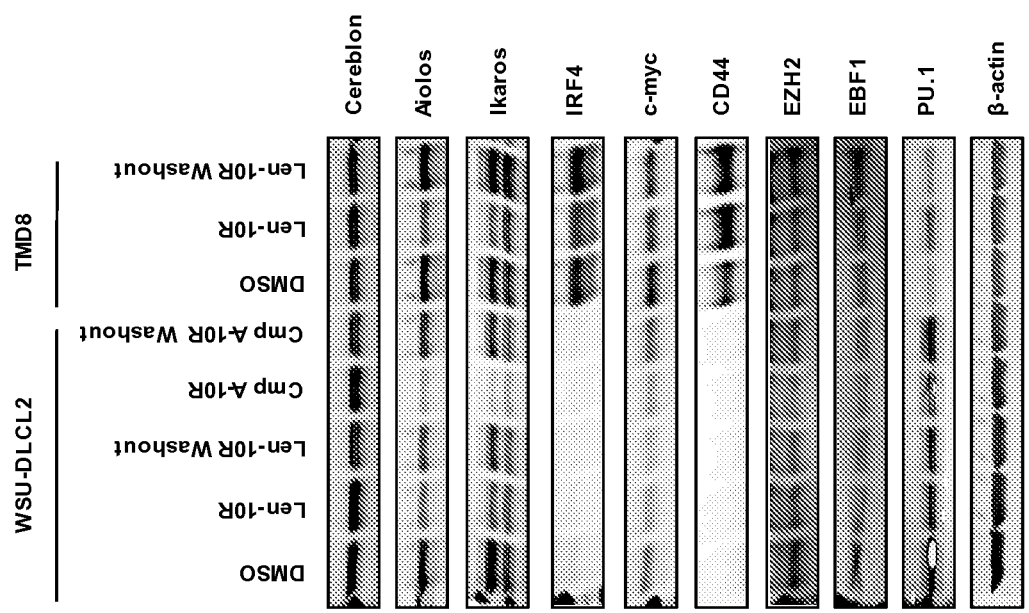

FIG. 5 shows the resistance to lenalidomide and Compound A mechanism of action. As shown in FIG. 5A, acquired resistance in two DLBCL does not involve down-regulation of CRBN levels as is observed in multiple myeloma however, acquired resistance may be achieved through down-regulation of CRBN or other unidentified mechanisms in other DLBCL cells. However, Aiolos and Ikaros levels are slightly decreased in WSU-DLCL2 resistant cells compared to parental. Additionally, c-Myc levels are decreased in both WSU-DLCL2 and TMD8 resistant cells while CD44, a marker of aggressive disease, is increased in the ABC DLBCL cell line (TMD8).

In addition, WSU-DLCL2 (GCB) or Compound A-resistant WSU-DLCL2 (Cmp A-R) cells were treated with DMSO (control) or 1 or 10 μM lenalidomide or Compound A (Cmp A), and Aiolos and β-actin (control) levels were assessed by Western blot 24 or 72 hours later, essentially as described in Section 6.8.

Figure 5B:
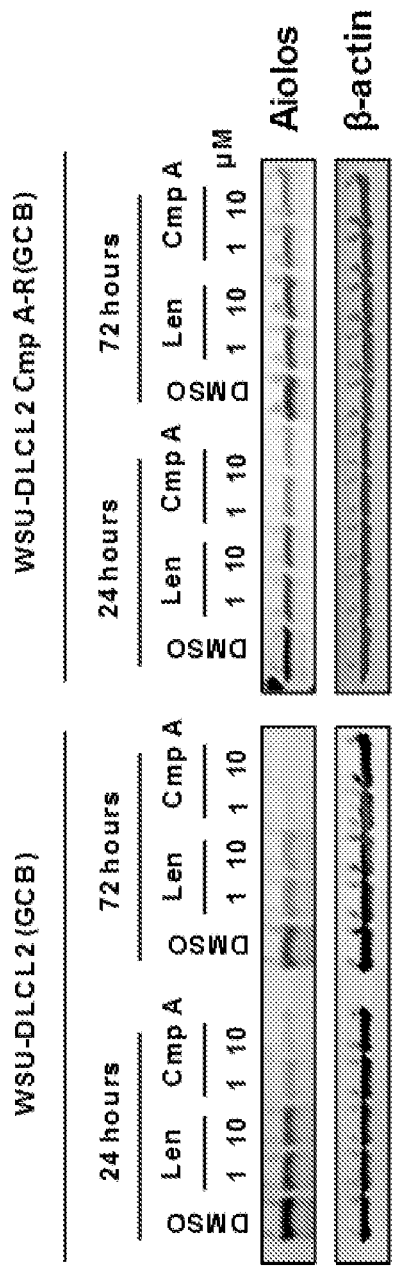

As shown in FIG. 5B, the rate of destruction of Aiolos in the WSU-DLCL2 Cmp A-R (Compound A resistant) cell line is decreased compared to the parental cell line.

6.13 Dynamic Range of Expression Levels of CRBN, Aiolos and Ikaros in DLBCL Patients Tumor cells were harvested an prepared from human patients, and immunohistochemistry to detect CRBN, Aiolos or Ikaros was performed, essentially as described in Section 6.9.

Figure 6A:
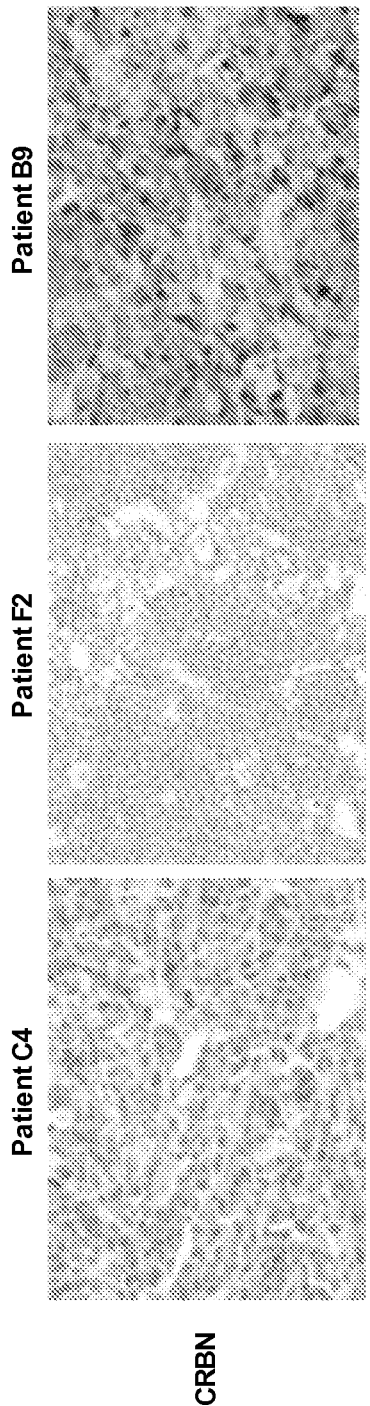
Figure 6B:
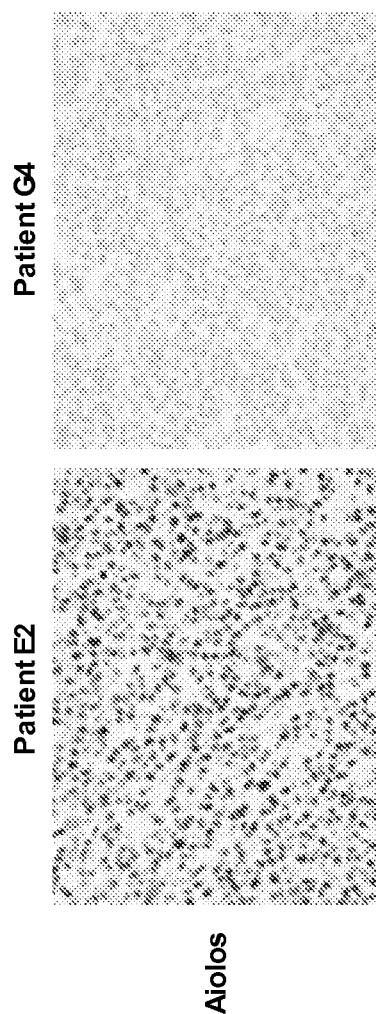
Figure 6C:
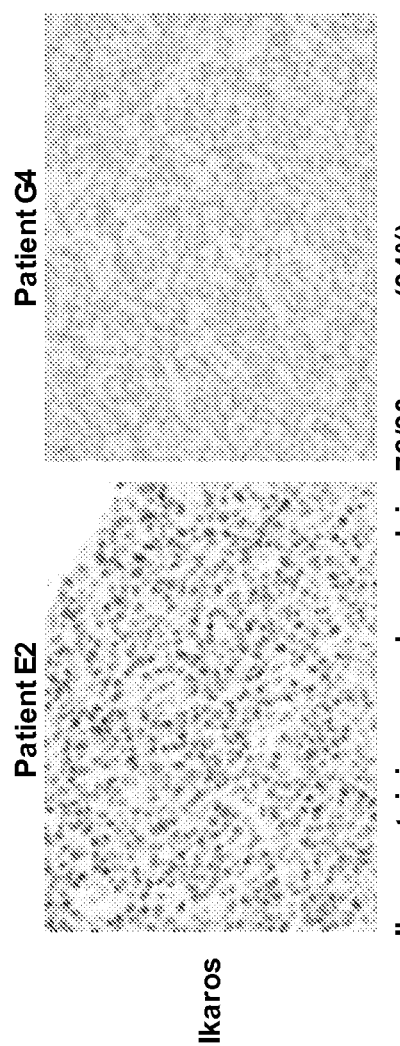

FIG. 6 depicts the dynamic range of expression levels of CRBN, Aiolos and Ikaros in DLBCL patients. IHC of a FFPE samples from 90 patients for CRBN, Aiolos and Ikaros indicates a wide range of expression levels in primary DLBCL. FIG. 6A shows the range of CRBN expression in three exemplary clinical trial patients, C4, F2 and B9. CRBN staining was observed in 76/90 cases (84%). Nuclear CRBN was observed in 23/76 positive CRBN tumors. FIG. 6B shows the range of Aiolos expression in two exemplary clinical trial patients, E2 and G4. Aiolos staining was observed in 85/90 cases (94%). Aiolos was strongly expressed in 61/85 patients. FIG. 6C shows the range of Ikaros expression in two exemplary clinical trial patients, E2 and G4. Ikaros staining was observed in 76/90 cases (84%).

The dynamic range of CRBN, Aiolos and Ikaros in DLBCL can be used as a positive inclusion process for participation in a Compound A (or other compound) clinical trial.

6.14 Differential Activity of Lenalidomide and Compound A

Lenalidomide and Compound A at varying concentrations from 1 to 100 μM were tested for their activity and effect on various diffuse large B-cell lymphoma (DLBCL) cell lines: SUDHL-10 (GCB), HT (GCB), Karpas 422 (GCB), WSU-DLCL2 (GCB), SUDHL-6 (GCB), Farange (GCB), OCI-Ly-3 (ABC), TMD8 (ABC), and OCI-Ly10 (ABC). The cells were then analyzed for proliferation using a $^3$H-thymidine incorporation assay.

Figure 7A:
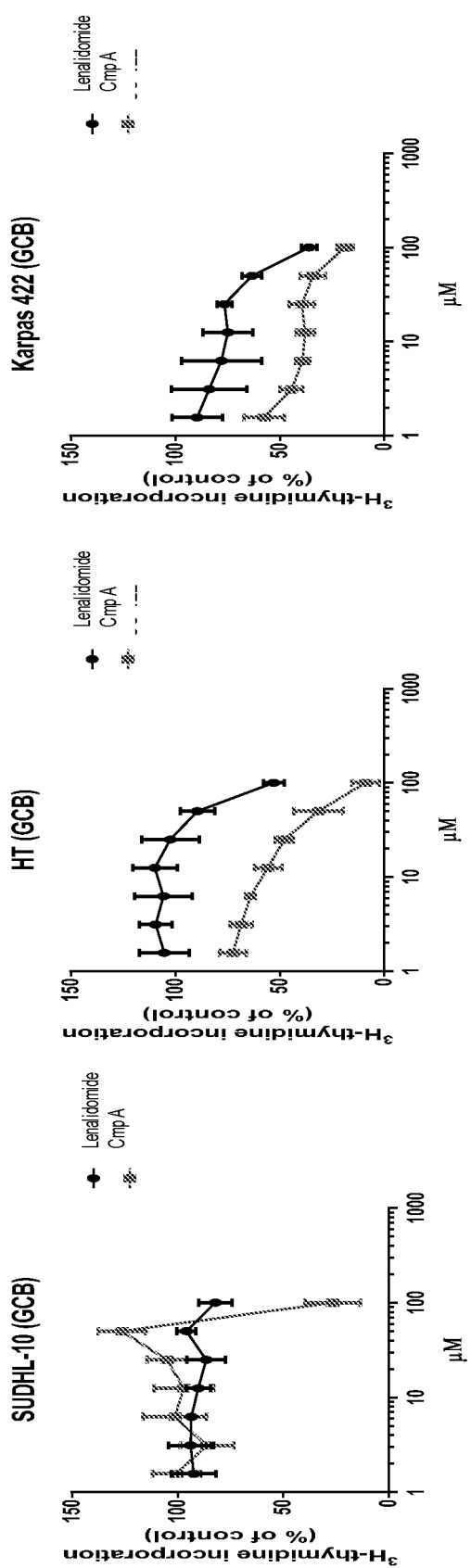
Figure 7B:
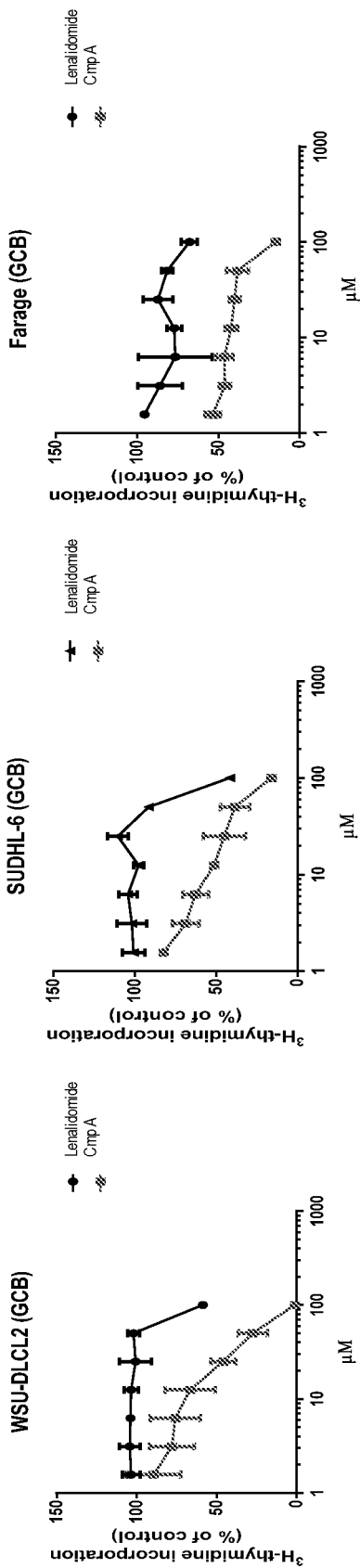
Figure 7C:
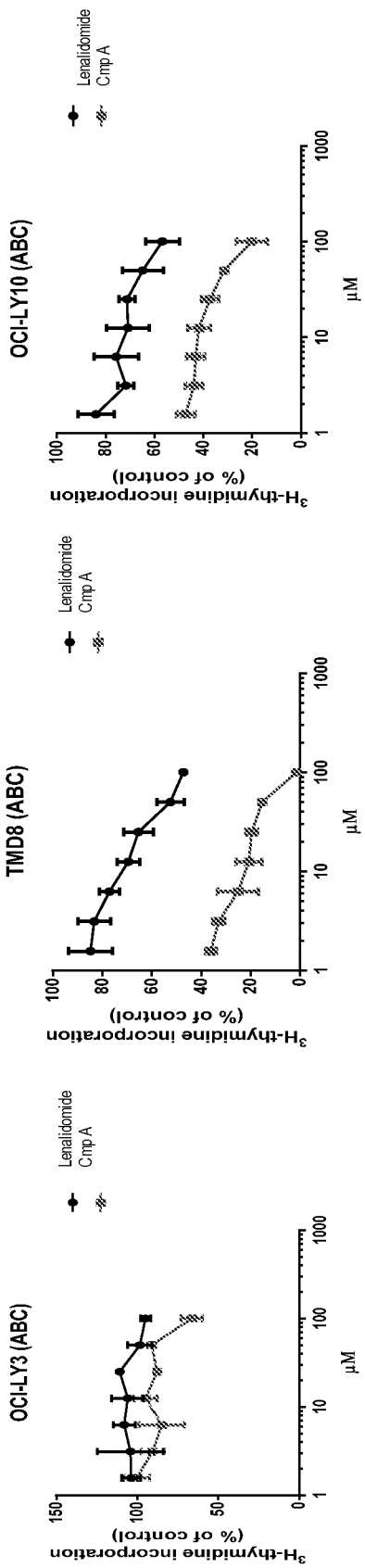

FIG. 7 depicts the differential activity of lenalidomide and Compound A in GCB and ABC DLBCL. Multiple DLBCL cell lines were culture with either lenalidomide or Compound A for 3 days. Proliferation was assessed through tritiated thymidine incorporation. Three phenomena were observed; inherent resistance, differential activity of Compound A compared to Lenalidomide or a distinct potency difference between the two molecules. Differential activity of Compound A is observed in some GCB DLBCL compared to lenalidomide. However, Compound A is more potent than lenalidomide in ABC DLBCL 6.15 Lenalidomide Competes with Compound a and Compound C for CRBN TMD8 (ABC) or Karpas 422 (GCB) cells were treated with either lenalidomide; Compound A; and 100 μM lenalidomide, 1-(3-chloro-4-methylphenyl)-3-((2-(2,6-dioxopiperidin-3-yl)-1-oxoisoindolin-5-yl)methyl)urea (Compound C (Cmp C)); or Compound C and 100 μM lenalidomide. They were cultured and cell-passaged long-term in lenalidomide or Compound A. The cells were then analyzed for proliferation using a $^3$H-thymidine incorporation assay.

Figure 8A:
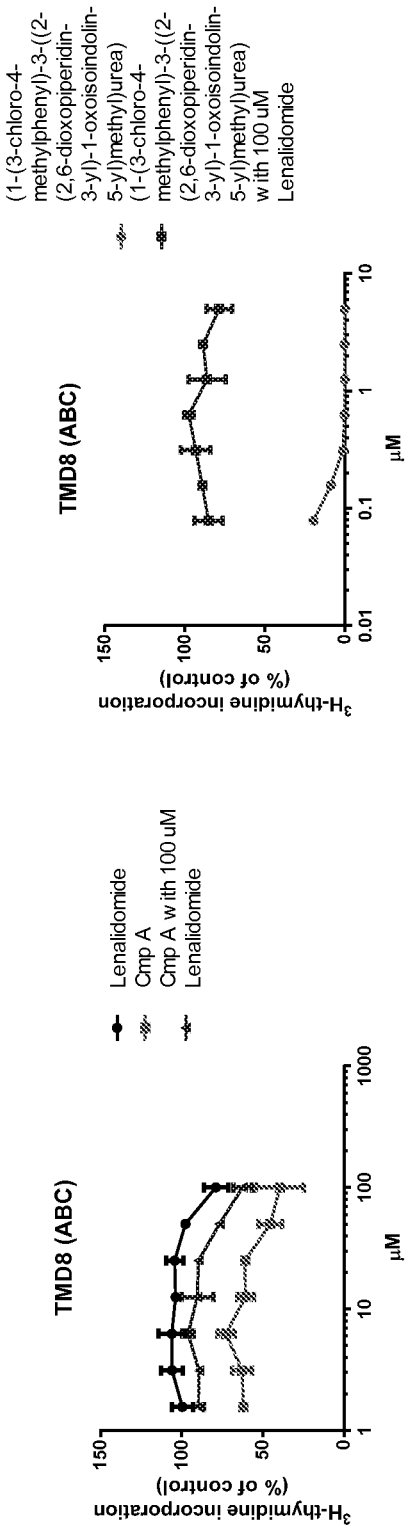
Figure 8B:
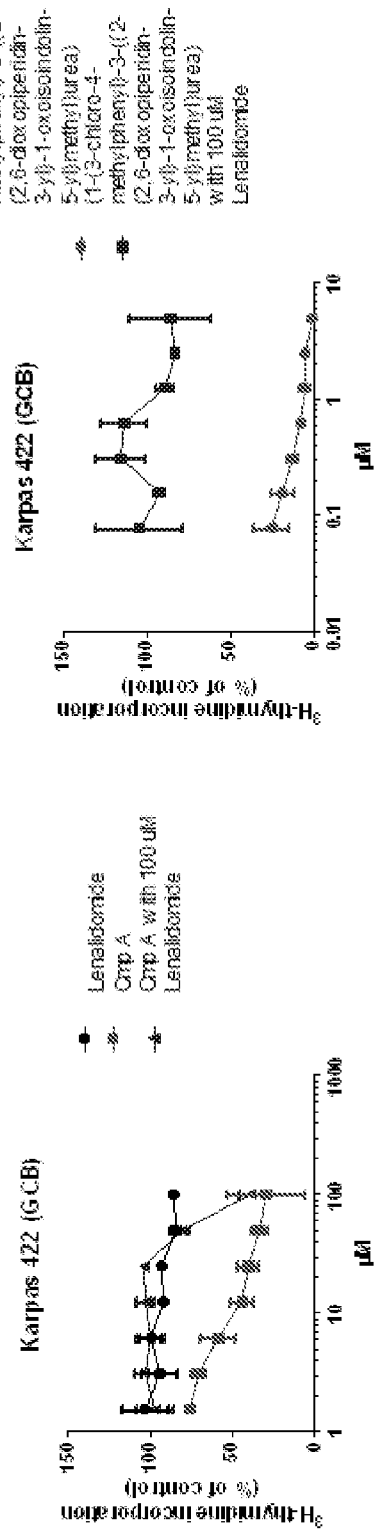

FIG. 8 shows that lenalidomide competes with Compound A and Compound C for CRBN. FIG. 8A shows that co-treatment with Compound A and 10 μM lenalidomide blocks anti-proliferative effects of Compound A, though competition of binding to the CRBN complex. Likewise, FIG. 8B shows that co-treatment with Compound C and 10 μM lenalidomide blocks anti-proliferative effects of Compound C, though competition of binding to the CRBN complex. Co-culture of Lenalidomide with either Compound A or Compound C dampens the activity of these compounds as they target the same binding pocket with relative affinity.

6.16 Differentiation of Lenalidomide and Compound a in DLBCL Using TMT Mass Spectrometry GCB cell lines (WSU-DLCL2, WSU-DLCL2-Cmp A-Resistant (Compound A resistant), Karpas 422 and HT) and ABC cell lines (TMD8, TMD8-Cmp A-Resistant, OCT-LY10 and U2932) were treated with either lenalidomide or Compound A for 24 or 72 hours. Aiolos or β-actin (control) protein levels were analyzed by Western blotting, essentially as described in Section 6.8. Proteins from these cells are also labeled and analyzed with Tandem Mass Tag proteomics to quantitatively measure differences in protein levels differentially affected by lenalidomide and Compound A.

Figure 9:
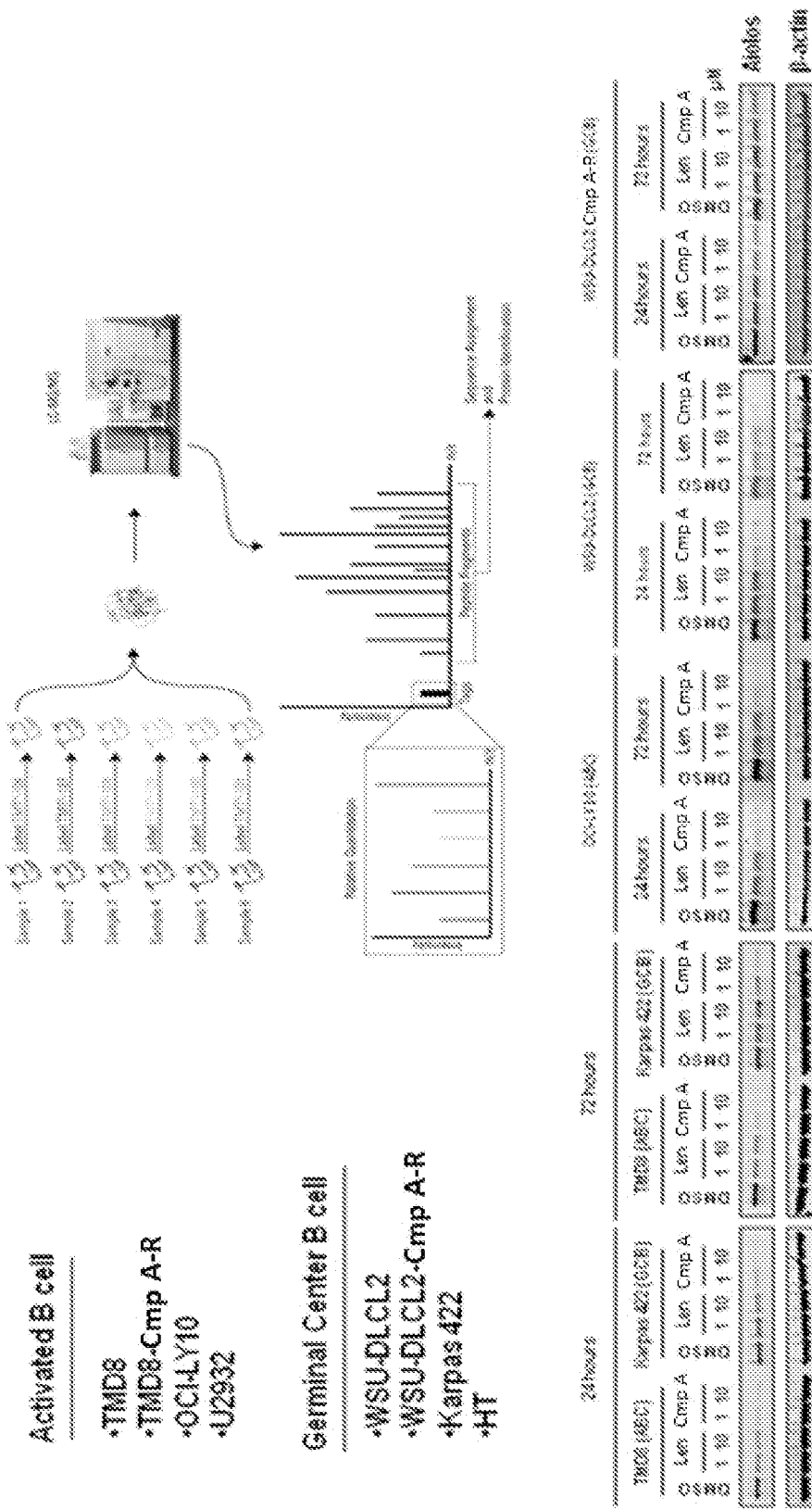

FIG. 9 shows the differentiation of lenalidomide and Compound A in DLBCL using TMT mass spectrometry. Aiolos protein levels decrease in a dose-dependent manner in as little as 24 hours in both ABC and GCB DLBCL (bottom panels).

6.17 Compound a and shAiolos Induce IFN Response Proteins

U2932 (ABC) cells were cultured and cell-passaged long-term in Compound A as described in Section 6.10. Levels of Aiolos, IRF7, and β-actin (control) were assessed using Western blotting, essentially as described above in Section 6.8.

Karpas 422 (GCB) cells were transfected with negative control siRNA (luciferase) or Aiolos specific siRNA at a concentration of 0, or 10 ng/ml. After 72 hours, Aiolos, c-myc, IRF7, and β-actin (control) were measured by Western blot, essentially as described in Section 6.8. Alternatively, after 3 or 5 days, the cells were analyzed for proliferation using a $^3$H-thymidine incorporation assay.

Figure 10A:
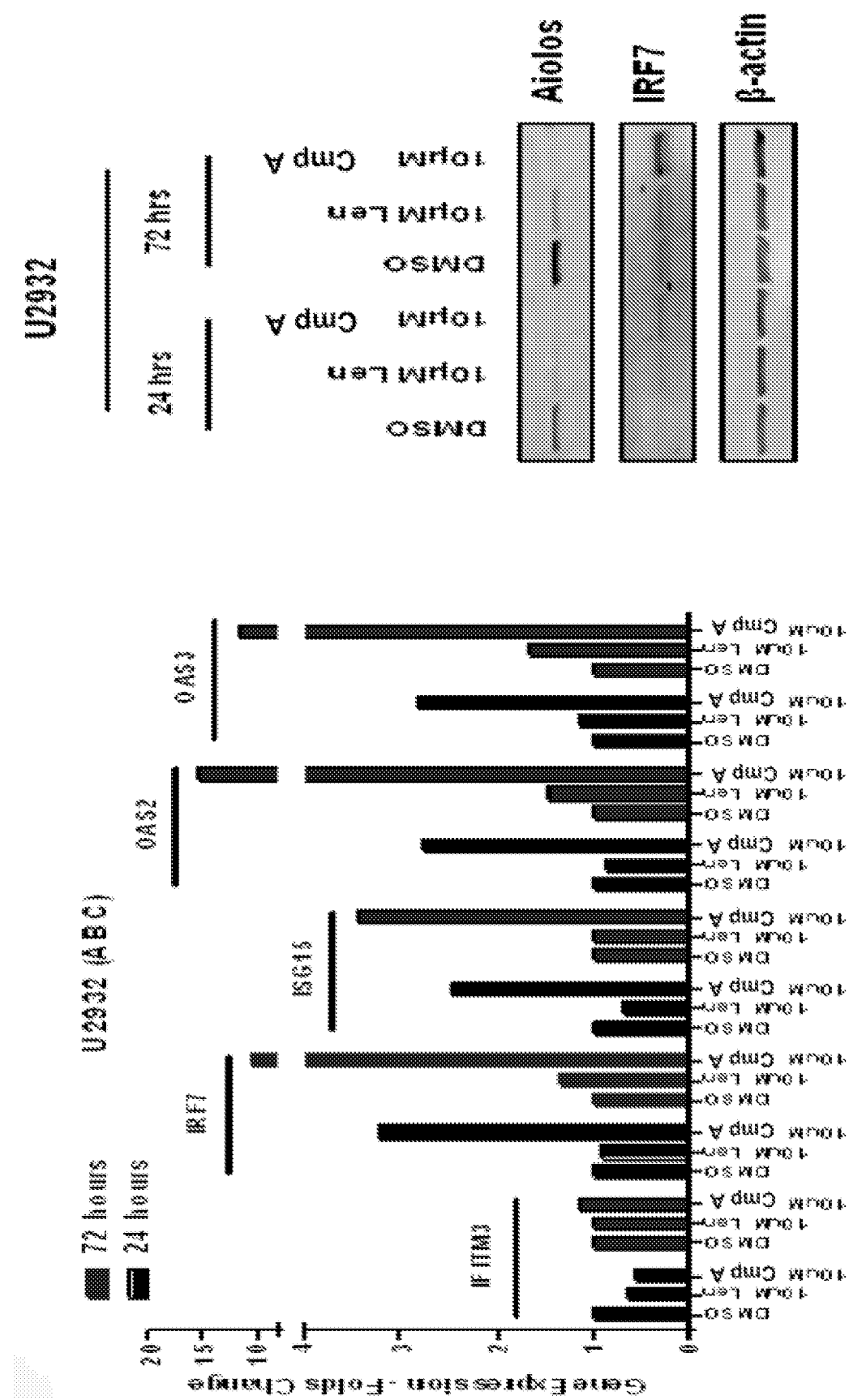
Figure 10B:
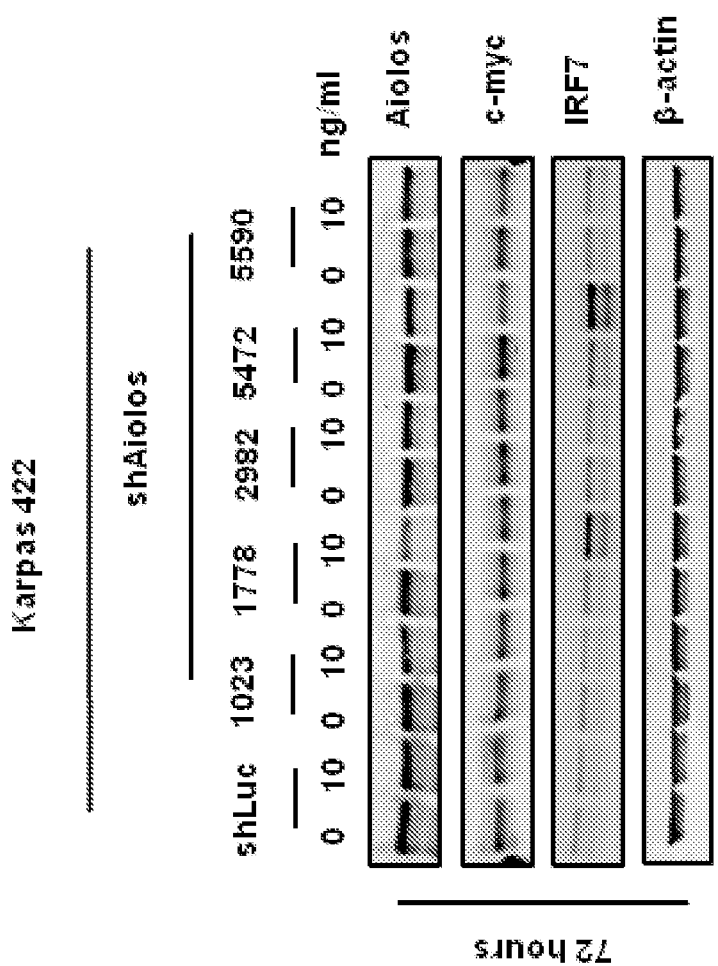

FIG. 10A shows that Compound A up-regulates IFN response gene expression and upregulates IRF7 protein expression. FIG. 10B shows that shAiolos upregulates IRF7 protein expression.

Figure 11:
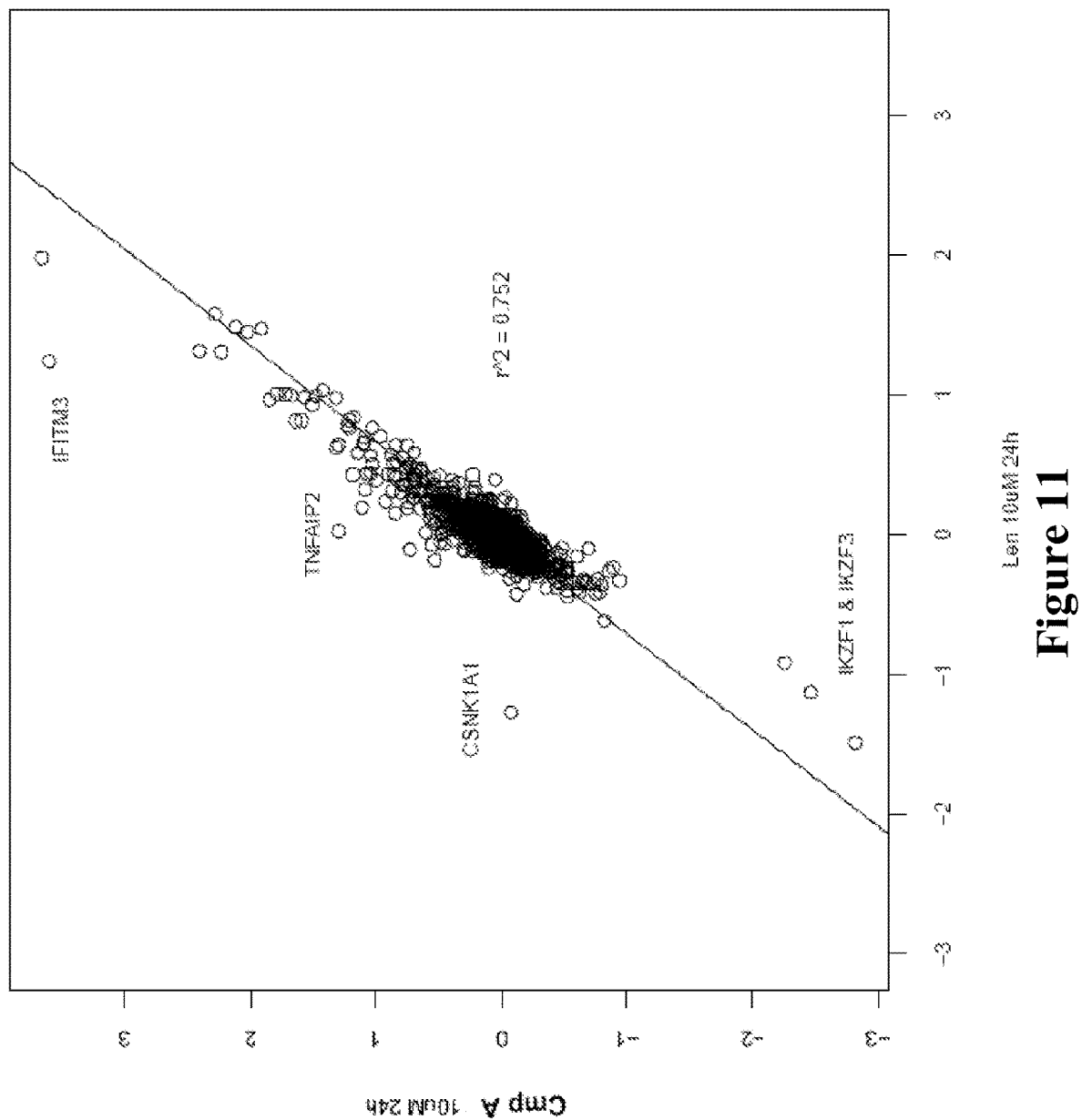
FIG. 11 shows that CSNK1A1 protein is one of few proteins affected by lenalidomide exposure to a manifestly greater extent than by Compound A.

6.18 Proteomic Screening Shows Compound a Affects CSNK1A1 Protein (ABC-DLBCL) cell line was treated with either lenalidomide or Compound A for 24 and 72 hours. Cells were harvested and proteins were fractionated using a basic pH reverse gradient method. Fractionated samples were labeled using a Tandem Mass Tag method. Log 2 ratios, averaged across replicates, of 10 uM lenalidomide and 10 uM Compound A relative abundances against those of the 24 h DMSO control treatment after 24 h exposure are plotted against each other in FIG. 11. The regression line displayed has r2=0.752, gradient 1.45 and intercept 0.03, suggesting generally stronger effect of Compound A compared to lenalidomide at this concentration. The protein CSNK1A1 (Casein Kinase 1, alpha 1 or CK1α), located in the q32 region of chr5 commonly associated with the del5q MDS sub-type, stands out as one of few proteins affected by lenalidomide exposure to a manifestly greater extent than by Compound A.

Thus, it was shown that Compound A does not appear to affect CSNK1A1 protein, while Lenalidomide decreases it.

6.19 Lenalidomide, Pomalidomide, Compound a, or shAiolos Affects IFN Pathway

As shown in FIG. 13A-G, lenalidomide, pomalidomide, or Compound A affects IFN pathway. FIG. 13A shows that lenalidomide, pomalidomide, or Compound A upregulates IFIT1, IFIT3, DDX58, XAF1, IFIH1, and OAS3 protein expression. FIG. 13B shows that lenalidomide, pomalidomide, or Compound A upregulates DDX58, IFI27, IFIT1, IFIT3, DDX58, and XAF1 gene expression. FIG. 13C shows that lenalidomide, pomalidomide, or Compound A upregulates ISG15 and OAS3 gene expression. FIG. 13D shows that shAiolos induces IFN pathway genes and upregulates IFIT1 protein expression. FIG. 13E shows that lenalidomide, pomalidomide, or Compound A induces IRF changes. FIG. 13F shows that lenalidomide, pomalidomide, or Compound A upregulates IFIT1 and IFIT3 protein expression, upregulates TBK1 phosphorylation (TBK1-PO$_4$), and reduces IKKE protein level. FIG. 13G shows that lenalidomide, pomalidomide, or Compound A upregulates IFIT1 and IFIT3 protein expression, and induces changes of levels of STAT or phosphorylated STAT.

6.20 Proteomics Analysis Shows the Level of ZFP91 Reduces in Response to Treatment with Various Compounds in Lymphoma Cell Lines Lymphoma cells from cells lines OCI-LY10, TMD8, and WSU-DLCL2, were treated with either DMSO, lenalidomide or Compound A for 24 and 72 hours. Cells were harvested and proteins were fractionated using a basic pH reverse gradient method. Fractionated samples were labeled using a Tandem Mass Tag (TMT) method. Relative abundance was calculated. Those proteins with decreased or increased relative abundance compared to DMSO control are listed in Table 1 below. As shown, the level of ZFP91 reduces in response to Compound A treatment in these lymphoma cell lines. The proteins upregulated or downregulated as shown in Table 1 can be used as a biomarker for selecting a patient for treatment with Compound A or for predicting/monitoring efficacy of Compound A in treating lymphomas according to the methods provided herein.

TABLE 1

Upregulated and Downregulated Proteins in Response to Compound A Treatment in Lymphoma Cell Lines

| OCI-LY10 | | TMD8 | | WSU-DLCL2 | |
|---|---|---|---|---|---|
| Upregulated | Downregulated | Upregulated | Downregulated | Upregulated | Downregulated |
| AHNAK | ARHGAP19 | ADAM19 | 3-Sep | ACSS1 | ADIPOR2 |
| ALOX5 | ASNS | AIF1 | ADIPOR2 | ACY3 | ATF5 |
| AMPD3 | ASPM | ALDH1A1 | AHR | ADAM19 | BACH2 |
| ANXA4 | B4GALT3 | ALDH2 | ALCAM | ADCY7 | BANK1 |
| ANXA6 | BANK1 | ALOX5 | ALDOC | AIF1 | BCDIN3D |
| ATP2B4 | BCDIN3D | AMPD3 | ALKBH6 | ALDH2 | CD320 |
| BMF | BLZF1 | APOBEC3G | ALPL | AMPD3 | CSNK1A1 |
| BST2 | CA2 | APOE | AP1S3 | ANK3 | DEPTOR |
| C10orf76 | CA8 | APOH | APBB1IP | ANXA4 | ETS1 |
| C19orf66 | CAMSAP3 | ARHGAP10 | ARHGAP24 | ANXA6 | GLIPR1L1 |
| CD36 | CCDC69 | ATP2B4 | ARHGAP27 | APOBEC3G | GNG7 |
| CLN3 | CCNB1 | BST2 | ARNT | APOBR | GPT2 |
| CNN3 | CDC7 | C4A | BCL11A | B2M | HSBP1 |
| CORO1B | CDCA3 | C4BPA | BCL2A1 | BCL9L | ICAM2 |
| CPNE2 | CENPF | C4orf33 | BCL2L1 | BST2 | IKZF1 |
| CSRP2 | CSNK1A1 | CAPN2 | BCLAF1 | C19orf66 | IKZF3 |
| CTNND1 | DHPS | CASP4 | BNIP3L | CASP10 | KRT1 |
| CTSH | DLGAP5 | CCR7 | C19orf22 | CCDC28B | KRT14 |
| DAPK2 | DOK3 | CD1D | C9orf40 | CD40 | KRT2 |
| DDX58 | ECT2 | CD63 | CANX | CD59 | KRT6B |
| DLG2 | EFCAB4B | CD86 | CD22 | CD83 | KRT9 |
| DTX3L | EHMT1 | CDR2 | CD44 | CGN | MED12L |
| EIF2AK2 | EHMT2 | CORO1B | CD5 | CLSTN1 | NEIL1 |
| EPB41L1 | EPCAM | CPNE2 | CDC42SE2 | CMPK2 | NUGGC |
| ETV6 | ESRP1 | CYTH4 | CENPJ | COL23A1 | OMA1 |
| EXTL2 | FAM195A | DAPK2 | CEP97 | CORO1B | PDE6D |
| F13A1 | FBRSL1 | DDX58 | CFLAR | CORO1C | PDZRN3 |
| FAM65B | FHOD1 | DDX60 | CLDN23 | CTNND1 | PODXL |
| FCGR2B | FIGNL1 | DDX60L | CLEC17A | CTSH | SYNGR3 |
| FES | GPT2 | DHX58 | COX17 | CTTNBP2NL | SYTL1 |
| FMNL3 | GRAMD1A | DNASE1L3 | CROCC | CYTH1 | WIZ |
| GBP1 | GRAMD1B | DTX3L | CRYM | CYTH4 | ZFP91 |
| GMFG | GRPEL2 | EIF2AK2 | CSNK1A1 | DDX58 | ZMYM2 |
| GMPR | HJURP | ELOVL7 | DBN1 | DDX60 | |
| HIP1 | HMCES | EPB41L1 | DENND1C | DTX3L | |
| HLA-B | HMMR | F13A1 | DNM2 | EIF2AK2 | |
| HLA-DMA | HOXC4 | FAM129A | DOK3 | ETHE1 | |
| HPSE | ICAM2 | FBLN1 | DTWD1 | F11R | |
| ID3 | IKZF1 | FCRLA | EHD1 | FADS2 | |
| IFI35 | IKZF3 | FERMT3 | EIF4H | FAM76A | |
| IFIH1 | IRS2 | FGD6 | ENO2 | FDFT1 | |
| IFIT1 | KIF18B | FLNA | EPHA4 | FGD4 | |
| IFIT3 | KIF22 | GALNT7 | EPHA7 | FLNA | |
| IFIT5 | KIF2C | GBP1 | EPHB1 | FLNB | |
| IFITM2 | LIPG | GBP2 | ERCC6 | FRRS1 | |
| IL4I1 | LPXN | GBP4 | ETS1 | FSCN1 | |
| IRF7 | MINA | GIPC1 | EVI2B | GCH1 | |
| IRF9 | MIS18BP1 | GPD1 | EVL | GMFG | |
| ISG15 | NEIL1 | GPX3 | FAR1 | GNB4 | |
| ISG20 | NFKBID | HABP2 | FCRL2 | GNG2 | |
| ITGB7 | NPIPB5 | HBA1 | FCRL3 | H1F0 | |
| JAK3 | OMA1 | HBD | FCRL5 | HECTD1 | |
| LAP3 | ORC6 | HERC3 | GABPB1 | HELZ2 | |
| LGALS1 | PARVB | HERC6 | GAMT | HGF | |
| LGALS3BP | PBK | HGF | GAPT | HGSNAT | |
| LIMD1 | PDE6D | HIGD1A | GAS7 | HGSNAT | |
| MAN2A2 | PKMYT1 | HMOX1 | GATM | HLA-A | |
| MARCKS | PLK1 | HSPA8 | GLRX | HLA-B | |
| MFI2 | PODXL | HSPB1 | GNG2 | HLA-G | |
| MGARP | PODXL2 | IFI35 | GRPEL2 | HSPB1 | |
| MOV10 | POLE2 | IFI44 | GYPC | HYI | |
| MPP7 | PRDM15 | IFI44L | GZMB | IFI35 | |
| MUC1 | PRNP | IFIH1 | HK2 | IFIT1 | |
| MX1 | PTAFR | IFIT1 | HLTF | IFIT3 | |
| MX2 | PTTG1 | IFIT2 | HTRA3 | IFIT5 | |
| MYO1G | PYROXD1 | IFIT3 | IFNAR2 | IL4I1 | |
| NCF2 | RASA4B | IFIT5 | IKZF1 | IPCEF1 | |

TABLE 1-continued

Upregulated and Downregulated Proteins in Response to Compound A Treatment in Lymphoma Cell Lines

| OCI-LY10 | | TMD8 | | WSU-DLCL2 | |
|---|---|---|---|---|---|
| Upregulated | Downregulated | Upregulated | Downregulated | Upregulated | Downregulated |
| NME3 | RASSF6 | IFITM3 | IKZF3 | IRF9 | |
| NMI | RGS1 | IL3RA | IL16 | ISG15 | |
| NT5C3A | RGS2 | IRF7 | INF2 | ISG20 | |
| OAS1 | SEC14L1 | IRF9 | IQSEC1 | JADE2 | |
| OAS2 | SGOL1 | ISG15 | IRF4 | KIAA0101 | |
| OAS3 | SGOL2 | ISG20 | ISYNA1 | LAT2 | |
| PARP14 | SLCO3A1 | ITGA1 | ITGAL | LGALS1 | |
| PARP9 | SLCO4A1 | ITGB3 | ITGB2 | LGALS3BP | |
| PBXIP1 | TACC3 | ITGB7 | KDM5B | LGALS9 | |
| PLD4 | TIMM8B | ITPKB | KHK | LGALS9B | |
| PLEKHO1 | TOP2A | KIAA1618 | L1CAM | LMCD1 | |
| PLSCR1 | TPX2 | L1TD1 | LAT2 | LMNA | |
| PLXNB2 | TRIB3 | LAP3 | LBH | LY75 | |
| POMP | WIZ | LDB3 | LNX1 | LYSMD2 | |
| PPFIBP1 | WSB1 | LGALS1 | LRRC25 | MAGED4 | |
| PTMS | WWC1 | LGALS3BP | LUC7L | MAPK10 | |
| QPRT | ZFP91 | LGALS9 | LYSMD2 | MBD1 | |
| RAB13 | ZMYM2 | LGALS9B | MEF2B | MEA1 | |
| RCN1 | ZNF385B | LMNA | MEF2D | MT2A | |
| RGCC | ZNF581 | LPIN1 | MICAL3 | MX1 | |
| RNF213 | ZNF644 | MAP3K11 | MYH11 | MX2 | |
| S100A13 | | MCAM | NARF | MYBPC2 | |
| SAMD9L | | MCM8 | NBR1 | NCOA7 | |
| SAMHD1 | | MGLL | NEDD9 | NCOA7 | |
| SERPINH1 | | MPP7 | NEFL | NEXN | |
| SLFN11 | | MUC1 | OMA1 | NT5C3A | |
| SLFN13 | | MX1 | PARVB | OAS1 | |
| SLFN5 | | MX2 | PDK1 | OAS2 | |
| SP110 | | MYL4 | PFKFB4 | OAS3 | |
| SP140 | | NCF4 | PGM1 | OSBPL10 | |
| SPN | | NMI | PIR | PARP10 | |
| SPR | | NQO1 | PLEKHG1 | PARP14 | |
| STAP1 | | NUB1 | PMS2CL | PARP9 | |
| STAT1 | | OAS1 | PODXL2 | PCDHGC3 | |
| STAT2 | | OAS2 | POU2AF1 | PLG | |
| TAP1 | | OAS3 | PPP1R2 | PLSCR1 | |
| TAX1BP3 | | OASL | PTPRCAP | PRCP | |
| THEMIS2 | | ORMDL2 | PTPRE | PTTG1IP | |
| THTPA | | OTOF | PTPRF | PYGO2 | |
| TNFAIP8L2 | | P2RY6 | PTPRO | QPCT | |
| TNFSF8 | | PAPSS2 | PTTG1 | S100A13 | |
| TP53I3 | | PARP14 | PVRL1 | SAMHD1 | |
| TREX1 | | PARP9 | RAB33A | SERPINH1 | |
| TRIM22 | | PBXIP1 | RANBP3 | SIRPB1 | |
| TTC39C | | PHF11 | RASGRP3 | SLC23A2 | |
| TXNIP | | PHF15 | RASSF6 | SLC25A33 | |
| UBA7 | | PLG | RBBP5 | SLC7A7 | |
| UBE2L6 | | PLSCR1 | RHOF | SLFN5 | |
| USP41 | | PREX1 | RPS29 | SOWAHD | |
| VCL | | PREX2 | RPS4Y2 | SP110 | |
| VNN2 | | PRIC285 | SAMD1 | SP140 | |
| ZBTB38 | | PRKCI | SC5DL | SPR | |
| | | PSAP | SEC14L1 | STAT1 | |
| | | PTMS | SEMA7A | STAT2 | |
| | | RAB13 | SERPINB9 | STK3 | |
| | | RASSF4 | SETD8 | SYBU | |
| | | RCN1 | SH2D3C | TAP1 | |
| | | RGL1 | SIT1 | TAP2 | |
| | | RGS13 | SLAMF7 | TDRD7 | |
| | | RNF213 | SLC16A3 | THEMIS2 | |
| | | RTN2 | SLC19A2 | TNFAIP8L2 | |
| | | RTP4 | SNAP23 | TNFSF9 | |
| | | RUNX3 | SNX11 | TRIM14 | |
| | | S100A13 | SP140 | TRIM21 | |
| | | SAMD9 | SPIB | TRIM22 | |
| | | SAMD9L | SPTAN1 | TYMP | |
| | | SAMHD1 | SPTB | UBE2L6 | |
| | | SERPINA7 | SSBIP1 | USP40 | |
| | | SERPINF2 | STK17B | VPREB1 | |
| | | SERPINH1 | SYNCRIP | | |
| | | SIPA1L3 | TCP11L1 | | |
| | | SLAMF1 | TGM2 | | |
| | | SLC1A3 | TJAP1 | | |

TABLE 1-continued

Upregulated and Downregulated Proteins in Response to Compound A Treatment in Lymphoma Cell Lines

| OCI-LY10 | | TMD8 | | WSU-DLCL2 | |
| --- | --- | --- | --- | --- | --- |
| Upregulated | Downregulated | Upregulated | Downregulated | Upregulated | Downregulated |
| | | SLC23A2 | TNFAIP3 | | |
| | | SLC27A3 | TNFRSF13B | | |
| | | SLFN5 | TNFRSF1B | | |
| | | SOD2 | TOM1 | | |
| | | SPN | TOR1AIP1 | | |
| | | SPR | TP53I11 | | |
| | | SRC | TSTD1 | | |
| | | STAT1 | TUBB2B | | |
| | | STAT2 | UBE2J1 | | |
| | | SYNJ2BP | VAT1 | | |
| | | TAX1BP3 | VIM | | |
| | | TBC1D13 | WIPF1 | | |
| | | TDRD7 | WIZ | | |
| | | TGOLN2 | ZBTB32 | | |
| | | TLR7 | ZFP91 | | |
| | | TMEM87A | ZMYM2 | | |
| | | TMOD2 | ZNF316 | | |
| | | TNFAIP2 | ZNF644 | | |
| | | TNFAIP8L2 | ZNF805 | | |
| | | TRANK1 | | | |
| | | TRIM14 | | | |
| | | TRPC4 | | | |
| | | TRPM4 | | | |
| | | TSPAN14 | | | |
| | | TSPAN3 | | | |
| | | UBA7 | | | |
| | | UBE2L6 | | | |
| | | USP18 | | | |
| | | USP41 | | | |
| | | VNN2 | | | |
| | | VTN | | | |
| | | XAF1 | | | |
| | | ZCCHC2 | | | |
| | | ZER1 | | | |
| | | ZNF385A | | | |
| | | ZNF480 | | | |
| | | ZNF770 | | | |

6.21 Western Analysis Shows the Levels of ZFP91 and Aiolos Reduce in Response to Treatment with Various Compounds in Lymphoma Cell Lines OCI-LY10 cells treated with DMSO, 100 µM thalidomide, 10 µM lenalidomide, 1 µM pomalidomide, 1 µM Compound A, 10 µM Compound A, 100 µM Compound B, or 100 µM Compound C for 6 hours. Cells were harvested with RIPA buffer, and proteins from cell lysates were separated by 10% sodium dodecyl sulfate polyacrylamide (SDS-PAGE) gel electrophoresis (Bio-Rad), and transferred to PVDF membranes (Invitrogen). Immunoblots were probed with antibodies recognizing Aiolos (9-9-7; Celgene), CK1α(Abcam), GSPT1 (Sigma), ZFP91 (LSBio) and β-actin (Li-Cor). Signals were detected with a Li-Cor Odyssey imager. The results were shown in FIG. 14A, and as shown, the levels of ZFP91 and Aiolos reduce in response to treatment with various compounds in the lymphoma cells OCI-LY10 cells treated with DMSO, 100 µM thalidomide, 10 µM lenalidomide, 1 µM pomalidomide, 1 µM Compound A, 10 µM Compound A, 100 µM Compound B, or 100 µM Compound C for 6 hours. Additionally, one sample was pretreated with 10 µM MLN-4924 for 1 hour prior to drug treatment with Compound A. Cells were harvested with RIPA buffer and Proteins from cell lysates were separated by 10% sodium dodecyl sulfate polyacrylamide (SDS-PAGE) gel electrophoresis (Bio-Rad), and transferred to PVDF membranes (Invitrogen). Immunoblots were probed with antibodies recognizing Aiolos (9-9-7; Celgene), GSPT1 (Sigma), ZFP91 (LSBio) and β-actin (Li-Cor). Signals were detected with a Li-Cor Odyssey imager. The results were shown in FIG. 14B. As shown, MLN-4924 blocked Aiolos and ZFP91 degradation in response to Compound A.

6.22 Western Analysis Shows the Level of ZFP91, CRBN, Ikaros, or Aiolos Changes in Response to Treatment with Compounds in Myeloma, Lymphoma, and Primary B Cell Lines Multiple myeloma cells (U266, DF15, RPMI8226), diffuse large B cell lymphoma cells (OCI-LY10, WSU-DLCL2, WSU-DLCL2 Compound A resistant), and primary B cells were treated with DMSO, 1 mM pomalidomide or 1 mM Compound A for 8 hours. Cells were harvested and were treated in cell lysis buffer to generate cell lysates. Proteins from cell lysate were separated by gel electrophoresis (10% SDS-PAGE) and transferred to nitrocellulose membranes. Immunoblots were then probed with antibodies recognizing Aiolos, CRBN, Ikaros, ZFP91 (LSBio), IRF4, IRF7, Myc, and β-actin (Li-Cor). The results were shown in FIG. 15. As shown, in all these cell lines, treatment with compounds reduced the levels of Aiolos, Ikaros, and ZFP91.

6.23 Compounds Induce Reduction of ZFP91 Level in a CRBN Dependent Pathway in Multiple Myeloma Cells As shown in FIG. 16A, pomalidomide induced ZFP91 degradation is CRBN dependent in U266 cells. U266 cells were transduced with inducible shRNA constructs targeting CRBN or targeting luciferase as control. Cells were grown in the presence or in the absence of 10 ng/ml Doxycycline, and in the presence or in the absence of 1 μM pomalidomide. Cells were harvested and were treated in cell lysis buffer to generate cell lysates. Proteins from cell lysate were separated by gel electrophoresis and transferred to nitrocellulose membranes. Immunoblots were then probed with antibodies recognizing Aiolos, CRBN, Ikaros, ZFP91, IRF4, IFIT1, IFIT3, P-STAT1, and β-actin (Li-Cor). As shown, when CRBN was knocked down by shRNA, the pomalidomide induced reductions of Aiolos, Ikaros, and ZFP91 were blocked.

Also as shown in FIG. 16B, thalidomide, lenalidomide, pomalidomide, or Compound A induced destruction of Aiolos, Ikaros, and ZFP91 in a CRBN dependent pathway. CRBN shRNA expression was induced for 48 hours in U266 cells with 10 ng/ml doxycycline prior to a 6 hour compound treatment (using DMSO, 100 mM thal, 10 mM len, 1 mM pom, or 1 mM Compound A). Cells were harvested, and lysates were run on 10% SDS-PAGE and immunoblotted with the appropriate antibodies. As shown, when CRBN was down regulated, reduction of Aiolos, Ikaros, and ZFP91 proteins induced by the compounds was blocked.

Similarly, when NAE1 or proteasome inhibitors were used to treat the cells, the compounds induced reduction of Aiolos, Ikaros, and ZFP91 proteins was blocked, as shown in FIG. 16C. MG132 activates c-Jun N-terminal kinase (JNK1), which initiates apoptosis. MG132 also inhibits NF-κB activation with an IC50 of 3 μM and prevents β-secretase cleavage. MLN4924 is a NAE1 inhibitor that blocks the activity of Cullin Ring Ligases (CRLs), such as CRL4$^{CRBN}$. U266 cells were pretreated with 10 mM MLN4924 or MG132 for 1 hr and then compounds were added for 6 hr (DMSO, 100 mM thal, 10 mM len, 1 mM pom, 1 mM Compound A, or 0.1 mM Compound B). Cells were harvested and lysates were run on 10% SDS-PAGE, transferred to nitrocellulose and immunoblotted with the corresponding antibodies. As shown, when CRBN activity was inhibited, reduction of Aiolos, Ikaros, and ZFP91 proteins induced by the compounds (thalidomide, lenalidomide, pomalidomide, or Compound A) was blocked. The results indicate that ZFP91 is a substrate of CRBN and ZFP91 is down-regulated in response to the compounds provided herein in a CRBN dependent pathway.

6.24 Compounds Induce Reduction of ZFP91 Level in a CRBN Dependent Pathway in Diffuse Large B Cell Lymphoma Cells OCI-LY10 cells treated with DMSO or various drugs for 6 hrs. Cells were harvested with RIPA buffer and proteins from cell lysates were separated by 10% sodium dodecyl sulfate polyacrylamide (SDS-PAGE) gel electrophoresis (Bio-Rad), and transferred to PVDF membranes (Invitrogen). Immunoblots were probed with antibodies recognizing: Aiolos (9-9-7; Celgene), CK1α(Abcam), GSPT1 (Sigma), ZFP91 (LSBio) and β-actin (Li-Cor). Signals were detected with a Li-Cor Odyssey imager. The results were shown in FIG. 17A-B. As shown in FIG. 17A, 100 mM thalidomide, 10 mM lenalidomide, 1 mM pomalidomide, 1 μM or 10 μM Compound A, or 100 nM Compound B reduced the levels of ZFP91 and Aiolos in OCI-LY10 cells. As shown in FIG. 17B, 1 μM lenalidomide, 10 μM lenalidomide, 0.1 μM Compound A, 1 μM Compound A, and 10 μM Compound A reduced the levels of ZFP91 and Aiolos.

OCI-LY10 cells were then treated with DMSO or various drugs for 6 hrs. Additionally, one sample was pretreated with 10 μM MLN-4924 for 1 hour prior to drug treatment. Cells were harvested with RIPA buffer and Proteins from cell lysates were separated by 10% sodium dodecyl sulfate polyacrylamide (SDS-PAGE) gel electrophoresis (Bio-Rad), and transferred to PVDF membranes (Invitrogen). Immunoblots were probed with antibodies recognizing: Aiolos (9-9-7; Celgene), ZFP91 (LSBio), ZNF198 (LSBio) and β-actin (Li-Cor). Signals were detected with a Li-Cor™ Odyssey imager. The results were shown in FIG. 17C, and as shown, pre-treatment by MLN-4924 restored the level of both Aiolos and ZFP91.

OCI-LY10 cells stably transduced with shCRBN 11 were induced for 48 hrs with either 0 or 10 ng/ml of doxycycline. Cells were then treated with either DMSO, lenalidomide, or Compound A for an additional 6 hours. Where MLN4924 treatments were present, MLN4924 was pre-incubated for 1 hr prior to drug treatment. Cells were harvested with RIPA buffer and Proteins from cell lysates were separated by 10% sodium dodecyl sulfate polyacrylamide (SDS-PAGE) gel electrophoresis (Bio-Rad), and transferred to PVDF membranes (Invitrogen). Immunoblots were probed with antibodies recognizing: CRBN-65, Aiolos (9-9-7; Celgene), Ikaros (Millipore), ZFP91 (LSBio) and β-actin (Li-Cor). Signals were detected with a Li-Cor Odyssey imager. The results were shown in FIG. 17D. Again, as shown, pre-treatment by MLN-4924 restored the level of both Aiolos and ZFP91 in cells treated with all the compounds tested, indicating that these compounds induce reduction of ZFP91 level in a CRBN dependent pathway in diffuse large B cell lymphoma cells.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

6.25 Dual Staining Immunohistochemistry Assay for Measuring CRBN-Associated Proteins This example exemplifies using dual staining immunohistochemistry (IHC) to measure CRBN, Aiolos and Ikaros proteins. Dual staining immunohistochemistry was performed on the Bond-Max automated slide stainer (Leica Microsystems) using Bond Polymer Refine Detection Kit and Bond Polymer Refine Red Detection Kit. Multiple myeloma cell model (DF15, pomalidomide-resistant DF15R, and U266 CRBN shRNA) and 25 cases of commercially available multiple myeloma patient bone marrow clots or biopsies were used in the assay. Formalin-fixed paraffin-embedded (FFPE) tissues or cell pellets were sectioned and deparaffinized on the instrument. Antigen retrieval was performed with Epitope Retrieval 2 (pH 9.0) for 20 minutes at 100° C. The slides were blocked for endogenous peroxidase activity with Peroxide Block for 5 minutes at room temperature. Sections were then incubated with a first antibody-rabbit monoclonal antibody to CRBN (CGN-6-4-5 available from Celgene), rabbit monoclonal antibody to Aiolos (9B-9-7 available from Celgene), or rabbit polyclonal antibody to Ikaros (Santa Cruz, sc-13039), for 15 minutes at room temperature, followed by incubation with HRP labeled Polymer for 8 minutes at room temperature. The sample was treated with hydrogen peroxide substrate and diaminobenzidine tetrahydrochloride (DAB) chromogen at room temperature for 10 minutes, and then in bound Wash buffer at 90° C. for 5 minutes. The sections were then incubated with an anti-CD128 mouse monoclonal antibody (Dako, M7228) for 15 minutes, followed by incubation with AP labeled Polymer for 8 minutes at room temperature. The sample was treated with hydrogen peroxide substrate and Refine Red at room temperature for 10 minutes. Slides were counterstained with Hematoxylin for 5 minutes at room temperature. Slides were then analyzed under light microscope and final scores were assigned using 40× objective.

Results were analyzed using H-score method. The H-score is a method of assessing the extent of immunoreactivity. The score is obtained by the formula: 3×percentage of strongly staining cells+2×percentage of moderately staining cells+1×percentage of weakly staining cells+0×percentage of negative staining cells, which gives a range of 0 to 300. The entire area of viable sample is scored for maker immunoreactivity based on the distribution and intensity. Scoring was given to those samples with 20 or more well-preserved CD128 positive cells, and areas compromised by artifact, e.g., edge staining, folding, shrinking, smearing, and incomplete fixation, are avoided.

As shown in Table 2 below, dual staining immunohistochemistry detected a range of CRBN levels in 22 MM cases.

TABLE 2

CRBN Levels Detected by Dual Staining Immunohistochemistry

| Sample No. | Average Cytoplasmic H-score | Average nuclear H-score | Average total H-scores |
|---|---|---|---|
| MM12 | 193 | 213 | 407 |
| MM13 | 150 | 193 | 343 |
| MM14 | 207 | 177 | 383 |
| MM15 | 183 | 180 | 363 |
| MM16 | 240 | 250 | 490 |
| MM17 | 100 | 110 | 210 |
| MM18 | 267 | 233 | 500 |
| MM19 | 163 | 100 | 263 |
| MM20 | 67 | 17 | 83 |
| MM21 | 240 | 193 | 433 |
| MM22 | 110 | 127 | 237 |
| MM23 | 217 | 240 | 457 |
| MM24 | 190 | 173 | 363 |
| MM25 | 93 | 40 | 133 |
| MM26 | 117 | 87 | 203 |
| MM27 | 137 | 160 | 297 |
| MM28 | 83 | 110 | 193 |
| MM30 | 63 | 50 | 113 |
| MM33 | 137 | 87 | 223 |
| MM34 | 177 | 157 | 333 |
| MM35 | 80 | 47 | 127 |
| MM36 | 67 | 40 | 107 |

As shown in FIG. 18, pathologic evaluation of 22 MM samples using the dual assay and the H-score method demonstrated high concordance in H-scores.

As shown in FIG. 19A, the dual staining assay differentiated high and low CRBN expression levels in multiple myeloma cell line DF15 and pomlidomide-resistant DF15R, respectively. FIG. 19B shows the CRBN staining results and H-score for Sample MM12. FIG. 19C shows the CRBN staining results and H-score for Samples MM13 and MM15. FIG. 20 and FIG. 21 shows the Aiolos staining and nuclear H-score and Ikaros staining and nuclear H-score, respectively, in Sample MM23.

As shown, these results demonstrate that dual staining immunohistochemistry assay can accurately measure a broad range of immunoreactivity. The dual CD138/CRBN, CD138/Aiolos, and CD138/Ikaros immunohistochemistry assays are effective in both bone marrow core biopsies and aspirate clots from 22 MM patients, for detection of a range of CRBN, Aiolos and Ikaros levels, respectively. Pathologic evaluation of MM samples using the dual assay and the H-score method demonstrated high concordance in H-scores. Thus, dual staining immunohistochemistry assay provides reliable and accurate semi-quantitative methods to evaluate CAPs in a cancer patient.

6.26 Lenalidomide Promotes Degradation of Casein Kinase 1α (CSNK1A1 or CK1α) in MDS and AML Cells Sensitivity to lenalidomide treatment in a panel of myeloid cancer cell lines was evaluated by tritiated thymidine and/or BrdU assays. 13 MDS/AML and 1 MM cell lines were evaluated for sensitivity to lenalidomide (LEN) in a 4 d BrdU cell assay. The results are shown in FIG. 22A, and as shown, across a panel of myeloid cancer cell lines evaluated for sensitivity to lenalidomide, HNT-34 and MDS-L cells show the greatest sensitivity to lenalidomide, with EC50's of 0.6 and 1.5 uM, respectively, while other cell lines were predominantly insensitive (EC50>10 uM). As shown in FIG. 22B, both HNT-34 and MDS-L cells were sensitive to lenalidomide, while only MDS-L cells were sensitive to Compound A, indicating of the selectivity of these compounds. As shown in FIG. 22C, the sensitivity of myeloid cancer cell lines to lenalidomide (LEN) and Compound A. As shown in FIG. 22D, lenalidomide promotes the degradation of casein kinase 1, alpha 1 (CSNK1A1; also interchangeably referred to as "CK1a" and "CK1α" herein) in the sensitive cell lines (HNT-34, MDS-L), but does not degrade CSNK1A1 in the insensitive line (e.g., MOLM-13, THP). Lenalidomide also promoted degradation of CSNK1A1 in the insensitive cell lines KG-1 and HL-60. FIG. 23E shows a Western Blot analysis of CK1α, Ikaros, and CRBN protein levels in untreated and lenalidomide (LEN)-treated myeloid cancer cells.

As shown in FIG. 23E, CK1α and Ikaros levels were reduced in LEN-treated myeloid cancer cell lines in vitro. In particular, decreased CK1α and Ikaros protein levels with LEN treatment were confirmed in MDS-L and HNT-34 cells. Decreased CK1α protein levels with LEN treatment were also observed in KG-1 and HL-60, but not in THP-1 or MOLM-13 AML cells. Decreased Ikaros protein levels with LEN treatment were also observed in KG-1, but not in THP-1 cells; HL-60 and MOLM-13 cells did not express detectable Ikaros. In addition, CRBN was expressed at higher levels in MDS-L, HNT-34, and KG-1 versus HL-60, THP-1, and MOLM-13 cells.

Changes in global cellular protein levels were measured by tandem-mass-tagged proteomics in a del(5q) MDS cell line (MDS-L) and an AML cell line (HNT-34), following treatment with vehicle or 10 uM lenalidomide or 1 uM Compound A for 8, 24 and 72 hours. Samples were subjected to multiplexed quantitative mass spectrometry analysis. In particular, cell lysate was prepared from the samples, and was subjected to tandem protein digestion using LysC and trypsin, peptide labeling with either Tandem Mass Tag 6-plex or 10-plex reagents, and peptide fractionation. Multiplexed quantitative mass spectrometry data were collected on an Orbitrap Fusion mass spectrometer operating in a MS3 mode using synchronous precursor selection for the MS2 to MS3 fragmentation. MS/MS data were searched against a Uniprot human database with both the forward and reverse sequences using the SEQUEST algorithm. Additional data processing steps included controlling peptide and protein level false discovery rates, assembling proteins from peptides, and protein quantification from peptides. Each drug-treated sample has 3 replicates, each DMSO sample has 4 replicates.

Protein levels were measured by tandem-mass-tagged proteomics in a del(5q) MDS cell line (MDS-L), following treatment with vehicle or 10 uM lenalidomide for 8, 24 and 72 hours (data not shown). Protein levels were also measured by tandem-mass-tagged proteomics in an AML cell line (HNT-34), following treatment with vehicle or 10 uM lenalidomide for 8, 24 and 72 hours (data not shown).

Selected results of proteomics studies are shown in Tables 3-8. The average relative abundance of the protein is shown in the tables. T is the statistic calculated for the t.test. P.value represents statistical significance for the test. Adj.P.value represents FDR multiple testing correction of the P.values in previous parameter. B log odds that the protein is differentially abundant between the conditions (compound vs control).

TABLE 3

MDS-L treated with LENALIDOMIDE (10 micromolar) for 8 hours

| Protein ID | Gene-Symbol | AveExpr | t | P. Value | adj. P. Val | B | $\log_2 FC$ |
|---|---|---|---|---|---|---|---|
| sp|Q13422|IKZF1_HUMAN | IKZF1 | 16.66668 | −65.9319 | 5.47E−11 | 2.58E−07 | 7.912138 | −2.1 |
| sp|P48729-2|KC1A_HUMAN | CSNK1A1 | 16.66666 | −38.7034 | 2.20E−09 | 5.20E−06 | 7.503006 | −1.6 |

TABLE 4

MDS-L treated with LENALIDOMIDE (10 micromolar) for 24 hours

| Protein ID | Gene-Symbol | AveExpr | t | P. Value | adj. P. Val | B | $\log_2 FC$ |
|---|---|---|---|---|---|---|---|
| sp|Q13422|IKZF1_HUMAN | IKZF1 | 13.22343 | −22.6587 | 2.68E−08 | 4.16E−05 | 9.70494 | −2.4 |
| sp|P48729-2|KC1A_HUMAN | CSNK1A1 | 9.210851 | −31.7149 | 2.09E−09 | 9.84E−06 | 11.5767 | −1.4 |
| sp|Q96JP5|ZFP91_HUMAN | ZFP91 | 12.78383 | −5.13461 | 0.001019 | 1.99E−02 | −0.81158 | −1.4 |
| sp|P20248|CCNA2_HUMAN | CCNA2 | 11.77519 | −11.7181 | 3.66E−06 | 5.22E−04 | 5.133116 | −1.1 |
| sp|P50454|SERPH_HUMAN | SERPINH1 | 7.916993 | 21.84346 | 3.53E−08 | 4.16E−05 | 9.476948 | 1.1 |

TABLE 5

MDS-L treated with LENALIDOMIDE (10 micromolar) for 72 hours

| ProteinID | Gene-Symbol | AveExpr | t | P. Value | adj. P. Val | B | $\log_2 FC$ |
|---|---|---|---|---|---|---|---|
| sp|Q13422|IKZF1_HUMAN | IKZF1 | 13.28264 | −60.4486 | 8.08E−12 | 2.10E−08 | 16.53253 | −2.4 |
| sp|P48729-2|KC1A_HUMAN | CSNK1A1 | 9.162276 | −38.45 | 2.85E−10 | 1.49E−07 | 14.11412 | −1.5 |
| sp|Q9NRR1|CYTL1_HUMAN | CYTL1 | 11.87789 | −33.6499 | 8.13E−10 | 3.19E−07 | 13.25043 | −1.2 |
| sp|Q9NQX7|ITM2C_HUMAN | ITM2C | 10.84549 | −33.6487 | 8.13E−10 | 3.19E−07 | 13.25018 | −1.2 |
| sp|Q96JP5|ZFP91_HUMAN | ZFP91 | 12.26652 | −32.6506 | 1.03E−09 | 3.24E−07 | 13.04713 | −1.1 |
| sp|Q9NQ75|CASS4_HUMAN | CASS4 | 9.256984 | 47.4336 | 5.46E−11 | 5.15E−08 | 15.34211 | 1.0 |
| sp|Q8N392|RHG18_HUMAN | ARHGAP18 | 8.574636 | 31.80469 | 1.27E−09 | 3.31E−07 | 12.8679 | 1.0 |
| sp|Q86W92|LIPB1_HUMAN | PPFIBP1 | 8.101329 | 47.64304 | 5.28E−11 | 5.15E−08 | 15.36599 | 1.2 |
| sp|P98082|DAB2_HUMAN | DAB2 | 7.79408 | 26.70875 | 4.97E−09 | 8.50E−07 | 11.62743 | 1.3 |
| sp|Q9BR76|COR1B_HUMAN | CORO1B | 7.752687 | 59.70966 | 8.90E−12 | 2.10E−08 | 16.47832 | 1.4 |
| sp|P04792|HSPB1_HUMAN | HSPB1 | 6.52062 | 42.98706 | 1.19E−10 | 8.52E−08 | 14.7879 | 1.5 |
| sp|P50454|SERPH_HUMAN | SERP1NH1 | 7.243517 | 56.70681 | 1.34E−11 | 2.10E−08 | 16.24365 | 1.7 |
| sp|Q9ULM3|YETS2_HUMAN | YEATS2 | 5.942486 | 3.831903 | 0.005123 | 1.41E−02 | −2.99583 | 2.5 |

TABLE 6

HNT-34 treated with LENALIDOMIDE (10 micromolar) for 8 hours

| ProteinID | Gene-Symbol | AveExpr | t | P. Value | adj. P. Val | B | $\log_2 FC$ |
|---|---|---|---|---|---|---|---|
| sp|Q13422|IKZF1_HUMAN | IKZF1 | 16.66665 | −39.2188 | 2.17E−09 | 1.02E−05 | 6.949087 | −2.1 |
| sp|P48729-2|KC1A_HUMAN | CSNK1A1 | 16.66665 | −29.6732 | 1.48E−08 | 3.49E−05 | 6.600017 | −1.6 |

TABLE 7

HNT-34 treated with LENALIDOMIDE (10 micromolar) for 24 hours

| ProteinID | Gene-Symbol | AveExpr | t | P. Value | adj. P. Val | B | log$_2$FC |
|---|---|---|---|---|---|---|---|
| sp\|Q13422\|IKZF1_HUMAN | IKZF1 | 13.77724 | −58.0432 | 3.27E−12 | 1.54E−08 | 15.99616 | −2.4 |
| sp\|P48729-2\|KC1A_HUMAN | CSNK1A1 | 9.102643 | −38.8985 | 9.25E−11 | 1.45E−07 | 14.30879 | −1.4 |
| sp\|Q96JP5\|ZFP91_HUMAN | ZFP91 | 12.41087 | −17.6126 | 6.51E−08 | 2.56E−05 | 9.039443 | −1.4 |
| sp\|P20248\|CCNA2_HUMAN | CCNA2 | 9.790186 | −5.24916 | 0.000667 | 1.11E−02 | −0.54051 | −1.1 |
| sp\|P62158\|CALM_HUMAN | CALM1 | 10.44533 | −3.48985 | 0.007632 | 4.70E−02 | −3.12054 | −1.1 |
| sp\|P50454\|SERPH_HUMAN | SERP1NH1 | 9.343343 | 18.40491 | 4.54E−08 | 2.38E−05 | 9.380643 | 1.1 |

TABLE 8

HNT-34 treated with LENALIDOMIDE (10 micromolar) for 72 hours

| Protein ID | GeneSymbol | AveExpr | t | P. Value | adj. P. Val | B | log$_2$FC |
|---|---|---|---|---|---|---|---|
| sp\|Q13422\|IKZF1_HUMAN | IKZF1 | 13.75679 | −41.0369 | 4.14E−11 | 4.88E−08 | 15.85308 | −2.4 |
| sp\|P48729-2\|KC1A_HUMAN | CSNK1A1 | 9.116471 | −27.5365 | 1.22E−09 | 6.20E−07 | 12.94428 | −1.5 |
| sp\|Q9NQX7\|ITM2C_HUMAN | ITM2C | 9.634643 | −3.19291 | 0.011717 | 3.97E−02 | −3.92038 | −1.2 |
| sp\|Q96JP5\|ZFP91_HUMAN | ZFP91 | 12.30761 | −44.9548 | 1.91E−11 | 3.57E−08 | 16.43863 | −1.1 |
| sp\|Q9NQ75\|CASS4_HUMAN | CASS4 | 9.6162 | 21.43315 | 1.01E−08 | 2.07E−06 | 10.90606 | 1.0 |
| sp\|Q8N392\|RHG18_HUMAN | ARHGAP18 | 9.713329 | 10.6197 | 3.28E−06 | 1.18E−04 | 4.864909 | 1.0 |
| sp\|Q86W92\|LIPB1_HUMAN | PPFIBP1 | 9.469486 | 17.68031 | 5.05E−08 | 6.10E−06 | 9.274738 | 1.2 |
| sp\|P98082\|DAB2_HUMAN | DAB2 | 9.292657 | 14.1321 | 3.23E−07 | 2.34E−05 | 7.339317 | 1.3 |
| sp\|Q9BR76\|COR1B_HUMAN | CORO1B | 9.277457 | 22.95871 | 5.66E−09 | 1.33E−06 | 11.47692 | 1.4 |
| sp\|P04792\|HSPB1_HUMAN | HSPB1 | 8.910686 | 12.15958 | 1.10E−06 | 5.65E−05 | 6.034471 | 1.5 |
| sp\|P50454\|SERPH_HUMAN | SERPINH1 | 9.026871 | 19.55829 | 2.17E−08 | 3.66E−06 | 10.13554 | 1.7 |

Proteomic analysis of lenalidomide-regulated proteins showed that CSNK1A1 and Ikaros were down-regulated in response to lenalidomide treatment, as shown in FIG. 23A (bars correspond to the average log 2 fold-change of 3 replicates and error bars correspond to 95% confidence interval for the mean). Proteomic analysis of lenalidomide-regulated proteins in MDS-L cells revealed Ikaros as the most down-regulated protein at 72 hrs (about 5 fold), and CSNK1A1 was the second most down-regulated protein (about 3 fold), as shown in FIG. 23B.

Western blot analysis was used to subsequently validate proteins that were differentially regulated in these lenalidomide-sensitive cell lines. The decrease of Ikaros and CSNK1A1 proteins by lenalidomide were confirmed by Western blot analysis in MDS-L cells as shown in FIG. 23C. The decrease of Ikaros and CSNK1A1 proteins by lenalidomide were also confirmed by Western blot analysis in HNT-34 cells as shown in FIG. 23C. As shown in FIG. 24, degradations of CSNK1A1 and Ikaros in HNT-34 cells treated with lenalidomide were time- and dose-dependent.

Mechanistic studies addressing CSNK1A1 regulation in HNT-34 cells revealed that CSNK1A1 protein levels were reduced by lenalidomide treatment in a time- and dose-dependent manner, with maximal reduction of 3.3-fold observed at 4 hrs using 10 uM lenalidomide, and CSNK1A1 degradation observed with lenalidomide at a dose as low as 0.1 uM, as shown in FIG. 24.

The effects of lenalidomide on CSNK1A1 level were validated in clinical studies. Five patients with acute myeloid leukemia (not previously treated and age 65 or older) were treated with 50 mg lenalidomide daily, and bone marrow or blood samples were obtained from the patients and processed to bone marrow mononuclear cells (BMMC) or peripheral blood mononuclear cells (PBMC). 3-5 µg total protein from each sample was evaludated for CSNK1A1, Ikaros, and GAPDH expressions by western analysis. The results were shown in FIG. 25. As shown In FIG. 25A, both CSNK1A1 and Ikaros were modulated (down-regulated) in 4 of 5 patients treated with lenalidomide. In addition, FIG. 25B shows that CK1α and Ikaros protein levels were reduced in bone marrow or peripheral blood of lenalidomide (LEN)-treated patients with AML in vivo.

6.27 MG-132 or Compound a Pre-Treatment Blocks Lenalidomide-Induced Degradation of CK1α and IKAROS in HNT-34 Cells HNT-34 cells were pre-treated with or without 3 µM or 10 µM MG-132 for 30 min. Then cells were treated with 10 µM lenalidomide for 3 h or 6 h. The results were shown in FIG. 26, and as shown lenalimoide treatment decreased both CSNK1A1 and Ikaros proteins levels at 3 h or 6 h, and pre-treating HNT-34 cells with the proteasome inhibitor MG-132 stabilized CSNK1A1 protein levels in the presence of lenalidomide, demonstrating proteasome-dependent degradation.

A competition experiment performed by pre-treating HNT-34 cells with Compound A. HNT-34 cells were pre-treated with 10 µM Compound A for 1.5 h. Then cells were treated with 0.1-10 µM lenalidomide for 3 h or 6 h. Western analysis of Ikaros and CSNK1A1 were shown in FIG. 27. As shown in FIG. 27A, 10 µM Compound A blocks 0.3 µM or less lenalidomide induced CSNK1A1 degradation at 3 h or 6 h. Compound A binds CRBN, and as a result, CSNK1A1 protein is stabilized in the presence of lenalidomide, demonstrating CRBN-dependence of the lenalidomide-induced degradation. FIG. 27B shows that the LEN-mediated reduction of CK1α levels are cullin-dependent and CRBN-dependent. For example, pretreatment with proteosome inhibitor (MG-132) and neddylation inhibitor (MLN-4924)

abrogated LEN-mediated CK1α reduction in HNT-34 cells (FIG. 27B, left panel). In addition, pretreatment with CRBN RNAi inhibited LEN-mediated CK1α reduction in HNT-34 cells (FIG. 27B, right panel).

These results indicate that CSNK1A1 is a lenalidomide-induced substrate of CRL4-CRBN. As the CSNK1A1 gene is located at 5q32, a commonly deleted region in MDS, further reduction of haplo-insufficient expression of CSNK1A1 is a potential mechanism of sensitivity to lenalidomide in del(5q) MDS.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of determining whether a compound is effective as an immunomodulatory compound or anti-tumor agent, or treating a cancer, comprising:
   (a) contacting a first cell from a subject with the compound;
   (b) obtaining a first sample from the first cell from step (a);
   (c) determining the level of a biomarker in the first sample;
   (d) comparing the level of the biomarker from step (c) to the level of the biomarker in a reference sample,
      (i) wherein when the biomarker is CYTL1, ITM2C, CCNA2, or ZFP91, a decreased level of the biomarker in the first sample as compared to the reference sample indicates that the compound is likely to be efficacious as an immunomodulatory compound or an anti-tumor agent, and an increased level of the biomarker in the first sample as compared to the reference sample indicates that the compound is unlikely to be efficacious as an immunomodulatory compound or an anti-tumor agent;
      (ii) wherein when the biomarker is ARHGAP18, CASS4, CORO1B, DAB2, HSPB1, PPFIBP1, SERPINH1, or YEATS2, an increased level of the biomarker in the first sample as compared to the reference sample indicates that the compound is likely to be efficacious as an immunomodulatory compound or an anti-tumor agent, and a decreased level of the biomarker in the first sample as compared to the reference sample indicates that the compound is unlikely to be efficacious as an immunomodulatory compound or an anti-tumor agent; and
   (e) administering to the subject a therapeutically effective amount of the compound when the compound is indicated as likely to be efficacious as an immunomodulatory compound or an anti-tumor agent, or not administering to the subject the compound when the compound is indicated as unlikely to be efficacious as an immunomodulatory compound or an anti-tumor agent;
   wherein the biomarker is ARHGAP18, CASS4, CCNA2, CORO1B, CYTL1, DAB2, HSPB1, ITM2C, PPFIBP1, SERPINH1, YEATS2 or ZFP91, or any combination thereof;
   wherein the reference sample is prepared by using a second sample obtained from the subject prior to contacting with the compound; and
   lenalidomide, pomalidomide, thalidomide, 3-(5-amino-2-methyl-4-oxo-4H-quinazolin-3-yl)-piperidine-2,6-dione (Compound A), or 3-(4-((4-(morpholinomethyl) benzyl)oxy)-1-oxoisoindolin-2-yl)piperidine-2,6-dione (Compound B), a stereoisomer thereof, or a pharmaceutically acceptable salt, solvate, hydrate, co-crystal, clathrate, or polymorph thereof.

2. The method of claim 1, wherein the cancer is selected from the group consisting of diffuse large B-cell lymphoma (DLBCL), multiple myeloma (MM), myelodysplastic syndrome (MDS), acute myeloid leukemia (AML), mantle cell lymphoma (MCL), follicular lymphoma (FL), chronic lymphocytic leukemia (CLL), non-Hodgkin's lymphoma (NHL), hairy cell leukemia, chronic myelogenous leukemia (CML), AIDS-related Kaposi sarcoma, and malignant melanoma.

3. The method of claim 1, wherein the biomarker is ZFP91.

4. The method of claim 1, wherein the first cell is a cancer cell.

5. The method of claim 1, wherein the first cell is an immune cell.

6. The method of claim 1, wherein the contacting in step (a) is in vitro.

7. The method of claim 1, wherein the contacting in step (a) is in vivo.

8. The method of claim 1, wherein the first sample is obtained from a tumor biopsy, node biopsy, or a biopsy from bone marrow, spleen, liver, brain or breast.

9. The method of claim 1, wherein the second sample is from the same source as the first sample.

10. The method of claim 1, wherein the cancer is diffuse large B-cell lymphoma (DLBCL).

11. The method of claim 1, wherein the cancer is multiple myeloma (MM).

12. The method of claim 1, wherein the cancer is myelodysplastic syndrome (MDS).

13. The method of claim 1, wherein the cancer is acute myeloid leukemia (AML).

14. The method of claim 1, wherein the compound is lenalidomide, or a stereoisomer thereof, or a pharmaceutically acceptable salt, solvate, hydrate, co-crystal, clathrate, or polymorph thereof.

15. The method of claim 1, wherein the compound is pomalidomide, or a stereoisomer thereof, or a pharmaceutically acceptable salt, solvate, hydrate, co-crystal, clathrate, or polymorph thereof.

16. The method of claim 1, wherein the compound is thalidomide, or a stereoisomer thereof, or a pharmaceutically acceptable salt, solvate, hydrate, co-crystal, clathrate, or polymorph thereof.

17. The method of claim 1, wherein the compound is 3-(5-amino-2-methyl-4-oxo-4H-quinazolin-3-yl)-piperidine-2,6-dione (Compound A), or a stereoisomer thereof, or a pharmaceutically acceptable salt, solvate, hydrate, co-crystal, clathrate, or polymorph thereof.

18. The method of claim 1, wherein the compound is 3-(4-((4-(morpholinomethyl)benzyl)oxy)-1-oxoisoindolin-2-yl)piperidine-2,6-dione (Compound B), a stereoisomer thereof, or a pharmaceutically acceptable salt, solvate, hydrate, co-crystal, clathrate, or polymorph thereof.

19. A method of predicting or monitoring the responsiveness of a subject having or suspected of having a cancer to a compound, comprising:
   (a) administering the compound to a subject having or suspected of having a cancer;
   (b) obtaining a first sample from the subject;
   (c) determining the level of a biomarker in the first sample;

(d) comparing the level of the biomarker from step (c) to the level of the same biomarker in a reference sample, (i) wherein when the biomarker is CYTL1, ITM2C, CCNA2, or ZFP91, a decreased level of the biomarker in the first sample as compared to the reference sample indicates that the subject is likely to be responsive to the compound, and an increased level of the biomarker in the first sample as compared to the reference sample indicates that the subject is unlikely to be responsive to the compound;

(ii) wherein when the biomarker is ARHGAP18, CASS4, CORO1B, DAB2, HSPB1, PPFIBP1, SERPINH1, or YEATS2, an increased level of the biomarker in the first sample as compared to the reference sample indicates that the subject is likely to be responsive to the compound, and a decreased level of the biomarker in the first sample as compared to the reference sample indicates that the subject is unlikely to be responsive to the compound; and (e) administering to the subject a therapeutically effective amount of the compound when the subject is indicated as likely to be responsive to the compound, or not administering to the subject the compound when the subject is indicated as unlikely to be responsive to the compound;

wherein the biomarker is ARHGAP18, CASS4, CCNA2, CORO1B, CYTL1, DAB2, HSPB1, ITM2C, PPFIBP1, SERPINH1, YEATS2 or ZFP91, or any combination thereof;

wherein the reference sample is prepared by using a second sample obtained from the subject prior to administration of the compound; and wherein the compound is lenalidomide, pomalidomide, thalidomide, 3-(5-amino-2-methyl-4-oxo-4H-quinazolin-3-yl)-piperidine-2,6-dione (Compound A), or 3-(4-((4-(morpholinomethyl)benzyl)oxy)-1-oxoisoindolin-2-yl)piperidine-2,6-dione (Compound B), a stereoisomer thereof, or a pharmaceutically acceptable salt, solvate, hydrate, co-crystal, clathrate, or polymorph thereof.

20. The method of claim 19, wherein the cancer is selected from the group consisting of diffuse large B-cell lymphoma (DLBCL), multiple myeloma (MM), myelodysplastic syndrome (MDS), acute myeloid leukemia (AML), mantle cell lymphoma (MCL), follicular lymphoma (FL), chronic lymphocytic leukemia (CLL), non-Hodgkin's lymphoma (NHL), hairy cell leukemia, chronic myelogenous leukemia (CML), AIDS-related Kaposi sarcoma, and malignant melanoma.

21. The method of claim 19, wherein the biomarker is ZFP91.

\* \* \* \* \*